ND## United States Patent
Chianelli et al.

(10) Patent No.: US 9,682,939 B2
(45) Date of Patent: Jun. 20, 2017

(54) COMPOSITIONS AND METHODS FOR MODULATING FARNESOID X RECEPTORS

(71) Applicants: Donatella Chianelli, San Diego, CA (US); Xiaodong Liu, San Diego, CA (US); Valentina Molteni, San Diego, CA (US); John Nelson, San Diego, CA (US); Jason Thomas Roland, San Diego, CA (US); Paul Vincent Rucker, Carlsbad, CA (US); David Charles Tully, Danville, CA (US)

(72) Inventors: Donatella Chianelli, San Diego, CA (US); Xiaodong Liu, San Diego, CA (US); Valentina Molteni, San Diego, CA (US); John Nelson, San Diego, CA (US); Jason Thomas Roland, San Diego, CA (US); Paul Vincent Rucker, Carlsbad, CA (US); David Charles Tully, Danville, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/034,280

(22) PCT Filed: Nov. 4, 2014

(86) PCT No.: PCT/US2014/063948
§ 371 (c)(1),
(2) Date: May 4, 2016

(87) PCT Pub. No.: WO2015/069666
PCT Pub. Date: May 14, 2015

(65) Prior Publication Data
US 2016/0340317 A1 Nov. 24, 2016

Related U.S. Application Data

(60) Provisional application No. 61/900,013, filed on Nov. 5, 2013.

(51) Int. Cl.
*C07D 231/54* (2006.01)
*C07D 491/052* (2006.01)
*C07D 471/06* (2006.01)
*A61K 31/4162* (2006.01)
*A61K 31/4745* (2006.01)
*A61K 31/4439* (2006.01)
*C07D 471/04* (2006.01)
*A61K 31/416* (2006.01)

(52) U.S. Cl.
CPC .......... *C07D 231/54* (2013.01); *A61K 31/416* (2013.01); *A61K 31/4162* (2013.01); *A61K 31/4439* (2013.01); *A61K 31/4745* (2013.01); *C07D 471/04* (2013.01); *C07D 471/06* (2013.01); *C07D 491/052* (2013.01)

(58) Field of Classification Search
None
See application file for complete search history.

(56) References Cited

FOREIGN PATENT DOCUMENTS

WO WO2007140183 A1 12/2007
WO WO2009012125 A1 1/2009

*Primary Examiner* — Kamal Saeed
(74) *Attorney, Agent, or Firm* — Emily Tongco Wu; Genomics Institute of the Novartis Research Foundation

(57) ABSTRACT

The present invention relates to compounds of Formula I,

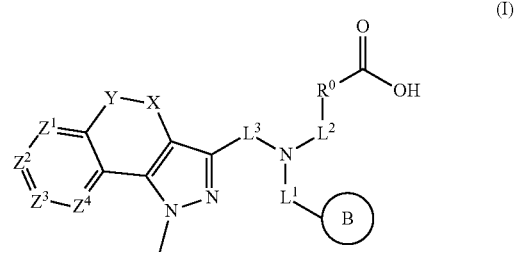

a stereoisomer, enantiomer, a pharmaceutically acceptable salt or an amino acid conjugate thereof; wherein variables are as defined herein; and their pharmaceutical compositions, which are useful as modulators of the activity of Farnesoid X receptors (FXR).

27 Claims, No Drawings

COMPOSITIONS AND METHODS FOR MODULATING FARNESOID X RECEPTORS

CROSS-REFERENCE TO RELATED APPLICATIONS

This application is a 371 U.S. national phase application of international application number PCT/US2014/063948 filed Nov. 4, 2014; which application claims the benefit of U.S. provisional application Ser. No. 61/900,013, filed Nov. 5, 2013. Each of these applications is incorporated by reference herein in its entirety.

FIELD OF THE INVENTION

The present invention relates to compositions and methods for modulating the activity of farnesoid X receptors (FXRs).

BACKGROUND OF THE INVENTION

The farnesoid X receptor (FXR) is a member of the nuclear hormone receptor superfamily and is primarily expressed in the liver, kidney and intestine (see, e.g., Seol et al. (1995) Mol. Endocrinol. 9:72-85 and Forman et al. (1995) Cell 81:687-693). It functions as a heterodimer with the retinoid X receptor (RXR) and binds to response elements in the promoters of target genes to regulate gene transcription. The FXR-RXR heterodimer binds with highest affinity to an inverted repeat-1 (IR-1) response element, in which consensus receptor-binding hexamers are separated by one nucleotide. FXR is part of an interrelated process, in that FXR is activated by bile acids (the end product of cholesterol metabolism) (see, e.g., Makishima et al. (1999) Science 284: 1362-1365, Parks et al. (1999) Science 284: 1365-1368, Wang et al. (1999) Mol. Cell. 3:543-553), which serve to inhibit cholesterol catabolism. See also, Urizar et al. (2000) J. Biol. Chem. 275:39313-39317.

FXR is a key regulator of cholesterol homeostasis, triglyceride synthesis and lipogenesis. (Crawley, Expert Opinion Ther. Patents (2010), 20(8): 1047-1057). In addition to the treatment of dyslipidemia, multiple indications for FXR have been described, including treatment of liver disease, diabetes, vitamin D-related diseases, drug-induced side effects and hepatitis. (Crawley, supra). While advances have been made in the development of novel FXR agonists, there remains significant room for improvement.

SUMMARY OF THE INVENTION

The present invention relates to compositions and methods for modulating the activity of farnesoid X receptors (FXRs). For example, the present invention provides novel compounds that are agonists or partial agonists of FXR, and are useful as pharmaceuticals to treat FXR-mediated conditions.

In one aspect, the compounds of the invention are defined by Formula (I):

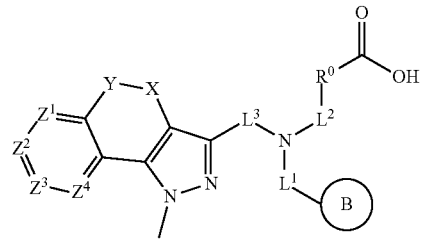

or a pharmaceutical acceptable salt thereof, wherein, $R^0$ is Ring A or $C_{1-6}$ alkyl;

Ring A is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring A is unsubstituted or substituted by 1-2 substituents independently represented by $R^2$;

Ring B is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring B is unsubstituted or substituted by 1-2 substituents independently represented by $R^2$;

X is —($CR^4R^5$)— or —C(O)—;

Y is —O—, —($CR^4R^5$)—, *—O($CR^4R^5$)— or —NR—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *[1]—($CR^4R^5$)$_{1-2}$— or *[1]—($CR^4R^5$)—C(O)—NR—, wherein "*[1]" indicates the point of attachment of $L^1$ to N;

$L^2$ is *[2]—($CR^4R^5$)$_{1-2}$—, *[2]—($CR^4R^5$)—C(O)—, *[2]—($CR^4R^5$)—C(O)—NR—, *[2]—($CR^4R^5$)$_2$—O—, *[2]—($CR^4R^5$)$_2$—NR—, *[2]—($CR^4R^5$)$_2$—SO$_2$—, *[2]—($CR^4R^5$)$_2$—NR—C(O)—, or *[2]—($CR^4R^5$)—C(O)—NR—($CR^4R^5$)—; wherein "*[2]" indicates the point of attachment of $L^2$ to N;

$L^3$ is —($CR^4R^5$)— or —C(O)—;

each $R^2$ is independently halo, hydroxyl, $C_{1-6}$ alkyl, or halo-substituted $C_{1-6}$ alkyl;

each $R^3$ is independently hydrogen, halo, or $C_{1-6}$ alkyl; and

R, $R^4$ and $R^5$ are independently hydrogen or $C_{1-6}$ alkyl.

In one embodiment, the compounds of the invention are defined by Formula (II):

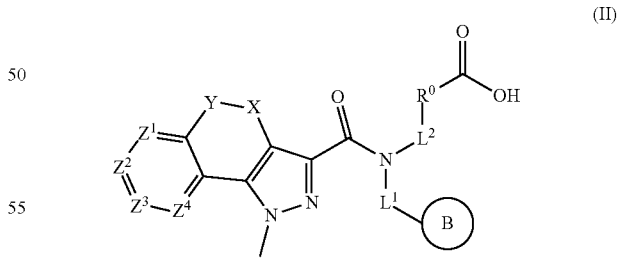

or a pharmaceutically acceptable salt thereof; wherein, $R^0$ is Ring A or $C_{1-6}$ alkyl; wherein Ring A is phenyl, pyridyl or cyclopropyl, each of which is unsubstituted or substituted by 1-2 substituents independently represented by $R^2$;

Ring B is selected from phenyl, pyridyl, 1H-indolyl, and $C_{3-7}$ cycloalkyl, each of which is unsubstituted or substituted by 1-2 substituents independently represented by $R^2$;

X is —(CR$^4$R$^5$)—;

Y is —O—, —(CR$^4$R$^5$)— or *—O(CR$^4$R$^5$)—, wherein "*" indicates the point of attachment of Y to the ring containing the Z ring atoms;

Z$^1$, Z$^2$, Z$^3$, and Z$^4$ are each independently —CR$^3$— or —N—;

L$^1$ is *$^1$—(CR$^4$R$^5$)$_{1\text{-}2}$— wherein "*$^1$" indicates the point of attachment of L$^1$ to N;

L$^2$ is *$^2$—(CR$^4$R$^5$)$_{1\text{-}2}$—, *$^2$—(CR$^4$R$^5$)—C(O)—NR—, *$^2$—(CR$^4$R$^5$)$_2$—O—, *$^2$—(CR$^4$R$^5$)$_2$—NR— or *$^2$—(CR$^4$R$^5$)—C(O)—NR—(CR$^4$R$^5$)—; where "*$^2$" indicates the point of attachment of L$^2$ to N;

each R$^2$ is independently halo, C$_{1\text{-}6}$ alkyl, or halo-substituted C$_{1\text{-}6}$ alkyl;

each R$^3$ is independently hydrogen, halo, or C$_{1\text{-}6}$ alkyl; and

R, R$^4$ and R$^5$ are independently hydrogen or C$_{1\text{-}6}$ alkyl.

In another embodiment, the compounds of the invention are represented by Formula (III):

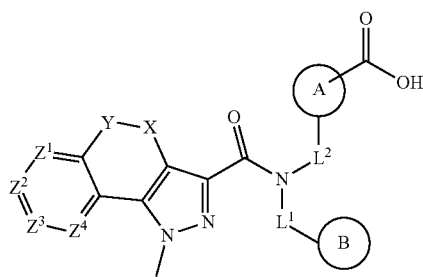

(III)

or a pharmaceutically acceptable salt thereof; wherein

Ring A is phenyl or pyridyl, each of which is unsubstituted or substituted by 1-2 substituents independently represented by R$^2$;

Ring B is selected from phenyl, pyridyl, 1H-indolyl, and cyclopentyl, each of which is unsubstituted or substituted by 1-2 substituents independently represented by R$^2$;

L$^1$ is —(CR$^4$R$^5$)—;

L$^2$ is selected from —(CH$_2$)—, *$^2$—CH$_2$C(O)NH—, *$^2$—CH(CH$_3$)C(O)NH—, *$^2$—CH$_2$C(O)NHCH$_2$—, *$^2$—(CH$_2$)$_2$O—, and *$^2$—(CH$_2$)$_2$NH—; wherein "*$^2$" indicates the point of attachment of L$^2$ to N;

X is CH$_2$;

Y is selected from —O—, —CH$_2$—, —C(CH$_3$)$_2$— and *—O—CH$_2$—, wherein "*" indicates the point of attachment of Y to the ring containing the Z ring atoms;

Z$^1$ is CR$^3$ or N;

Z$^2$ is CR$^3$;

Z$^3$ is CR$^3$;

Z$^4$ is CR$^3$ or N;

each R$^2$ is independently selected from halo, methyl, and trifluoromethyl;

each R$^3$ is independently hydrogen, halo, or C$_{1\text{-}6}$ alkyl; and each of R$^4$ and R$^5$ is independently hydrogen or methyl.

In yet another embodiment, the compounds of the invention are represented by Formula (IV):

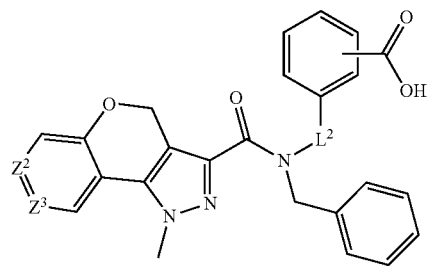

(IV)

or a pharmaceutically acceptable salt thereof; wherein each phenyl ring is optionally further substituted by 1-2 substituents independently represented by R$^2$, wherein R$^2$ is fluoro or methyl;

L$^2$ is selected from —CH$_2$—, *$^2$—CH$_2$CH$_2$NH—, *$^2$—CH$_2$CH$_2$O—, and *$^2$—CH$_2$C(O)NH—, wherein "*$^2$" indicates the point of attachment of L$^2$ to N;

Z$^2$ is selected from CH, CF, CCl, and CCH$_3$; and

Z$^3$ is selected from CH, CF, CCl, and CCH$_3$.

The present invention also provides a compound represented by Formula (V):

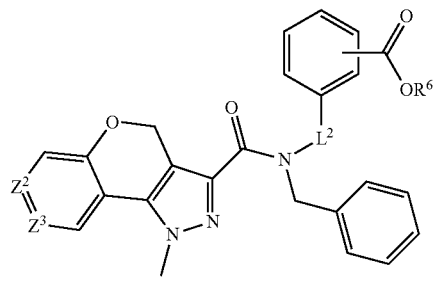

(V)

wherein each phenyl ring is optionally further substituted by 1-2 substituents independently represented by R$^2$, wherein R$^2$ is fluoro or methyl;

L$^2$ is selected from —CH$_2$—, *$^2$—CH$_2$CH$_2$NH—, *$^2$—CH$_2$CH$_2$O—, and *$^2$—CH$_2$C(O)NH—, wherein "*$^2$" indicates the point of attachment of L$^2$ to N;

Z$^2$ is selected from CH, CF, CCl, and CCH$_3$;

Z$^3$ is selected from CH, CF, CCl, and CCH$_3$; and

R$^6$ is C$_{1\text{-}6}$ alkyl.

The compounds of Formula I, II, III, IV and V, and their pharmaceutically acceptable salts exhibit valuable pharmacological properties when tested in vitro in cell-free kinase assays and in cellular assays, and are therefore useful as pharmaceuticals.

In one aspect, the invention relates to methods for modulating FXR in a cell, comprising contacting the cell with an effective amount of a compound of Formula I, II, III, IV or V, or a pharmaceutically acceptable salt thereof; and optionally in combination with a second therapeutic agent.

In another aspect, the invention relates to methods to treat, ameliorate or prevent a FXR-mediated disorder in a subject suffering there from, comprising administering to the subject a therapeutically effective amount of a compound of Formula I, II, III, IV or V, or a pharmaceutically acceptable salt thereof; and optionally in combination with a second therapeutic agent. The present invention also provides for the use of a compound of Formula I, II, III, IV or V, or a pharmaceutically acceptable salt thereof; and optionally in combination with a 15 second therapeutic agent, in the manufacture of a medicament for treating a FXR-mediated disorder. In yet another aspect, the present invention relates to a combination comprising a therapeutically effective amount of a compound of Formula I, II, III, IV or V, or a pharmaceutically acceptable salt thereof, and a second therapeutic agent. Where a second therapeutic agent is used, the second therapeutic agent may also be useful in the treatment of a FXR-mediated disorder.

In one embodiment, the compounds (alone or in combination with a second therapeutic agent) are useful for treating a liver disease or a gastrointestinal disease, including but not limited to liver diseases selected from intrahepatic cholestasis, estrogen-induced cholestasis, drug-induced cholestasis, cholestasis of pregnancy, parenteral nutrition-associated cholestasis, progressive familiar cholestasis (PFIC), Alagille syndrome, primary biliary cirrhosis (PBC), primary sclerosing cholangitis, ductopenic liver transplant rejection, liver transplant associated graft versus host disease, cystic fibrosis liver disease, non-alcoholic fatty liver disease (NAFLD), non-alcoholic steatohepatitis (NASH), alcoholic liver disease, and parenteral nutrition-associated liver disease; and gastrointestinal diseases selected from bile acid malabsorption (including primary bile acid diarrhea and secondary bile acid diarrhea), bile reflux gastritis, and inflammatory bowel disease such as Crohn's disease, ulcerative colitis, collagenous colitis, lymphocytic colitis, diversion colitis, indeterminate colitis and Behçet's disease.

DETAILED DESCRIPTION OF THE INVENTION

Definitions

For purposes of interpreting this specification, the following definitions will apply and whenever appropriate, terms used in the singular will also include the plural and vice versa.

As used herein, "$C_{1-6}$ alkyl" denotes an alkyl radical having from 1 up to 6, in some cases from 1 up to 4 carbon atoms, the radicals being either linear or branched with single or multiple branching. For example, "$C_{1-6}$ alkyl" includes but is not limited n-butyl, sec-butyl, isobutyl, tert-butyl; propyl, such as n-propyl, 2-methylpropyl or iso-propyl; ethyl or methyl.

As used herein, the term "alkylene" refers to divalent alkyl group as defined herein above having 1 to 4 carbon atoms. Representative examples of alkylene include, but are not limited to, methylene, ethylene, n-propylene, iso-propylene, n-butylene, sec-butylene, iso-butylene, tert-butylene, and the like.

As used herein, "$C_{3-7}$ cycloalkyl" refers to a non-aromatic saturated or partially unsaturated monocyclic, bicyclic, bridged or spirocyclic hydrocarbon groups of 3-7 carbon ring atoms. Exemplary monocyclic hydrocarbon groups include, but are not limited to, cyclopropyl, cyclobutyl, cyclopentyl, cyclopentenyl, cyclohexyl and cyclohexenyl and the like.

As used herein, "halogen" or "halo" refers to fluoro, chloro, bromo, and iodo; and more particularly, fluoro or chloro.

As used herein, "halo $C_{1-6}$ alkyl" or "halo-substituted $C_{1-6}$ alkyl" refers to an alkyl radical, as defined above that is substituted by one or more halo radicals, as defined above, and is particularly fluoro $C_{1-6}$ alkyl, more particularly trifluoromethyl.

As used herein, a "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposable mirror images of one another.

As used herein, the term "amino acid conjugate" refers to conjugates of the compound of Formula I, II, III, IV or V with any suitable amino acid. Preferably, such suitable amino acid conjugates of the compound of Formula I, II, III, IV or V will have the added advantage of enhanced integrity in bile or intestinal fluids. Suitable amino acids include but are not limited to glycine, taurine and acyl glucuronide. Thus, the present invention encompasses the glycine, taurine and acyl glucuronide conjugates of the compound of Formula I, II, III, IV or V.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

As used herein, the term "therapeutically effective amount" refers to an amount of the compound of formula (I) which is sufficient to achieve the stated effect. Accordingly, a therapeutically effective amount of a compound of formula (I) used in for the treatment of a condition mediated by FXR will be an amount sufficient for the treatment of the condition mediated by FXR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "dyslipidemia" refers to an abnormality in, or abnormal amounts of lipids and lipoproteins in the blood and the disease states resulting, caused by, exacerbated by, or adjunct to such abnormality (see, Dorland's Illustrated Medical Dictionary, 29th edition or subsequent versions thereof, W.B. Saunders Publishing Company, New York, N.Y.). Disease states encompassed within the definition of dyslipidemia as used herein include hyperlipidemia, hypertriglyceridemia, low plasma HDL, high plasma LDL, high plasma VLDL, liver cholestasis, and hypercholesterolemia.

As used herein, the phrase "diseases related to dyslipidemia" as used herein refers to diseases including but not limited to atherosclerosis, thrombosis, coronary artery disease, stroke, and hypertension. Diseases related to dyslipidemia also include metabolic diseases such as obesity, diabetes, insulin resistance, and complications thereof.

As used herein, the term "cholestasis" refers to any condition in which the flow of bile from the liver is blocked, and may be intrahepatic (i.e., occurring inside the liver) or extrahepatic (i.e., occurring outside the liver).

As used herein, "liver fibrosis" includes liver fibrosis due to any cause, including but not limited to virally-induced liver fibrosis such as that due to hepatitis B and C; exposure to alcohol (alcoholic liver disease), pharmaceutical compounds, oxidative stress, cancer radiation therapy or industrial chemicals; and diseases such as primary biliary cirrhosis, fatty liver, obesity, non-alcoholic steatohepatitis, cystic fibrosis, hemochromatosis, and auto-immune hepatitis.

As used herein, "FXR agonist" refers to an agent that directly binds to and upregulates the activity of FXR.

As used herein, the term "a," "an," "the" and similar terms used in the context of the present invention (especially in the context of the claims) are to be construed to cover both the singular and plural unless otherwise indicated herein or clearly contradicted by the context.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

Modes of Carrying Out the Invention

The present invention relates to compositions and methods for FXR. Various embodiments of the invention are described herein. It will be recognized that features specified in each embodiment may be combined with other specified features to provide further embodiments.

In a first embodiment, the compounds of the present invention are defined by Formula (I):

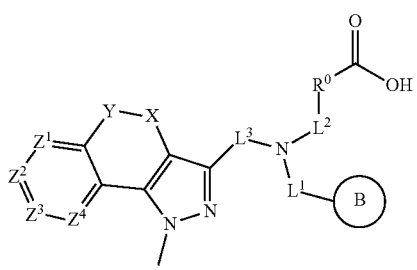

(I)

or a pharmaceutical acceptable salt thereof, wherein, $R^0$ is Ring A or $C_{1-6}$ alkyl;

Ring A is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring A is unsubstituted or substituted by 1-2 substituents independently represented by $R^2$;

Ring B is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring B is unsubstituted or substituted by 1-2 substituents independently represented by $R^2$;

X is —($CR^4R^5$)— or —C(O)—;

Y is —O—, —($CR^4R^5$)—, *—O($CR^4R^5$)— or —NR—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *$^1$—($CR^4R^5$)$_{1-2}$— or *$^1$—($CR^4R^5$)—C(O)—NR—, wherein "*$^1$" indicates the point of attachment of $L^1$ to N;

$L^2$ is *$^2$—($CR^4R^5$)$_{1-2}$—, *$^2$—($CR^4R^5$)—C(O)—, *$^2$—($CR^4R^5$)—C(O)—NR—, *$^2$—($CR^4R^5$)$_2$—O—, *$^2$—($CR^4R^5$)$_2$—NR—, *$^2$—($CR^4R^5$)$_2$—SO$_2$—, *$^2$—($CR^4R^5$)$_2$—NR—C(O)—, or *$^2$—($CR^4R^5$)—C(O)—NR—($CR^4R^5$)—; wherein "*$^2$" indicates the point of attachment of $L^2$ to N;

$L^3$ is —($CR^4R^5$)— or —C(O)—;

each $R^2$ is independently halo, hydroxyl, $C_{1-6}$ alkyl, or halo-substituted $C_{1-6}$ alkyl;

each $R^3$ is independently hydrogen, halo, or $C_{1-6}$ alkyl; and

R, $R^4$ and $R^5$ are independently hydrogen or $C_{1-6}$ alkyl.

In a second embodiment, the compounds of the present invention are defined by Formula (I) as defined in the first embodiment, wherein $R^0$ is Ring A or $C_{1-6}$ alkyl;

Ring A is aryl; 5-10 membered heteroaryl comprising 1-3 N, O or S heteroatoms; or $C_{3-7}$ cycloalkyl; and said Ring A is unsubstituted or substituted by 1-2 substituents independently represented by $R^2$;

Ring B is aryl; 5-10 membered heteroaryl comprising 1-3 N, O or S heteroatoms; or $C_{3-7}$ cycloalkyl; and said Ring B is unsubstituted or substituted by 1-2 substituents independently represented by $R^2$;

X is —($CR^4R^5$)—;

Y is —O—, —($CR^4R^5$)—, or *—O($CR^4R^5$)—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *$^1$—($CR^4R^5$)$_{1-2}$— wherein "*$^1$" indicates the point of attachment of $L^1$ to N;

$L^2$ is *$^2$—($CR^4R^5$)$_{1-2}$—, *$^2$—($CR^4R^5$)—C(O)—NR—, *$^2$—($CR^4R^5$)$_2$—O—, *$^2$—($CR^4R^5$)$_2$—NR— or *$^2$—($CR^4R^5$)—C(O)—NR—($CR^4R^5$)—; wherein "*$^2$" indicates the point of attachment of $L^2$ to N;

$L^3$ is —C(O)—;

each $R^2$ is independently halo, $C_{1-6}$ alkyl, or halo-substituted $C_{1-6}$ alkyl;

each $R^3$ is independently hydrogen, halo, or $C_{1-6}$ alkyl;

R, $R^4$ and $R^5$ are independently hydrogen or $C_{1-6}$ alkyl.

In a third embodiment, the compounds of the present invention are defined by Formula (II):

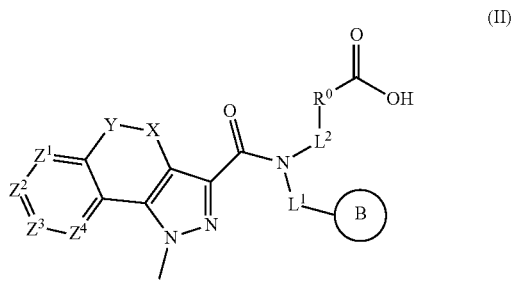

(II)

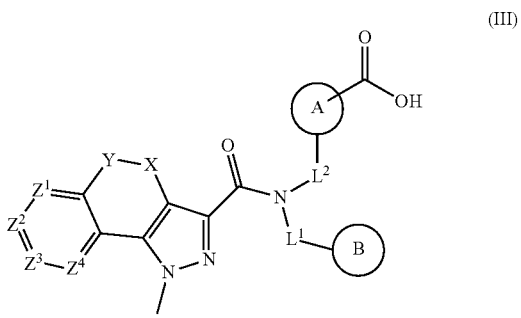

(III)

or a pharmaceutically acceptable salt thereof; wherein, $R^0$ is Ring A or $C_{1-6}$ alkyl; wherein Ring A is phenyl, pyridyl or cyclopropyl, each of which is unsubstituted or substituted by 1-2 substituents independently represented by $R^2$;

Ring B is selected from phenyl, pyridyl, 1H-indolyl, and $C_{3-7}$ cycloalkyl, each of which is unsubstituted or substituted by 1-2 substituents independently represented by $R^2$;

X is —$(CR^4R^5)$—;

Y is —O—, —$(CR^4R^5)$— or *—$O(CR^4R^5)$—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *¹—$(CR^4R^5)_{1-2}$— wherein "*¹" indicates the point of attachment of $L^1$ to N;

$L^2$ is *²—$(CR^4R^5)_{1-2}$—, *²—$(CR^4R^5)$—C(O)—NR—, *²—$(CR^4R^5)_2$—O—, *²—$(CR^4R^5)_2$—NR— or *²—$(CR^4R^5)$—C(O)—NR—$(CR^4R^5)$—; where "*²" indicates the point of attachment of $L^2$ to N;

each $R^2$ is independently halo, $C_{1-6}$ alkyl, or halo-substituted $C_{1-6}$ alkyl;

each $R^3$ is independently hydrogen, halo, or $C_{1-6}$ alkyl; and

R, $R^4$ and $R^5$ are independently hydrogen or $C_{1-6}$ alkyl.

In a fourth embodiment, $R^0$ in any of the above embodiments is selected from *³—$CH_2C(CH_3)_2$—, *³—$CH_2CH(CH_3)$—, and *³-cyclopropane-1,1,-diyl, wherein "*³" indicates the point of attachment of $R^0$ to $L^2$.

With reference to any one of the above embodiments, Y can be selected from —O—, —$CH_2$—, —$C(CH_3)_2$—, and *—O—$CH_2$—, wherein "*" indicates the point of attachment of Y to the six membered ring containing the Z ring atoms.

With reference to any one of the above embodiments, $L^1$ can be —$(CR^4R^5)$— or —$CH_2$—. In one variation, $L^1$ is —$(CR^4R^5)$—.

With reference to any one of the above embodiments, $L^2$ can be selected from —$(CH_2)$—, *²—$CH_2C(O)NH$—, *²—$CH(CH_3)C(O)NH$—, *²—$CH_2C(O)NHCH_2$—, *²—$(CH_2)_2O$—, and *²—$(CH_2)_2NH$—, wherein "*²" indicates the point of attachment of $L^2$ to N.

With reference to any one of the above embodiments, each $R^2$ when present can independently be selected from halo, methyl, and trifluoromethyl.

In a fifth embodiment, the compounds of the present invention are represented by Formula (III):

or a pharmaceutically acceptable salt thereof; wherein

Ring A is phenyl or pyridyl, each of which is unsubstituted or substituted by 1-2 substituents independently represented by $R^2$;

Ring B is selected from phenyl, pyridyl, 1H-indolyl, and cyclopentyl, each of which is unsubstituted or substituted by 1-2 substituents independently represented by $R^2$;

$L^1$ is —$(CR^4R^5)$—;

$L^2$ is selected from —$(CH_2)$—, *²—$CH_2C(O)NH$—, *²—$CH(CH_3)C(O)NH$—, *²—$CH_2C(O)NHCH_2$—, *²—$(CH_2)_2O$—, and *²—$(CH_2)_2NH$—; wherein "*²" indicates the point of attachment of $L^2$ to N;

X is $CH_2$;

Y is selected from —O—, —$CH_2$—, —$C(CH_3)_2$— and *—O—$CH_2$—, wherein "*" indicates the point of attachment of Y to the ring containing the Z ring atoms;

$Z^1$ is $CR^3$ or N;

$Z^2$ is $CR^3$;

$Z^3$ is $CR^3$;

$Z^4$ is $CR^3$ or N;

each $R^2$ is independently selected from halo, methyl, and trifluoromethyl;

each $R^3$ is independently hydrogen, halo, or $C_{1-6}$ alkyl; and each of $R^4$ and $R^5$ is independently hydrogen or methyl.

In a sixth embodiment, Y in any of the above embodiments is —O—. In an alternative embodiment, Y is —$CH_2$—. In another alternative embodiment, Y is *—O—$CH_2$—, wherein "*" indicates the point of attachment of Y to the ring containing the Z ring atoms.

In a seventh embodiment, $L^1$ in any of the above embodiments is —$CH_2$—.

In an eighth embodiment, $L^2$ in any of the above embodiments is selected from —$(CH_2)$—, *²—$CH_2C(O)NH$—, *²—$(CH_2)_2O$—, and *²—$(CH_2)_2NH$—; wherein "*²" indicates the point of attachment of $L^2$ to N.

In a ninth embodiment, $L^2$ in any of the above embodiments is —$(CH_2)$—.

In a tenth embodiment, $R^2$ when present in any one of the above embodiments is independently fluoro or methyl. In one variation, each $R^2$ is fluoro. In another variation, each $R^2$ is methyl.

In an eleventh embodiment, $R^3$ in any of the above embodiments is selected from hydrogen, fluoro, chloro, and methyl.

In a twelfth embodiment, with reference to any one of the above embodiments, $Z^1$ is selected from CH, CF, $CCH_3$, and N; $Z^2$ is selected from CH, CF, CCl, and $CCH_3$; $Z^3$ is selected from CH, CF, CCl, and $CCH_3$; and $Z^4$ is CH or N.

With reference to any one of the above embodiments, each of R, $R^4$, $R^5$ and $R^6$ when present, can independently be hydrogen or methyl. In one variation, R, $R^4$, $R^5$ and $R^6$ when present, is hydrogen.

In a thirteenth embodiment, the compounds of the present invention are represented by Formula (IV):

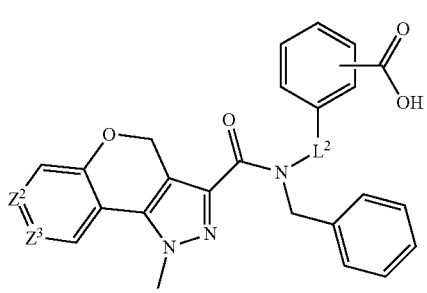

(IV)

each phenyl ring is optionally further substituted by 1-2 substituents independently represented by $R^2$, wherein $R^2$ is fluoro or methyl;

$L^2$ is selected from —$CH_2$—, $*^2$—$CH_2CH_2NH$—, $*^2$—$CH_2CH_2O$—, and $*^2$—$CH_2C(O)NH$—, wherein "$*^2$" indicates the point of attachment of $L^2$ to N;

$Z^2$ is selected from CH, CF, CCl, and $CCH_3$; and
$Z^3$ is selected from CH, CF, CCl, and $CCH_3$.

In one embodiment, $L^2$ in any of the above embodiments is —($CH_2$)—. In an alternative embodiment, $L^2$ is $*^2$—($CH_2$)$_2$NH—. In another alternative embodiment, $L^2$ is $*^2$—$CH_2C(O)NH$—. In each embodiment, "$*^2$" indicates the point of attachment of $L^2$ to N.

Particular compounds according to the present invention include, but are not limited to: 4-fluoro-3-(2-(8-fluoro-N-(2-fluorobenzyl)-1-methyl-1,4-dihydrochromeno[4,3-c]pyrazole-3-carboxamido)acetamido)benzoic acid; 4-fluoro-3-(2-(8-fluoro-N-(3-fluorobenzyl)-1-methyl-1,4-dihydrochromeno[4,3-c]pyrazole-3-carboxamido)acetamido)benzoic acid; 3-(2-(8-chloro-1-methyl-N-(3-methylbenzyl)-1,4-dihydrochromeno[4,3-c]pyrazole-3-carboxamido)acetamido)-4-fluorobenzoic acid; 4-fluoro-3-(2-(1-methyl-N-(3-methylbenzyl)-1,4-dihydrochromeno[4,3-c]pyrazole-3-carboxamido)acetamido)benzoic acid; 3-(2-(N-(2-fluorobenzyl)-1,8-dimethyl-1,4-dihydrochromeno[4,3-c]pyrazole-3-carboxamido)acetamido)benzoic acid; 3-(2-(N-(2-fluorobenzyl)-1,6-dimethyl-1,4-dihydrochromeno[4,3-c]pyrazole-3-carboxamido)acetamido)benzoic acid; 3-(2-(8-fluoro-N-(2-fluorobenzyl)-1-methyl-1,4-dihydrochromeno[4,3-c]pyrazole-3-carboxamido)acetamido)benzoic acid; 3-(2-(7-fluoro-N-(2-fluorobenzyl)-1-methyl-1,4-dihydrochromeno[4,3-c]pyrazole-3-carboxamido)acetamido)benzoic acid; 3-(2-(7-chloro-N-(2-fluorobenzyl)-1-methyl-1,4-dihydrochromeno[4,3-c]pyrazole-3-carboxamido)acetamido)benzoic acid; N-(2-fluorobenzyl)-1-methyl-1,4-dihydrochromeno[4,3-c]pyrazole-3-carboxamido)acetamido)benzoic acid; 3-(2-(6,8-difluoro-N-(2-fluorobenzyl)-1-methyl-1,4-dihydrochromeno[4,3-c]pyrazole-3-carboxamido)acetamido)benzoic acid; 3-(2-(N-(2-fluorobenzyl)-1-methyl-1,4-dihydrochromeno[4,3-c]pyrazole-3-carboxamido)acetamido)benzoic acid; 3-(2-(8-chloro-N-(2-fluorobenzyl)-1,7-dimethyl-1,4-dihydrochromeno[4,3-c]pyrazole-3-carboxamido)acetamido)benzoic acid; 3-(2-(8-chloro-N-(2-fluorobenzyl)-1,6-dimethyl-1,4-dihydrochromeno[4,3-c]pyrazole-3-carboxamido)acetamido)benzoic acid; 3-(2-(8-chloro-6-fluoro-N-(2-fluorobenzyl)-1-methyl-1,4-dihydrochromeno[4,3-c]pyrazole-3-carboxamido)acetamido)benzoic acid; 4-fluoro-3-(2-(N-(2-fluorobenzyl)-1-methyl-1,4-dihydrochromeno[4,3-c]pyrazole-3-carboxamido)acetamido)benzoic acid; 3-(2-(7,8-difluoro-N-(2-fluorobenzyl)-1-methyl-1,4-dihydrochromeno[4,3-c]pyrazole-3-carboxamido)acetamido)-4-fluorobenzoic acid; 3-(2-(7,8-difluoro-N-(3-fluorobenzyl)-1-methyl-1,4-dihydrochromeno[4,3-c]pyrazole-3-carboxamido)acetamido)-4-fluorobenzoic acid; 3-(2-(N-benzyl-7,8-difluoro-1-methyl-1,4-dihydrochromeno[4,3-c]pyrazole-3-carboxamido)acetamido)-4-fluorobenzoic acid; 4-fluoro-3-(2-(8-fluoro-1-methyl-N-(3-methylbenzyl)-1,4-dihydrochromeno[4,3-c]pyrazole-3-carboxamido)acetamido)benzoic acid; 4-fluoro-3-(2-(N-(2-fluorobenzyl)-1-methyl-4,5-dihydro-1H-pyrazolo[4,3-h]quinoline-3-carboxamido)acetamido)benzoic acid; 4-fluoro-3-(2-(N-(2-fluorobenzyl)-1-methyl-4,5-dihydro-1H-pyrazolo[3,4-f]quinoline-3-carboxamido)acetamido)benzoic acid; (S)-4-fluoro-3-(2-(8-fluoro-N-(2-fluorobenzyl)-1-methyl-1,4-dihydrochromeno[4,3-c]pyrazole-3-carboxamido)propanamido)benzoic acid; 3-(2-(8-chloro-N-(2-fluorobenzyl)-1-methyl-4,5-dihydro-1H-benzo[g]indazole-3-carboxamido)acetamido)benzoic acid; 3-(2-(8-chloro-7-fluoro-N-(2-fluorobenzyl)-1-methyl-1,4-dihydrochromeno[4,3-c]pyrazole-3-carboxamido)acetamido)benzoic acid; 4-fluoro-3-(2-(N-(3-fluorobenzyl)-1,5,5-trimethyl-4,5-dihydro-1H-benzo[g]indazole-3-carboxamido)acetamido)benzoic acid; 4-fluoro-3-(2-(N-(3-fluorobenzyl)-1-methyl-1,4-dihydrochromeno[4,3-c]pyrazole-3-carboxamido)acetamido)benzoic acid; 3-(2-(8-chloro-N-(3-fluorobenzyl)-1-methyl-1,4-dihydrochromeno[4,3-c]pyrazole-3-carboxamido)acetamido)-4-fluorobenzoic acid; 3-(2-(N-benzyl-8-chloro-1-methyl-1,4-dihydrochromeno[4,3-c]pyrazole-3-carboxamido)acetamido)-4-fluorobenzoic acid; 3-(2-(8-chloro-N-(2-fluorobenzyl)-1-methyl-1,4-dihydrochromeno[4,3-c]pyrazole-3-carboxamido)acetamido)-4-fluorobenzoic acid; 3-(2-(N-benzyl-8-chloro-1-methyl-1,4-dihydrochromeno[4,3-c]pyrazole-3-carboxamido)acetamido)benzoic acid; 3-(2-(N-benzyl-8-fluoro-1-methyl-1,4-dihydrochromeno[4,3-c]pyrazole-3-carboxamido)acetamido)-4-fluorobenzoic acid; 3-(2-(N-benzyl-1-methyl-1,4-dihydrochromeno[4,3-c]pyrazole-3-carboxamido)acetamido)-4-fluorobenzoic acid; 3-(2-(9-chloro-N-(2-fluorobenzyl)-1-methyl-4,5-dihydro-1H-benzo[2,3]oxepino[4,5-c]pyrazole-3-carboxamido)acetamido)-4-fluorobenzoic acid; 3-(2-(8-chloro-N-(2-fluorobenzyl)-1-methyl-1,4-dihydrochromeno[4,3-c]pyrazole-3-carboxamido)acetamido)benzoic acid; 3-(2-(8-chloro-N-(cyclopentylmethyl)-1-methyl-1,4-dihydrochromeno[4,3-c]pyrazole-3-carboxamido)acetamido)-4-fluorobenzoic acid; 3-(2-(8-chloro-N-(cyclopentylmethyl)-1-methyl-1,4-dihydrochromeno[4,3-c]pyrazole-3-carboxamido)acetamido)benzoic acid; 3-(2-(8-chloro-N-(2-fluorobenzyl)-1-methyl-1,4-dihydrochromeno[4,3-c]pyrazole-3-carboxamido)acetamido)-5-fluorobenzoic acid; 3-(2-(8-chloro-N-(2-fluorobenzyl)-1-methyl-1,4-dihydrochromeno[4,3-c]pyrazole-3-carboxamido)acetamido)-4-methylbenzoic acid; 3-(2-(8-chloro-N-(2-fluorobenzyl)-1-methyl-1,4-dihydrochromeno[4,3-c]pyrazole-3-carboxamido)acetamido)-2-methylpropanoic acid; 3-(2-(8-chloro-N-(2-fluorobenzyl)-1-methyl-1,4-dihydrochromeno[4,3-c]pyrazole-3-carboxamido)acetamido)-2,2-dimethylpropanoic acid; 1-((2-(8-chloro-N-(2-fluorobenzyl)-1-methyl-1,4-dihydrochromeno[4,3-c]pyrazole-3-carboxamido)acetamido)methyl)cyclopropanecarboxylic acid; 4-(2-(8-chloro-N-(2-fluorobenzyl)-1-methyl-1,4-dihydrochromeno[4,3-c]pyrazole-3-carboxamido)ethoxy)-3-fluorobenzoic acid; 3-(2-(8-chloro-N-(2-fluorobenzyl)-1-methyl-1,4-dihydrochromeno[4,3-c]pyrazole-3-carboxamido)ethoxy)benzoic acid; 4-(2-(8-chloro-N-(2-fluorobenzyl)-1-methyl-1,4-dihydrochromeno[4,3-c]pyrazole-3-carboxamido)ethoxy)benzoic acid; N-(2-fluorobenzyl)-1-methyl-1,4-dihydrochromeno[4,3-c]pyrazole-3-carboxamido)ethoxy)-3-methylbenzoic acid; 4-(2-(8-chloro-N-(2-fluorobenzyl)-1-methyl-1,4-dihydrochromeno[4,3-c]pyrazole-3-carboxamido)ethoxy)-3,5-dimethylbenzoic acid; 3-(2-(8-chloro-N-(2-fluorobenzyl)-1-methyl-1,4-dihydrochromeno[4,3-c]pyrazole-3-carboxamido)ethoxy)-4-fluorobenzoic acid; 4-(2-(8-chloro-N-(cyclopentylmethyl)-1-methyl-1,4-dihydrochromeno[4,3-c]pyrazole-3-carboxamido)ethoxy)-3,5-dimethylbenzoic acid; 4-(2-(8-chloro-N-(2-fluorobenzyl)-1-methyl-1,4-dihydrochromeno[4,3-c]pyrazole-3-carboxamido)ethoxy)-3,5-difluorobenzoic acid; 4-(2-(8-chloro-N-(2-fluorobenzyl)-1-methyl-1,4-dihydrochromeno[4,3-c]pyrazole-3-carboxamido)ethoxy)-3-(trifluoromethyl)benzoic acid; 4-(2-(N-benzyl-8-chloro-1-methyl-1,4-dihydrochromeno[4,3-c]pyrazole-3-carboxamido)ethoxy)-3,5-difluorobenzoic acid; 3,5-difluoro-4-(2-(8-fluoro-N-(2-fluorobenzyl)-1-methyl-1,4-dihydrochromeno[4,3-c]pyrazole-3-carboxamido)ethoxy)benzoic acid; 4-(2-(N-benzyl-8-fluoro-1-methyl-1,4-dihydrochromeno[4,3-c]pyrazole-3-carboxamido)ethoxy)-3,5-difluorobenzoic acid; 4-(2-(N-benzyl-8-chloro-1-methyl-1,4-dihydrochromeno[4,3-c]pyrazole-3-carboxamido)ethoxy)-3-fluorobenzoic acid; 4-(2-(N-benzyl-8-fluoro-1-methyl-1,4-dihydrochromeno[4,3-c]pyrazole-3-carboxamido)ethoxy)-3-fluorobenzoic acid; 4-(2-(N-benzyl-7,8-difluoro-1-methyl-1,4-dihydrochromeno[4,3-c]pyrazole-3-carboxamido)ethoxy)-3-fluorobenzoic acid; 3-fluoro-4-(2-(8-fluoro-N-(3-fluorobenzyl)-1-methyl-1,4-dihydrochromeno[4,3-c]pyrazole-3-carboxamido)ethoxy)benzoic acid; 4-(2-(7,8-difluoro-N-(3-fluorobenzyl)-1-methyl-1,4-dihydrochromeno[4,3-c]pyrazole-3-carboxamido)ethoxy)-3-fluorobenzoic acid; 4-(2-(8-chloro-N-(3-fluorobenzyl)-1-methyl-1,4-dihydrochromeno[4,3-c]pyrazole-3-carboxamido)ethoxy)-3-fluorobenzoic acid; 3-fluoro-4-(2-(8-fluoro-N-(2-fluorobenzyl)-1-methyl-1,4-dihydrochromeno[4,3-c]pyrazole-3-carboxamido)ethoxy)benzoic acid; 4-(2-(7,8-difluoro-N-(2-fluorobenzyl)-1-methyl-1,4-dihydrochromeno[4,3-c]pyrazole-3-carboxamido)ethoxy)-3-fluorobenzoic acid; 3-((2-(8-chloro-N-(2-fluorobenzyl)-1-methyl-1,4-dihydrochromeno[4,3-c]pyrazole-3-carboxamido)ethyl)amino)benzoic acid; 3-(2-(8-chloro-N-(2-fluorobenzyl)-1-methyl-1,4-dihydrochromeno[4,3-c]pyrazole-3-carboxamido)acetamido)-4-fluorobenzoic acid; 3-((2-(8-chloro-N-(3-fluorobenzyl)-1-methyl-1,4-dihydrochromeno[4,3-c]pyrazole-3-carboxamido)ethyl)amino)-4-fluorobenzoic acid; 3-((2-(8-chloro-1-methyl-N-(3-methylbenzyl)-1,4-dihydrochromeno[4,3-c]pyrazole-3-carboxamido)ethyl)amino)-4-fluorobenzoic acid; 4-fluoro-3-((2-(8-fluoro-1-methyl-N-(3-methylbenzyl)-1,4-dihydrochromeno[4,3-c]pyrazole-3-carboxamido)ethyl)amino)benzoic acid; 3-((2-(7,8-difluoro-1-methyl-N-(3-methylbenzyl)-1,4-dihydrochromeno[4,3-c]pyrazole-3-carboxamido)ethyl)amino)-4-fluorobenzoic acid; 4-fluoro-3-((2-(8-fluoro-N-(2-fluorobenzyl)-1-methyl-1,4-dihydrochromeno[4,3-c]pyrazole-3-carboxamido)ethyl)amino)benzoic acid; 4-fluoro-3-((2-(N-(2-fluorobenzyl)-1-methyl-1,4-dihydrochromeno[4,3-c]pyrazole-3-carboxamido)ethyl)amino)benzoic acid; 3-((2-(N-benzyl-8-fluoro-1-methyl-1,4-dihydrochromeno[4,3-c]pyrazole-3-carboxamido)ethyl)amino)-4-fluorobenzoic acid; 3-((2-(N-benzyl-8-chloro-1-methyl-1,4-dihydrochromeno[4,3-c]pyrazole-3-carboxamido)ethyl)amino)-4-fluorobenzoic acid; 3-((2-(7,8-difluoro-N-(3-fluorobenzyl)-1-methyl-1,4-dihydrochromeno[4,3-c]pyrazole-3-carboxamido)ethyl)amino)-4-fluorobenzoic acid; 3-((2-(N-benzyl-7,8-difluoro-1-methyl-1,4-dihydrochromeno[4,3-c]pyrazole-3-carboxamido)ethyl)amino)-4-fluorobenzoic acid; 4-((N-benzyl-8-chloro-1-methyl-1,4-dihydrochromeno[4,3-c]pyrazole-3-carboxamido)methyl)benzoic acid; 4-((N-benzyl-8-chloro-1-methyl-1,4-dihydrochromeno[4,3-c]pyrazole-3-carboxamido)methyl)-3-fluorobenzoic acid; 4-((8-fluoro-N-(3-fluorobenzyl)-1-methyl-1,4-dihydrochromeno[4,3-c]pyrazole-3-carboxamido)methyl)benzoic acid; 4-((8-chloro-N-(3,5-difluorobenzyl)-1-methyl-1,4-dihydrochromeno[4,3-c]pyrazole-3-carboxamido)methyl)benzoic acid; 4-((N-benzyl-8-fluoro-1-methyl-1,4-dihydrochromeno[4,3-c]pyrazole-3-carboxamido)methyl)-3-fluorobenzoic acid; 4-((8-chloro-1-methyl-N-(3-methylbenzyl)-1,4-dihydrochromeno[4,3-c]pyrazole-3-carboxamido)methyl)benzoic acid; 4-((8-chloro-N-(2,3-difluorobenzyl)-1-methyl-1,4-dihydrochromeno[4,3-c]pyrazole-3-carboxamido)methyl)benzoic acid; 4-((8-chloro-N-(3-fluoro-5-methylbenzyl)-1-methyl-1,4-dihydrochromeno[4,3-c]pyrazole-3-carboxamido)methyl)benzoic acid; 4-((N-(3,5-difluorobenzyl)-8-fluoro-1-methyl-1,4-dihydrochromeno[4,3-c]pyrazole-3-carboxamido)methyl)benzoic acid; 4-((8-chloro-1-methyl-N-(3-methylbenzyl)-1,4-dihydrochromeno[4,3-c]pyrazole-3-carboxamido)methyl)-3-fluorobenzoic acid; 3-fluoro-4-((8-fluoro-1-methyl-N-(3-methylbenzyl)-1,4-dihydrochromeno[4,3-c]pyrazole-3-carboxamido)methyl)benzoic acid; 4-((N-((1H-indol-5-yl)methyl)-8-chloro-1-methyl-1,4-dihydrochromeno[4,3-c]pyrazole-3-carboxamido)methyl)benzoic acid; 5-((8-chloro-N-(3-fluorobenzyl)-1-methyl-1,4-dihydrochromeno[4,3-c]pyrazole-3-carboxamido)methyl)picolinic acid; 4-((8-chloro-N-((5-fluoropyridin-3-yl)methyl)-1-methyl-1,4-dihydrochromeno[4,3-c]pyrazole-3-carboxamido)methyl)benzoic acid; 4-((8-chloro-N-((5-chloropyridin-3-yl)methyl)-1-methyl-1,4-dihydrochromeno[4,3-c]pyrazole-3-carboxamido)methyl)benzoic acid; 4-((8-chloro-N-(3-fluorobenzyl)-1-methyl-1,4-dihydrochromeno[4,3-c]pyrazole-3-carboxamido)methyl)-2-fluorobenzoic acid; 4-((N-benzyl-8-chloro-1-methyl-1,4-dihydrochromeno[4,3-c]pyrazole-3-carboxamido)methyl)-2-fluorobenzoic acid; N-benzyl-N-(4-carbamoylbenzyl)-8-chloro-1-methyl-1,4-dihydrochromeno[4,3-c]pyrazole-3-carboxamide; 4-((8-chloro-N-(2-fluorobenzyl)-1-methyl-1,4-dihydrochromeno[4,3-c]pyrazole-3-carboxamido)methyl)benzoic acid; 4-((8-chloro-N-(2-fluorobenzyl)-1-methyl-1,4-dihydrochromeno[4,3-c]pyrazole-3-carboxamido)methyl)-3-fluorobenzoic acid; 3-fluoro-4-((8-fluoro-N-(2-fluorobenzyl)-1-methyl-1,4-dihydrochromeno[4,3-c]pyrazole-3-carboxamido)methyl)benzoic acid; 4-((8-chloro-N-(3-fluorobenzyl)-1-methyl-1,4-dihydrochromeno[4,3-c]pyrazole-3-carboxamido)methyl)benzoic acid; 4-((8-chloro-N-(3-fluorobenzyl)-1-methyl-1,4-dihydrochromeno[4,3-c]pyrazole-3-carboxamido)methyl)-3-fluorobenzoic acid; 4-((8-chloro-N-(2-fluorobenzyl)-1-methyl-1,4-dihydrochromeno[4,3-c]pyrazole-3-carboxamido)methyl)-2-fluorobenzoic acid; 6-((8-chloro-N-(3-fluorobenzyl)-1-methyl-1,4-dihydrochromeno[4,3-c]pyrazole-3-carboxamido)methyl)nicotinic acid; 5-((8-chloro-N-(3-fluorobenzyl)-1-methyl-1,4-dihydrochromeno[4,3-c]pyrazole-3-carboxamido)methyl)-6-methylpicolinic acid; 4-fluoro-3-((2-(8-fluoro-N-(3-fluorobenzyl)-1-methyl-1,4-dihydrochromeno[4,3-c]pyrazole-3-carboxamido)ethyl)amino)benzoic acid; and 3-((2-(8-chloro-N-(2-fluorobenzyl)-1-methyl-1,4-dihydrochromeno[4,3-c]pyrazole-3-carboxamido)ethyl)amino)-4-fluorobenzoic acid; or a pharmaceutically acceptable salt, tautomer or stereoisomer thereof.

More particular examples of the compounds according to the present invention include but are not limited to: 4-fluoro-3-(2-(8-fluoro-N-(2-fluorobenzyl)-1-methyl-1,4-dihydrochromeno[4,3-c]pyrazole-3-carboxamido)acetamido)benzoic acid; 4-fluoro-3-(2-(8-fluoro-N-(3-fluorobenzyl)-1-methyl-1,4-dihydrochromeno[4,3-c]pyrazole-3-carboxamido)acetamido)benzoic acid; 3-(2-(7-chloro-N-(2-fluorobenzyl)-1-methyl-1,4-dihydrochromeno[4,3-c]pyrazole-3-carboxamido)acetamido)benzoic acid; 3-(2-(7,8-difluoro-N-(2-fluorobenzyl)-1-methyl-1,4-dihydrochromeno[4,3-c]pyrazole-3-carboxamido)acetamido)-4-fluorobenzoic acid; 3-(2-(8-chloro-N-(2-fluorobenzyl)-1-methyl-1,4-dihydrochromeno[4,3-c]pyrazole-3-carboxamido)ethoxy)benzoic acid; 3-((2-(8-chloro-N-(2-fluorobenzyl)-1-methyl-1,4-dihydrochromeno[4,3-c]pyrazole-3-carboxamido)ethyl)amino)benzoic acid; 3-((2-(8-chloro-N-(3-fluorobenzyl)-1-methyl-1,4-dihydrochromeno[4,3-c]pyrazole-3-carboxamido)ethyl)amino)-4-fluorobenzoic acid; 4-((N-benzyl-8-chloro-1-methyl-1,4-dihydrochromeno[4,3-c]pyrazole-3-carboxamido)methyl)benzoic acid; 4-((8-chloro-N-(2-fluorobenzyl)-1-methyl-1,4-dihydrochromeno[4,3-c]pyrazole-3-carboxamido)methyl)benzoic acid; 4-((8-chloro-N-(3-fluorobenzyl)-1-methyl-1,4-dihydrochromeno[4,3-c]pyrazole-3-carboxamido)methyl)benzoic acid; and 4-fluoro-3-((2-(8-fluoro-N-(3-fluorobenzyl)-1-methyl-1,4-dihydrochromeno[4,3-c]pyrazole-3-carboxamido)ethyl)amino)benzoic acid; or a pharmaceutically acceptable salt, tautomer or stereoisomer thereof.

In one embodiment, the present invention provides a compound according to any one of the above embodiments, wherein the compound is in the form of a pharmaceutically acceptable salt selected from TRIS (2-amino-2-hydroxymethyl-1,3-propanediol), arginine, lysine, sodium and meglumine salt.

The present invention also provides a compound of Formula (V):

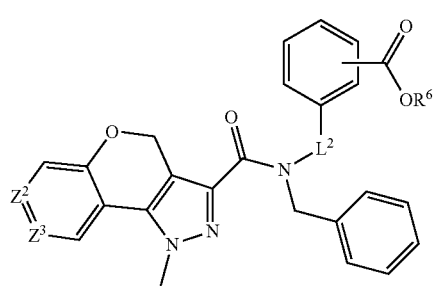

wherein each phenyl ring is unsubstituted or substituted by 1-2 substituents independently represented by $R^2$, wherein $R^2$ is fluoro or methyl;

$L^2$ is selected from $*^2$—$CH_2$—, $*^2$—$CH_2CH_2NH$—, $*^2$—$CH_2CH_2O$—, and $*^2$—$CH_2C(O)NH$—, wherein "$*^2$" indicates the point of attachment of $L^2$ to N;

$Z^2$ is selected from CH, CF, CCl, and $CCH_3$;

$Z^3$ is selected from CH, CF, CCl, and $CCH_3$; and $R^6$ is $C_{1-6}$ alkyl.

In another aspect, the present invention provides a pharmaceutical composition comprising a therapeutically effective amount of a compound according to any one of the above embodiments and variations or a pharmaceutically acceptable salt thereof, and a pharmaceutically acceptable carrier, diluent or excipient.

In yet another aspect, the present invention provides a combination comprising a therapeutically effective amount of a compound according to any one of the above embodiments and variations or a pharmaceutically acceptable salt thereof, and a second therapeutic agent.

In still another aspect, the invention provides a method for treating a condition mediated by farnesoid X receptors (FXR) in a subject suffering therefrom, comprising administering to the subject a therapeutically effective amount of a compound of any one of the above embodiments and variations or a pharmaceutically acceptable salt thereof; and optionally in combination with a second therapeutic agent.

In still another aspect, the invention provides a compound according to any of the above embodiments and variations or a pharmaceutically acceptable salt thereof, and optionally in combination with a second therapeutic agent, for use in treating a condition mediated by FXR.

In yet another aspect, the invention provides the use of a compound of any one of the above embodiments and variations or a pharmaceutically acceptable salt thereof, and optionally in combination with a second therapeutic agent, for the preparation of a medicament for the treatment of a condition mediated by FXR in a subject.

In one embodiment, the condition mediated by FXR with respect to any of the above methods, uses or combinations, is a liver disease or a gastrointestinal disease. For example, the compounds of the invention may be used for treating a liver disease mediated by FXR, wherein the liver disease is selected from cholestasis (e.g., intrahepatic cholestasis, estrogen-induced cholestasis, drug-induced cholestasis, cholestasis of pregnancy, parenteral nutrition-associated cholestasis, progressive familiar cholestasis (PFIC)); Alagille syndrome, primary biliary cirrhosis (PBC), primary sclerosing cholangitis, ductopenic liver transplant rejection, liver transplant associated graft versus host disease, cystic fibrosis liver disease, non-alcoholic fatty liver disease (NAFLD), non-alcoholic steatohepatitis (NASH), alcoholic liver disease, and parenteral nutrition-associated liver disease. The compounds of the invention may be also be used for treating a gastrointestinal disease mediated by FXR, wherein the gastrointestinal disease is selected from bile acid malabsorption (including primary bile acid diarrhea and secondary bile acid diarrhea), bile reflux gastritis, and inflammatory bowel disease such as Crohn's disease, ulcerative colitis, collagenous colitis, lymphocytic colitis, diversion colitis, indeterminate colitis and Behçet's disease.

More particularly, the condition mediated by FXR is non-alcoholic fatty liver disease (NAFLD) or non-alcoholic steatohepatitis (NASH). With reference to combination therapies of the invention, the other therapeutic agent can also be useful in the treatment of non-alcoholic fatty liver disease (NAFLD) or non-alcoholic steatohepatitis (NASH).

In one embodiment, the compounds of the invention are administered enterally; and more particularly, orally.

Unless specified otherwise, the term "compounds of the present invention" refers to compounds of Formula I, II, III, IV or V, pharmaceutically acceptable salt thereof, prodrugs, and inherently formed moieties (e.g., polymorphs, solvates and/or hydrates). The compounds of the present invention may be stereoisomers (including diastereoisomers and enantiomers), and may be a mixture of stereoisomers or a single stereoisomer. The compounds of the present invention may also be tautomers and isotopically labeled compounds (including deuterium substitutions). Further compounds of the invention are detailed in the Examples, infra.

Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$ and $^{125}I$ respectively. The invention includes various isotopically labeled compounds as defined herein, for example those into which radioactive isotopes, such as $^{3}H$, $^{13}C$, and $^{14}C$, are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula I, II, III, IV and V can generally be prepared by conventional techniques known to those skilled in the art or by processes analogous to those described in the accompanying Examples and Processes using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of Formula I, II, III, IV and V that contain groups capable of acting as donors and/or acceptors for hydrogen bonds may be capable of forming co-crystals with suitable co-crystal formers. These co-crystals may be prepared from compounds of Formula I, II, III, IV or V by known co-crystal forming procedures. Such procedures include grinding, heating, co-subliming, co-melting, or contacting in solution compounds of Formula I, II, III, IV or V with the co-crystal former under crystallization conditions and isolating co-crystals thereby formed. Suitable co-crystal formers include those described in WO 2004/078163. Hence the invention further provides co-crystals comprising a compound of Formula I, II, III, IV or V.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Pharmacology and Utility

The compounds of Formula I, II, III, IV and V in free form or in salt form, exhibit valuable pharmacological properties, e.g. FXR modulating properties, e.g. as indicated in in vitro and/or in vivo tests as provided in the next sections, and are therefore indicated for therapy in treating a disorder which may be treated by modulating FXR, such as those described below.

With the development of the first synthetic FXR ligand GW4064 as a tool compound (Maloney et al., J. Med. Chem. 2000, 43(16), 2971-2974; Willson et al., Med. Res. Rev. 2001, 21(6) 513-22), and the development of the semisynthetic artificial bile acid ligand 6-alpha-ethyl-CDCA, the effects of superstimulation of FXR by potent agonists could be analyzed. It was shown that both ligands induce bile flow in bile duct ligated animals. In addition to choleretic effects, hepatoprotective effects could also be demonstrated (Pellicciari et al., J. Med. Chem. 2002, 45(17), 3569-3572; Liu et al., J. Clin. Invest. 2003, 112(11), 1678-1687). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 (MMP-2) in hepatic stellate cells and the subsequent reduction of alpha-collagen mRNA and Transforming growth factor beta (TGF-beta) mRNA which are both pro-fibrotic factors by FXR agonists (Fiorucci et al., Gastroenterology 2004, 127(5), 1497-1512; Fiorucci et al., Pharmacol. Exp. Ther. 2005, 314(2), 584-595).

The anti-fibrotic activity of FXR is at least partially mediated by the induction of PPARγ, a further nuclear receptor, with which anti-fibrotic activity is associated (Fiorucci et al., J. Pharmacol. Exp. Ther. 2005, 315(1), 58-68; Galli et al., Gastroenterology 2002, 122(7), 1924-1940; Pineda Torra et al., Mol. Endocrinol. 2003, 17(2), 259-272). Furthermore, anti-cholestatic activity was demonstrated in bile-duct ligated animal models as well as in animal models of estrogen-induced cholestasis (Fiorucci et al., J. Pharmacol. Exp. Ther. 2005, 313(2), 604-612).

Genetic studies demonstrate that in hereditary forms of cholestasis (Progressive Familiar Intrahepatic Cholestasis=PFIC, Type I-IV), either nuclear localization of FXR itself is reduced as a consequence of a mutation in the FIC1 gene (in PFIC Type I, also called Byler's Disease) (Chen et al., Gastroenterology. 2004, 126(3), 756-64; Alvarez et al., Hum. Mol. Genet. 2004; 13(20), 2451-60) or levels of the FXR target gene encoding MDR-3 phospholipid export pump are reduced (in PFIC Type III). Taken together, there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: Rizzo et al., Curr. Drug Targets Immune Endocr. Metabol. Disord. 2005, 5(3), 289-303; Zollner, Mol. Pharm. 2006, 3(3), 231-51, Cai et al., Expert Opin. Ther. Targets 2006, 10(3), 409-421).

Furthermore, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (Claudel et al., Arterioscler. Thromb. Vasc. Biol. 2005, 25(10), 2020-2030; Westin et al., Mini Rev. Med. Chem. 2005, 5(8), 719-727).

FXR has also been shown to be a key regulator of serum triglycerides (Maloney et al., J. Med. Chem. 2000, 43(16), 2971-2974; Willson et al., Med. Res. Rev. 2001, 21(6), 513-22). Recent reports indicate that activation of FXR by synthetic agonists leads to significant reduction of serum triglycerides, mainly in the form of reduced VLDL, but also to reduced total serum cholesterol (Figge et al., J. Biol. Chem. 2004, 279(4), 2790-2799; Bilz et al., Am. J. Physiol. Endocrinol. Metab. 2006, 290(4), E716-22). However, the lowering of serum triglycerides is not a stand-alone effect. Treatment of db/db or ob/ob mice with synthetic FXR agonist GW4064 resulted in marked and combined reduction of serum triglycerides, total cholesterol, free fatty acids, and ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (Stayrook et al., Endocrinology 2005, 146(3), 984-91; Zhang et al., Proc. Natl. Acad. Sci. USA 2006, 103(4), 1006-1011; Cariou et al., J. Biol. Chem. 2006, 281, 11039-11049; Ma et al., J. Clin. Invest. 2006, 116(4), 1102-1109; Duran-Sandoval et al., Biochimie 2005, 87(1), 93-98).

The compounds of the invention are also useful for the treatment of gastrointestinal diseases, including but not limited to bile acid malabsorption (including primary bile acid diarrhea and secondary bile acid diarrhea), bile reflux gastritis and inflammatory bowel diseases (IBD). Bile acid malabsorption, which leads to excessive fecal bile acid excretion and diarrhea in patients, is characterized by a cycle wherein the feedback regulation of bile acid synthesis is interrupted, resulting in additional bile acid production. Feedback regulation of bile acid synthesis is under the control of an endocrine pathway, wherein activation of the nuclear bile acid receptor FXR induces enteric expression of fibroblast growth factor 15 (FGF15) in rodents or FGF19 in humans. In liver, FGF15 or FGF19 act together with FXR-mediated expression of small heterodimer partner to repress bile acid synthesis (Jung et al., Journal of Lipid Research 48: 2693-2700 (2007) Walters J R, Nat Rev Gastroenterol Hepatol. 11(7):426-34 (2014)).

In another embodiment, the compounds according to the invention are useful for beneficially altering lipid profiles, including but not limited to lowering total cholesterol levels, lowering LDL cholesterol levels, lowering VLDL cholesterol levels, raising HDL cholesterol levels, and/or lowering triglyceride levels. Thus, the present invention provides a method for treating FXR mediated conditions such as dyslipidemia and diseases related to dyslipidemia comprising administering a therapeutically effective amount of a compound of the present invention to a subject in need thereof.

In a further embodiment, the compound or pharmaceutical composition is used for treating a disease selected from the group consisting of lipid and lipoprotein disorders such as hypercholesterolemia, hypertriglyceridemia, and atherosclerosis as a clinically manifest condition which can be ameliorated by FXR's beneficial effect on raising HDL cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the preparation of a medicament where the combined lipid lowering, anti-cholestatic and anti-fibrotic effects of FXR-targeted medicaments can be exploited for the treatment of liver steatosis and associated syndromes such as non-alcoholic steatohepatitis (NASH), or for the treatment of cholestatic and fibrotic effects that are associated with alcohol-induced cirrhosis, or with viral-borne forms of hepatitis.

FXR seems also to be involved in the control of antibacterial defense in the intestine (Inagaki et al., Proc. Natl. Acad. Sci. USA. 2006, 103(10), 3920-3905), and may have a beneficial impact in the therapy of Inflammatory Bowel Disorders (IBD), particularly those forms where the upper (ileal) part of the intestine is affected (e.g. ileal Crohn's disease) because this seems to be the site of action of FXR's control on bacterial growth. In IBD, the desensitization of the adaptive immune response is somehow impaired in the intestinal immune system.

Bacterial overgrowth might then be the causative trigger towards establishment of a chronic inflammatory response. Hence, dampening of bacterial growth by FXR-borne mechanisms might be a key mechanism to prevent acute inflammatory episodes. Thus, the invention also relates to a compound according to formula (I) or a pharmaceutical composition comprising said compound for treating a disease related to Inflammatory Bowel Diseases such as Crohn's disease or ulcerative colitis. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the treatment of obesity and associated disorders such as metabolic syndrome (combined conditions of dyslipidemias, diabetes and abnormally high body-mass index), which can be overcome by FXR-mediated lowering of serum triglycerides, blood glucose and increased insulin sensitivity and FXR-mediated weight loss. The compounds or pharmaceutical composition of the present invention are also useful in the preparation of a medicament for treating clinical complications of Type I and Type II Diabetes such as diabetic nephropathy, diabetic retinopathy, and Peripheral Arterial Occlusive Disease (PAOD).

Furthermore, conditions and diseases which result from chronic fatty and fibrotic degeneration of organs due to enforced lipid and specifically triglyceride accumulation and subsequent activation of profibrotic pathways may also be treated by applying the compounds or pharmaceutical composition of the present invention. Such conditions and diseases encompass Non-Alcoholic Steatohepatitis (NASH) and chronic cholestatic conditions in the liver, glomerulosclerosis and diabetic nephropathy in the kidney, macular degeneration and diabetic retinopathy in the eye and neurodegenerative diseases such as Alzheimer's disease in the brain or diabetic neuropathies in the peripheral nervous system.

Examples of other FXR-mediated disease include drug-induced bile duct injury, bile duct obstruction, gallstones, cholelithiasis, liver fibrosis, liver cirrhosis, alcohol-induced cirrhosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, erectile dysfunction, and other FXR-mediated conditions leading to extrahepatic cholestasis.

Administration and Pharmaceutical Compositions

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

In a particular embodiment, the pharmaceutical composition is formulated for oral administration. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of Formula I, II, III, IV or V, and at least one other therapeutic agent as a combined preparation for simultaneous, separate or sequential use in therapy. In one embodiment, the therapy is the treatment of a disease or condition mediated by FXR. Products provided as a combined preparation include a composition comprising a compound of Formula I, II, III, IV or V, and the other therapeutic agent(s) together in the same pharmaceutical composition, or the compound of Formula I, II, III, IV or V and the other therapeutic agent(s) in separate form, e.g. in the form of a kit.

In one embodiment, the invention provides a pharmaceutical composition comprising a compound of Formula I, 11, III, IV or V, and another therapeutic agent(s). It is contemplated that the invention provides a pharmaceutical composition comprising a compound of Formula I, II, III, IV or V in combination with a naturally occurring non-toxic bile acid, such as ursodeoxycholic acid, as an aid in preventing possible depletion of fat-soluble vitamins secondary to treatment with an FXR agonist. Accordingly, the compounds of the invention may be administered concurrently with the naturally occurring non-toxic bile acid, either as separate entities or as a single formulation comprising a compound of Formula I, II, III, IV or V, and naturally occurring bile acid.

Optionally, the pharmaceutical composition may comprise a pharmaceutically acceptable excipient, as described above.

In one embodiment, the invention provides a kit comprising two or more separate pharmaceutical compositions, at least one of which contains a compound of Formula I, II, III, IV or V. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides for the use of a compound of Formula I, II, III, IV or V for treating a disease or condition mediated by FXR, wherein the medicament is prepared for administration, or administered with, another therapeutic agent. The invention also provides a compound of Formula I, II, III, IV or V for use in a method of treating a disease or condition mediated by FXR, wherein the compound of Formula I, II, III, IV or V is prepared for administration, or administered with, another therapeutic agent. The invention also provides another therapeutic agent for use in a method of treating a disease or condition mediated by FXR, wherein the other therapeutic agent is prepared for administration, or administered with, a compound of Formula I, II, III, IV or V.

The invention also provides for the use of a compound of Formula I, II, III, IV or V for treating a disease or condition mediated by FXR, wherein the patient has previously (e.g. within 24 hrs) been treated with another therapeutic agent. Alternatively, the invention provides for the use of another therapeutic agent for treating a disease or condition mediated by FXR, wherein the patient has previously (e.g. within 24 hrs) been treated with a compound of Formula I, II, III, IV or V.

Additional Embodiments

The present invention further encompasses additional embodiments described herein.

Embodiment 1. A compound according to formula (I), or a pharmaceutical acceptable salt, tautomer or stereoisomer thereof,

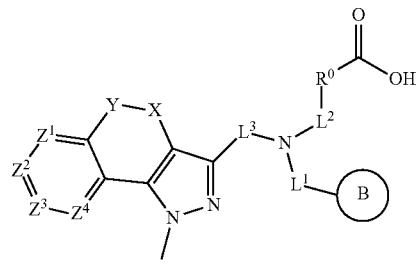

wherein,
$R^0$ is Ring A or $C_{1-6}$ alkyl; wherein
Ring A is aryl; 5-10 membered heteroaryl comprising 1-3 N, O or S heteroatoms; 4-6 membered heterocycle comprising 1-2 N, O or S heteroatoms; or $C_{3-7}$ cycloalkyl; each of which is unsubstituted or substituted by 1-2 substituents each independently represented by $R^2$; wherein $L^3$ and $R^0$ can be attached to the same or different ring atoms of Ring A; and the $C_{1-6}$ alkyl is optionally substituted by 1 to 2 $C_{1-6}$ alkyl;
Ring B is aryl; 5-10 membered heteroaryl comprising 1-3 N, O or S heteroatoms; 4-6 membered heterocycle comprising 1-2 N, O or S heteroatoms; or $C_{3-7}$ cycloalkyl; each of which is unsubstituted or substituted by 1-2 substituents each independently represented by $R^2$;
X is $(CR^4R^5)$ or $C(O)$;
Y is O, $(CR^4R^5)$, *$O(CR^4R^5)$ or NR, wherein "*" indicates the point of attachment of Y to the ring containing the Z ring atoms;
$Z^1$, $Z^2$, $Z^3$, and $Z^4$ are each independently $CR^3$ or N;
$L^1$ is *$^1$—$(CR^4R^5)_{1-2}$— or *$^1$—$(CR^4R^5)$—$C(O)$—NR—, wherein "*$^1$" indicates the point of attachment of $L^1$ to N;
$L^2$ is *$^2$—$(CR^4R^5)_{1-2}$—, *$^2$—$(CR^4R^5)$—$C(O)$, *$^2$—$(CR^4R^5)$—$C(O)$—NR, *$^2$—$(CR^4R^5)_2$—O—, *$^2$—$(CR^4R^5)_2$—NR—, *$^2$—$(CR^4R^5)_2$—$SO_2$—, *$^2$—$(CR^4R^5)_2$—NR—$C(O)$—, or *$^2$—$(CR^4R^5)$—$C(O)$—NR—$(CR^4R^5)$; wherein "*$^2$" indicates the point of attachment of $L^2$ to N;
$L^3$ is —$(CR^4R^5)$— or —$C(O)$—;
each $R^2$ is independently halo, hydroxyl, $C_{1-6}$ alkyl, or halo-substituted $C_{1-6}$ alkyl;
each $R^3$ is independently hydrogen, halo, or $C_{1-6}$ alkyl; and
R, $R^4$ and $R^5$ are independently hydrogen or $C_{1-6}$ alkyl.

Embodiment 2. A compound according to embodiment 1, or a salt, tautomer or stereoisomer thereof, wherein the compound is represented by Formula (II),

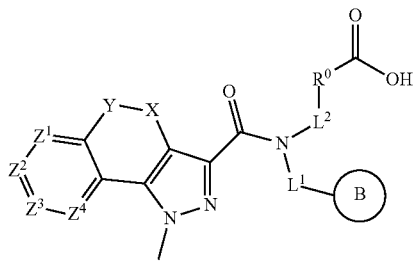

wherein
$R^0$ is Ring A or $C_{1-6}$ alkyl; wherein
Ring A is selected from phenyl, pyridyl, pyridazinyl, pyrimidinyl, pyrazinyl and $C_{3-7}$ cycloalkyl, each of which is unsubstituted or substituted by 1-3 substituents each independently represented by $R^2$; wherein $L^3$ and $R^0$ can be attached to the same or different ring atoms of Ring A; and the $C_{1-6}$ alkyl is optionally substituted by 1-2 $C_{1-6}$ alkyl;

Ring B is selected from phenyl, pyridyl, pyridazinyl, pyrimidinyl, pyrazinyl, 1H-indolyl, and $C_{3-7}$ cycloalkyl, each of which is unsubstituted or substituted by 1-2 substituents each independently represented by $R^2$;

X is $(CR^4R^5)$;

Y is O, $(CR^4R^5)$ or $*O(CR^4R^5)$, where "*" indicates the point of attachment of Y to the ring containing the Z ring atoms;

$Z^1$, $Z^2$, $Z^3$, and $Z^4$ are each independently $CR^3$ or N;

$L^1$ is $—(CR^4R^5)_{1-2}—$, $L^2$ is $*^2—(CR^4R^5)_{1-2}—$, $*^2—(CR^4R^5)—C(O)—NR—$, $*^2—(CR^4R^5)_2—O—$, or $*^2—(CR^4R^5)_2—NR—$; where "$*^2$" indicates the point of attachment of $L^2$ to N; and each $R^2$ is independently halo, hydroxyl, $C_{1-6}$ alkyl, or halo-substituted $C_{1-6}$ alkyl;

each $R^3$ is independently hydrogen, halo, or $C_{1-6}$ alkyl;

R, $R^4$ and $R^5$ are independently hydrogen or $C_{1-6}$ alkyl.

Embodiment 3. A compound according to embodiment 1 or 2, or a pharmaceutically acceptable salt, tautomer or stereoisomer thereof, wherein $R^0$ is selected from $*^3—CH_2C(CH_3)_2—$, $*^3—CH_2CH(CH_3)—$, and $*^3$-cyclopropane-1,1-diyl-, wherein "$*^3$" indicates the point of attachment of $R^0$ to $L^2$.

Embodiment 4. A compound according to embodiment 1 or 2, or a pharmaceutically acceptable salt, tautomer or stereoisomer thereof, wherein the compound is represented by Formula (III):

(III)

wherein

Ring A is phenyl or pyridyl, each of which is unsubstituted or substituted by 1-2 substituents each independently represented by $R^2$;

Ring B is selected from phenyl, pyridyl, 1H-indolyl, and cyclopentyl, each of which is unsubstituted or substituted by 1-2 substituents each independently represented by $R^2$;

$L^1$ is $—(CR^4R^5)$;

$L^2$ is selected from $*^2—(CH_2)—$, $*^2—CH_2C(O)NH—$, $*^2—CH(CH_3)C(O)NH—$, $*^2—CH_2C(O)NHCH_2—$, $*^2—(CH_2)_2O—$, and $*^2—(CH_2)_2NH—$; wherein "$*^2$" indicates the point of attachment of $L^2$ to N;

X is $CH_2$;

Y is selected from O, $CH_2$, $C(CH_3)_2$, and $*O—CH_2$, wherein "*" indicates the point of attachment of Y to the ring containing the Z ring atoms;

$Z^1$ is $CR^3$ or N;

$Z^2$ is $CR^3$;

$Z^3$ is $CR^3$;

$Z^4$ is $CR^3$ or N; and each $R^2$ is independently selected from halo, methyl, and trifluoromethyl;

each $R^3$ is independently hydrogen, halo, or $C_{1-6}$ alkyl; and each of $—R^4$ and $R^5$ is independently hydrogen or methyl.

Embodiment 5. A compound according to any one of embodiments 1 to 4, or a pharmaceutically acceptable salt, tautomer or stereoisomer thereof, wherein Y is O.

Embodiment 6. A compound according to any one of embodiments 1 to 5, or a pharmaceutically acceptable salt, tautomer or stereoisomer thereof, wherein $L^1$ is $—CH_2—$.

Embodiment 7. A compound according to any one of embodiments 1 to 6, or a pharmaceutically acceptable salt, tautomer or stereoisomer thereof, wherein $L^2$ is selected from $*^2—(CH_2)—$, $*^2—CH_2C(O)NH—$, $*^2—(CH_2)_2O—$, and $*^2—(CH_2)_2NH—$; wherein "$*^2$" indicates the point of attachment of $L^2$ to N.

Embodiment 8. A compound according to any one of embodiments 1 to 6, or a pharmaceutically acceptable salt, tautomer or stereoisomer thereof, wherein $L^2$ is $*^2—(CH_2)—$.

Embodiment 9. A compound according to any one of embodiments 1 to 8, or a pharmaceutically acceptable salt, tautomer or stereoisomer thereof, wherein each $R^2$ is independently fluoro or methyl.

Embodiment 10. A compound according to any one of embodiments 1 to 9, or a pharmaceutically acceptable salt, tautomer or stereoisomer thereof, wherein each $R^3$ is independently selected from hydrogen, fluoro, chloro, and methyl.

Embodiment 11. A compound according to any one of embodiments 1 to 9, or a pharmaceutically acceptable salt, tautomer or stereoisomer thereof, wherein $Z^1$ is selected from CH, CF, $CCH_3$, and N;

$Z^2$ is selected from CH, CF, CCl, and $CCH_3$;

$Z^3$ is selected from CH, CF, CCl, and $CCH_3$; and $Z^4$ is CH or N.

Embodiment 12. A pharmaceutical composition comprising a therapeutically effective amount of a compound according to any one of embodiments 1-11 and a pharmaceutically acceptable carrier.

Embodiment 13. A combination comprising a therapeutically effective amount of a compound according to any one of embodiments 1-11, and a second therapeutic agent being useful in the treatment of cholestasis, intrahepatic cholestasis, estrogen-induced cholestasis, drug-induced cholestasis, cholestasis of pregnancy, parenteral nutrition-associated cholestasis, primary biliary cirrhosis (PBC), primary sclerosing cholangitis (PSC), progressive familiar cholestasis (PFIC), non-alcoholic fatty liver disease (NAFLD), non-alcoholic steatohepatitis (NASH), drug-induced bile duct injury, gallstones, liver cirrhosis, alcohol-induced cirrhosis, cystic fibrosis, bile duct obstruction, cholelithiasis, liver fibrosis, dyslipidemia, atherosclerosis, diabetes, diabetic nephropathy, colitis, newborn jaundice, prevention of kernicterus, veno-occlusive disease, portal hypertension, metabolic syndrome, hypercholesterolemia, intestinal bacterial overgrowth, or erectile dysfunction.

Embodiment 14. A method for treating a condition mediated by farnesoid X receptors (FXR) in a subject suffering therefrom, comprising administering to the subject a therapeutically effective amount of a compound of any one of embodiments 1-11, or a pharmaceutical composition thereof, and optionally in combination with a second therapeutic agent.

Embodiment 15. A pharmaceutical composition which comprises a compound according to any one of embodiments 1-11 for use in the treatment of a condition mediated by FXR.

Embodiment 16. A compound of Formula (VI)

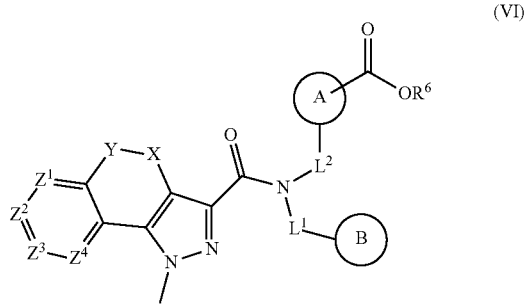

(VI)

wherein:

Ring A is phenyl or pyridyl, each of which is unsubstituted or substituted by 1-2 substituents each independently represented by $R^2$;

Ring B is selected from phenyl, pyridyl, 1H-indolyl, and cyclopentyl, each of which is unsubstituted or substituted by 1-2 substituents each independently represented by $R^2$;

$L^1$ is —$(CR^4R^5)$;

$L^2$ is selected from *²—$(CH_2)$—, *²—$CH_2C(O)NH$—, *²—$CH(CH_3)C(O)NH$—, *²—$(CH_2)_2O$—, and *²—$(CH_2)_2NH$—; wherein "*²" indicates the point of attachment of $L^2$ to N;

X is $CH_2$;

Y is selected from O, $CH_2$, $C(CH_3)_2$, and *O—$CH_2$, wherein "*" indicates the point of attachment of Y to the ring containing the Z ring atoms;

$Z^1$ is $CR^3$ or N;
$Z^2$ is $CR^3$;
$Z^3$ is $CR^3$;
$Z^4$ is $CR^3$ or N;

each $R^2$ is independently selected from halo, methyl, and trifluoromethyl;

each $R^3$ is independently hydrogen, halo, or $C_{1-6}$ alkyl;

each of $R^4$ and $R^5$ is independently hydrogen or methyl; and $R^6$ is $C_{1-6}$ alkyl.

Embodiment 17. The compound according to embodiment 16, wherein Y is O.

Embodiment 18. The compound according to embodiment 16, wherein $L^1$ is —$CH_2$—.

Embodiment 19. The compound according to embodiment 16, wherein $L^2$ is selected from *²—$(CH_2)$—, *²—$CH_2C(O)NH$—, *²—$(CH_2)_2O$—, and *²—$(CH_2)_2NH$—; wherein "*²" indicates the point of attachment of $L^2$ to N; and more particularly, wherein $L^2$ is —$CH_2$—.

Embodiment 20. The compound according to embodiment 16, wherein each $R^2$ is independently fluoro or methyl.

Embodiment 21. The compound according to embodiment 16, wherein each $R^3$ is independently selected from hydrogen, fluoro, chloro, and methyl.

Embodiment 22. A method for preparing a crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid, comprising the step of reacting 4-fluoro-3-(2-(8-fluoro-N-(3-fluorobenzyl)-1-methyl-1,4-dihydrochromeno[4,3-c]pyrazole-3-carboxamido) acetamido)benzoic acid with 2-amino-2-hydroxymethyl-propane-1,3-diol in a solvent such as a methanol:dichloromethane solvent (1:1 by volume).

Embodiment 23. A crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid produced according to embodiment 22; and more particularly, wherein said crystalline form has a melting point of about 125° C. as determined by differential scanning calorimetry.

Embodiment 24. A method for preparing a crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid, comprising the step of: (i) reacting 4-fluoro-3-(2-(8-fluoro-N-(3-fluorobenzyl)-1-methyl-1,4-dihydrochromeno[4,3-c]pyrazole-3-carboxamido) acetamido)benzoic acid in a solvent such as methanol with aqueous L-arginine; and (ii) optionally, further crystallizing the solid obtained from (i) in a solvent such as an acetonitrile: methanol solvent (2:1 by volume).

Embodiment 25. A crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid produced according to embodiment 24; and more particularly, wherein said crystalline form has a melting point of about 206° C. as determined by differential scanning calorimetry.

Embodiment 26. A method for preparing a crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid, comprising the step of: (i) reacting 4-fluoro-3-(2-(8-fluoro-N-(3-fluorobenzyl)-1-methyl-1,4-dihydrochromeno[4,3-c]pyrazole-3-carboxamido) acetamido)benzoic acid in a solvent such as methanol with aqueous L-lysine; and (ii) optionally, further crystallizing the solid obtained in (i) in a solvent such as acetonitrile.

Embodiment 27. A crystalline form of 4-fluoro-3-(2-(8-fluoro-N-(3-fluorobenzyl)-1-methyl-1,4-dihydrochromeno[4,3-c]pyrazole-3-carboxamido) acetamido)benzoic acid produced according to embodiment 26.

Embodiment 28. A method for preparing a crystalline form of 4-fluoro-3-((2-(8-fluoro-N-(3-fluorobenzyl)-1-methyl-1,4-dihydrochromeno[4,3-c]pyrazole-3-carboxamido)ethyl)amino)benzoic acid, comprising the step of reacting 4-fluoro-3-((2-(8-fluoro-N-(3-fluorobenzyl)-1-methyl-1,4-dihydrochromeno[4,3-c]pyrazole-3-carboxamido)ethyl)amino)benzoic acid with 2-amino-2-hydroxymethyl-propane-1,3-diol in a solvent such as methanol.

Embodiment 29. A crystalline form of 4-fluoro-3-((2-(8-fluoro-N-(3-fluorobenzyl)-1-methyl-1,4-dihydrochromeno[4,3-c]pyrazole-3-carboxamido)ethyl)amino)benzoic acid produced according to embodiment 28; and more particularly, wherein said crystalline form has a melting point of about 160° C. as determined by differential scanning calorimetry.

Embodiment 30. A method for preparing a crystalline form of 4-fluoro-3-((2-(8-fluoro-N-(3-fluorobenzyl)-1-methyl-1,4-dihydrochromeno[4,3-c]pyrazole-3-carboxamido)ethyl)amino)benzoic acid, comprising the step of: (i) reacting 4-fluoro-3-((2-(8-fluoro-N-(3-fluorobenzyl)-1-methyl-1,4-dihydrochromeno[4,3-c]pyrazole-3-carboxamido)ethyl)amino)benzoic acid in a solvent such as methanol with aqueous L-arginine; and (ii) optionally, further crystallizing the solid obtained from (i) in a solvent such as acetonitrile.

Embodiment 31. A crystalline form of 4-fluoro-3-((2-(8-fluoro-N-(3-fluorobenzyl)-1-methyl-1,4-dihydrochromeno[4,3-c]pyrazole-3-carboxamido)ethyl)amino)benzoic acid produced according to embodiment 30; and more particularly, wherein said crystalline form has a melting point of about 161° C. as determined by differential scanning calorimetry.

Embodiment 32. A method for preparing a crystalline form of 4-fluoro-3-(2-(8-fluoro-N-(2-fluorobenzyl)-1-methyl-1,4-dihydrochromeno[4,3-c]pyrazole-3-carboxamido)acetamido)benzoic acid, comprising the step of reacting 4-fluoro-3-(2-(8-fluoro-N-(2-fluorobenzyl)-1-methyl-1,4-dihydrochromeno[4,3-c]pyrazole-3-carboxamido)acetamido)benzoic acid in a solvent such as methanol with aqueous L-arginine.

Embodiment 33. A crystalline form of 4-fluoro-3-(2-(8-fluoro-N-(2-fluorobenzyl)-1-methyl-1,4-dihydrochromeno[4,3-c]pyrazole-3-carboxamido)acetamido)benzoic acid produced according to embodiment 32; and more particularly, wherein said crystalline form has a melting point of about 206° C. as determined by differential scanning calorimetry.

Embodiment 34. A method for preparing a crystalline form of 4-fluoro-3-(2-(8-fluoro-N-(2-fluorobenzyl)-1-methyl-1,4-dihydrochromeno[4,3-c]pyrazole-3-carboxamido)acetamido)benzoic acid, comprising the step of: (i) reacting 4-fluoro-3-(2-(8-fluoro-N-(2-fluorobenzyl)-1-methyl-1,4-dihydrochromeno[4,3-c]pyrazole-3-carboxamido)acetamido)benzoic acid in a solvent such as methanol with aqueous sodium hydroxide; and (ii) optionally, further crystallizing the solid obtained in (i) in a solvent such as acetonitrile.

Embodiment 35. A crystalline form of 4-fluoro-3-(2-(8-fluoro-N-(2-fluorobenzyl)-1-methyl-1,4-dihydrochromeno[4,3-c]pyrazole-3-carboxamido)acetamido)benzoic acid produced according to embodiment 34; and more particularly, wherein said crystalline form has a melting point of about 161° C. as determined by differential scanning calorimetry.

Embodiment 36. A method for preparing a crystalline form of 4-((N-benzyl-8-chloro-1-methyl-1,4-dihydrochromeno[4,3-c]pyrazole-3-carboxamido)methyl)benzoic acid, comprising the step of reacting 4-((N-benzyl-8-chloro-1-methyl-1,4-dihydrochromeno[4,3-c]pyrazole-3-carboxamido)methyl)benzoic acid with 2-amino-2-hydroxymethyl-propane-1,3-diol in a solvent such as methanol.

Embodiment 37. A crystalline form of 4-((N-benzyl-8-chloro-1-methyl-1,4-dihydrochromeno[4,3-c]pyrazole-3-carboxamido)methyl)benzoic acid produced according to embodiment 36; and more particularly, wherein said crystalline form has a melting point of about 195.6° C. as determined by differential scanning calorimetry.

Embodiment 38. A method for preparing a crystalline form of 4-((N-benzyl-8-chloro-1-methyl-1,4-dihydrochromeno[4,3-c]pyrazole-3-carboxamido)methyl)benzoic acid, comprising the step of: (i) reacting 4-((N-benzyl-8-chloro-1-methyl-1,4-dihydrochromeno[4,3-c]pyrazole-3-carboxamido)methyl)benzoic acid in a solvent such as acetone with aqueous meglumine; and (ii) optionally, further comprising heating the solid obtained in (i) at a temperature ranging from 60-90° C. (e.g., about 80° C.).

Embodiment 39. A crystalline form of 4-((N-benzyl-8-chloro-1-methyl-1,4-dihydrochromeno[4,3-c]pyrazole-3-carboxamido)methyl)benzoic acid produced according to embodiment 38, step (i) having a dehydration point at about 71° C. as determined by differential scanning calorimetry; or obtained upon further heating in step (ii) having a melting point of about 167.5° C. as determined by differential scanning calorimetry.

Embodiment 40. A method for preparing a crystalline form of 4-((N-benzyl-8-chloro-1-methyl-1,4-dihydrochromeno[4,3-c]pyrazole-3-carboxamido)methyl)benzoic acid, comprising the step of: (i) reacting 4-((N-benzyl-8-chloro-1-methyl-1,4-dihydrochromeno[4,3-c]pyrazole-3-carboxamido)methyl)benzoic acid and meglumine in a solvent such as methanol; and (ii) further comprising heating the reactants at a temperature ranging from 60-90° C.

Embodiment 41. A crystalline form of 4-((N-benzyl-8-chloro-1-methyl-1,4-dihydrochromeno[4,3-c]pyrazole-3-carboxamido)methyl)benzoic acid produced according to embodiment 40; and more particularly, wherein the crystalline form has a melting point of about 180.6° C. as determined by differential scanning calorimetry.

Processes for Making Compounds of the Invention

The compounds of the present invention may be prepared by the routes described in the following schemes or in the Examples. All methods described herein can be performed in any suitable order unless otherwise indicated herein or otherwise clearly contradicted by context.

Compounds of Formula (I) wherein $L^1$ is methyl, $L^2$ is $*^2$—$CH_2C(O)NH$—, $L^3$ is $C(O)$ and $R^0$ is Ring A may be prepared according to Scheme 1:

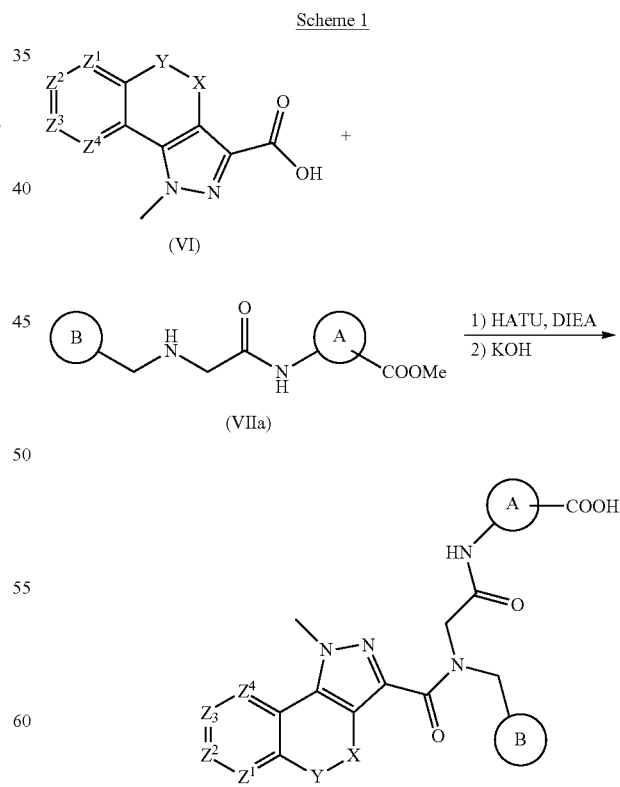

Compounds of Formula (I) wherein $L^1$ is methyl, $L^2$ is $*^2$—$CH_2C(O)NH$—, $L^3$ is $C(O)$ and $R^0$ is Ring A may be prepared according to Scheme 2:

Scheme 2

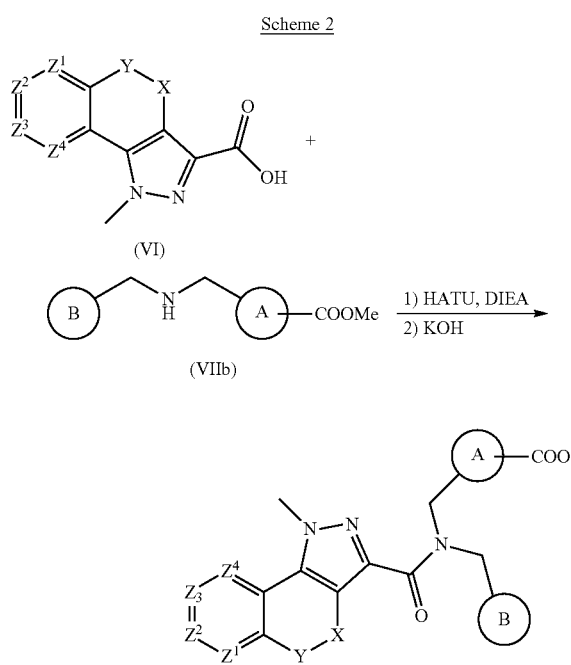

Compounds of Formula (I) wherein $L^1$ is methyl, $L^2$ is $*^2$—$(CH_2)_2NH$—, $L^3$ is C(O) and $R^0$ is Ring A may be prepared according to Scheme 3:

Scheme 3

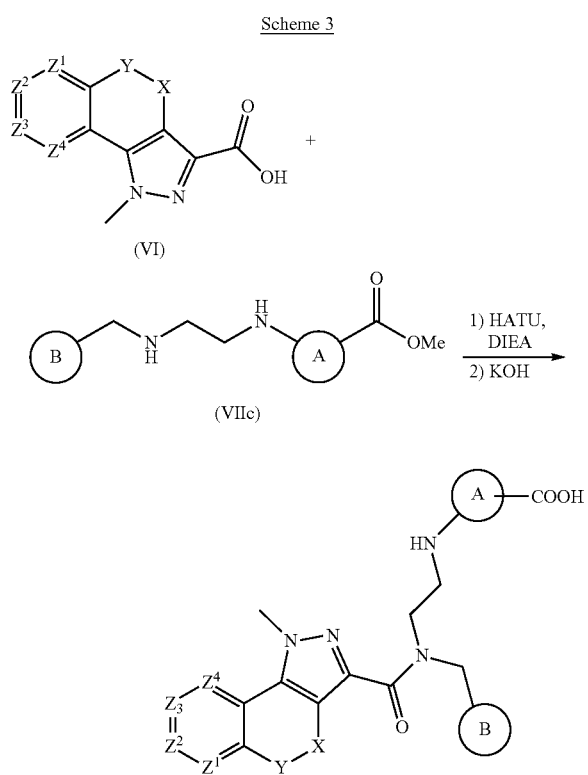

Compounds of Formula (I) wherein $L^1$ is methyl, $L^2$ is $*^2$—$(CH_2)_2O$—, $L^3$ is C(O) and $R^0$ is Ring A may be prepared according to Scheme 4:

Scheme 4

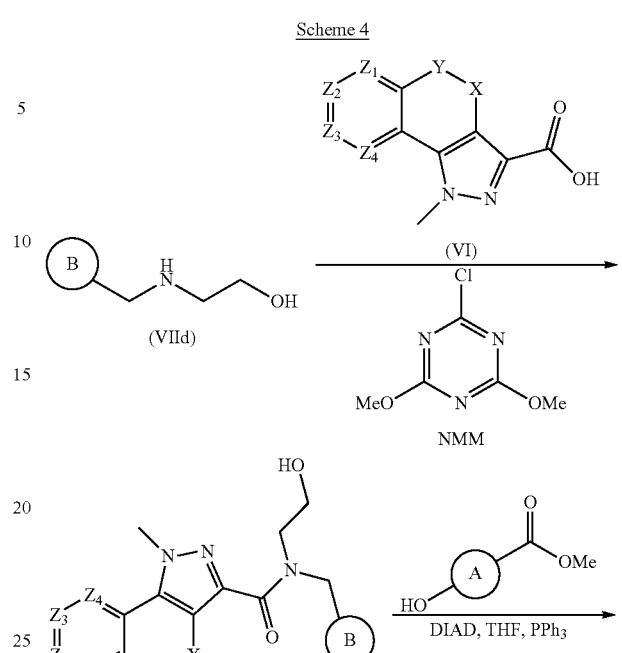

Compounds of Formula (I) wherein $L^1$ is methyl, $L^2$ is $*^2$—$CH_2C(O)NH$—, $L^3$ is C(O) and $R^0$ is $C_{1-6}$alkyl may be prepared according to Scheme 5:

Scheme 5

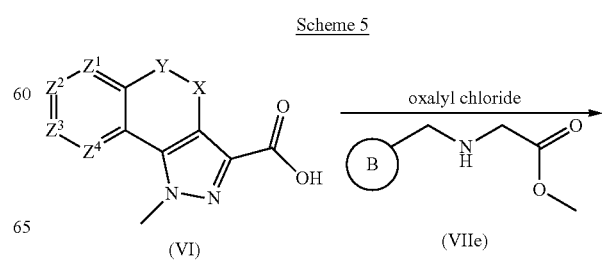

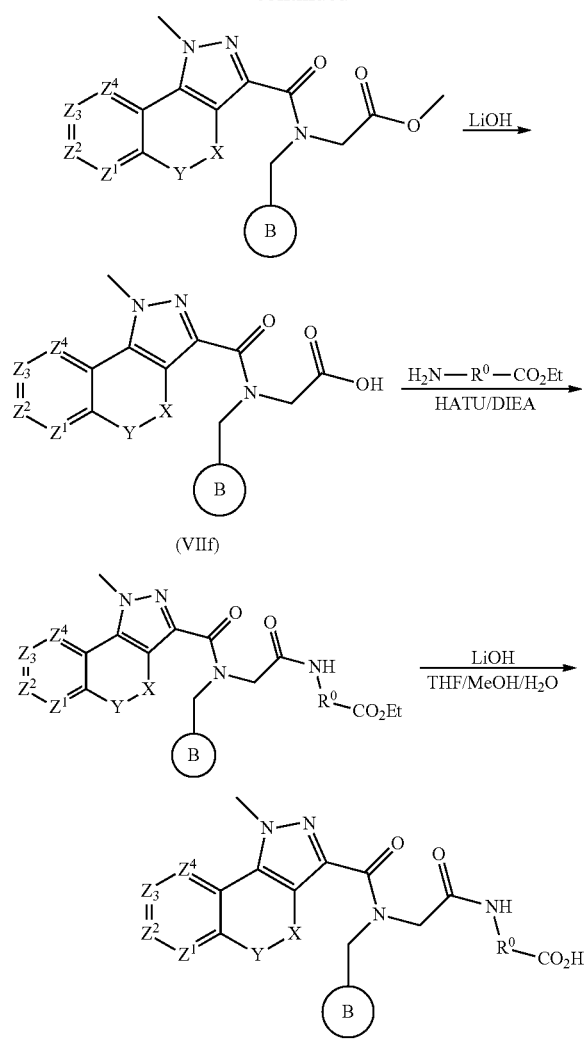

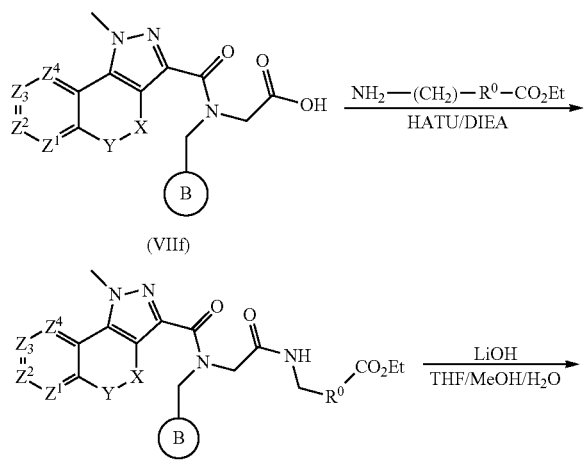

Compounds of Formula (I) wherein $L^1$ is methyl, $L^2$ is *²—(CH$_2$)—C(O)NH(CH$_2$) $L^3$ is C(O) and $R^0$ is Ring A may be prepared according to Scheme 6:

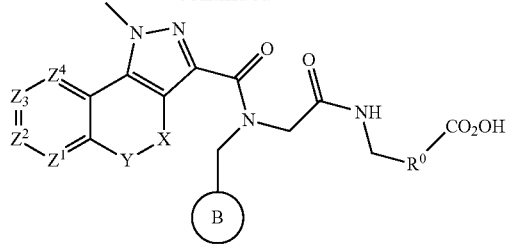

In each of the above Schemes 1-6, X, Y, $Z^1$, $Z^2$, $Z^3$, $Z^4$, A and B are as defined in any of the above embodiments. Generally, the tricyclic core (VI) is coupled to an amide side chain (VIIa, VIIb, VIIc, VIId or VIIe) with or without the use of a suitable amide coupling agent such as HATU; followed by hydrolysis to provide a compound of Formula (I).

In each of the above Schemes 1-5, the tricyclic core (VI) may be prepared according to Scheme 7 wherein X, Y, $Z^1$, $Z^2$, $Z^3$ and $Z^4$ are as defined in any of the above embodiments. Typical conditions are exemplified in the syntheses of ethyl 2-(6-chloro-4-oxochroman-3-yl)-2-oxoacetate (I-1), ethyl 8-chloro-1-methyl-1,4-dihydrochromeno[4,3-c]pyrazole-3-carboxylate (I-3) and 8-chloro-1-methyl-1,4-dihydrochromeno[4,3-c]pyrazole-3-carboxylic acid (I-4), infra.

Scheme 7

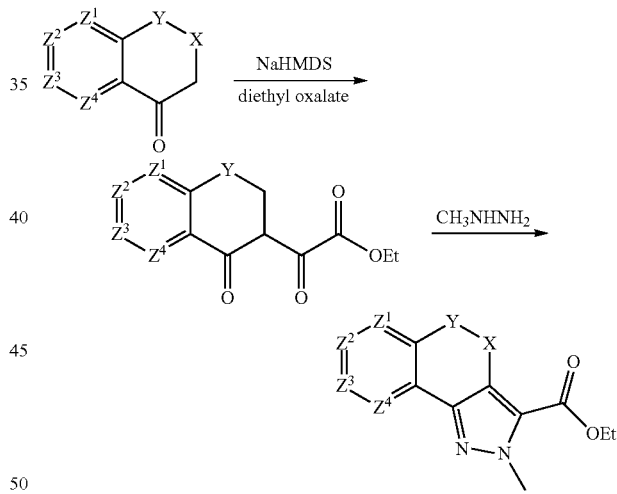

-continued

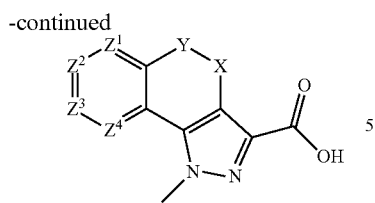

In the above Scheme 1, the amide side chain (VIIa) may be prepared according to Scheme 8, wherein A and B are as defined in any of the above embodiments. Typical conditions are exemplified in the synthesis of methyl 4-fluoro-3-(2-((3-fluorobenzyl)amino) acetamido)benzoate (I-16), infra.

Scheme 8

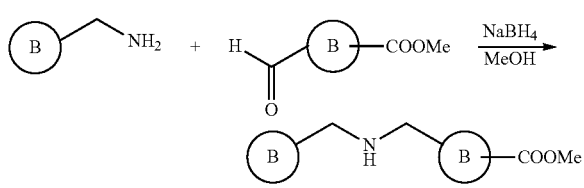

In the above Scheme 2, the amide side chain (VIIb) may be prepared according to Scheme 8, wherein A and B are as defined in any of the above embodiments. Typical conditions are exemplified in the synthesis of methyl 4-((benyzlamino) methyl)benzoate (I-23), infra.

Scheme 9

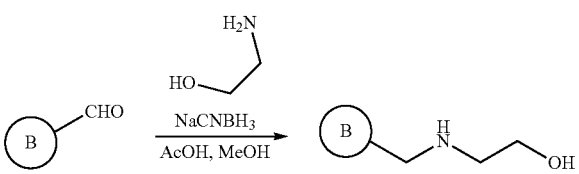

In the above Scheme 3, the amide side chain (VIIc) may be prepared according to Scheme 10, wherein A and B are as defined in any of the above embodiments. Typical conditions are exemplified in the synthesis of methyl 3-((2-((tert-butoxycarbonyl)amino)ethyl) amino)-4-fluorobenzoate (I-44), methyl 3-((2-aminoethyl)amino)-4-fluorobenzoate (I-45) and methyl 4-fluoro-3-((2-((3-fluorobenzyl)amino)ethyl)amino)benzoate (I-46), infra.

Scheme 10

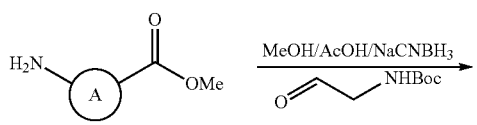

-continued

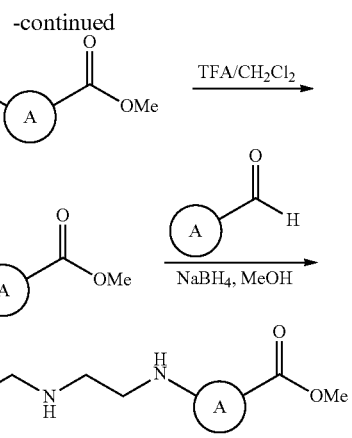

In the above Scheme 4, the amide side chain (VIId) may be prepared according to Scheme 11, wherein B is as defined in any of the above embodiments. Typical conditions are exemplified in the synthesis of 2-((2-fluorobenzyl)amino) ethanol (I-72), infra.

Scheme 11

Each reaction step can be carried out in a manner known to those skilled in the art. For example, a reaction can be carried in the presence of a suitable solvent or diluent or of mixture thereof. A reaction can also be carried, if needed, in the presence of an acid or a base, with cooling or heating, for example in a temperature range from approximately −30° C. to approximately 150° C. In particular examples, a reaction is carried in a temperature range from approximately 0° C. to 100° C., and more particularly, in a temperature range from room temperature to approximately 80° C., in an open or closed reaction vessel and/or in the atmosphere of an inert gas, for example nitrogen.

The invention also relates to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. Compounds of the invention and intermediates can also be converted into each other according to methods generally known to those skilled in the art. Intermediates and final products can be worked up and/or purified according to standard methods, e.g. using chromatographic methods, distribution methods, (re-) crystallization, and the like.

In the reactions described, reactive functional groups, for example hydroxyl, amino, imino, thio or carboxy groups, where these are desired in the final product, may be protected to avoid their unwanted participation in the reactions. A characteristic of protecting groups is that they can be removed readily (i.e. without the occurrence of undesired secondary reactions) for example by solvolysis, reduction, photolysis or alternatively under physiological conditions (e.g. by enzymatic cleavage). Conventional protecting groups may be used in accordance with standard practice (see e.g., T. W. Greene and P. G. M. Wuts in "Protective Groups in Organic Chemistry," 4th Ed., Wiley-lnterscience, 2006, and subsequent versions thereof).

All the above-mentioned process steps mentioned herein before and hereinafter can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers. Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic or heteroaromatic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules. In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers. Salts can be converted into the free compounds in accordance with methods known to those skilled in the art. Metal and ammonium salts can be converted, for example, by treatment with suitable acids, and acid addition salts, for example, by treatment with a suitable basic agent.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Other pharmaceutically acceptable salts can be derived from L-arginine, TRIS (2-amino-2-hydroxymethyl-1,3-propanediol), adipic acid (adipate), L-ascorbic acid (ascorbate), capric acid (caprate), sebacic acid (sebacate), 1-hydroxy-2-naphthoic acid (xinafoate), L-glutamic acid (glutamate), glutaric acid (glutarate), triphenylacetic acid (trifenatate) and galactaric acid/mucic acid (mucate).

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington: The Science and Practice of Pharmacy," $21^{st}$ Ed., Pharmaceutical Press 2011; and in "Pharmaceutical Salts: Properties, Selection, and Use" by Stahl and Wermuth ($2^{nd}$ Rev. Ed., Wiley-VCH 2011, and subsequent versions thereof).

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. (See, The Practice of Medicinal Chemistry, Ch. 31-32 (Ed. Wermuth, Academic Press, San Diego, Calif., 2001, and subsequent versions thereof). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., alkyl esters, cycloalkyl esters, alkenyl esters, benzyl esters, mono- or di-substituted alkyl esters, such as the ω-(amino, mono- or di-alkylamino, carboxy, alkoxycarbonyl) alkyl esters, the α-(alkanoyloxy, alkoxycarbonyl or di-alkylaminocarbonyl) alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, J. Med. Chem. 2503 (1989), and subsequent versions thereof). Moreover, drugs containing an acidic NH group, such as imidazole, imide, indole and the like, have been masked with N-acyloxymethyl groups (Bundgaard, Design of Prodrugs, Elsevier (1985), and subsequent versions thereof). Hydroxy groups have been masked as esters and ethers. EP 039,051 (Sloan and Little) discloses Mannich-base hydroxamic acid prodrugs, their preparation and use.

Furthermore, the compounds of the present invention, including their salts, may also be obtained in the form of hydrates, or their crystals may, for example, include the solvent used for crystallization. Different crystalline forms may be present. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

EXAMPLES

The examples provided herein are offered to illustrate but not limit the compounds of the invention, as well as the preparation of such compounds and intermediates. It is understood that if there appears to be a discrepancy between the name and structure of a particular compound, the structure is to be considered correct as the compound names were generated from the structures. All the variables are as defined herein.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl Science of Synthesis volumes 1-48, Georg Thieme Verlag, and subsequent versions thereof). Furthermore, the compounds of the present invention can be produced by organic synthesis methods known to one of ordinary skill in the art as shown in the following examples.

Temperatures are given in degrees Celsius. If not mentioned otherwise, all evaporations are performed under reduced pressure, typically between about 15 mm Hg and 100 mm Hg (20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Unless mentioned otherwise, melting points were calculated by differential scanning calorimetry (DSC) using TA Q2000 or TA Discovery differential scanning calorimeters at a scanning rate of 10° C./min. The accuracy of the measured sample temperature is generally within about ±1° C.

NMR and LC-MS methodologies are well-known in the art. The methods described herein are merely illustrative, and are not considered limiting.

NMR. NMR spectra were recorded on either a Bruker AVANCE-400 operating at a proton frequency of 400.13 MHz equipped with a 5 mm QNP cryoprobe ($^1$H/$^{13}$C/$^{19}$F/$^{31}$P); or a Bruker AVANCE-600 spectrometer operating at a frequency of 600.13 MHz equipped with a 5 mm Z-gradient TCI cryoprobe or a 5-mm TXI cryoprobe. Unless otherwise indicated, samples were acquired at a temperature of 300° K, and spectra were referenced to the appropriate solvent peak.

LC-MS Methods. Mass spectra were acquired on LC-MS systems using electrospray, chemical and electron impact ionization methods from a range of instruments. Typical methods are described below.

Method 1:
Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H$_2$O+0.025% TFA and (B) Acetonitrile+0.025% TFA. Gradient: 0.4 mL/min, initial 15% B ramp to 95% B over 3.0 mins, then hold until 4.0 mins, return to 15% B at 4.1 mins until end of run, then equilibrated the column for 2.0 mins. MS Scan: 100 to 1000 amu in 0.5 seconds per channel; Diode Array Detector: 200 nm and 400 nm.

Method 2:
Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H$_2$O+0.025% TFA and (B) Acetonitrile+0.025% TFA. Gradient: 0.4 mL/min, initial 20% B ramp to 90% B over 2.0 mins, then hold until 4.0 mins, return to 20% B at 4.1 mins until end of run, then equilibrated the column for 2.0 mins. MS Scan: 100 to 1000 amu in 0.5 seconds per channel; Diode Array Detector: 200 nm and 400 nm.

Method 3:
Agilent 1200 sl/6140 system; UPLC Column: Waters Acquity; HSS T3; C18 1.8 um 50×2.0 mm; Mobile Phase: (A) H$_2$O+0.05% TFA and (B) Acetonitrile+0.035% TFA. Gradient: 0.9 mL/min, initial 10% B ramp to 100% B over 1.95 mins, then return to 10% B at 2.00 mins until end of run. MS Scan: 100 to 1000 amu in 0.5 seconds per channel; Diode Array Detector: 190 nm and 400 nm; Drift tube temperature: 50° C. and N$_2$ gas flow: 40 Psi for ELSD Detector.

Method 4:
Agilent 1100 sl/1946 system; UPLC Column: Waters Atlantis; C18 1.8 um 50×2.0 mm; Mobile Phase: (A) H$_2$O+0.05% TFA and (B) Acetonitrile+0.035% TFA. Gradient: 1.0 mL/min, initial 10% B ramp to 90% B over 3.00 mins, then return to 10% B at 3.5 mins until end of run. MS Scan: 100 to 1000 amu in 0.5 seconds per channel; Diode Array Detector: 190 nm and 400 nm; Drift tube temperature: 50° C. and N$_2$ gas flow: 40 Psi for ELSD Detector.

Analytical method: WATERS ZQ SHIMADZU LEAP CTC, ZORBAX SB-C8 30*4.6 mm, 3.5 um, UV1:220 nm, UV 2:254 nm, A:H$_2$O (0.03% TFA), B:CH$_3$CN (0.05% TFA), Flow: 2.000 (ml/min), Time/% B: 0/5, 1.90/95, 2.30/95, 2.31/5, 2.50/5.

Abbreviations

Boc tertiary butyl carboxy
br broad
d doublet
dd doublet of doublets
DIAD diisopropyl azodicarboxylate
DIEA diethylisopropylamine
DMF N,N-dimethylformamide
DMSO dimethylsulfoxide
ESI electrospray ionization
EtOAc ethyl acetate
HATU 2-(1H-7-Azabenzotriazol-1-yl)-1,1,3,3-tetramethyl uronium hexafluorophosphate
hr(s) hour(s)
HPLC high pressure liquid chromatography
LCMS liquid chromatography and mass spectrometry
MeOH methanol
MS mass spectrometry
m multiplet
mg milligram
min(s) minute(s)
ml milliliter
mmol millimol
m/z mass to charge ratio
NaHDMS sodium bis(trimethylsilyl)amide
NMM N-methylmorpholine
NMR nuclear magnetic resonance
PPh$_3$ triphenylphosphine
r.t. retention time
s singlet
t triplet
TFA trifluoroacetic acid
THF tetrahydrofuran
TRIS (2-amino-2-hydroxymethyl-1,3-propanediol)
Tris.HCl aminotris(hydroxymethyl)methane hydrochloride

Intermediates

Ethyl 2-(6-chloro-4-oxochroman-3-yl)-2-oxoacetate (I-1)

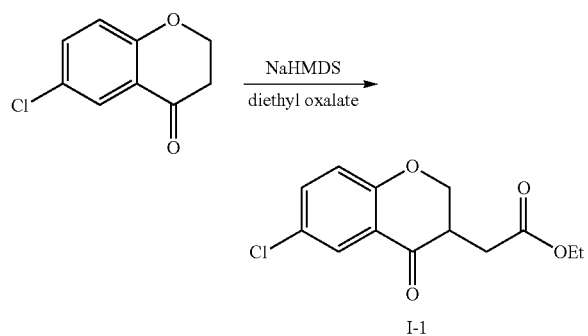

A solution of 6-chloro-2,3-dihydrochromen-4-one (109 mmol) in THF was treated with a solution of NaHMDS (60 mL, 120 mmol, 1.1 eq., 2M in THF) in THF at −78° C. under nitrogen. After stirring for 30 min, diethyl oxalate (22 mL, 163 mmol, 1.5 eq.) was added at −78° C. dropwise and then stirred for 1 hr at room temperature. Subsequently the reaction was quenched with 1N HCl until the pH value was adjusted to 3. The resulting mixture was extracted with EtOAc (200 mL×3). The combined organic phase was washed with brine and dried over $Na_2SO_4$. The solvent was removed in vacuo to give I-1 as a yellow solid. MS (m/z): 283 $(M+H)^+$.

Ethyl 8-chloro-1-methyl-1,4-dihydrochromeno[4,3-c]pyrazole-3-carboxylate (I-3)

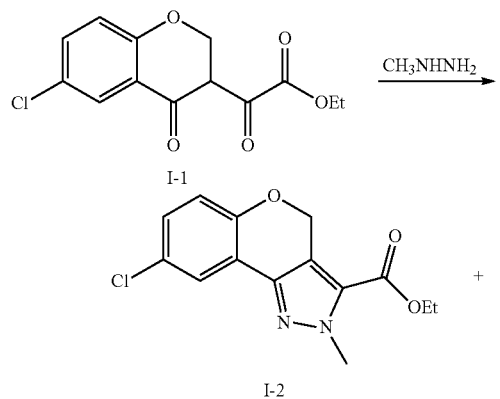

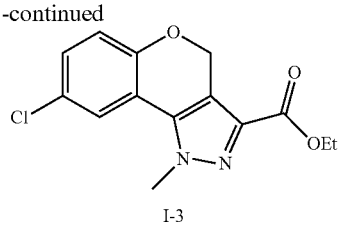

To a warm solution of I-1 (109 mmol) in ethanol was added 1-methylhydrazine (109 mmol) and the solution was stirred for 12 hrs at room temperature. After the solvent was removed in vacuo, the residue was purified by column chromatography (petroleum ether: ethyl acetate=95:5) to give I-2 and the desired product I-3 as a yellow solid. $^1$H-NMR: (300 MHz, $CDCl_3$): δ 7.69 (d, J=2.7 Hz, 1H), 7.13 (dd, J=2.4 Hz, J=8.7 Hz, 1H), 6.86 (d, J=8.7 Hz, 1H), 5.43 (s, 2H), 4.38 (q, J=7.2 Hz, 2H), 4.22 (s, 3H), 1.41 (t, J=7.2 Hz, 3H). MS (m/z): 293 $(M+H)^+$.

8-chloro-1-methyl-1,4-dihydrochromeno[4,3-c]pyrazole-3-carboxylic acid (I-4)

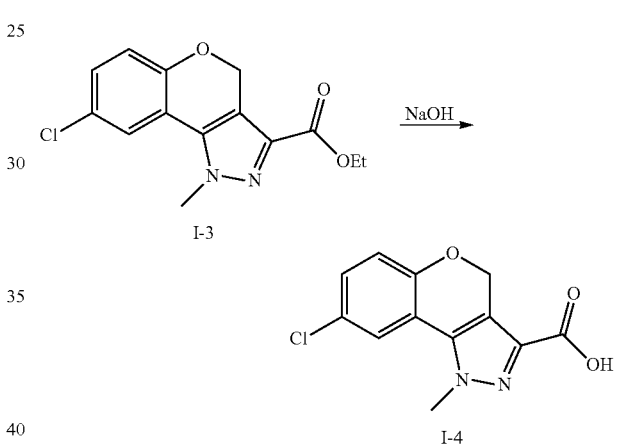

To a solution of I-3 (44 mmol) in 100 mL of THF/water (4:1) was added NaOH (89 mmol, 2 eq.) and the mixture was heated at 60° C. for 8 hrs. Subsequently the resulting white solid was filtrated and washed with methanol and the solid was treated with 100 mL of 1 N HCl. The resulting solid was collected by filtration, washed with methanol thoroughly and dried in vacuum to give I-4 as a white solid. $^1$H-NMR (300 MHz, $CDCl_3$): δ 13.05 (brs, 1H), 7.72 (d, J=2.7 Hz, 1H), 7.34 (dd, J=2.7 Hz, J=8.7 Hz, 1H), 7.06 (d, J=8.7 Hz, 1H), 5.41 (s, 2H), 4.19 (s, 3H). MS (m/z): 265 $(M+H)^+$.

The following intermediates were prepared according to the procedures described for the synthesis of I-4 using the appropriate reagents.

| Compound | Structure | Characterization Data |
|---|---|---|
| I-5 | 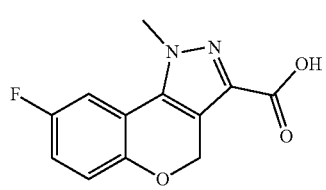 | $^1$H NMR (400 MHz, DMSO): δ 7.57 (dd, J = 3.0, 9.3 Hz, 1H), 7.15 (td, J = 3.0, 8.7 Hz, 1H), 7.06 (dd, J = 4.9, 9.0 Hz, 1H), 5.36 (s, 2H), 4.18 (s, 3H). |

-continued

| Compound | Structure | Characterization Data |
|---|---|---|
| I-6 | 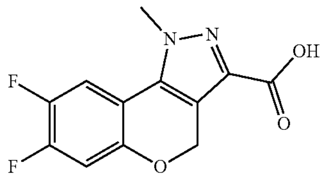 | $^1$H NMR (400 MHz, DMSO): δ 7.82 (dd, J = 8.8, 11.3 Hz, 1H), 7.23 (dd, J = 7.2, 11.8 Hz, 1H), 5.38 (s, 2H), 4.16 (s, 3H). |
| I-7 | 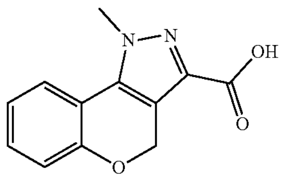 | Commercial |
| I-8 | 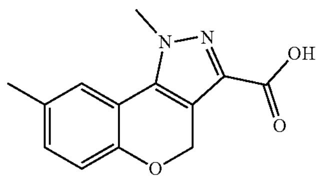 | MS (m/z): 245 (M + H)$^+$ |
| I-9 | 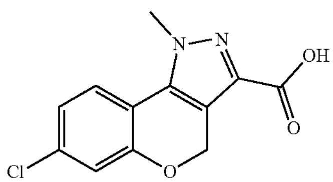 | $^1$H NMR (400 MHz, DMSO): δ 7.79-7.69 (m, 1H), 7.19-7.09 (m, 2H), 5.43 (s, 2H), 4.16 (s, 3H). |
| I-10 | 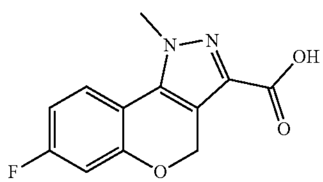 | $^1$H NMR (400 MHz, DMSO): δ 7.81-7.73 (m, 1H), 6.98-6.90 (m, 2H), 5.42 (s, 2H), 4.16 (s, 3H). |
| I-11 | 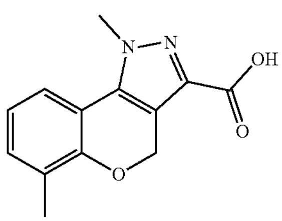 | MS (m/z): 245 (M + H)$^+$ |
| I-12 | 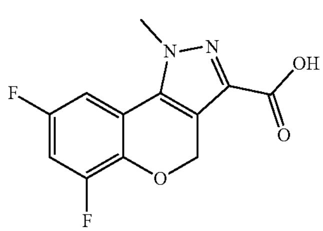 | $^1$H NMR (400 MHz, DMSO): δ 7.47 (ddd, J = 9.1, 2.9, 1.7 Hz, 1H), 7.38 (ddd, J = 11.0, 9.0, 2.9 Hz, 1H), 5.46 (s, 2H), 4.19 (s, 3H). |
| I-13 | 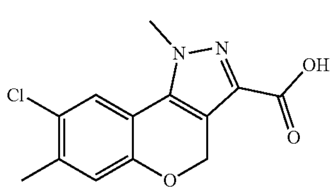 | $^1$H NMR (400 MHz, DMSO): δ 7.69 (s, 1H), 7.06 (d, J = 0.4 Hz, 1H), 5.38 (s, 2H), 4.17 (s, 3H), 2.30 (s, 3H). |

-continued

| Compound | Structure | Characterization Data |
|---|---|---|
| I-14 | 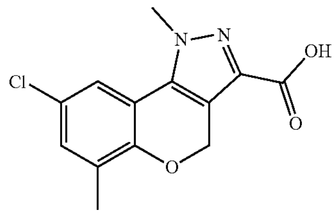 | $^1$H NMR (400 MHz, DMSO): δ 7.51 (d, J = 2.4, 1H), 7.23 (d, J = 2.1 Hz, 1H), 5.40 (s, 2H), 4.10 (s, 3H), 2.18 (s, 3H). |
| I-15 | 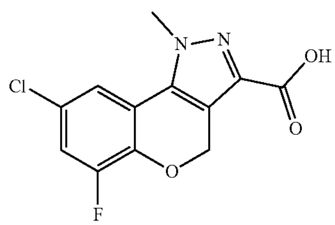 | $^1$H NMR (400 MHz, DMSO): δ 7.53-7.50 (m, 1H), 7.44 (dd, J = 2.3, 10.6 Hz, 1H), 5.47 (s, 2H), 4.10 (s, 3H). |

Methyl 4-fluoro-3-(2-((3-fluorobenzyl)amino)acetamido)benzoate (I-16)

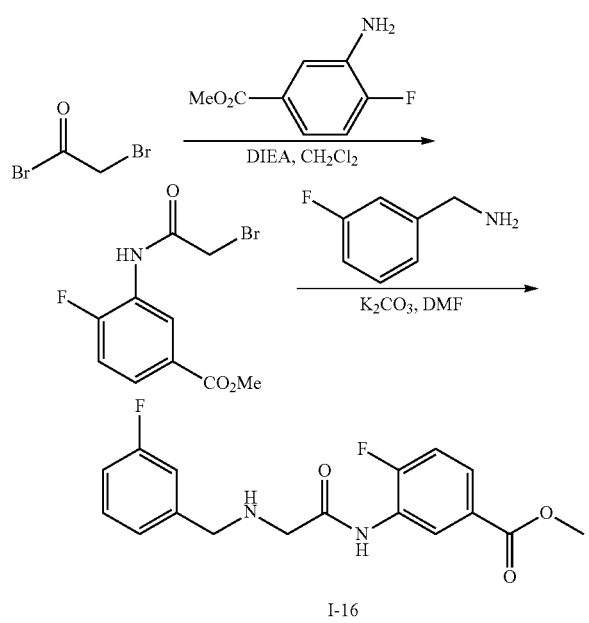

Bromoacetyl bromide (1.1 mL, 12.5 mmol) was added dropwise to a mixture of the methyl 3-amino-4-fluorobenzoate (10.9 mmol) and diisopropylethylamine (2.8 mL, 16.4 mmol) in dichloromethane at 0° C. After stirring for 30 mins at 0° C., the reaction mixture was diluted with dichloromethane and water. The layers were separated and the aqueous phase was washed with dichloromethane (2×). the combined organic layers were dried over MgSO$_4$ and concentrated (aspirator) to give a dark brown liquid. LCMS showed that the amide was the major component and the aniline was a minor component. The mixture was dissolved in DMF (30 mL) and potassium carbonate (12.3 mmol) was added. To the mixture was added 3-fluorobenzylamine (10.9 mmol) and the reaction stirred at room temperature for 16 hrs. The reaction was diluted with water (300 mL) and the aqueous solution was extracted with ethyl acetate (3×). The combined organic layers were washed with water, brine, and were dried over MgSO$_4$. The mixture was filtered and concentrated and the crude residue was purified by flash chromatography (silica gel, 0-60% ethyl acetate/hexanes) to give I-16. $^1$H NMR (400 MHz, d$_4$-MeOH): δ 8.80 (dd, J=8.0, 4.0 Hz, 1H), 7.89-7.85 (m, 1H), 7.56-7.51 (m, 1H), 7.38-7.29 (m, 3H), 7.25 (app dt, J=8.3, 6.0 Hz, 1H), 4.35 (s, 2H), 4.09 (s, 2H), 3.91 (s, 3H).

The following intermediates were prepared according to the procedures described for the synthesis of I-16 using the appropriate reagents.

| Compound | Structure | Characterization Data |
|---|---|---|
| I-17 | 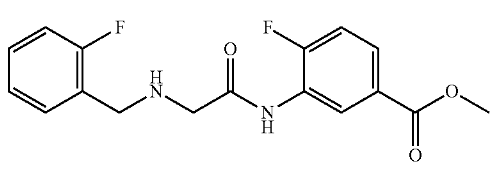 | $^1$H NMR (400 MHz, CDCl$_3$): δ 9.70 (br s, 1H), 9.02 (dd, J = 2.2, 7.6 Hz, 1H), 7.80 (ddd, J = 2.2, 5.1, 8.6 Hz, 1H), 7.34-7.26 (m, 2H), 7.19-7.03 (m, 3H), 3.93-3.88 (m, 5H), 3.47 (s, 2H). |

| Compound | Structure | Characterization Data |
|---|---|---|
| I-18 | 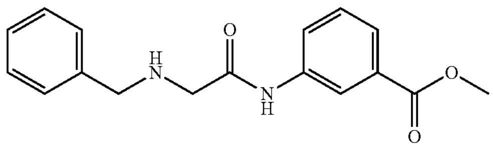 | $^1$H NMR (400 MHz, CDCl$_3$): δ 9.41 (s, 1H), 8.05 (t, J = 1.9 Hz, 1H), 8.00 (ddd, J = 1.0, 2.2, 8.1 Hz 1H), 7.82-7.78 (m, 1H), 7.46-7.30 (m, 7H), 3.95 (s, 3H), 3.89 (s, 2H), 3.47 (s, 2H). MS (m/z): 299.1 (M + H)$^+$ |
| I-19 | 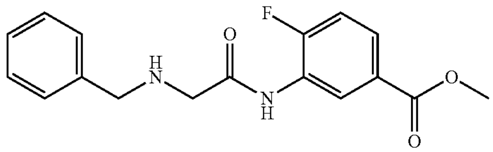 | MS (m/z): 317.1 (M + H)$^+$ |
| I-20 | 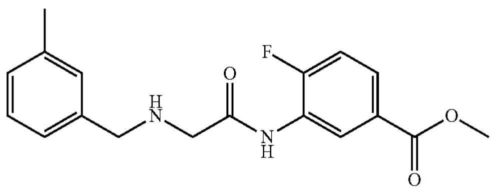 | MS (m/z): 331.1 (M + H)$^+$ |

2-(8-chloro-N-(2-fluorobenzyl)-1-methyl-1,4-dihydrochromeno[4,3-c]pyrazole-3-carboxamido)acetic acid (I-22)

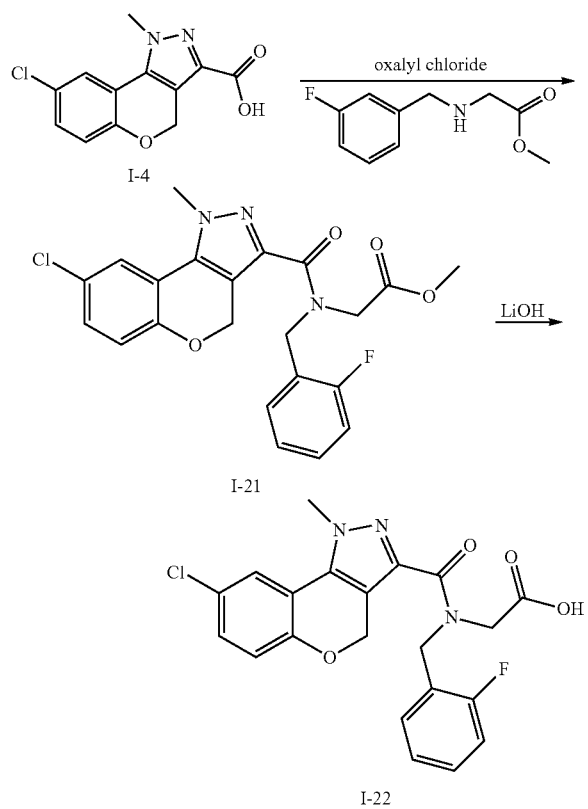

Step 1

To a suspension of the 8-chloro-1-methyl-1,4-dihydrochromeno[4,3-c]pyrazole-3-carboxylic acid (I-4) (1.9 mmol) in CH$_2$Cl$_2$ (10 mL) was added catalytic amount of DMF (25 uL) and dropwise oxalyl chloride (0.78 mL, 8.9 mmol) at 0° C. The resulting suspension was warmed up to room temperature and stirred for 1 hr. The solvent was removed under vacuum to dryness completely (need to remove oxalyl chloride completely). The obtained residue was dissolved with CH$_2$Cl$_2$ (10 mL) and then dropwise into a solution of methyl 2-((3-fluorobenzyl)amino)acetate (1.9 mmol) in CH$_2$Cl$_2$ (10 mL) in the presence of DIEA (0.56 mL, 3.8 mmol). The reaction mixture was stirred for 30 min at room temperature and then was charged 50 mL water. Organic layer was separated and aqueous layer was extracted with CH$_2$Cl$_2$ (50 mL). Combined organic layers were washed with H$_2$O and brine successively, dried over Na$_2$SO$_4$, filtered and concentrated to give the crude product which was purified by column chromatography (0-60% EtOAc in hexanes) to yield methyl 2-(8-chloro-N-(2-fluorobenzyl)-1-methyl-1,4-dihydrochromeno[4,3-c]pyrazole-3-carboxamido)acetate (I-21). $^1$H NMR (400 MHz, CDCl$_3$): δ 7.47-7.43 (m, 2H), 7.34-7.29 (m, 1H), 7.23-7.19 (m, 1H), 7.18-7.04 (m, 2H), 6.97 (dd, J=2.3, 8.7 Hz, 1H), 5.57-4.12 (m, 9H), 3.77-3.74 (m, 3H). Mixture of rotamers. MS (m/z): 444.1 (M+H)$^+$.

Step 2

Methyl 2-(8-chloro-N-(2-fluorobenzyl)-1-methyl-1,4-dihydrochromeno[4,3-c]pyrazole-3-carboxamido)acetate (I-21) (1.62 mmol) was dissolved in THF/MeOH/H$_2$O (3:2:1, 10 mL) and followed by addition of LiOH monohydrate (0.408 g, 9.72 mmol). The reaction mixture was stirred at room temperature for 1 hr and diluted with 10 ml of water and acidified to pH=2.0. Solid was collected and dried to yield 2-(8-chloro-N-(2-fluorobenzyl)-1-methyl-1,4-dihydrochromeno[4,3-c]pyrazole-3-carboxamido)acetic acid (I-22). $^1$H NMR (400 MHz, DMSO): δ 12.73 (s, 1H), 7.71 (t, J=2.6 Hz, 1H), 7.42-7.30 (m, 3H), 7.24-7.15 (m, 2H), 7.07-7.02 (m, 1H), 5.41-4.10 (m, 9H). Mixture of rotamers. MS (m/z) 430.0 (M+H)$^+$.

Methyl 4-((benzylamino)methyl)benzoate (I-23)

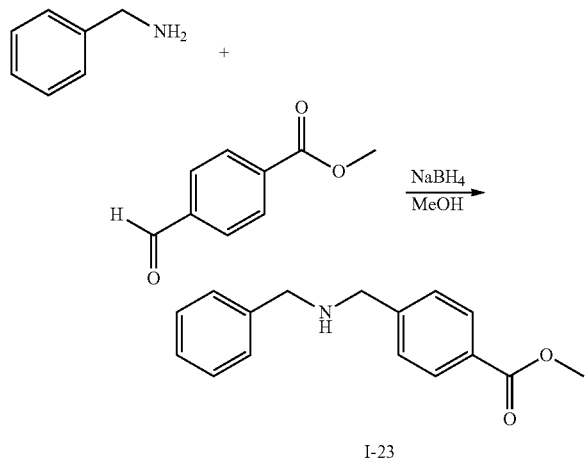

Benzyl amine (8.65 mL, 79 mmol) (Aldrich) and methyl 4-formylbenzoate (79 mmol) (Aldrich) were dissolved in methanol (Volume: 350 mL) and the mixture was stirred for 2 hr at room temperature, resulting in a white precipitate. The reaction mixture was cooled to 0° C. and sodium borohydride (158 mmol) (Aldrich) was added portion-wise over the course of 15 min. After stirring for 1 hr at 0° C. the mixture was allowed to warm to room temperature. After stirring for an additional 1 hr the mixture was cooled in an ice bath and the reaction was quenched slowly with water (15 mL, 833 mmol). The resulting mixture was allowed to stir for 15 min. After removal of solvent (aspirator) the mixture was dissolved in EtOAc and washed with $H_2O$. The aqueous phase was washed with EtOAc and the combined organic layers were dried ($MgSO_4$). The crude material was purified by chromatography (silica gel, loaded neat with DCM rinse, 0-40% DCM/(10% MeOH in DCM)) to give I-23. $^1$H NMR (400 MHz, DMSO): δ 9.17 (bs, 2H), 7.95-7.96 (m, 2H), 7.56-7.54 (m, 2H), 7.44-7.34 (m, 5H), 4.19 (s, 1H), 4.12 (s, 1H), 3.78 (s, 3H).

The following intermediates were prepared according to the procedures described for the synthesis of I-23 using the appropriate reagents.

| Compound | Structure | Characterization Data |
|---|---|---|
| I-24 | 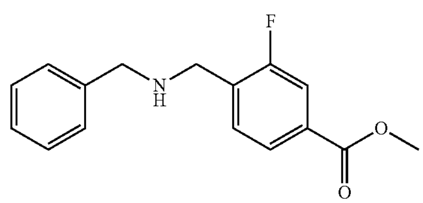 | MS (m/z): 274.2 (M + H)$^+$; r.t. = 1.281 |
| I-25 | 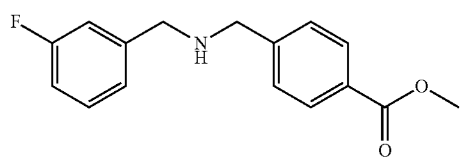 | $^1$H NMR (400 MHz, DMSO): δ 9.42 (br s, 1H, NH), 8.04 (d, J = 8.2 Hz, 2H), 7.78 (d, J = 8.2 Hz, 2H), 7.62 (dd, J = 8.0 Hz, 4.0, 1H), 7.44-7.32 (m, 3H), 4.36 (br s, 2H), 4.30 (s, 2H), 3.88 (s, 3H). MS (m/z): 274.1 (M + H)$^+$; r.t. = 1.38. |
| I-26 | 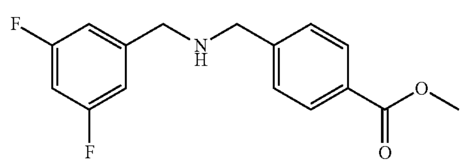 | MS (m/z): 292.1 (M + H)$^+$ |
| I-27 | 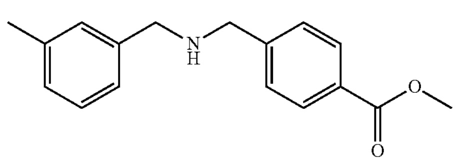 | MS (m/z): 270.1 (M + H)$^+$ |
| I-28 | 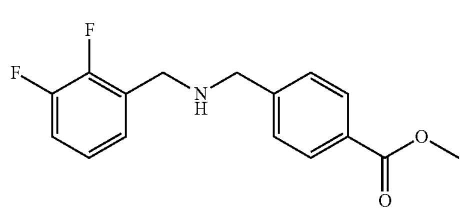 | MS (m/z): 292.1 (M + H)$^+$ |

-continued

| Compound | Structure | Characterization Data |
|---|---|---|
| I-29 | 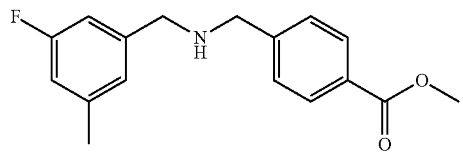 | MS (m/z): 288.1 (M + H)+ |
| I-30 | 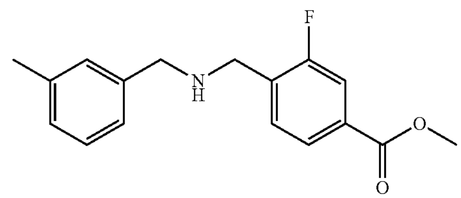 | MS (m/z): 288.1 (M + H)+ |
| I-31 | 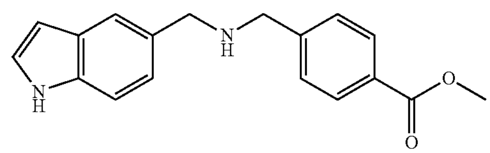 | MS (m/z): 295.2 (M + H)+; r.t. = 1.133 |
| I-32 | 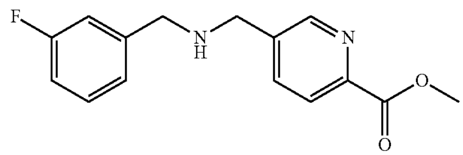 | MS (m/z): 275.2 (M + H)+; r.t. = 1.147 |
| I-33 | 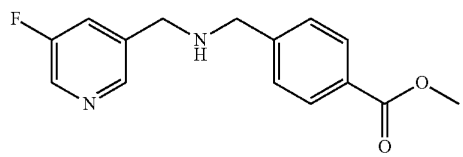 | MS (m/z): 275.1 (M + H)+; r.t. = 1.151 |
| I-34 | 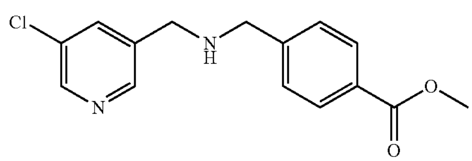 | MS (m/z): 291.1 (M + H)+; r.t. = 1.304 |
| I-35 | 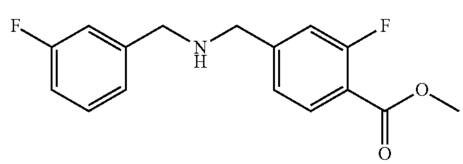 | MS (m/z): 292.2 (M + H)+; r.t. = 1.088 |
| I-36 | 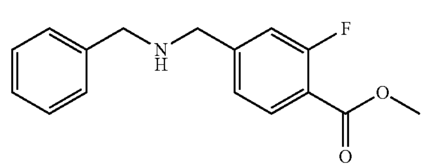 | MS (m/z): 274.2 (M + H)+; r.t. = 1.081 |
| I-37 | 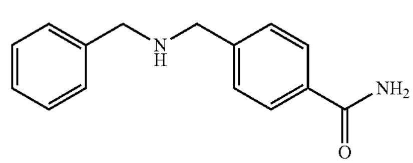 | $^1$H NMR (400 MHz, DMSO): δ 7.83 (s, 1H), 7.73 (d, J = 8.2 Hz, 2H), 7.32 (d, J = 8.2 Hz, 2H), 7.24 (m, 5H), 7.14 (m, 1H), 3.62 (d, J = 19.2 Hz, 4H), 3.25 (s, 1H). |

| Compound | Structure | Characterization Data |
|---|---|---|
| I-38 | 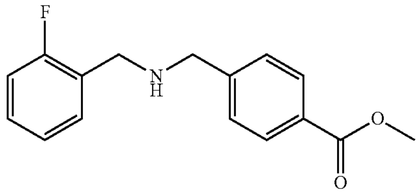 | $^1$H NMR (400 MHz, DMSO): δ 9.76 (br s, 1H, NH), 8.06 (d, J = 8.2 Hz, 2H), 7.76 (d, J = 8.2 Hz, 2H), 7.62 (t, J = 8.0 Hz, 1H), 7.50 (app q, J = 7.8 Hz, 1H), 7.34-7.28 (m, 2H), 4.34 (br s, 2H), 4.28 (s, 2H), 3.80 (s, 3H). MS (m/z): 274.1 (M + H)$^+$; r.t. = 0.239. |
| I-39 | 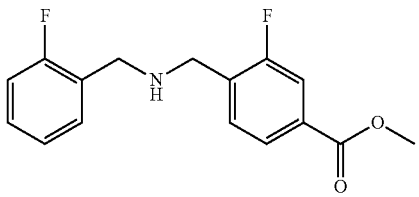 | $^1$H NMR (400 MHz, d$_4$-MeOH): δ 7.99 (d, J = 3.2 Hz, 1H), 7.89 (d, J = 8.0 Hz, 1H), 7.72 (t, J = 8.0 Hz, 1H), 7.63-7.56 (m, 2H), 7.28-7.20 (m, 2H), 4.45 (br s, 2H), 4.38 (s, 2H), 3.91 (s, 3H). MS (m/z): 292.1 (M + H)$^+$; r.t. = 1.42. |
| I-40 | 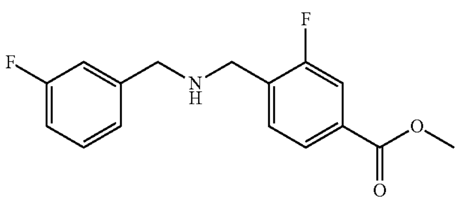 | $^1$H NMR (400 MHz, DMSO): δ 9.52 (s, 1H), 7.89 (d, J = 8.2 Hz, 2H), 7.80-7.64 (m, 2H), 7.28-7.19 (m, 2H), 7.20 (t, J = 7.7 Hz, 1H), 4.40 (br s, 4H), 3.91 (s, 3H). MS (m/z): 292.1 (M + H)$^+$; r.t. = 1.52. |
| I-41 | 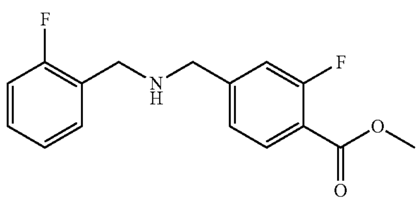 | $^1$H NMR (400 MHz, DMSO): δ 7.80 (d, J = 7.2 Hz, 1H), 7.80-7.55 (m, 5H), 7.33-7.26 (m, 2H), 4.20 (br s, 2H), 4.14 (s, 2H), 3.90 (s, 3H). MS (m/z): 292.1 (M + H)$^+$; r.t. = 1.22. |
| I-42 | 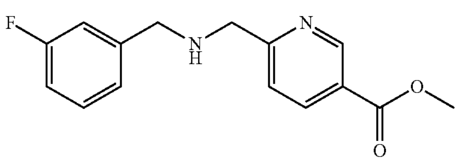 | $^1$H NMR (400 MHz, d$_4$-MeOH): δ 9.22 (d, J = 2.2 Hz, 1H), 8.34 (d, J = 8.2 Hz, 1H), 7.48-7.40 (m, 2H), 7.33-7.27 (m, 3H). 7.10 (t, J = 8.1 Hz, 1H), 4.40 (br s, 2H), 4.34 (s, 2H), 3.94 (s, 3H). MS (m/z): 275.1 (M + H)$^+$; r.t. = 1.02. |
| I-43 | 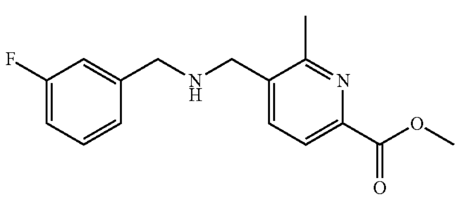 | $^1$H NMR (400 MHz, DMSO): δ 9.42 (s, 1H), 8.00 (app q, J = 8.2 Hz, 2H), 7.52 (q, J = 8.1 Hz, 1H), 7.30-7.26 (m, 2H), 7.15 (t, J = 7.5 Hz, 1H), 4.30 (br s, 4H), 3.87 (s, 3H), 2.52 (s, 3H). MS (m/z): 289.1 (M + H)$^+$; r.t. = 1.372. |

Methyl 3-((2-((tert-butoxycarbonyl)amino)ethyl)amino)-4-fluorobenzoate (I-44)

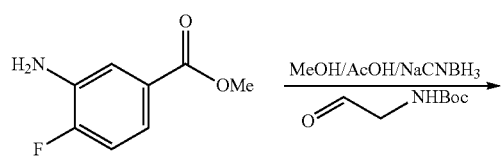

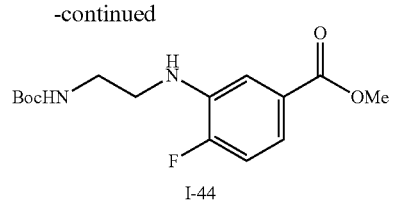

I-44

Methyl 3-amino-4-fluorobenzoate (8.4 mmol) and tert-butyl (2-oxoethyl)carbamate (12.6 mmol) were dissolved in MeOH (100 mL) and AcOH (10 mL). After stirring for 1 hr at room temperature the reaction mixture was treated with NaCNBH$_3$ (16.6 mmol) and stirred for 2 hrs. After removal of solvent (aspirator) the mixture was dissolved in EtOAc and washed with NaHCO$_3$ (sat., 1×). The aqueous phase was washed with EtOAc (1×) and the combined organic layers were dried (MgSO$_4$). The product (I-44) was taken on crude for the next step. $^1$H NMR (400 MHz, CDCl3): δ 7.40-7.38 (m, 2H), 7.02 (dd, J=8.8 Hz, 11.1, 1 H), 4.88 (s, 1H), 3.91 (s, 3H), 3.40-3.38 (m, 4H), 1.47 (s, 9H). MS (m/z): 313.1 (M+H)$^+$.

Methyl 3-((2-aminoethyl)amino)-4-fluorobenzoate (I-45)

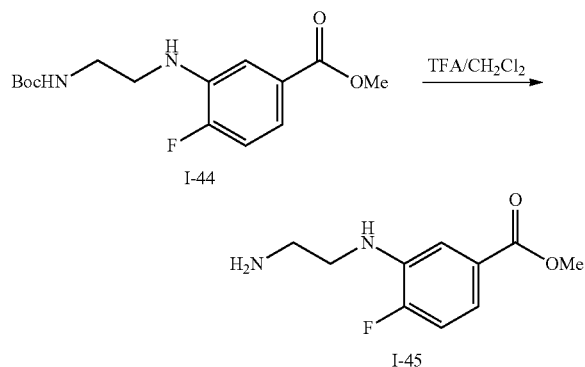

Methyl 3-((2-((tert-butoxycarbonyl)amino)ethyl)amino)-4-fluorobenzoate (1.57 g) was dissolved in dichloromethane (10 mL) and treated with TFA (10 mL). The reaction stirred at room temperature for 1 hr. The solvent was azeotropically removed with dichloromethane and the cream colored solid (I-45) was used directly for the next step. $^1$H NMR (400 MHz, DMSO): δ 7.78 (s, 3H), 7.24 (m, 3H), 5.93 (s, 1H), 3.83 (s, 3H), 3.50-3.22 (m, 5H), 3.04 (s, 2H). MS (m/z): 213.1 (M+H)$^+$.

Methyl 4-fluoro-3-((2-((3-fluorobenzyl)amino)ethyl)amino)benzoate (I-46)

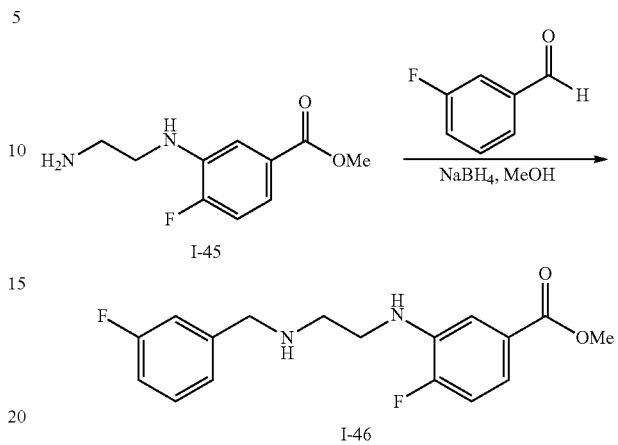

A mixture of methyl 3-((2-aminoethyl)amino)-4-fluorobenzoate (5.0 mmol), sodium bicarbonate (5.0 mmol) and methanol (30 mL) stirred at room temperature for 30 mins. 3-fluoro-benzadehyde (5.0 mmol) was added and stirred at room temperature for 2 hrs. Sodium Borohydride (7.4 mmol) was added in portions. The reaction stirred at room temperature for 30 mins. LCMS showed that the reaction was complete. The solvent was removed and the residue was diluted with ethyl acetate (50 mL). The organic solution was washed with water and brine, dried over MgSO$_4$, and concentrated. The crude material was purified by flash chromatography (silica 5-40% ethyl acetate/hexanes) to give (I-46) as a white solid. $^1$H NMR (400 MHz, DMSO): δ 7.33 (td, J=6.3, 8.1 Hz, 1H), 7.25 (dd, J=1.9, 8.6 Hz, 1H), 7.23-7.10 (m, 4H), 7.08-6.98 (m, 1H), 5.67 (s, 1H), 3.82 (s, 3H), 3.74 (s, 2H), 3.20 (q, J=6.2 Hz, 2H), 2.72 (t, J=6.3 Hz, 2H). MS (m/z): 321.1 (M+H)$^+$.

The following intermediates were prepared according to the procedures described for the synthesis of I-46 using the appropriate reagents.

| Compound | Structure | Characterization Data |
|---|---|---|
| I-47 | ![structure] | MS (m/z): 317.1 (M + H)$^+$; r.t. = 1.274 |
| I-48 | ![structure] | $^1$H NMR (400 MHz, CDCl$_3$): δ 7.38-7.31 (m, 3H), 7.27-7.21 (m, 1H), 7.11 (1H, td, J = 1.1, 7.4 Hz, 1H), 7.07-6.96 (m, 2H), 4.50 (m, 1H), 3.91-3.85 (m, 5H), 3.34-3.24 (m, 2H), 2.98-2.90 (m, 2H). |
| I-49 | ![structure] | $^1$H NMR (400 MHz, DMSO): δ 8.88 (br s, 1H), 7.78-7.66 (m, 3H), 7.60 (d, J = 8.0 Hz, 2H), 7.34-7.22 (m, 3H), 5.02 (br s, 1H), 4.32 (t, J = 4.9 Hz, 2H), 3.91 (s, 3H), 3.63 (t, J = 4.9 Hz, 2H), 3.12 (br s, 2H). MS (m/z): 303.1 (M + H)$^+$; r. t. = 1.71. |

Methyl 4-(2-aminoethoxy)-3-fluorobenzoate (I-51)

Methyl 4-(2-(benzylamino)ethoxy)-3-fluorobenzoate (I-52)

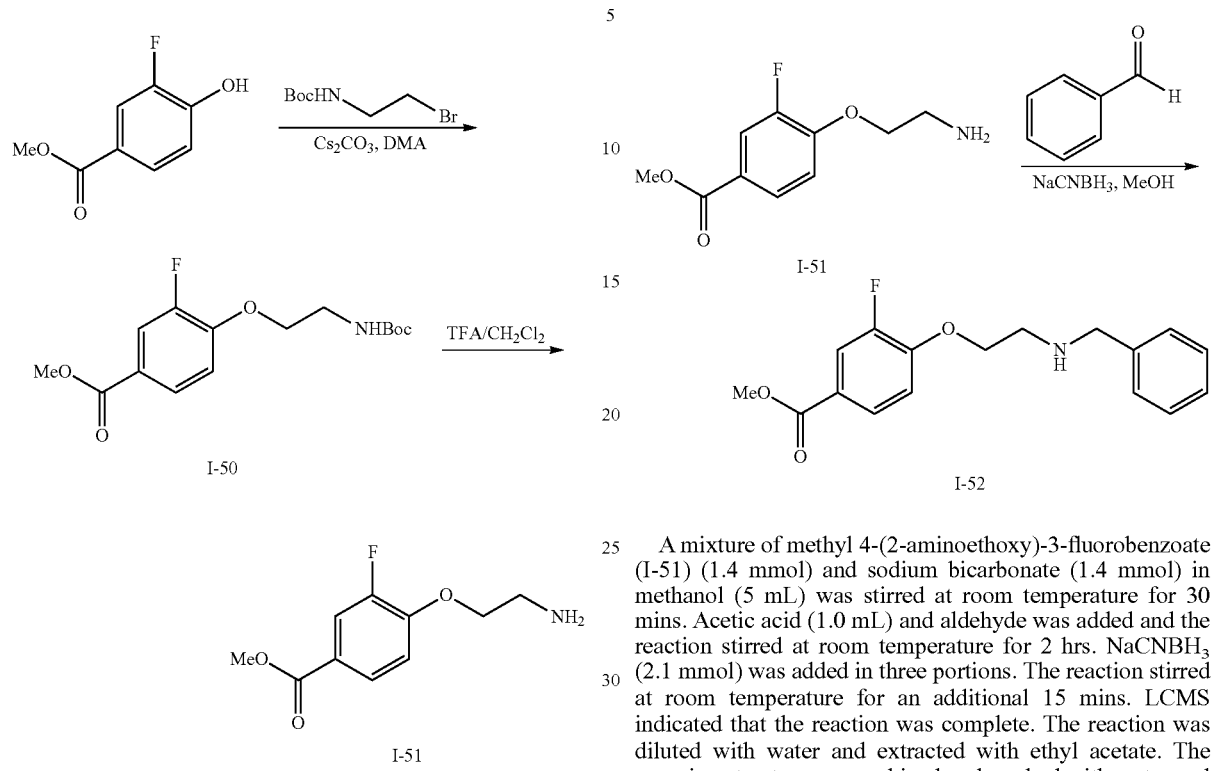

To a mixture of methyl 3-fluoro-4-hydroxybenzoate (17 mmol), cesium carbonate (25 mmol) and DMF (30 mL) was added tert-butyl (2-bromoethyl)carbamate (20 mmol). The resulting suspension stirred at 60° C. for 4 hrs. The reaction was diluted with water (100 mL) and the resulting precipitate was collected by vacuum filtration. The filter cake was washed with water and dried under vacuum to give pure I-50. I-50 (17 mmol) was taken up in dichloromethane (12 mL) and treated with TFA (5 mL). The reaction stirred at room temperature for 30 mins. LCMS showed that the reaction was complete. The reaction was concentrated to dryness. The crude material was taken up in dichloromethane and stirred with solid sodium bicarbonate for 8 hrs to remove any residual TFA. The mixture was filtered and the filtrate was dried to give I-51 as a clear oil. $^1$H NMR (400 MHz, DMSO): δ 7.79 (d, J=9.4 Hz, 1H), 7.73 (dd, J=1.6, 11.8 Hz, 1H), 7.33 (t, J=8.6 Hz, 1H), 4.22 (t, J=5.4 Hz, 2H), 3.84 (s, 3H), 3.12 (t, J=5.4 Hz, 2H).

A mixture of methyl 4-(2-aminoethoxy)-3-fluorobenzoate (I-51) (1.4 mmol) and sodium bicarbonate (1.4 mmol) in methanol (5 mL) was stirred at room temperature for 30 mins. Acetic acid (1.0 mL) and aldehyde was added and the reaction stirred at room temperature for 2 hrs. NaCNBH$_3$ (2.1 mmol) was added in three portions. The reaction stirred at room temperature for an additional 15 mins. LCMS indicated that the reaction was complete. The reaction was diluted with water and extracted with ethyl acetate. The organic extracts were combined and washed with water and brine, dried over MgSO$_4$ and concentrated to give I-52. No further purification was necessary. MS (m/z): 304.1 (M+H)$^+$.

The following intermediate was prepared according to the procedure described for the synthesis of I-52 using the appropriate reagents.

| Compound | Structure | Characterization Data |
|---|---|---|
| I-53 | ![structure] | MS (m/z): 322.1 (M+H)$^+$; r.t. = 1.31 |

Methyl 4-(2-((tert-butoxycarbonyl)(2-fluorobenzyl)amino)ethoxy)-3-fluorobenzoate (I-55)

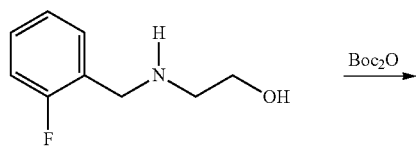

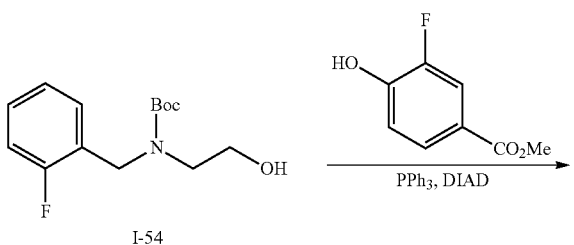

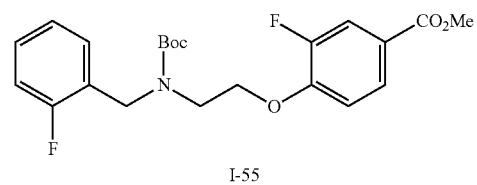

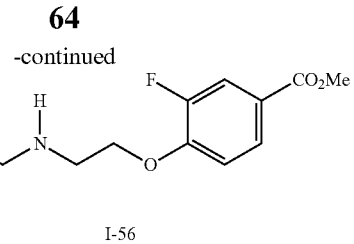

Trifluoroacetic acid (2 mL) was added to a solution of I-55 (0.9 mmol) in dichloromethane (8 mL) at room temperature. After stirring for 1 hr the reaction mixture was concentrated (aspirator), diluted with MeOH and neutralized by passing the mixture through SPE-carbonate polymer bound cartridges (6 cartridges, 100 mg units each). The solvent was removed (aspirator) to give I-56. MS (m/z): 322.1 (M+H)+; r.t.=0.981.

Di-tert-butyl dicarbonate (3.0 mmol) was added to a mixture of 2-((2-fluorobenzyl)amino)ethanol (3.0 mmol) in dichloromethane (25 mL) and NaOH (1 M in H₂O, 9.6 mL, 9.6 mmol) at room temperature. The reaction mixture was stirred for 16 hrs and then diluted with H₂O (50 mL) and dichloromethane (25 mL). Upon separation of the layers, the aqueous phase was washed with dichloromethane (2×, 50 mL) and the combined organic extracts were washed with H₂O (1×50 mL), dried (Na₂SO₄) and concentrated (aspirator). The crude mixture was purified by chromatography (silica gel, 0-60% EtOAc/hexanes) to give I-54 as an oil. Diisopropyl azodicarboxylate (0.41 mL, 2.1 mmol) was added dropwise to a mixture of I-54 (1.0 mmol), methyl 3-fluoro-4-hydroxybenzoate (2.0 mmol) and PPh₃ (2.0 mmol) in THF (15 mL) at 0° C. After stirring for 10 mins, the reaction mixture was allowed to warm to room temperature on its own accord and stirred for an additional 4 hrs. The reaction mixture was diluted with Et₂O (50 mL) and H₂O (50 mL) and the layers were separated. The aqueous phase was washed with Et₂O (2×, 50 mL) and the combined organic extracts were dried (MgSO₄) and then concentrated (aspirator). The crude mixture was purified by chromatography (silica gel, 0-25% EtOAc/hexanes) to give an inseparable mixture of I-55 and methyl 3-fluoro-4-hydroxybenzoate. The mixture was concentrated, diluted with EtOAc (100 mL) and then washed with NaOH (×2, 1 M, 25 mL) to remove methyl 3-fluoro-4-hydroxybenzoate from the mixture. The organic phase was dried (MgSO₄) and concentrated (aspirator) to give I-55. ¹H NMR (400 MHz, CDCl₃): δ 7.69-7.55 (m, 2H), 7.23-7.06 (m, 2H), 7.00-6.86 (m, 2H), 6.86-6.71 (m, 1H), 4.56-4.45 (m, 2H), 4.14-3.99 (m, 2H), 3.75 (s, 3H), 3.59-3.44 (m, 2H), 1.40-1.25 (m, 9H).

Methyl 3-fluoro-4-(2-((2-fluorobenzyl)amino)ethoxy)benzoate (I-56)

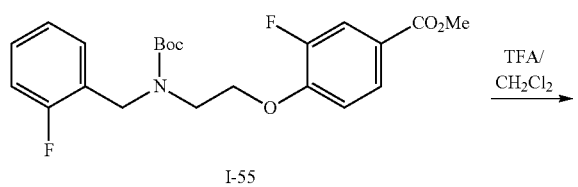

Methyl 3-(2-aminoacetamido)-4-fluorobenzoate (I-58)

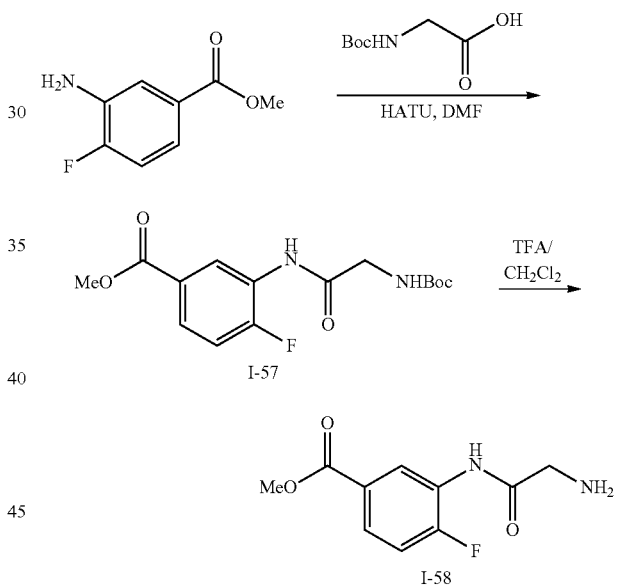

HATU (8.2 mmol) was added to a mixture of N-Boc glycine (6.8 mmol), methyl 3-amino-4-fluorobenzoate (6.2 mmol), diisopropylethylamine (3.6 mL, 20.5 mmol) and DMF (15 mL). The reaction was stirred at room temperature for 1 hr. LCMS indicated that the reaction was complete. The reaction was diluted with water and extracted with ethyl acetate. The organic extracts were dried over MgSO₄ and concentrated. No further purification was necessary. The crude amide (I-57) (9.2 mmol) was dissolved in dichloromethane (15 mL) and treated with trifluoroacetic acid (8 mL). The reaction stirred at room temperature for 1 hr. LCMS indicated that the reaction was complete. The reaction was concentrated to dryness and the crude material was purified by preparative HPLC to give I-58. ¹H NMR (400 MHz, d₄-MeOH) δ 8.71 (br d, J=8.0 Hz, 1H), 7.79-7.75 (m, 1H), 7.21 (dd, J=10.3, 8.2 Hz, 1H), 3.87 (s, 2H), 3.82 (s, 3H). MS (m/z): 227.1 (M+H)+.

Methyl 4-fluoro-3-(2-((3-methylbenzyl)amino)acetamido)benzoate (I-59)

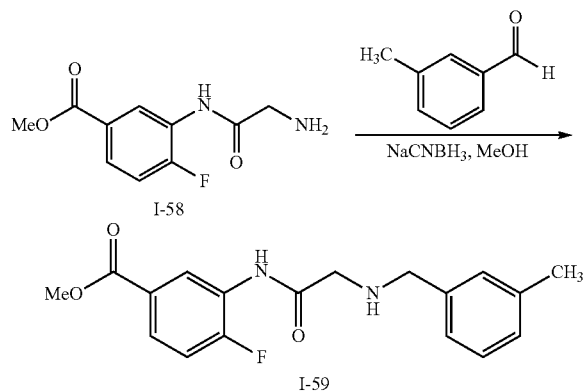

A mixture of methyl 3-(2-aminoacetamido)-4-fluorobenzoate (I-58) (1.5 mmol) and sodium bicarbonate (1.5 mmol) in methanol (5 mL) was stirred at room temperature for 30 mins. Acetic acid (1.0 mL) and 3-methylbenzaldehyde were added and the reaction stirred at room temperature for 2 hrs. NaCNBH₃ (2.2 mmol) was added in three portions. The reaction stirred at room temperature for an additional 15 mins. LCMS indicated that the reaction was complete. The reaction was concentrated and purified by preparative HPLC to give I-59. MS (m/z): 331.1 (M+H)⁺; r.t.=1.51.

The following intermediate was prepared according to the procedure described for the synthesis of I-59 using the appropriate reagents.

| Compound | Structure | Characterization Data |
|---|---|---|
| I-59A | 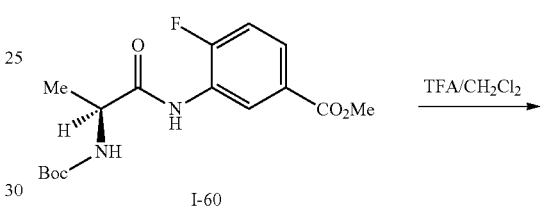 | $^1$H NMR (400 MHz, CDCl$_3$): δ 9.00 (s, 1H), 8.11 (s, 1H), 8.00 (d, J = 8.1, 1H), 7.81 (d, J = 7.8, 1H), 7.43 (t, J = 7.9, 1H), 7.31 (m, 2H), 7.19-7.12 (m, 3H), 4.41-4.38 (m, 2H), 3.92 (s, 3H), 3.47 (s, 2H). |

(S)-Methyl 3-(2-((tert-butoxycarbonyl)amino)propanamido)-4-fluorobenzoate (I-60)

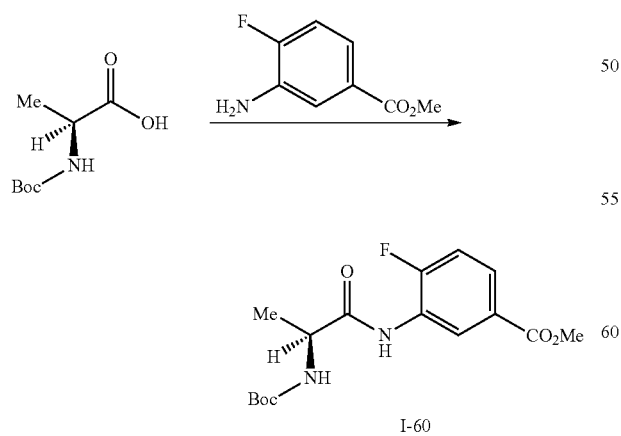

Iso-Butyl chloroformate (5.3 mmol) was added to a solution of N-(tert-butoxycarbonyl)-L-alanine (5.0 mmol) and N-methylmorpholine (5.3 mmol) in THF (25 mL) at 0° C. After stirring for min, methyl 3-amino-4-fluorobenzoate (5.3 mmol) was added as a solid and the resulting mixture was stirred for 16 hrs at room temperature. After removal of the solvent (aspirator), the residue was dissolved in EtOAc (50 mL) and washed with NaHCO₃ (sat., 50 mL), HCl (0.1 M in H₂O, 50 mL) and brine (50 mL). The organics was dried (MgSO₄) and concentrated (aspirator). The crude material was purified by chromatography (silica gel, 0-40% EtOAc/hexanes) to give 1-60. $^1$H NMR (600 MHz, CDCl$_3$): δ 8.96 (dd, J=2.0, 7.6 Hz, 1H), 8.67 (br s, 1H), 7.83-7.75 (m, 1H), 7.17-7.11 (m, 1H), 4.94 (br s, 1H), 4.36 (br s, 1H), 3.90 (s, 3H), 1.50-1.43 (m, 12H).

(S)-Methyl 4-fluoro-3-(2-((2-fluorobenzyl)amino)propanamido)benzoate (I-62)

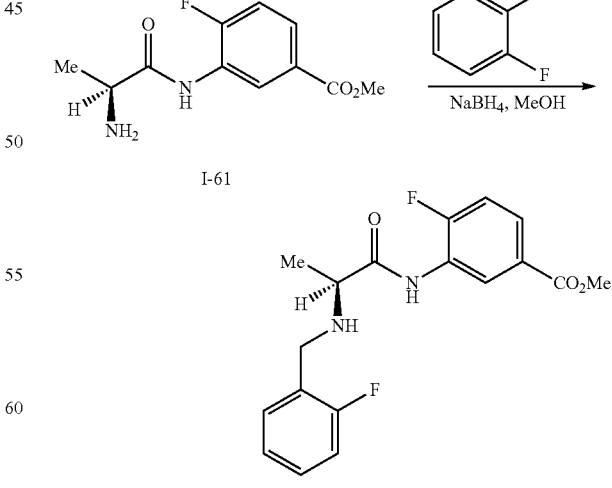

Trifluoroacetic acid (1.0 mL) was added to a solution of I-60 (0.9 mmol) in dichloromethane (5 mL) at room temperature. After stirring for 30 mins, the solvent was removed (aspirator) and the residue was dissolved in dichloromethane (25 mL) and washed with NaHCO₃ (sat., 25 mL). The aqueous phase was washed with dichloromethane (2×, 25 mL) and the combined organic extracts were dried (Na₂SO₄) and concentrated (aspirator) to give 190 mg of I-61 as an oil. 2-Fluorobenzaldehyde (94 mg, 0.8 mmol) was added to a solution of 1-61 (0.8 mmol) in MeOH (9 mL) and AcOH (1 mL). After stirring for 1 hr at room temperature, the reaction mixture was treated with NaBH₄ (1.6 mmol) and stirred for 30 mins. After removal of solvent (aspirator), the mixture was dissolved in EtOAc (25 mL) and washed with NaHCO₃ (sat., 25 mL). The aqueous phase was washed with EtOAc (2×, 25 mL) and the combined organic extracts were dried (MgSO₄) and concentrated (aspirator). The material was purified by chromatography (silica gel, 0-60% EtOAc/hexanes) to give I-62. MS (m/z): 349.2 (M+H)⁺; r.t.=1.097.

1-methyl-4,5-dihydro-1H-benzo[2,3]oxepino[4,5-c]pyrazole-3-carboxylic acid (I-64)

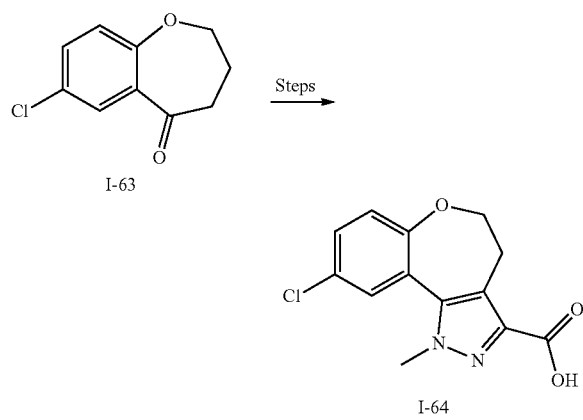

Intermediate 1-64 was prepared according to the procedure described for the preparation of intermediate 1-4, starting with 3,4-dihydrobenzo[b]oxepin-5(2H)-one (I-63, commercially available). ¹H NMR (400 MHz, DMSO): ¹H NMR (400 MHz, DMSO): δ 12.77 (s, 1H), 7.80 (d, J=2.6 Hz, 1H), 7.44 (dd, J=8.6, 2.6 Hz, 1H), 7.22 (d, J=8.7 Hz, 1H), 4.33 (t, J=6.3 Hz, 2H), 4.05 (s, 3H), 3.12 (t, J=6.3 Hz, 2H). MS (m/z): 279.0/281.0 (M+H)⁺ (chlorine isotope pattern); r.t.=1.302.

2-(8-chloro-N-(2-fluorobenzyl)-1-methyl-1,4-dihydrochromeno[4,3-c]pyrazole-3-carboxamido)acetic acid (I-66)

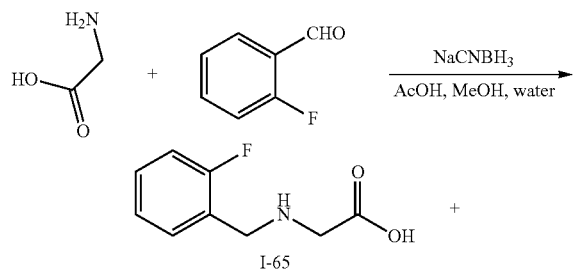

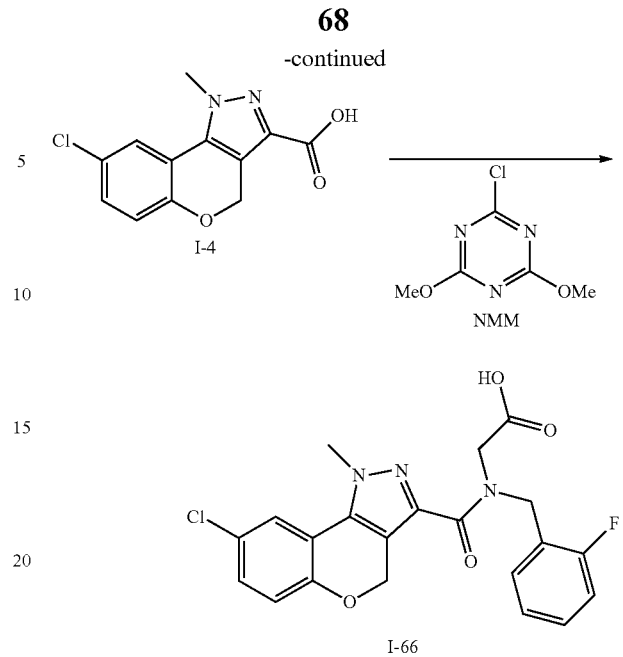

Step 1

To a 20 mL reaction vessel was added reagents in the following order: glycine (10 mmol), AcOH (2 mL), MeOH (12 mL), water (2 mL). This was stirred until complete dissolution. Next was added 2-fluorobenzaldehyde (5.0 mmol). After 20 mins, sodium cyanoborohydride (3.0 mmol) was added. The reaction was stirred 10 mins, at which time an additional portion of sodium cyanoborohydride was added (3.0 mmol). The reaction was stirred for 10 mins, filtered, and then purified by acetic acid modified (0.05%) reverse phase-chromatography (10 to 50%, water-ACN) and subsequently recrystalized by MeOH/water 1:5 (2 mL) to furnish 2-((2-fluorobenzyl)amino)acetic acid (I-65) as a white powder. ¹H NMR (400 MHz, DMSO): δ 7.61 (t, J=8.1 Hz, 1H), 7.54 (app q, J=7.8 Hz, 1H), 7.36-7.28 (m, 2H), 4.24 (s, 2H), 3.92 (s, 2H). MS (m/z): 184.1 (M+H)⁺.

Step 2

To a 100 mL reaction vessel was added reagents in the following order: 8-chloro-1-methyl-1,4-dihydrochromeno[4,3-c]pyrazole-3-carboxylic acid (I-4) (1.5 mmol), THF (15 mL), and N-methyl morpholine (NMM) (1 mL, 6.9 mmol). This was stirred until complete dissolution. Next was added 2-chloro-4,6-dimethoxy-1,3,5-triazine (1.6 mmol) and this solution was stirred for 40 mins at 50° C. until a white precipitate fully formed. The precipitate was physically agitated with rapid stirring to ensure all solids were well mixed. Next was added 2-((2-fluorobenzyl)amino)acetic acid (I-65) (2.3 mmol) and the reaction was stirred for 30 mins at 50° C. and then diluted with 5 mL of MeOH and then purified by acetic acid modified (0.05%) reverse phase chromatography (30 to 80%, water/ACN) and subsequently recrystallized by MeOH/water 1:1 (20 mL) to furnish a white powder (I-66). ¹H NMR (400 MHz, CDCl₃): δ 10.05 (br s, 1H), 7.39 (app t, J=7.8 Hz, 2H), 7.23-7.20 (m, 1H), 7.14 (d, J=8.3 Hz, 1H), 7.09 (t, J=8.2 Hz, 1H), 7.02 (t, J=8.2 Hz, 1H), 6.84 (d, J=8.3 Hz, 2H), 5.44-5.40 (m, 2H), 4.82 (br s, 1H), 4.59 (br s, 1H), 4.05-4.02 (m, 1H), 4.01 (s, 3H). MS (m/z): 430.1/432.1 (M+H)⁺ (chlorine isotope pattern).

2-(8-chloro-N-(2-fluorobenzyl)-1-methyl-1,4-dihydrochromeno[4,3-c]pyrazole-3-carboxamido)acetic acid (I-68)

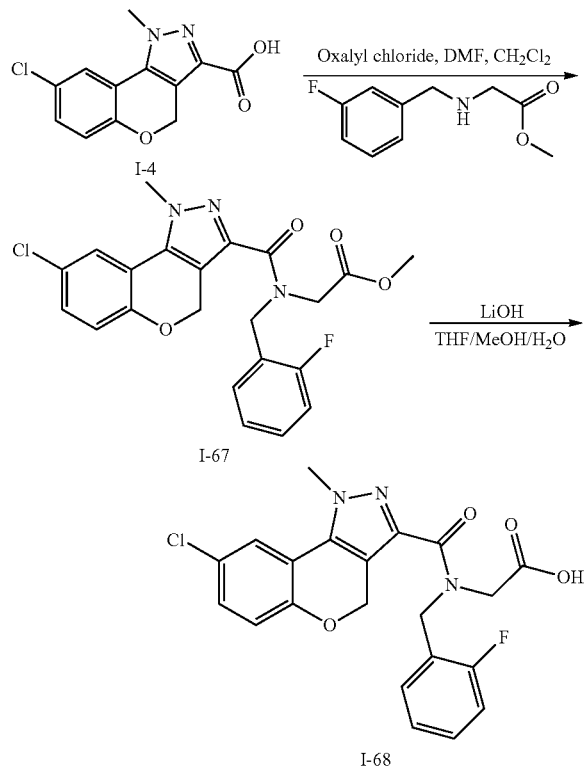

Step 1

To a suspension of the 8-chloro-1-methyl-1,4-dihydrochromeno[4,3-c]pyrazole-3-carboxylic acid (I-4) (1.9 mmol) in CH$_2$Cl$_2$ (10 mL) was added catalytic amount of DMF (25 uL) and dropwise oxalyl chloride (0.78 mL, 8.9 mmol) at 0° C. The resulting suspension was warmed up to room temperature and stirred for 1 hr. The solvent was removed under vacuum to dryness completely (need to remove oxalyl chloride completely). The obtained residue was dissolved with CH$_2$Cl$_2$ (10 mL) and then dropwise into a solution of methyl 2-((3-fluorobenzyl)amino)acetate (1.9 mmol) in CH$_2$Cl$_2$ (10 mL) in the presence of DIEA (0.56 mL, 3.8 mmol). The reaction mixture was stirred for 30 min at room temperature and then was charged 50 mL water. Organic layer was separated and aqueous layer was extracted with CH$_2$Cl$_2$ (50 mL). Combined organic layers were washed with H$_2$O and brine successively, dried over Na$_2$SO$_4$, filtered and concentrated to give the crude product, which was purified by column chromatography (0-60% EtOAc in hexanes) to give methyl 2-(8-chloro-N-(2-fluorobenzyl)-1-methyl-1,4-dihydrochromeno[4,3-c]pyrazole-3-carboxamido)acetate (I-67). $^1$H NMR (400 MHz, CDCl$_3$): δ7.47-7.43 (m, 2H), 7.34-7.29 (m, 1H), 7.23-7.19 (m, 1H), 7.18-7.04 (m, 2H), 6.97 (dd, J=2.3, 8.7 Hz, 1H), 5.57-4.12 (m, 9H), 3.77-3.74 (m, 3H). Mixture of rotamers. MS (m/z): 444.1 (M+H)$^+$.

Step 2

Methyl 2-(8-chloro-N-(2-fluorobenzyl)-1-methyl-1,4-dihydrochromeno[4,3-c]pyrazole-3-carboxamido)acetate (I-67) (1.6 mmol) was dissolved in THF/MeOH/H$_2$O (3:2:1, 10 mL) and followed by addition of LiOH monohydrate (0.408 g, 9.72 mmol). The reaction mixture was stirred at room temperature for 1 hr and diluted with 10 ml of water and acidified to pH=2.0. Solid was collected and dried to yield 2-(8-chloro-N-(2-fluorobenzyl)-1-methyl-1,4-dihydrochromeno[4,3-c]pyrazole-3-carboxamido)acetic acid (I-68). $^1$H NMR (400 MHz, DMSO): δ 12.73 (s, 1H), 7.71 (t, J=2.6 Hz, 1H), 7.42-7.30 (m, 3H), 7.24-7.15 (m, 2H), 7.07-7.02 (m, 1H), 5.41-4.10 (m, 9H). Mixture of rotamers. MS (m/z): 430.0 (M+H)$^+$.

Methyl 3-(2-((cyclopentylmethyl)amino)acetamido)-4-fluorobenzoate (I-70)

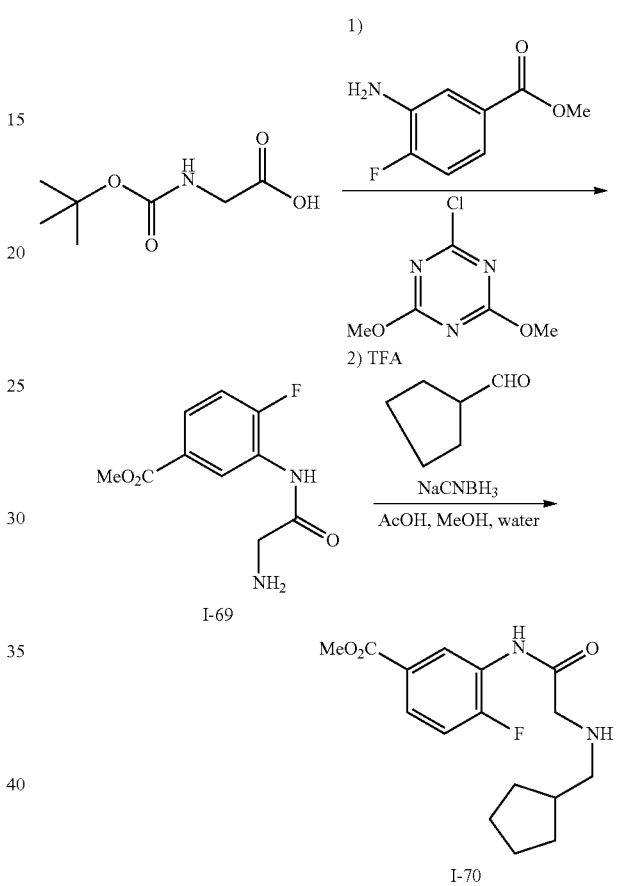

Step 1

To a 40 mL reaction vessel was added reagents in the following order: N-(tert-butoxycarbonyl)glycine (1.0 mmol), THF (4.0 mL), N-methyl morpholine (c.a. 0.2 mL, 2.0 mmol). This was stirred until complete dissolution. Next was added 2-chloro-4,6-dimethoxy-1,3,5-triazine (1.0 mmol) and this solution was stirred for 20 mins at 50° C. until a white precipitate fully formed. The precipitate was physically agitated to ensure all solids were well stirred. Next was added methyl 3-amino-4-fluorobenzoate (1.3 mmol) and the reaction was stirred for 30 mins at 50° C. and then at room temperature for 2 hrs, then diluted with 5 mL of MeOH and then purified by being poured into water (rapidly stirred, 25 mL). A white solid was collected and treated with dichloromethane (5 mL) and TFA (5 mL), and heated to 34° C. for about 1 hr until removal of the Boc group was complete (by LCMS monitoring). The material was concentrated to dryness and subjected to reverse-phase chromatography (10 to 40% water/ACN) to give I-69. The desired fractions were then passed through polymer bound ion-exchange free base cartridges to removal any residual TFA (using product StratoSpheres, SPE PL HCO3 MP SPE 0.9 mmol nominal load×2 units). Mobilizing eluent was MeOH (10 mL total flush volume). $^1$H NMR (400 MHz, d₄-MeOH): δ 8.71 (br d, J=8.0 Hz, 1H), 7.79-7.75 (m, 1H), 7.21 (dd, J=10.3, 8.2 Hz, 1H), 3.87 (s, 2H), 3.82 (s, 3H). MS (m/z): 227.1 (M+H)⁺.

Step 2

To a 20 mL reaction vessel was added reagents in the following order: methyl 3-(2-aminoacetamido)-4-fluorobenzoate (I-69) (0.63 mmol), AcOH (1 mL), MeOH (4 mL) and cyclopentanecarbaldehyde (1 mmol). After 30 mins, sodium cyanoborohydride (0.80 mmol) was added. The reaction was stirred 10 mins, at which time an additional portion of sodium cyanoborohydride was added (0.40 mmol). The reaction was stirred for 2 hrs, filtered, and then purified TFA modified (0.05%) reverse phase-chromatography (20 to 60%, water-ACN) and subsequently residual TFA was removed using a polymer bound ion exchange cartridge (SPE PL HCO₃ MP SPE 0.9 mmol nominal load×1 units and 8 mL MeOH as mobilizing eluent) to give the amine (I-70) as a glassy solid. ¹H NMR (400 MHz, d₄-MeOH): δ 8.80 (br d, J=8.0 Hz, 1H), 7.91-7.86 (m, 1H), 7.32 (dd, J=11.0, 8.0 Hz, 1H), 4.08 (s, 2H), 3.92 (s, 3H), 3.08 (app d, J=8.1 Hz, 2H), 2.31-2.22 (m, 1H), 1.97-1.92 (m, 2H), 1.77-1.64 (m, 4H), 1.36-1.30 (m, 2H). MS (m/z): 309.1 (M+H)⁺.

The following intermediates were prepared according to the procedures described for the synthesis of I-70 using the appropriate reagents.

| Compound | Structure | Characterization Data |
|---|---|---|
| I-71 | MeO₂C—[structure with NH-C(=O)-CH₂-NH-CH₂-cyclopentyl on phenyl] | MS (m/z): 291.1 (M + H)⁺; r.t. = 1.238 |

8-chloro-N-(2-fluorobenzyl)-N-(2-hydroxyethyl)-1-methyl-1,4-dihydrochromeno[4,3-c]pyrazole-3-carboxamide (I-73)

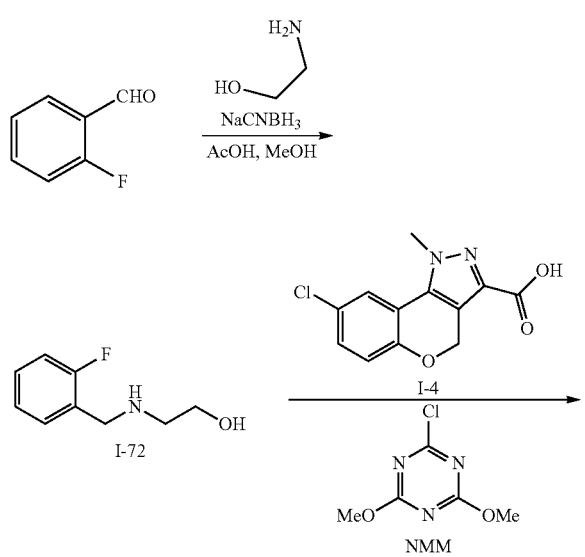

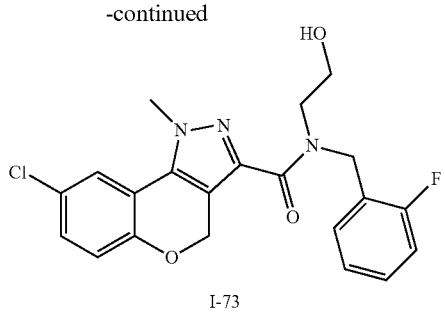

Step 1

To a 250 mL reaction vessel was added reagents in the following order: ethanol amine (40.0 mmol), AcOH (8 mL), MeOH (60 mL), and 2-fluorobenzaldehyde (20.0 mmol). After 30 mins, sodium cyanoborohydride (20.0 mmol) was added portionwise over 30 mins. The reaction was stirred 1 hr, and then partially concentrated (in vacuo) before direct purification by acetic acid modified (0.05%) reverse phase-chromatography (5 to 15%, water-ACN) to furnish upon drying 2-((2-fluorobenzyl)amino)ethanol (I-72) as a semi-solid. ¹H NMR (400 MHz, d₄-MeOH): δ 7.61 (dt, J=7.9, 1.8 Hz, 1H), 7.41-7.35 (m, 1H), 7.21 (app t, J=7.9 Hz, 1H), 7.13 (app t, J=8.9 Hz, 1H), 4.00 (s, 2H), 3.73 (t, J=6.2 Hz, 1H), 2.87 (t, J=6.2 Hz, 1H). MS (m/z): 170.1 (M+H)⁺.

Step 2

To a 100 mL reaction vessel was added reagents in the following order: 8-chloro-1-methyl-1,4-dihydrochromeno[4,3-c]pyrazole-3-carboxylic acid (I-4) (2.0 mmol, THF (10 mL) and N-methyl morpholine (0.72 mL, 5.0 mmol). This was stirred until complete dissolution. Next was added 2-chloro-4,6-dimethoxy-1,3,5-triazine (2.2 mmol) and this solution was stirred for 20 mins at 50 C until a white precipitate fully formed. The precipitate was physically agitated with rapid stirring to ensure all solids were well mixed. Next was added 2-((2-fluorobenzyl)amino)ethanol (I-72) (2.4 mmol) and the reaction was stirred for 30 mins at 50° C. and then diluted with 5 mL of MeOH and then purified by acetic acid modified (0.05%) reverse phase chromatography (30 to 80%, water/ACN) and subsequently recrystallized by MeOH/water 1:3 (10 mL) to furnish a white powder (I-73). ¹H NMR (400 MHz, DMSO): δ 7.74-7.70 (m, 1H), 7.38-7.28 (m, 5H), 7.04 (dd, J=8.4, 1.5 Hz, 1H), 5.40-5.35 (m, 3H), 4.80-4.75 (m, 2H), 4.20 (s, 3H), 3.93 (t, J=6.2 Hz, 1H) 3.63 (q, J=6.2 Hz, 1H), 3.55 (q, J=6.2 Hz, 1H), 3.41 (t, J=6.5 Hz, 1H). Mixture of rotamers. MS (m/z): 416.1/418.1 (M+H)⁺ (chlorine isotope pattern).

The following intermediates were prepared according to the procedures described for the synthesis of I-73 using the appropriate reagents.

| Compound | Structure | Characterization Data |
|---|---|---|
| I-74 | 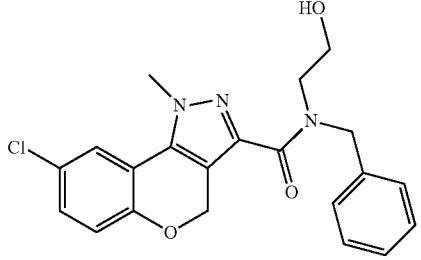 | ¹H NMR (400 MHz, DMSO): δ 7.78-7.75 (m, 2H), 7.30-7.16 (m, 5H), 5.40-5.35 (m, 2H), 4.80 (br s, 2H), 4.04 (s, 3H), 3.78 (app t, J = 5.0 Hz, 2H), 3.34 (app t, J = 5.0 Hz, 2H), 3.45 (t, J = 4.0 Hz, 1H). Mixture of rotamers. MS (m/z): 398.1 (M + H)⁺. |
| I-75 | 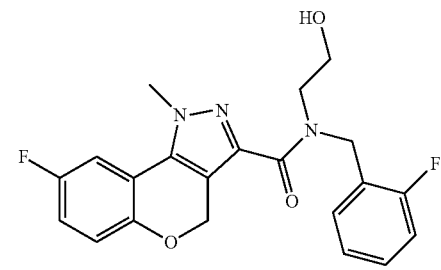 | ¹H NMR (400 MHz, DMSO): δ 7.73-7.70 (m, 2H), 7.36-7.00 (m, 5H), 5.35-5.30 (m, 2H), 4.78 (br s, 2H), 4.14 (s, 3H), 3.88 (app t, J = 5.0 Hz, 2H), 3.45-3.50 (m, 2H), 3.38-3.36 (m, 1H). Mixture of rotamers. MS (m/z): 400.1 (M + H)⁺. |
| I-76 | 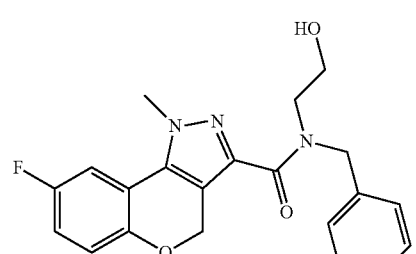 | ¹H NMR (400 MHz, DMSO): δ 7.75-7.69 (m, 2H), 7.46-6.92 (m, 6H), 5.25-5.15 (m, 2H), 4.73 (br s, 2H), 4.04 (s, 3H), 3.88-3.24 (m, 4H). Mixture of rotamers. MS (m/z): 382.1 (M + H)⁺. |
| I-77 | 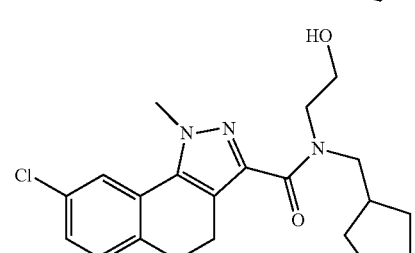 | MS (m/z): 390.1 (M + H)⁺; r.t. = 1.289 |

1,5,5-trimethyl-4,5-dihydro-1H-benzo[g]indazole-3-carboxylic acid (I-78)

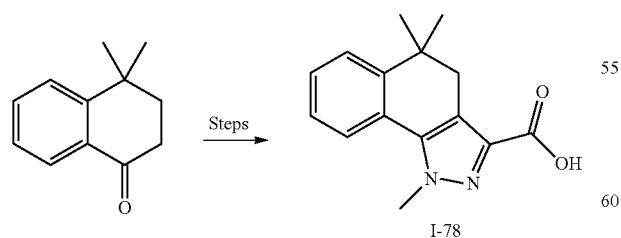

I-78

Intermediate I-78 was prepared according to the procedure described for the preparation of intermediate I-4, starting with 4,4-dimethyl-3,4-dihydronaphthalen-1(2H)-one. MS (m/z): 257.1 (M+H)⁺.

Example 1

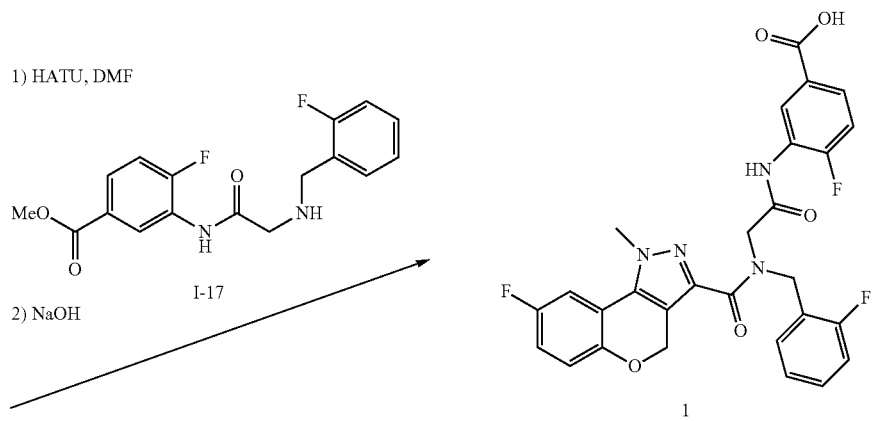

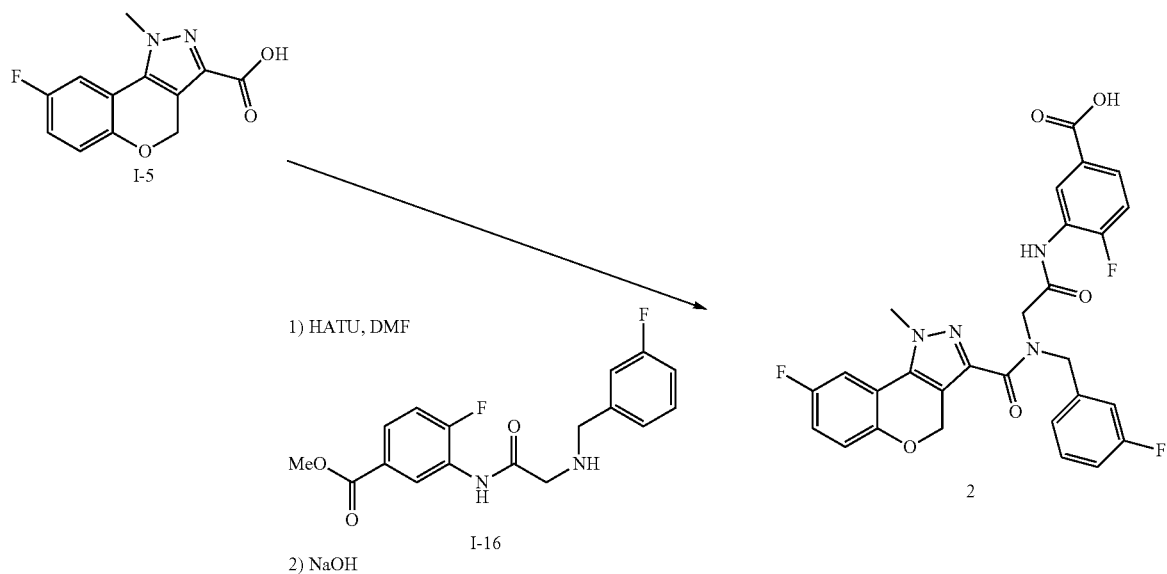

4-Fluoro-3-(2-(8-fluoro-N-(2-fluorobenzyl)-1-methyl-1,4-dihydrochromeno[4,3-c]pyrazole-3-carboxamido)acetamido)benzoic acid (Compound 1)

Step 1

To a solution of methyl 4-fluoro-3-(2-((2-fluorobenzyl)amino)acetamido)benzoate (I-17) (8.2 mmol) and HATU (8.2 mmol) in DMF (30 mL), diisopropylethylamine (30 mmol) and 8-fluoro-1-methyl-1,4-dihydrochromeno[4,3-c]pyrazole-3-carboxylic acid (I-5) (7.4 mmol) were added to give a yellowish solution. The reaction mix was stirred at room temperature for 3 hr. The reaction mixture was poured onto ice 300 mL resulting in a precipitate that was collected by vacuum filtration. The solid was then re-dissolved in EtOAc (600 mL) and washed with 5% $Na_2CO_3$, water, brine, dried and concentrated The solid was purified by trituration in hot MeOH. The resulting solid was filtered and dried. $^1$H NMR (400 MHz, DMSO): δ 10.14 (m, 1H), 8.79-8.46 (m, 1H), 7.80-7.66 (m, 1H), 7.56 (m, 1H), 7.50-7.29 (m, 3H), 7.22 (m, 3H), 7.06 (m, 1H), 5.38 (m, 3H), 4.82 (d, J=41.7 Hz, 3H), 4.35-4.03 (m, 3H), 3.85 (m, 3H). Mixture of rotamers.

Step 2

The resulting ester (5 mmol) was dissolved in a 4:1 THF-MeOH (100 mL) and treated with 1N KOH (20 mL). The white suspension was stirred at room temperature for 2 hrs resulting in a clear solution. The reaction was stirred at room temperature for an additional 16 hrs until the reaction was completed as indicated by LCMS. The organic solvent was removed in vacuo resulting in a white suspension. The resulting suspension was diluted with water (100 mL) and the pH was adjusted to ~5 w/AcOH. The white solid was collected by filtration, washed with water and dried under vacuum for 24 hrs. The carboxylic acid product was further purified by stirring in 8:2 MeOH-water solution (200 mL) at 70° C. for 2 hrs. After cooling to room temperature, the solid was collected by vacuum filtration to give 4-fluoro-3-(2-(8-fluoro-N-(2-fluorobenzyl)-1-methyl-1,4-dihydrochromeno[4,3-c]pyrazole-3-carboxamido)acetamido)benzoic acid. $^1$H NMR (400 MHz, DMSO): δ 10.06-10.01 (m, 1H), 8.58-8.56 (m, 1H), 8.51-8.49 (m, 1H), 7.72-7.69 (m, 1H), 7.58-7.53 (m, 1H), 7.46-7.33 (m, 3H), 7.24-7.12 (m, 3H), 7.08-7.04 (m, 1H), 5.40-5.37 (m, 3H), 4.86-4.76 (m, 3H), 4.24-4.12 (m, 4H). Mixture of rotamers. MS (m/z): 551.1 (M+H)$^+$.

In one embodiment, a solution of L-arginine (0.82 mmol) in deionized water (6 mL) was added to a suspension of 4-fluoro-3-(2-(8-fluoro-N-(2-fluorobenzyl)-1-methyl-1,4-dihydrochromeno[4,3-c]pyrazole-3 carboxamido)acetamido)benzoic acid (0.82 mmol) in MeOH (50 mL). The clear mixture was stirred for 0.5 hr at room temperature and then concentrated to give a white semi-solid residue. The residue was taken in anhydrous acetonitrile (25 mL) and the white suspension was slowly concentrated under reduced pressure. The process was repeated several times (5×) to give 4-fluoro-3-(2-(8-fluoro-N-(2-fluorobenzyl)-1-methyl-1,4-dihydrochromeno[4,3-c]pyrazole-3-carboxamido)acetamido) benzoic acid L-arginine salt. Melting point (157° C.). $^1$H NMR (400 MHz, DMSO): δ 9.88-9.77 (m, 1H), 8.37-8.26 (m, 1H), 8.03-7.68 (m, 5H), 7.66-7.51 (m, 2H), 7.48-7.31 (m, 3H), 7.15 (m, 6H), 5.43-5.35 (m, 2H), 4.86-4.72 (m, 3H), 4.22-4.10 (m, 4H), 3.26-3.18 (m, 1H), 3.17-2.99 (m, 2H), 1.76-1.52 (m, 4H).

In another embodiment, suspension of 4-fluoro-3-(2-(8-fluoro-N-(2-fluorobenzyl)-1-methyl-1,4-dihydrochromeno[4,3-c]pyrazole-3-carboxamido)acetamido)benzoic acid (0.84 mmol) in MeOH (20 mL) was heated to 70° C. A 1N solution of NaOH (0.84 mmol) was added drop wise. The clear solution was stirred at room temperature for 1 hr before the solvent was removed under reduced pressure. The crude material was triturated with MeOH and crystallized by slurring in acetonitrile (5 mL) to give 4-fluoro-3-(2-(8-fluoro-N-(2-fluorobenzyl)-1-methyl-1,4-dihydrochromeno[4,3-c]pyrazole-3-carboxamido)acetamido)benzoic acid sodium salt. Melting point (161° C.). $^1$H NMR (400 MHz, DMSO): δ 9.86-9.60 (m, 1H), 8.27-8.17 (m, 1H), 7.63-7.55 (m, 2H), 7.48-7.31 (m, 2H), 7.26-7.04 (m, 5H), 5.42-5.37 (m, 2H), 4.84-4.74 (m, 3H), 4.20-4.12 (m, 4H).

4-Fluoro-3-(2-(8-fluoro-N-(3-fluorobenzyl)-1-methyl-1,4-dihydrochromeno[4,3-c]pyrazole-3-carboxamido)acetamido)benzoic acid (Compound 2)

4-Fluoro-3-(2-(8-fluoro-N-(3-fluorobenzyl)-1-methyl-1,4-dihydrochromeno[4,3-c]pyrazole-3-carboxamido)acetamido)benzoic acid was prepared following the procedures for Compound 1. Melting point (246° C.). $^1$H NMR (400 MHz, DMSO): δ 10.14-10.04 (m, 1H), 8.71-8.58 (m, 1H), 7.79-7.69 (m, 1H), 7.62-7.51 (m, 1H), 7.47-7.36 (m, 2H), 7.29-7.02 (m, 5H), 5.42-5.32 (m, 2H), 4.84-4.72 (m, 2H), 4.23-4.08 (m, 3H), 3.88-3.80 (m, 3H). Mixture of rotamers. MS (m/z) (M+H)$^+$, 551.3. Anal. Calcd for $C_{28}H_{21}F_3N_4O_5$*0.15 $CH_4O$:C, 61.09; H, 3.85; N, 10.18. Found: C, 60.97; H, 4.02; N, 10.16.

Methanol (500 mL) and dichloromethane (500 mL) were added to a mixture of 4-fluoro-3-(2-(8-fluoro-N-(3-fluorobenzyl)-1-methyl-1,4-dihydrochromeno[4,3-c]pyrazole-3-carboxamido)acetamido) benzoic acid (22 mmol) and 2-amino-2-hydroxymethyl-propane-1,3-diol (TRIS; 22 mmol). The reaction was stirred at 25° C. for 3 hrs. The solvent was removed in vacuum, and dichloromethane (500 mL) was added to the solid and concentrated (repeated 2×). The solid was suspended in 100 mL of dichloromethane and collected by vacuum filtration to give 4-fluoro-3-(2-(8-fluoro-N-(3-fluorobenzyl)-1-methyl-1,4-dihydrochromeno[4,3-c]pyrazole-3-carboxamido)acetamido) benzoic acid TRIS salt. Melting point (125° C.). $^1$H NMR (400 MHz, DMSO) δ 10.01-9.65 (m, 1H), 8.59-8.30 (m, 1H), 7.76-6.95 (m, 10H), 5.53-4.00 (m, 9H), 3.58-3.10 (m, 10H). Anal. Calcd for $C_{32}H_{32}F_3N_5O_8$*1 $H_2O$: C, 55.73; H, 4.97; N, 10.16.

Found: C, 55.74; H, 4.99; N, 10.12.

In one embodiment, a solution of L-arginine (0.73 mmol) in deionized water (5.8 mL) was added to suspension of 4-fluoro-3-(2-(8-fluoro-N-(3-fluorobenzyl)-1-methyl-1,4-dihydrochromeno[4,3-c]pyrazole-3-carboxamido)acetamido)benzoic acid (0.73 mmol) in methanol (70 mL). The mixture was heated to 70° C. for 0.5 hrs. After cooling to room temperature, the solvent was removed in vacuum. A 2:1 mixture of acetonitrile and methanol (20 mL) was added to the solid and concentrated (repeated 2×). The solid was crystallized by slurring the solid residue in a 2:1 mixture of acetonitrile and methanol (5 mL) and stirring the suspension at room temperature for 24 hrs to give 4-fluoro-3-(2-(8-fluoro-N-(3-fluorobenzyl)-1-methyl-1,4-dihydrochromeno[4,3-c]pyrazole-3-carboxamido)acetamido) benzoic acid L-arginine salt as a white precipitate. Melting point (206° C.). $^1$H NMR (400 MHz, DMSO) δ 9.88-9.78 (m, 1H), 8.41-8.31 (m, 1H), 8.08-7.82 (m, 5H), 7.68-7.52 (m, 2H), 7.47-7.36 (m, 1H), 7.28-7.04 (m, 6H), 5.43-5.30 (m, 3H), 4.81-4.70 (m, 3H), 4.14 (s, 4H), 3.26-3.21 (m, 2H), 3.16-3.01 (m, 2H), 1.78-1.52 (m, 4H).

In another embodiment, a solution of L-lysine (0.20 mmol) in deionized water (3 mL) was added to a hot suspension of 4-fluoro-3-(2-(8-fluoro-N-(3-fluorobenzyl)-1-methyl-1,4-dihydrochromeno[4,3-c]pyrazole-3-carboxamido)acetamido)benzoic acid (0.20 mmol) in methanol (25 mL). The mixture was stirred at room temperature for 16 hrs. The solvent was removed under vacuum and the crude material was crystallized by slurring the solid residue in acetonitrile (5 mL). The mixture was stirred at room temperature for additional 24 hrs to give 4-fluoro-3-(2-(8-fluoro-N-(3-fluorobenzyl)-1-methyl-1,4-dihydrochromeno[4,3-c]pyrazole-3-carboxamido) benzoic acid L-lysine salt as a white precipitate. $^1$H NMR (400 MHz, DMSO): δ 9.86-9.77 (m, 1H), 8.40-8.28 (m, 1H), 7.68-7.51 (m, 2H), 7.48-7.36 (m, 1H), 7.29-7.02 (m, 7H), 5.43-5.36 (m, 2H), 5.36-5.31 (m, 1H), 4.80-4.71 (m, 3H), 4.19-4.11 (m, 4H), 3.17-3.09 (m, 1H), 2.76-2.64 (m, 2H), 1.77-1.31 (m, 7H); some peaks fall under solvent peaks.

The following compounds were prepared according to the procedures described in Example 1 using the appropriate intermediates.

| Compound | Structure | Characterization Data |
|---|---|---|
| 3 | 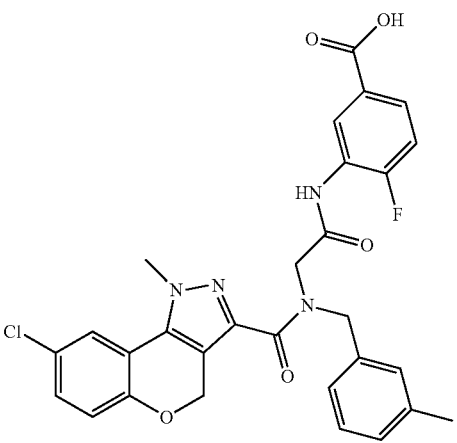 | ¹H NMR (400 MHz, DMSO): δ 10.03 (s, 1H), 8.72-8.39 (m, 1H), 7.81-7.59 (m, 2H), 7.48-6.86 (m, 7H), 5.54-5.19 (m, 3H), 4.79-4.61 (m, 2H), 4.22-4.03 (m, 4H), 2.30 (s, 3H). Mixture of rotamers. MS (m/z): 563.2/565.2 (M + H)⁺ (chlorine isotope pattern). |
| 4 | 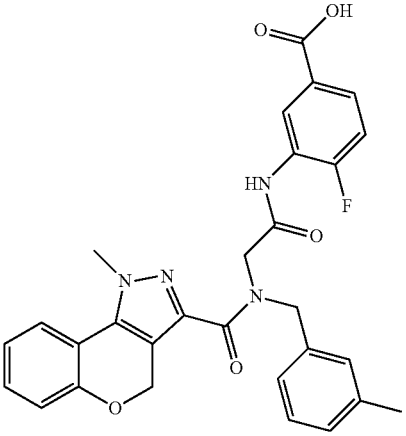 | ¹H NMR (400 MHz, DMSO): δ 10.06-9.86 (m, 1H), 8.60-8.45 (m, 1H), 7.80-7.61 (m, 2H), 7.42-6.92 (m, 8H), 5.48-5.22 (m, 3H), 4.77-4.66 (m, 2H), 4.20-4.02 (m, 4H), 2.30 (s, 3H). Mixture of rotamers. MS (m/z): 529.2 (M + H)⁺. |
| 5 | 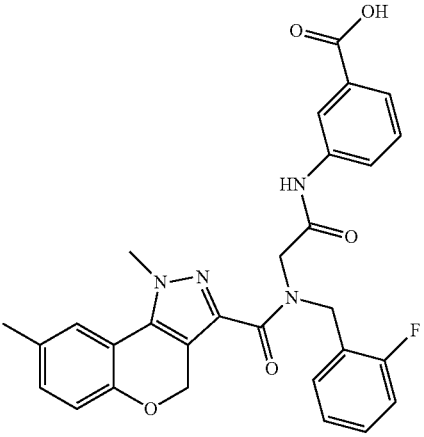 | ¹H NMR (400 MHz, DMSO): δ 10.31-10.18 (m, 1H), 8.28-8.16 (m, 1H), 7.83-7.74 (m, 1H), 7.65-7.58 (m, 1H), 7.56-7.31 (m, 4H), 7.26-7.17 (m, 2H), 7.13-7.06 (m, 1H), 6.96-6.85 (m, 1H), 5.48-5.25 (m, 3H), 4.88-4.70 (m, 2H), 4.21-4.00 (m, 4H), 2.34-2.25 (m, 3H). Mixture of rotamers. MS (m/z): 529.2 (M + H)⁺. |

| Compound | Structure | Characterization Data |
|---|---|---|
| 6 | 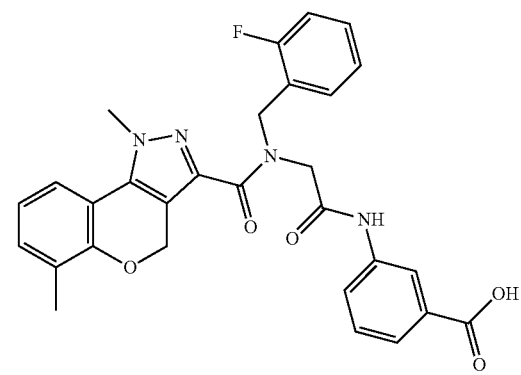 | $^1$H NMR (400 MHz, DMSO): δ 10.31-10.21 (m, 1H), 8.29-8.17 (m, 1H), 7.82-7.74 (m, 1H), 7.66-7.49 (m, 2H), 7.49-7.29 (m, 3H), 7.26-7.13 (m, 3H), 7.02-6.92 (m, 1H), 5.47-5.35 (m, 3H), 4.88-4.71 (m, 3H), 4.21-4.02 (m, 4H), 2.25-2.14 (m, 3H). Mixture of rotamers. MS (m/z): 529.2 (M + H)$^+$. |
| 7 | 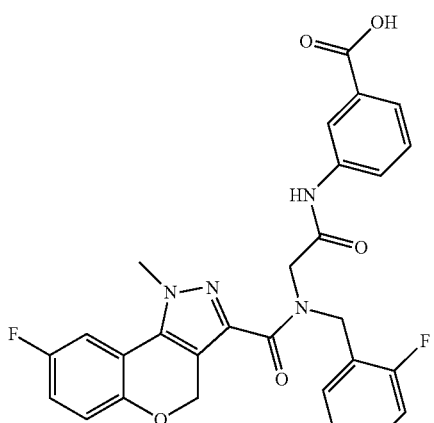 | $^1$H NMR (400 MHz, DMSO): δ 10.31-10.19 (m, J = 6.6 Hz, 1H), 8.26-8.16 (m, J = 9.7 Hz, 1H), 7.83-7.74 (m, J = 2.9, 5.1 Hz, 1H), 7.65-7.49 (m, 2H), 7.49-7.30 (m, 3H), 7.26-7.01 (m, 4H), 5.46-5.33 (m, J = 11.7 Hz, 3H), 4.85-4.73 (m, J = 26.4 Hz, 2H), 4.20-4.04 (m, J = 10.6 Hz, 22.1, 4H). Mixture of rotamers. MS (m/z): 533.1 (M + H)$^+$. |
| 8 | 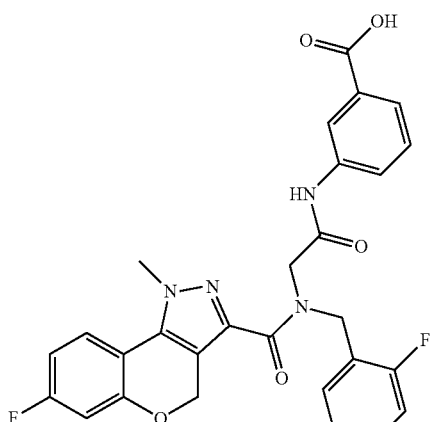 | $^1$H NMR (400 MHz, DMSO): δ 10.32-10.21 (m, 1H), 8.29-8.17 (m, 1H), 7.83-7.68 (m, 15.0, 2H), 7.65-7.59 (m, 1H), 7.47-7.30 (m, 3H), 7.24-7.16 (m, 2H), 6.98-6.87 (m, 2H), 5.49-5.38 (m, 3H), 4.88-4.69 (m, 2H), 4.18-4.02 (m, 4H). Mixture of rotamers. MS (m/z): 533.2 (M + H)$^+$. |

-continued
| Compound | Structure | Characterization Data |
|---|---|---|
| 9 | 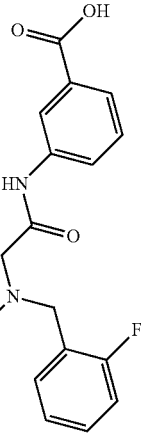 | ¹H NMR (400 MHz, DMSO): δ 10.31-10.20 (m, 1H), 8.27-8.17 (m, 1H), 7.82-7.58 (m, 3H), 7.48-7.30 (m, 3H), 7.26-7.08 (m, 4H), 5.48-5.38 (m, 3H), 4.85-4.72 (m, 2H), 4.19-4.02 (m, 4H). Mixture of rotamers. MS (m/z): 549.1 (M + H)⁺. |
| 10 | 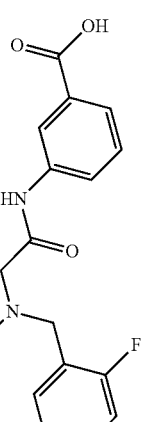 | ¹H NMR (400 MHz, DMSO): δ 10.30-10.20 (m, 1H), 8.26-8.17 (m, 1H), 7.86-7.72 (m, 2H), 7.66-7.58 (m, 1H), 7.48-7.30 (m, 3H), 7.27-7.16 (m, 3H), 5.45-5.38 (m, 3H), 4.85-4.72 (m, 2H), 4.18-4.05 (m, 4H). Mixture of rotamers. MS (m/z); 551.1 (M + H)⁺. |
| 11 | 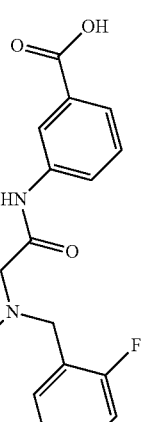 | ¹H NMR (400 MHz, DMSO): δ 10.29-10.21 (m, 1H), 8.28-8.15 (m, 1H), 7.82-7.74 (m, 1H), 7.66-7.58 (m, 1H), 7.49-7.30 (m, 5H), 7.26-7.16 (m, 2H), 5.49-5.38 (m, 3H), 4.87-4.73 (m, 2H), 4.19-4.06 (m, 4H). Mixture of rotamers. MS (m/z): 551.2 (M + H)⁺. |

| Compound | Structure | Characterization Data |
|---|---|---|
| 12 | 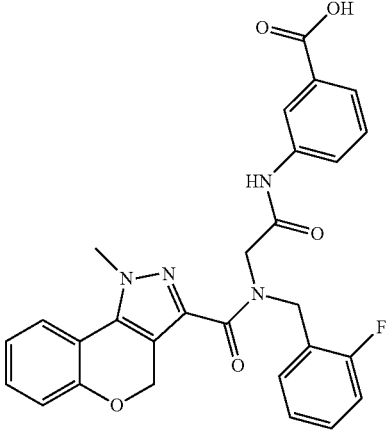 | ¹H NMR (400 MHz, DMSO): δ 10.32-10.19 (m, 1H), 8.26-8.18 (m, 1H), 7.83-7.57 (m, 3H), 7.48-7.16 (m, 6H), 7.13-6.96 (m, 2H), 5.47-5.35 (m, 3H), 4.86-4.72 (m, 2H), 4.18-4.04 (m, 4H). Mixture of rotamers. MS (m/z): 515.1 (M + H)⁺. |
| 13 | 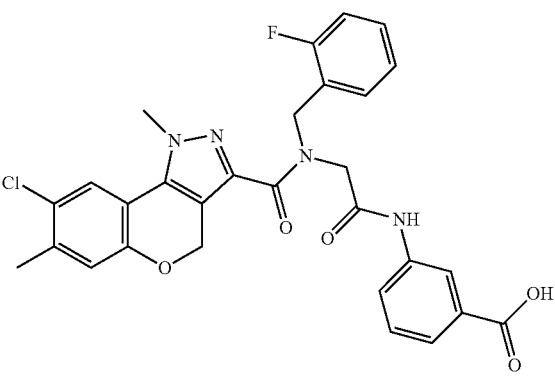 | ¹H NMR (400 MHz, DMSO): δ 10.23 (m, 1H), 8.23-8.14 (m, 1H), 7.82-7.72 (m, 1H), 7.70-7.57 (m, 2H), 7.47-7.30 (m, 3H), 7.25-7.16 (m, 2H), 7.08-7.02 (m, 1H), 5.44-5.33 (m, 3H), 4.84-4.72 (m, 2H), 4.18-4.04 (m, 4H), 2.32-2.25 (m, 3H). Mixture of rotamers. MS (m/z): 563.2 (M + H)⁺. |
| 14 | 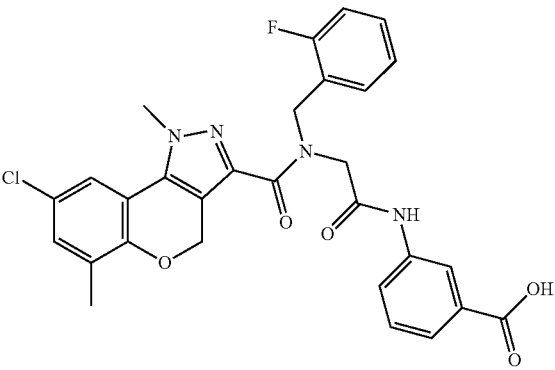 | ¹H NMR (400 MHz, DMSO): δ 10.29-10.19 (m, 1H), 8.25-8.17 (m, 1H), 7.82-7.73 (m, 1H), 7.64-7.48 (m, 2H), 7.48-7.30 (m, 3H), 7.30-7.15 (m, 3H), 5.45-5.38 (m, 3H), 4.84-4.72 (m, 2H), 4.17-4.05 (m, 4H), 2.21-2.14 (m, 3H). Mixture of rotamers. MS (m/z): 563.2 (M + H)⁺. |

| Compound | Structure | Characterization Data |
|---|---|---|
| 15 | 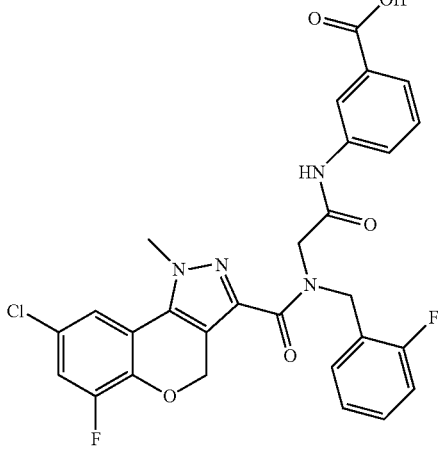 | $^1$H NMR (400 MHz, DMSO): δ 10.31-10.21 (m, 1H), 8.27-8.17 (m, 1H), 7.82-7.73 (m, 1H), 7.67-7.47 (m, 3H), 7.47-7.29 (m, 3H), 7.27-7.15 (m, 2H), 5.53-5.38 (m, 3H), 4.86-4.69 (m, 2H), 4.21-4.07 (m, 4H). Mixture of rotamers. MS (m/z): 567.1 (M + H)$^+$. |
| 16 | 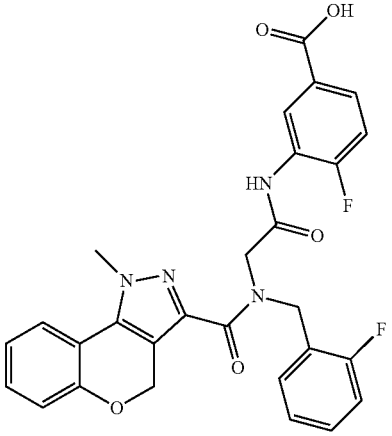 | $^1$H NMR (400 MHz, DMSO): δ 10.13-10.00 (m, 1H), 8.65-8.50 (m, 1H), 7.76-7.65 (m, 2H), 7.46-7.15 (m, 6H), 7.12-6.97 (m, 2H), 5.44-5.32 (m, 3H), 4.91-4.73 (m, 2H), 4.27-4.06 (m, 4H). Mixture of rotamers. MS (m/z): 533.2 (M + H)$^+$. |
| 17 | 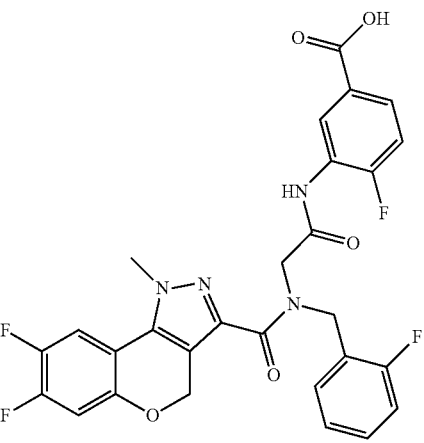 | $^1$H NMR (400 MHz, DMSO): δ 10.13-9.97 (m, 1H), 8.65-8.49 (m, 1H), 7.86-7.67 (m, 2H), 7.48-7.30 (m, 3H), 7.27-7.16 (m, 3H), 5.44-5.36 (m, 3H), 4.87-4.73 (m, 2H), 4.27-4.07 (m, 4H). Mixture of rotamers. MS (m/z): 569.2 (M + H)$^+$. |

-continued
| Compound | Structure | Characterization Data |
|---|---|---|
| 18 | 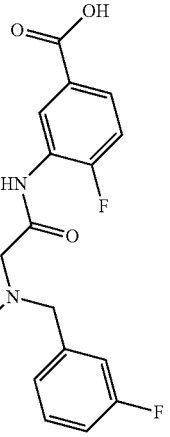 | ¹H NMR (400 MHz, DMSO): δ 10.11-9.98 (m, 1H), 8.69-8.47 (m, 1H), 7.87-7.65 (m, 2H), 7.48-7.30 (m, 2H), 7.30-7.06 (m, 4H), 5.49-5.29 (m, 3H), 4.83-4.70 (m, 2H), 4.22-4.05 (m, 4H). Mixture of rotamers. MS (m/z): 569.2 (M + H)⁺. |
| 19 | 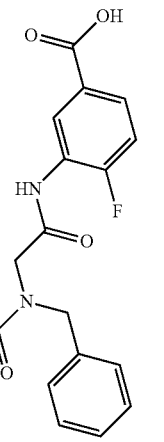 | ¹H NMR (400 MHz, DMSO): δ 10.09-9.96 (m, 1H), 8.67-8.52 (m, 1H), 7.87-7.65 (m, 2H), 7.43-7.16 (m, 7H), 5.49-5.29 (m, 3H), 4.79-4.69 (m, 2H), 4.20-4.06 (m, 4H). Mixture of rotamers. MS (m/z): 551.2 (M + H)⁺. |
| 20 | 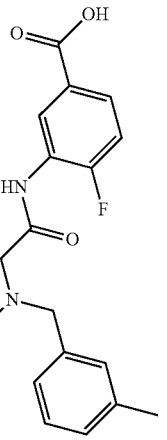 | ¹H NMR (400 MHz, DMSO): δ 10.08-9.94 (m, 1H), 8.66-8.53 (m, 1H), 7.76-7.66 (m, 1H), 7.61-7.50 (m, 1H), 7.44-7.31 (m, 1H), 7.30-7.21 (m, 1H), 7.21-7.02 (m, 5H), 5.43-5.26 (m, 3H), 4.79-4.66 (m, 2H), 4.19-4.05 (m, 4H), 2.31-2.27 (s, 3H). Mixture of rotamers. MS (m/z): 547.1 (M + H)⁺. |

| Compound | Structure | Characterization Data |
|---|---|---|
| 21 | 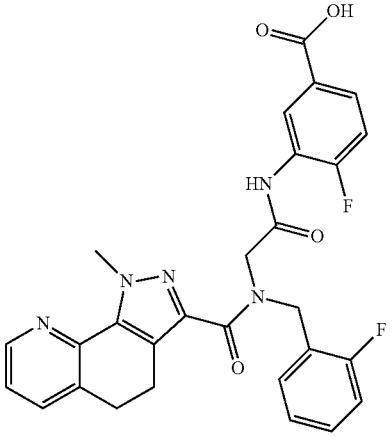 | ¹H NMR (400 MHz, DMSO): δ 10.03 (s, 1H), 8.66-8.42 (m, 2H), 7.78-7.65 (m, 2H), 7.52-7.14 (m, 6H), 5.25-5.13 (m, 1H), 4.82-4.66 (m, 2H), 4.29-4.20 (m, 4H), 3.01-2.83 (m, 4H). Mixture of rotamers. MS (m/z): 532.2 (M + H)⁺. |
| 22 | 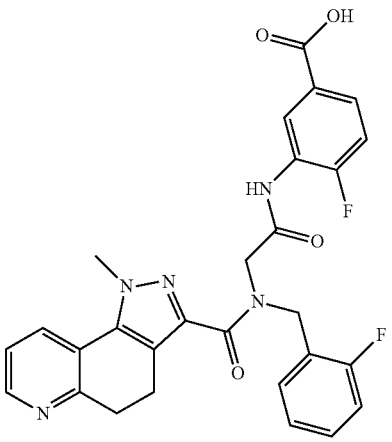 | ¹H NMR (400 MHz, DMSO): δ 10.07-9.97 (m, 1H), 8.67-8.51 (m, 1H), 8.43-8.37 (m, 1H), 8.12-8.03 (m, 1H), 7.75-7.66 (m, 1H), 7.49-7.28 (m, 4H), 7.28-7.14 (m, 2H), 5.25-5.15 (m, 1H), 4.82-4.67 (m, 2H), 4.28-4.05 (m, 4H), 3.06-2.84 (m, 4H). Mixture of rotamers. MS (m/z): 532.2 (M + H)⁺. |
| 23 | 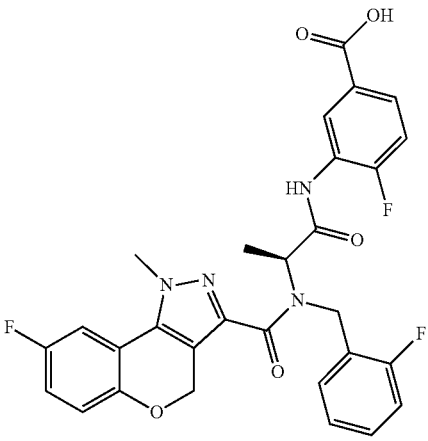 | ¹H NMR (400 MHz, DMSO): δ 10.26-9.80 (m, 1H), 8.48-8.31 (m, 1H), 7.76-7.68 (m, 1H), 7.64-7.49 (m, 1H), 7.44-7.34 (m, 1H), 7.30-7.02 (m, 6H), 6.02-5.86 (m, 1H), 5.59-4.97 (m, 3H), 4.94-4.59 (m, 1H), 4.33-3.95 (m, 3H), 1.54-1.30 (m, 3H). Mixture of rotamers. MS (m/z): 565.2 (M + H)⁺. |

| Compound | Structure | Characterization Data |
|---|---|---|
| 24 | 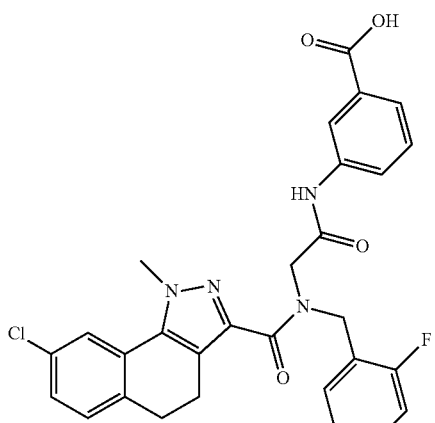 | ¹H NMR (400 MHz, DMSO): δ 10.42-10.12 (m, 1H), 8.37-8.08 (m, 1H), 7.90-7.67 (m, 2H), 7.67-7.55 (m, 1H), 7.55-7.30 (m, 5H), 7.30-7.13 (m, 2H), 5.32-5.18 (m, 1H), 4.90-4.62 (m, 2H), 4.27-3.91 (m, 4H), 3.11-2.93 (m, 2H), 2.93-2.78 (m, 2H). Mixture of rotamers. |
| 25 | 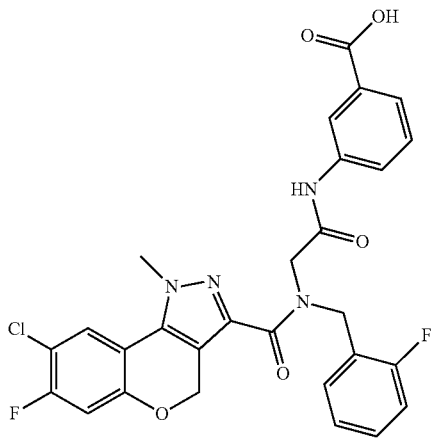 | ¹H NMR (400 MHz, DMSO): δ 10.29 (m, 1H), 8.22 (m, 1H), 7.84 (m, 2H), 7.61 (m, 1H), 7.41 (m, 3H), 7.29-7.11 (m, 3H), 5.63-5.20 (m, 3H), 4.79 (m, 2H), 4.15 (m, 4H). Mixture of rotamers. |
| 26 | 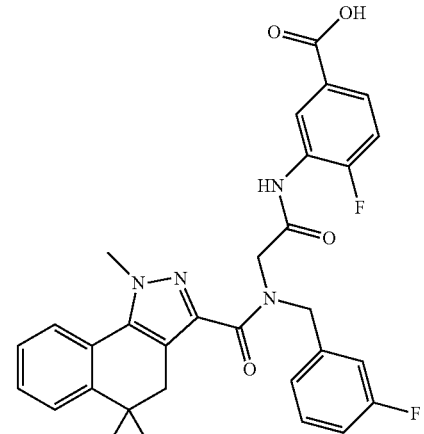 | ¹H NMR (400 MHz, DMSO): δ 10.15-9.81 (m, 1H), 8.77-8.50 (m, 1H), 8.07-6.95 (m, 10H), 5.34-5.00 (m, 1H), 4.90-4.47 (m, 2H), 4.12 (s, 4H), 2.89-2.73 (m, 2H), 1.21 (s, 6H). Mixture of rotamers. MS (m/z): 559.2 (M + H)⁺; r.t. = 1.781 |

| Compound | Structure | Characterization Data |
|---|---|---|
| 27 | 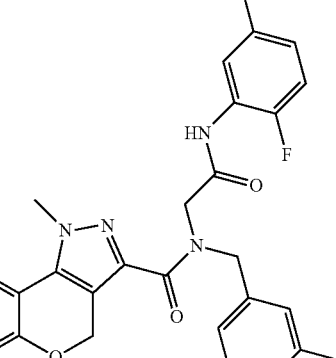 | MS (m/z): 533.2 (M + H)⁺: r.t. = 1.678 |
| 28 | 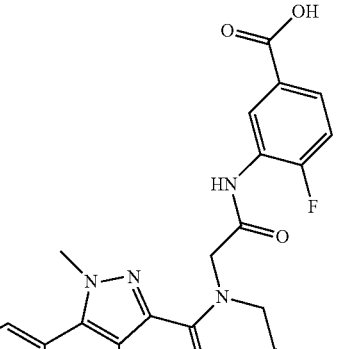 | NMR (400 MHz, DMSO): δ 12.23 (br s, 1H), 10.01-9.98 (m, 1H), 8.43-8.41 (m, 1H), 7.80-7.10 (m, 8H), 7.02 (app d, J = 8.4 Hz, 1H), 5.39-5.30 (m, 3H), 4.86-4.70 (m, 3H), 4.13 (app br s, 3H). Mixture of rotamers. MS (m/z): 567.1/569.1 (M + H)⁺ (chlorine isotope pattern). |

Example 2

3-(2-(N-benzyl-8-chloro-1-methyl-1,4-dihydro-chromeno[4,3-c]pyrazole-3-carboxamido)acet-amido)-4-fluorobenzoic acid (Compound 29)

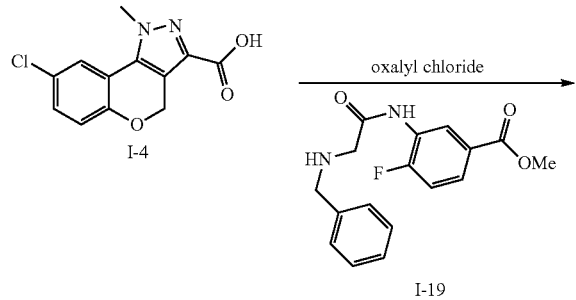

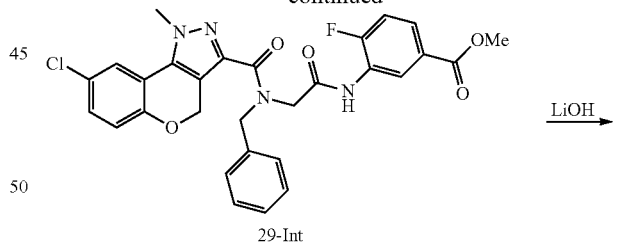

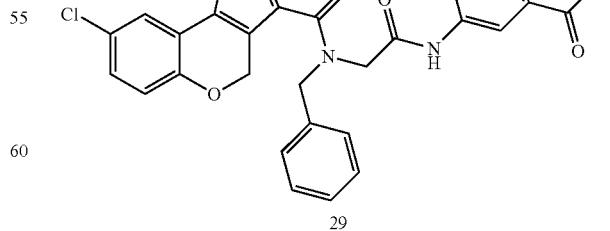

Step 1

To a suspension of the 8-chloro-1-methyl-1,4-dihydro-chromeno[4,3-c]pyrazole-3-carboxylic acid (I-4) (0.20 mmol) in CH₂Cl₂ (1 mL) was added a catalytic amount of DMF (2.5 μL) and dropwise oxalyl chloride (0.60 mmol) at 0° C. The resulting suspension was warmed up to room temperature and stirred for 1 hr. The solvent was removed under vacuum to dryness completely (need to remove oxalyl chloride completely). The obtained residue was dissolved with CH₂Cl₂ (1 mL) and then dropwise into a solution of methyl 3-(2-(benzylamino)acetamido)-4-fluorobenzoate (I-19) (0.2 mmol) in CH₂Cl₂ (1 mL) in the presence of DIEA (0.38 mmol). The reaction mixture was stirred for 15 mins at room temperature and then was charged 50 mL water. Organic layer was separated and aqueous layer was extracted with CH₂Cl₂ (50 mL). Combined organic layers were washed with H₂O and brine successively, dried over Na₂SO₄, filtered and concentrated to give the crude product which was purified by column chromatography (0-60% EtOAc in hexanes) to give methyl 3-(2-(N-benzyl-8-chloro-1-methyl-1,4-dihydrochromeno[4,3-c]pyrazole-3-carboxamido)acetamido)-4-fluorobenzoate (29-Int). ¹H NMR (400 MHz, CDCl₃): δ 9.94 (s, 1H), 9.10-8.85 (m, 1H), 7.82 (s, 1H), 7.54-7.30 (m, 6H), 7.26-7.21 (m, 1H), 7.21-7.10 (m, 1H), 7.01 (d, J=8.3 Hz, 1H), 5.64-4.45 (m, 5H), 4.36-4.06 (m, 4H), 3.95 (s, 3H). Mixture of rotamers. MS (m/z): 563.1 (M+H)⁺.

Step 2

Methyl 3-(2-(N-benzyl-8-chloro-1-methyl-1,4-dihydrochromeno[4,3-c]pyrazole-3-carboxamido)acetamido)-4-fluorobenzoate (29-Int) (0.14 mmol) was dissolved in THF/MeOH/H₂O (3:2:1, 5.0 mL) and followed by addition of LiOH monohydrate (0.85 mmol). The reaction mixture was stirred at room temperature for 2 hrs. Solvents were removed under vacuum and acidified to pH=3.0 by addition of 3N HCl. Solid was collected and dried to give 3-(2-(8-chloro-N-(2-fluorobenzyl)-1-methyl-1,4-dihydrochromeno[4,3-c]pyrazole-3-carboxamido)acetamido)-5-fluorobenzoic acid. ¹H NMR (400 MHz, DMSO): δ 10.11-9.96 (m, 1H), 8.67-8.53 (m, 1H), 7.78-7.66 (m, 2H), 7.43-7.26 (m, 7H), 7.11-7.03 (m, 1H), 5.48-4.10 (m, 9H). Mixture of rotamers. MS (m/z): 549.1 (M+H)⁺.

The following compounds were prepared according to the procedures described in Example 2 using the appropriate intermediates.

| Compound | Structure | Characterization Data |
| --- | --- | --- |
| 30 | 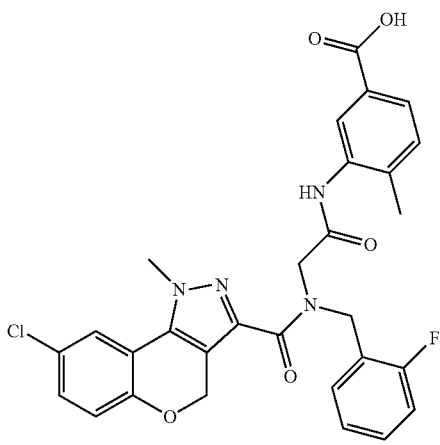 | ¹H NMR (400 MHz, DMSO): δ 10.17-10.01 (m, 1H), 8.64-8.49 (m, 1H), 7.75-7.67 (m, 2H), 7.48-7.30 (m, 4H), 7.26-7.17 (m, 2H), 7.09-7.02 (m, 1H), 5.43-4.12 (m, 9H). Mixture of rotamers. MS (m/z): 563.2 (M + H)⁺. |
| 31 | 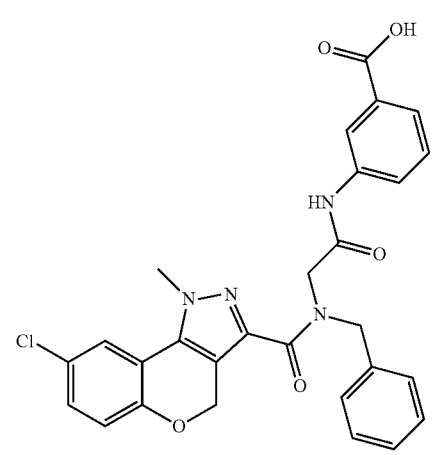 | ¹H NMR (400 MHz, DMSO): δ 10.26-10.18 (m, 1H), 8.27-8.19 (m, 1H), 7.82-7.76 (m, 1H), 7.74-7.66 (m, 1H), 7.65-7.59 (m, 1H), 7.47-7.40 (m, 1H), 7.40-7.26 (m, 6H), 7.10-7.00 (m, 1H), 5.49-4.04 (m, 9H). Mixture of rotamers. MS (m/z): 531.1 (M + H)⁺. |

-continued
| Compound | Structure | Characterization Data |
|---|---|---|
| 32 | 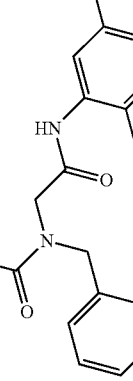 | $^1$H NMR (400 MHz, DMSO): δ 10.10-9.98 (m, 1H), 8.67-8.53 (m, 1H), 7.76-7.67 (m, 1H), 7.61-7.51 (m, 1H), 7.42-7.34 (m, 5H), 7.34-7.26 (m, 1H), 7.19-7.11 (m, 1H), 7.10-7.03 (m, 1H), 5.47-4.05 (m, 9H). Mixture of rotamers. MS (m/z): 533.1 (M + H)$^+$. |
| 33 | 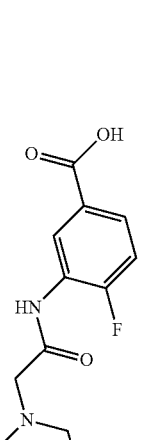 | $^1$H NMR (400 MHz, DMSO): δ 10.11-9.97 (m, 1H), 8.68-8.52 (m, 1H), 7.78-7.66 (m, 2H), 7.42-7.34 (m, 5H), 7.34-7.25 (m, 2H), 7.14-6.99 (m, 2H), 5.46-4.09 (m, 9H). Mixture of rotamers. MS (m/z): 515.1 (M + H)$^+$. |
Example 2A
3-(2-(9-chloro-N-(2-fluorobenzyl)-1-methyl-4,5-dihydro-1H-benzo[2,3]oxepino[4,5-c]pyrazole-3-carboxamido)acetamido)-4-fluorobenzoic acid (Compound 34)
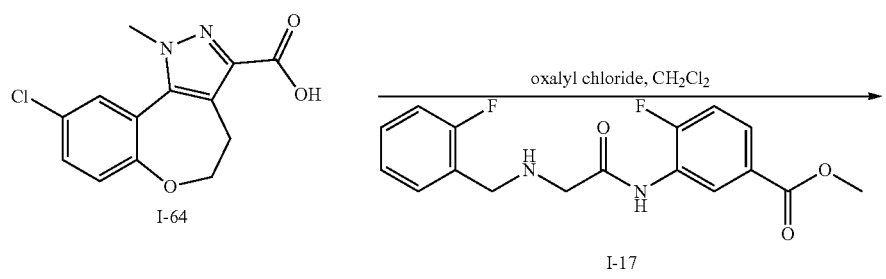

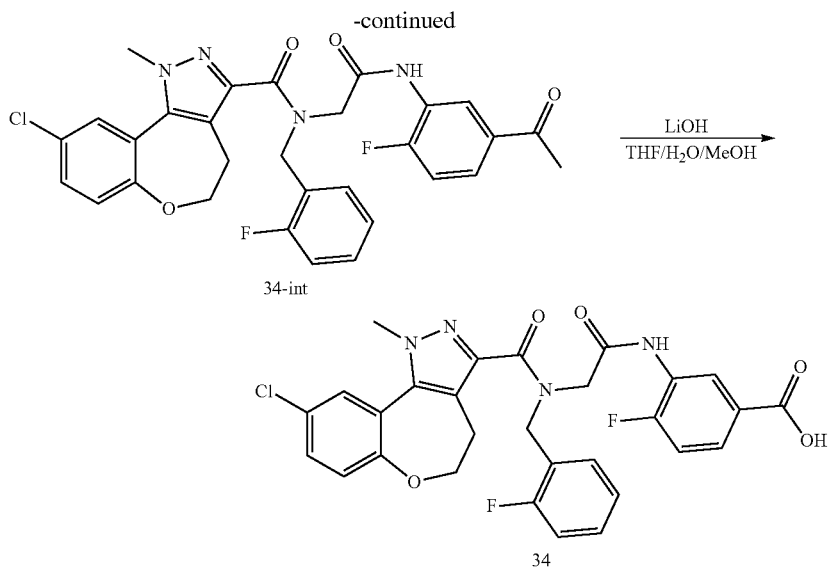

Step 1

To a suspension of the 9-chloro-1-methyl-4,5-dihydro-1H-benzo[2,3]oxepino[4,5-c]pyrazole-3-carboxylic acid (1.8 mmol) in $CH_2Cl_2$ (10 mL) was added catalytic amount of DMF (25 uL) and dropwise oxalyl chloride (8.9 mmol) at 0° C. The resulting suspension was warmed up to room temperature and stirred for 1 hr. The solvent was removed under vacuum to dryness completely. The obtained residue was dissolved with $CH_2Cl_2$ (10 mL) and then dropwise into a solution of methyl 4-fluoro-3-(2-((2-fluorobenzyl)amino)acetamido)benzoate (I-17) (1.8 mmol) in $CH_2Cl_2$ (10 mL) in the presence of DIEA (3.6 mmol). The reaction mixture was stirred for 30 mins at room temperature and then was charged with 50 mL water. Organic layer was separated and aqueous layer was extracted with $CH_2Cl_2$ (50 mL). Combined organic layers were washed with $H_2O$ and brine successively, dried over $Na_2SO_4$, filtered and concentrated to give the crude product which was purified by column chromatography (0-60% EtOAc in hexanes) to give N-(2-((5-acetyl-2-fluorophenyl)amino)-2-oxoethyl)-9-chloro-N-(2-fluorobenzyl)-1-methyl-4,5-dihydro-1H-benzo[2,3]oxepino[4,5-c]pyrazole-3-carboxamide. $^1$H NMR (400 MHz, $CDCl_3$): δ 10.11 (s, 1H), 8.74 (s, 1H), 7.72 (s, 1H), 7.38-7.31 (m, 3H), 7.27-7.22 (m, 1H), 7.12-6.97 (m, 3H), 5.28-4.79 (m, 2H), 4.38 (t, J=6.4 Hz, 3H), 4.05-3.94 (m, 4H), 3.84 (s, 3H), 3.13 (t, J=6.4 Hz, 2H). MS (m/z): 595.1 $(M+H)^+$.

Step 2

N-(2-((5-acetyl-2-fluorophenyl)amino)-2-oxoethyl)-9-chloro-N-(2-fluorobenzyl)-1-methyl-4,5-dihydro-1H-benzo[2,3]oxepino[4,5-c]pyrazole-3-carboxamide (1.6 mmol) was dissolved in $THF/MeOH/H_2O$ (3:2:1, 10 mL) and followed by addition of LiOH monohydrate (9.7 mmol). The reaction mixture was stirred at room temperature for 4 hr and diluted with 10 ml of water and acidified to pH=3.0. Solid was collected and dried to yield 3-(2-(9-chloro-N-(2-fluorobenzyl)-1-methyl-4,5-dihydro-1H-benzo[2,3]oxepino[4,5-c]pyrazole-3-carboxamido)acetamido)-4-fluorobenzoic acid. $^1$H NMR (400 MHz, DMSO): δ 10.03 (s, 1H), 8.69-8.48 (m, 1H), 7.84-7.66 (m, 2H), 7.52-7.30 (m, 4H), 7.28-7.12 (m, 3H), 5.18-4.20 (m, 6H), 4.05-3.92 (m, 3H), 3.11-2.93 (m, 2H). Mixture of rotamers. MS (m/z): 581.1 $(M+H)^+$.

Example 3

3-(2-(8-chloro-N-(2-fluorobenzyl)-1-methyl-1,4-dihydrochromeno[4,3-c]pyrazole-3-carboxamido)acetamido)benzoic acid (Compound 35)

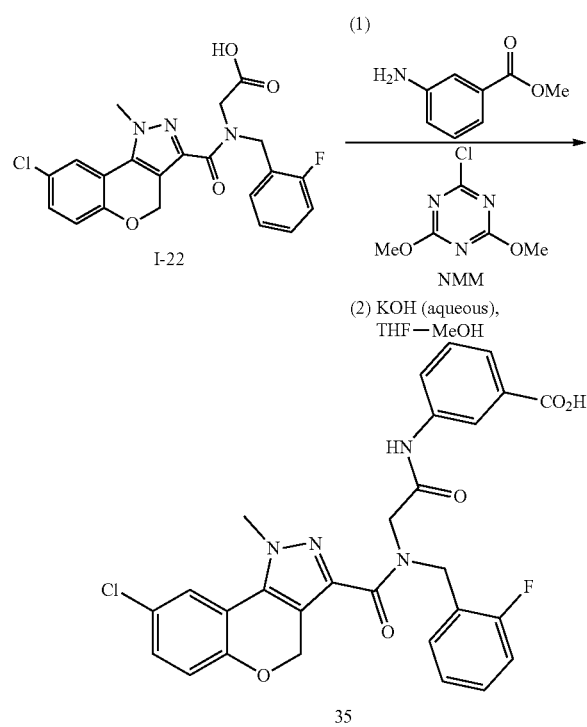

To a 40 mL reaction vessel was added reagents in the following order: 2-(8-chloro-N-(2-fluorobenzyl)-1-methyl-1,4-dihydrochromeno[4,3-c]pyrazole-3-carboxamido)acetic acid (I-22) (0.10 mmol), THF (2 mL), and N-methyl morpholine (1.4 mmol). This was stirred until complete dissolution. Next was added 2-chloro-4,6-dimethoxy-1,3,5-triazine (0.20 mmol) and this solution was stirred for 20 mins at 50° C. until a white precipitate fully formed. The precipitate was physically agitated to ensure all solids were well stirred. Next was added methyl 3-aminobenzoate (0.30 mmol) and the reaction was stirred for 30 mins at 50° C. and then diluted with 5 mL of MeOH and then directly purified by acetic acid modified (0.05%) reverse-phase chromatography (30 to 80%, ACN/water). Ester intermediate was used without further purification and was dissolved in 2 mL of MeOH, 2 mL of THF, and treated with 1 mL of 1 N KOH aqueous solution (1.0 mmol). After heating the homogenous solution to 60° C. for 30 mins the reaction was cooled to room temperature, quenched with AcOH (17 N, approx 0.06 mL) to about pH-6. The reaction was diluted with ethyl acetate (30 mL), rinsed with 2×5 mL of water, and the ethyl acetate fraction was partially concentrated to give 3-(2-(8-chloro-N-(2-fluorobenzyl)-1-methyl-1,4-dihydrochromeno[4,3-c]pyrazole-3-carboxamido)acetamido)benzoic acid as a white solid. $^1$H NMR (400 MHz, DMSO): δ 11.91 (br s, 1H), 10.15 (br s, 1H), 8.26-8.20 (m, 1H), 7.85-7.62 (m, 3H), 7.48-7.29 (m, 4H), 7.20 (app q, J=7.5 Hz, 2H), 7.05 (dd, J=1.7, 8.7 Hz, 1H), 5.39-5.35 (m, 2H), 4.84-4.70 (m, 2H), 4.23-4.10 (m, 5H). Mixture of rotamers. MS (m/z): 549.2/551.2 (M+H)$^+$ (chlorine isotope pattern).

Example 4

3-(2-(8-chloro-N-(cyclopentylmethyl)-1-methyl-1,4-dihydrochromeno[4,3-c]pyrazole-3-carboxamido) acetamido)-4-fluorobenzoic acid (Compound 36)

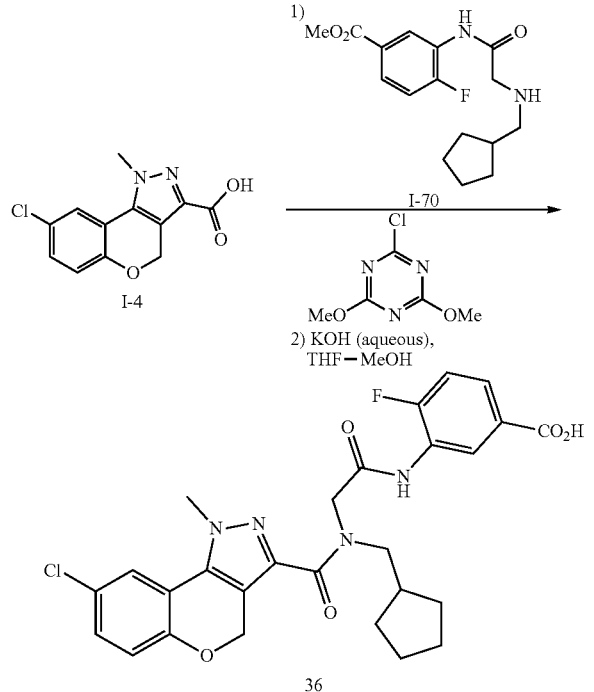

To a 40 mL reaction vessel was added reagents in the following order: 8-chloro-1-methyl-1,4-dihydrochromeno[4,3-c]pyrazole-3-carboxylic acid (I-4) (0.10 mmol, THF (3 mL) and N-methyl morpholine (1.0 mmol). This was stirred until complete dissolution. Next was added 2-chloro-4,6-dimethoxy-1,3,5-triazine (0.11 mmol) and this solution was stirred for 20 mins at 50 C until a white precipitate fully formed. The precipitate was physically agitated with rapid stirring to ensure all solids were well mixed. Next was added methyl 3-(2-((cyclopentylmethyl)amino) acetamido)-4-fluorobenzoate (I-70) (0.10 mmol) and the reaction was stirred for 30 mins at 50° C. and then diluted with 5 mL of MeOH and then purified by acetic acid modified (0.05%) reverse phase chromatography (30 to 80%, water/ACN). The intermediate ester was carried without further manipulation and was dissolved in 2 mL of MeOH, 2 mL of THF, and treated with 1 mL of 1 N KOH aqueous solution (1.0 mmol). After heating the homogenous solution to 60° C. for 30 mins the reaction was cooled to room temperature, quenched with AcOH (17 N, approx. 0.06 mL) to about pH=6. The reaction was diluted with 30 mL of ethyl acetate, rinsed with 2×5 mL of water, and the ethyl acetate fraction was partially concentrated to give 3-(2-(8-chloro-N-(cyclopentylmethyl)-1-methyl-1,4-dihydrochromeno[4,3-c]pyrazole-3-carboxamido)acetamido)-4-fluorobenzoic acid as a white solid. $^1$H NMR (400 MHz, DMSO): δ 10.06-10.01 (m, 1H), 8.46-8.40 (m, 1H), 7.82-7.78 (m, 2H), 7.36-7.32 (m, 2H), 7.03-7.00 (m, 1H), 5.32-5.20 (m, 2H), 4.89 (br s, 1H), 4.29 (br s, 2H), 4.24-3.90 (m, 4H), 2.10-2.05 (m, 1H), 1.87-1.67 (m, 6H), 1.09-1.02 (m, 2H). Mixture of rotamers. MS (m/z): 541.2/542.2 (M+H)$^+$ (chlorine isotope pattern).

Example 5

3-(2-(8-chloro-N-(cyclopentylmethyl)-1-methyl-1,4-dihydrochromeno[4,3-c]pyrazole-3-carboxamido) acetamido)benzoic acid (Compound 37)

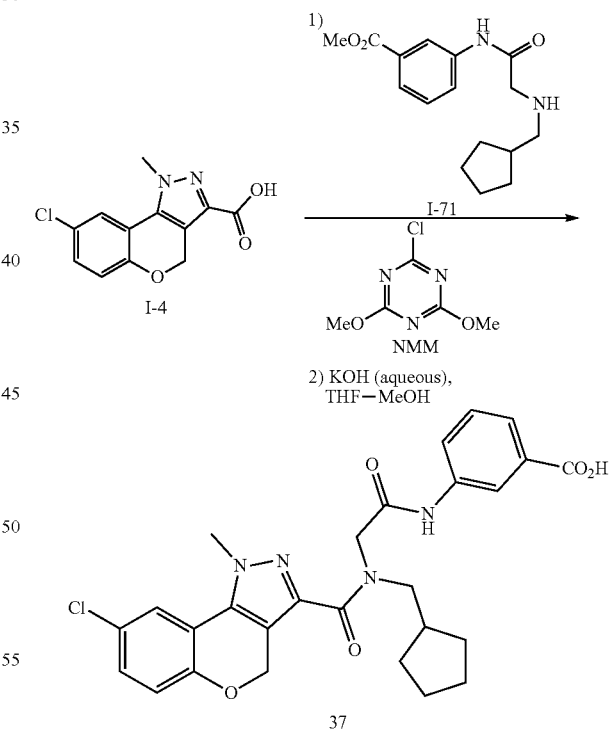

3-(2-(8-chloro-N-(cyclopentylmethyl)-1-methyl-1,4-dihydrochromeno[4,3-c]pyrazole-3-carboxamido)acetamido)benzoic acid was made following the procedures described in Example 4, except for the substitution of methyl 3-(2-((cyclopentylmethyl)amino)acetamido)benzoate (I-71) in the place of methyl 3-(2-((cyclopentylmethyl)amino)acetamido)-4-fluorobenzoate (I-70). $^1$H NMR (400 MHz, DMSO): δ 12.66 (br s, 1H), 10.18-10.14 (m, 1H), 8.23 (app d, J=10.0 Hz, 1H), 7.89-7.12 (m, 5H), 7.06-7.02 (m, 1H), 5.35-5.25 (m, 2H), 4.89 (br s, 1H), 4.72 (br s, 2H), 4.43 (br s, 1H), 4.14-4.00 (m, 3H), 1.99-0.96 (m, 9H). Mixture of rotamers. MS (m/z): 523.2/525.2 (M+H)$^+$ (chlorine isotope pattern).

Example 6

3-(2-(8-chloro-N-(2-fluorobenzyl)-1-methyl-1,4-dihydrochromeno[4,3-c]pyrazole-3-carboxamido)acetamido)-5-fluorobenzoic acid (Compound 38)

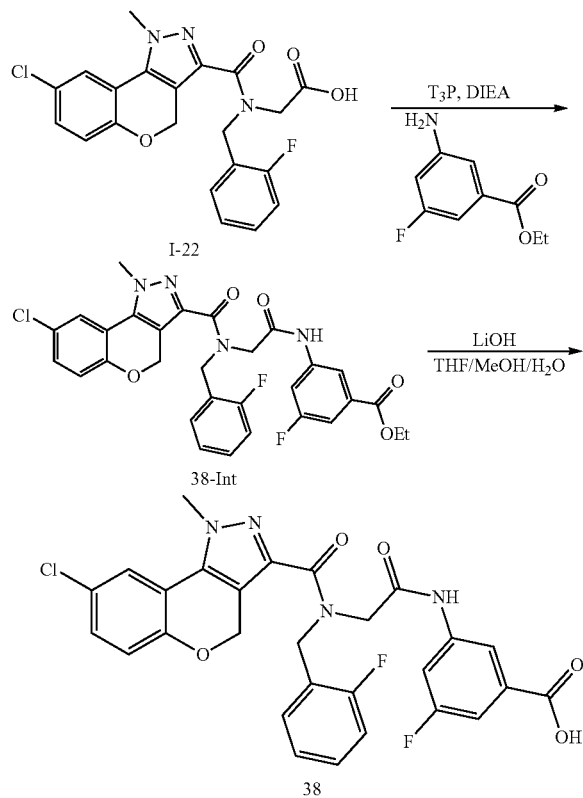

Step 1

To a mixture of 2-(8-chloro-N-(2-fluorobenzyl)-1-methyl-1,4-dihydrochromeno[4,3-c]pyrazole-3-carboxamido)acetic acid (I-22) (0.032 mmol), DIEA (0.16 mmol) and ethyl 3-amino-5-fluorobenzoate (0.05 mmol) in EtOAc (0.5 mL) was added T$_3$P (50% wt in EtOAc, 0.5 mL) and stirred at room temperature for 30 mins. Purification by HPLC yielded ethyl 3-(2-(8-chloro-N-(2-fluorobenzyl)-1-methyl-1,4-dihydrochromeno[4,3-c]pyrazole-3-carboxamido)acetamido)-5-fluorobenzoate (38-Int). $^1$H NMR (400 MHz, CDCl$_3$): δ 9.38-8.71 (m, 1H), 7.95-7.69 (m, 1H), 7.59 (s, 1H), 7.49-7.39 (m, 3H), 7.26-7.22 (m, 1H), 7.14 (td, J=1.1, 7.5 Hz, 1H), 7.08-7.02 (m, 1H), 7.00 (d, J=8.7 Hz, 1H), 5.53 (s, 2H), 5.08-4.81 (m, 1H), 4.67-4.47 (m, 1H), 4.40 (q, J=7.1 Hz, 2H), 4.17 (s, 3H), 1.42 (t, J=7.1 Hz, 3H). MS (m/z): 595.1 (M+H)$^+$.

Step 2

Ethyl 3-(2-(8-chloro-N-(2-fluorobenzyl)-1-methyl-1,4-dihydrochromeno[4,3-c]pyrazole-3-carboxamido)acetamido)-5-fluorobenzoate (38-Int) (8 mg, 0.0134 mmol) was dissolved in THF/MeOH/H$_2$O (3:2:1, 5.0 mL) and followed by addition of LiOH monohydrate (0.08 mmol). The reaction mixture was stirred at room temperature for 2 hrs. The solvents were removed under vacuum and acidified to pH=3.0 by addition of 3N HCl to give 3-(2-(8-chloro-N-(2-fluorobenzyl)-1-methyl-1,4-dihydrochromeno[4,3-c]pyrazole-3-carboxamido)acetamido)-5-fluorobenzoic acid as a solid. $^1$H NMR (400 MHz, DMSO): δ 10.59-10.47 (m, 1H), 7.99 (s, 1H), 7.87-7.79 (m, 1H), 7.79-7.72 (m, 1H), 7.53-7.43 (m, 1H), 7.43-7.36 (m, 3H), 7.32-7.23 (m, 2H), 7.14-7.08 (m, 1H), 5.51-4.13 (m, 9H). Mixture of rotamers. MS (m/z): 567.0 (M+H)$^+$.

The following compounds were prepared according to the procedures described in Example 6 using the appropriate intermediates.

| Compound | Structure | Characterization Data |
|---|---|---|
| 39 | 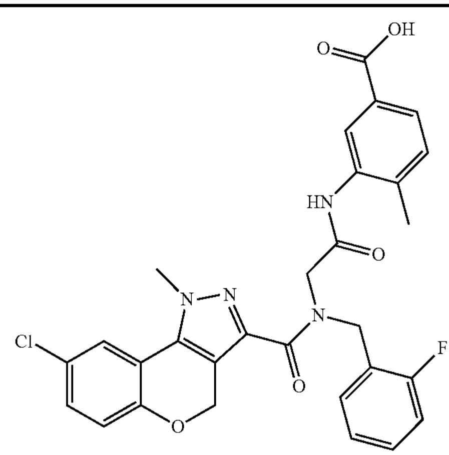 | MS (m/z) 563.1 (M + H)$^+$; r.t. = 1.886 |

Example 7

3-(2-(8-chloro-N-(2-fluorobenzyl)-1-methyl-1,4-dihydrochromeno[4,3-c]pyrazole-3-carboxamido)acetamido)-2-methylpropanoic acid (Compound 40)

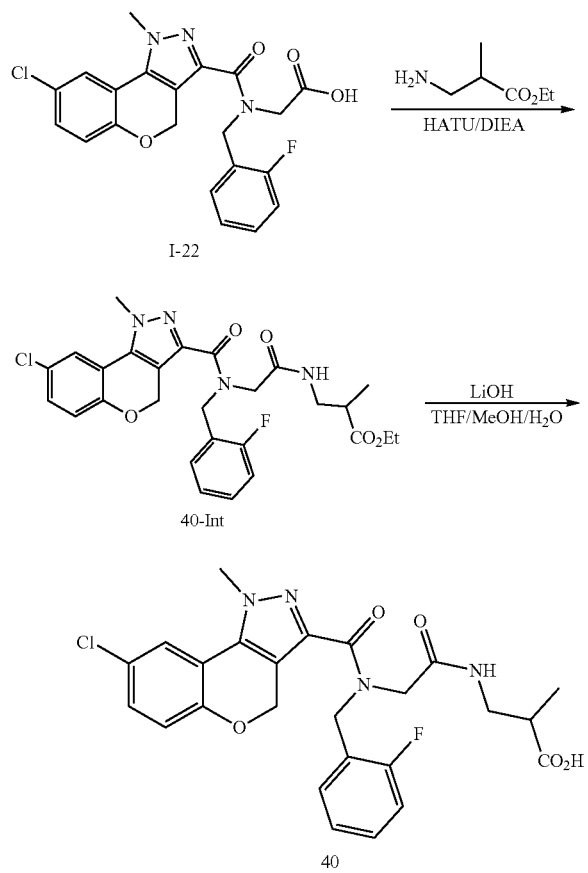

Step 1

To a mixture of 2-(8-chloro-N-(2-fluorobenzyl)-1-methyl-1,4-dihydrochromeno[4,3-c]pyrazole-3-carboxamido)acetic acid (I-22) (0.15 mmol), DIEA (0.45 mmol) and HATU (0.18 mmol) in DMF (1 mL) was added ethyl 3-amino-2-methylpropanoate (0.22 mmol) and stirred at room temperature for 10 mins. Then the reaction was diluted with 20 mL water and extracted with EtOAc (20 mL, twice). Combined organic layers were washed with H$_2$O and brine successively, dried over Na$_2$SO$_4$, filtered and concentrated to give the crude product which was purified by column chromatography (0-80% EtOAc in hexanes) to yield ethyl 3-(2-(8-chloro-N-(2-fluorobenzyl)-1-methyl-1,4-dihydrochromeno[4,3-c]pyrazole-3-carboxamido)acetamido)-2-methylpropanoate (40-Int). $^1$H NMR (400 MHz, CDCl$_3$): δ 7.47 (d, J=2.4 Hz, 1H), 7.43-7.33 (m, 1H), 7.33-7.29 (m, 1H), 7.22 (dd, J=2.4, 8.7 Hz, 1H), 7.14 (dt, J=3.8, 7.5 Hz, 1H), 7.08 (t, J=9.2 Hz, 1H), 6.98 (d, J=8.7 Hz, 1H), 5.60-4.74 (m, 5H), 4.25-3.89 (m, 6H), 3.62-3.39 (m, 1H), 3.40-3.24 (m, 1H), 2.72-2.61 (m, 1H), 1.23-1.14 (m, 6H). Mixture of rotamers. MS (m/z): 543.1 (M+H)$^+$.

Step 2

Ethyl 3-(2-(8-chloro-N-(2-fluorobenzyl)-1-methyl-1,4-dihydrochromeno[4,3-c]pyrazole-3-carboxamido)acetamido)-2-methylpropanoate (40-Int) (0.125 mmol) was dissolved in THF/MeOH/H$_2$O (3:2:1, 5.0 mL) and followed by addition of LiOH monohydrate (0.75 mmol). The reaction mixture was stirred at room temperature for 2 hr. The solvents were removed under vacuum then water (5 mL) was added and acidified to pH=3.0 by addition of 3N HCl to give 3-(2-(8-chloro-N-(2-fluorobenzyl)-1-methyl-1,4-dihydrochromeno[4,3-c]pyrazole-3-carboxamido)acetamido)-2-methylpropanoic acid. $^1$H NMR (400 MHz, DMSO): δ 12.26 (s, 1H), 8.10-7.99 (m, 1H), 7.73-7.67 (m, 1H), 7.40-7.29 (m, 3H), 7.24-7.16 (m, 2H), 7.09-7.02 (m, 1H), 5.43-3.89 (m, 9H), 3.32-3.06 (m, 2H), 1.06-0.97 (m, 3H). Mixture of rotamers. MS (m/z): 515.0 (M+H)$^+$.

The following compounds were prepared according to the procedures described in Example 7 using the appropriate intermediates.

| Compound | Structure | Characterization Data |
|---|---|---|
| 41 | 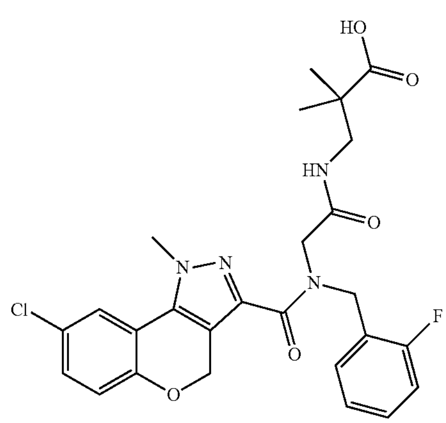 | $^1$H NMR (400 MHz, CDCl$_3$): δ 7.35 (s, 1H), 7.33-7.24 (m, 1H), 7.15-7.08 (m, 1H), 7.08-6.94 (m, 2H), 6.94-6.80 (m, 2H), 5.45-3.93 (m, 9H), 3.33-3.19 (m, 2H), 1.15-1.05 (m, 6H). Mixture of rotamers. MS (m/z): 529.1 (M + H)$^+$. |

| Compound | Structure | Characterization Data |
|---|---|---|
| 42 | 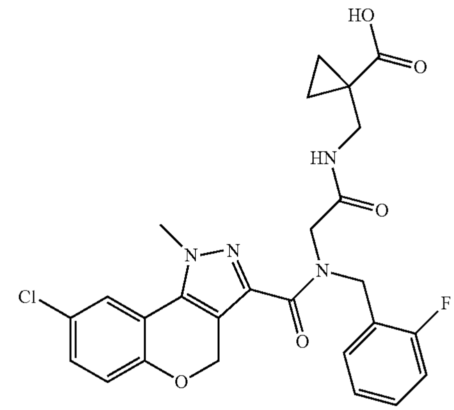 | $^1$H NMR (400 MHz, DMSO): δ 7.99-7.88 (m, 1H), 7.73-7.68 (m, 1H), 7.39-7.29 (m, 3H), 7.23-7.14 (m, 2H), 7.08-7.03 (m, 1H), 5.42-5.26 (m, 3H), 4.66-4.55 (m, 2H), 4.19-3.89 (m, 4H), 3.32-3.27 (m, 2H), 1.03-0.73 (m, 4H). Mixture of rotamers. MS (m/z): 527.3 (M + H)$^+$. |

Example 8

4-(2-(8-chloro-N-(2-fluorobenzyl)-1-methyl-1,4-dihydrochromeno[4,3-c]pyrazole-3-carboxamido)ethoxy)-3-fluorobenzoic acid (Compound 43)

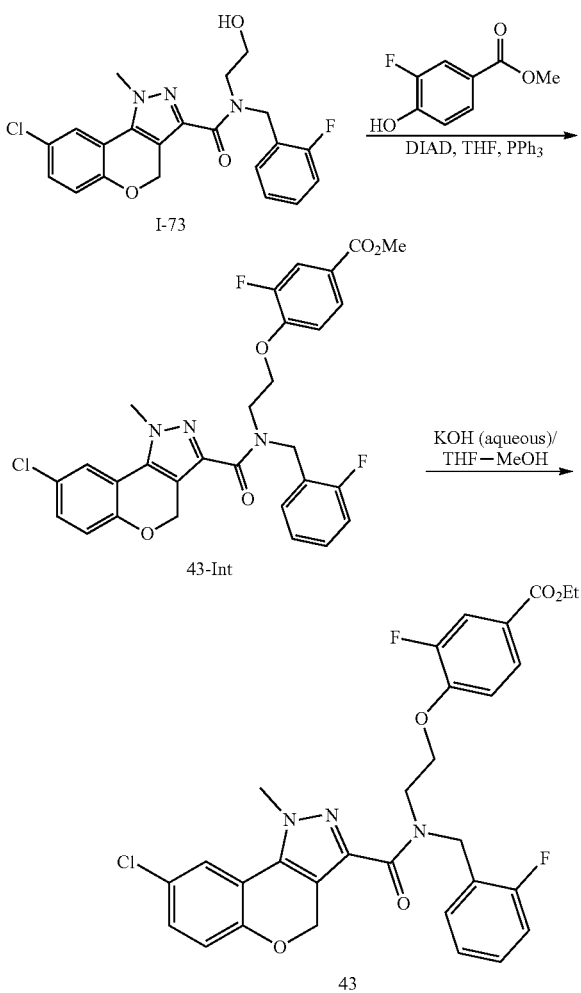

Step 1

To 8-chloro-N-(2-fluorobenzyl)-N-(2-hydroxyethyl)-1-methyl-1,4-dihydrochromeno[4,3-c]pyrazole-3-carboxamide (I-73) (0.45 mmol) was added THF (7 mL) and methyl 3-fluoro-4-hydroxybenzoate (0.88 mmol), triphenyl phosphine solid (0.90 mmol) the resulting solution cooled to 0° C. and lastly DIAD (diisopropyl azodicarboxylate) dropwise (0.20 mL, Aldrich™ commercial stock at 95% weight by weight content, 0.96 mmol). The internal temperature of the reaction maintained at 0° C. for 10 mins, then allowed to warm to room temperature over 20 mins. After a full hr at room temperature, the reaction was diluted with THF (5 mL), filtered, and directly purified by TFA modified (0.05%) reverse phase chromatography (40 to 90%, water/ACN). All fractions were reduced to dryness under vacuum and subjected to a free base event using polymer immobilized carbonate (SPE-CO3H Varian cartridge, 0.90 nominal load with MeOH mobilizer, 10 mL) to give the methyl ethyl intermediate as an off white powder (43-Int). $^1$H NMR (400 MHz, DMSO): δ 7.78-7.69 (m, 2H), 7.63 (br s, 1H), 7.42-7.38 (m, 3H), 7.18 (app dt, J=12.3, 8.0 Hz, 3H), 7.04 (app d, J=8.0 Hz, 1H), 5.40-5.35 (m, 2H), 5.29 (br s, 1H), 4.83 (br s, 1H), 4.52-4.38 (m, 2H), 4.15-4.10 (m, 2H), 3.93 (s, 3H) 3.73 (s, 3H). Mixture of rotamers. MS (m/z): 568.2/570.2 (M+H)$^+$ (chlorine isotope pattern).

Step 2

The ester, methyl 4-(2-(8-chloro-N-(2-fluorobenzyl)-1-methyl-1,4-dihydrochromeno[4,3-c]pyrazole-3-carboxamido)ethoxy)-3-fluorobenzoate (43-Int), generated in the previous step was then dissolved in THF (10 mL), MeOH (2 mL), and 1.0 M KOH (2.0 mmol). The resulting homogenous solution was heated to 60° C. for 2 hrs. At this time the reaction was cooled back to room temperature, quenched with 0.12 mL of AcOH (2 mmol, to PH-6 using Whatman-4 color-strip indicator paper to monitor). The reaction was then diluted with water (20 mL) and extracted with ethyl acetate (3×100 mL). The organic extracts were further washed with water (2×15 mL). The organic extracts were removed to dryness and allowed to precipitate from MeOH/water (10 mL, 9:1) to give 4-(2-(8-chloro-N-(2-fluorobenzyl)-1-methyl-1,4-dihydrochromeno[4,3-c]pyrazole-3-carboxamido)ethoxy)-3-fluorobenzoic acid as a white solid. $^1$H NMR (400 MHz, DMSO): δ 12.51 (br s, 1H), 7.89-7.19 (m, 9H), 7.07 (dd, J=1.7, 8.7 Hz, 1H), 5.30-5.15 (m, 3H), 4.85 (br s, 1H), 4.43-4.18 (m, 3H, 4.04-3.99 (m, 3H), 3.78 (m, 1H). Mixture of rotamers. MS (m/z): 554.1/556.1 (M+H)$^+$ (chlorine isotope pattern).

The following compounds were prepared according to the procedures described in Example 8 using the appropriate intermediates.

| Compound | Structure | Characterization Data |
|---|---|---|
| 44 | 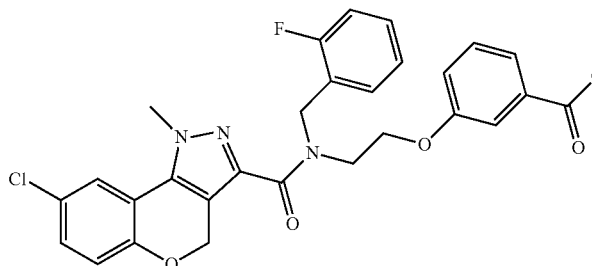 | $^1$H NMR (400 MHz, DMSO): δ 12.56 (br s, 1H), 7.79-7.10 (m, 10 H), 7.06 (dd, J = 1.7, 8.7 Hz, 1H), 5.40-5.25 (m, 3H), 4.82 (br s, 1H), 4.33-4.13 (m, 3H), 4.04 (br s, 3H), 3.75 (m, 1H). Mixture of rotamers. MS (m/z): 536.1/538.1 (M + H)$^+$ (chlorine isotope pattern). |
| 45 | 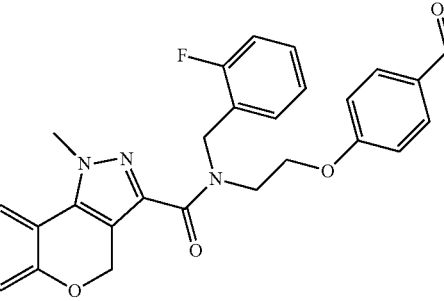 | MS (m/z): 536.2/538.2 (M + H)$^+$ (chlorine isotope pattern); r.t. = 1.608 |
| 46 | 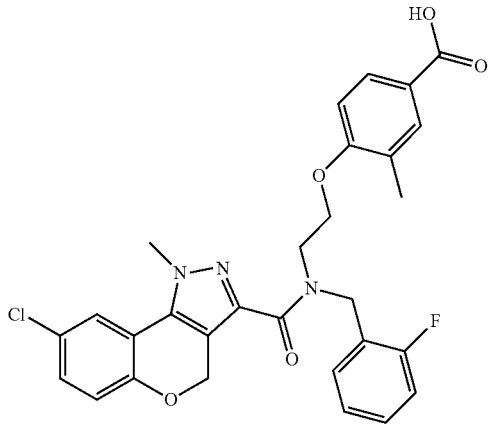 | MS (m/z): 550.2/552.2 (M + H)$^+$ (chlorine isotope pattern); r.t. = 1.632 |
| 47 | 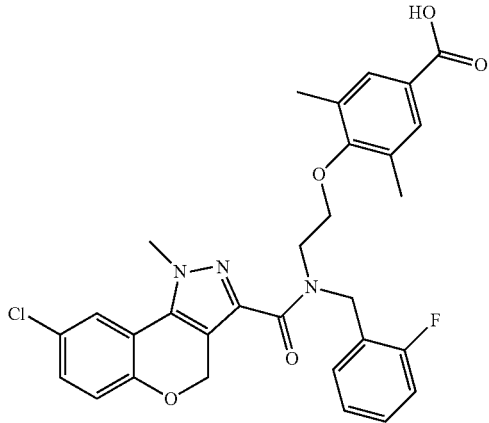 | MS (m/z): 564.2/566.2 (M + H)$^+$ (chlorine isotope pattern); r.t. = 1.759 |

| Compound | Structure | Characterization Data |
|---|---|---|
| 48 | 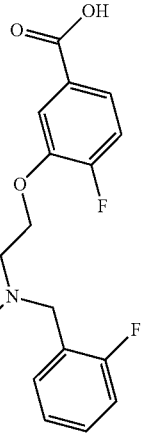 | MS (m/z): 554.2/556.2 (M + H)+ (chlorine isotope pattern); r.t. = 1.750 |
| 49 | 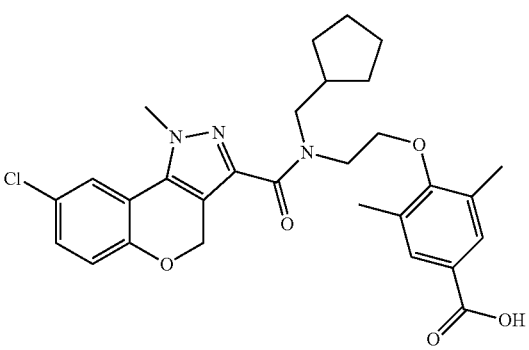 | ¹H NMR (400 MHz, DMSO): δ 12.50 (br s, 1H), 7.82 (app d, J = 8.0 Hz, 1H), 7.75 (br s, 2H), 7.30 (app d, J = 8.0 Hz, 1H), 7.03-7.00 (m, 1H), 5.40-5.30 (m, 2H), 4.30 (br s, 1H), 4.22-3.88 (m, 6H), 3.82-3.78 (m, 1H), 3.56-3.54 (m, 1H), 2.13-2.10 (m, 1H), 2.06 (s, 3H), 2.02 (s, 3H), 1.69-1.38 (m, 6 H), 1.24-1.15 (m, 2H). Mixture of rotamers. MS (m/z): 538.1/540.1 (M + H)+ (chlorine isotope pattern). |
| 50 | 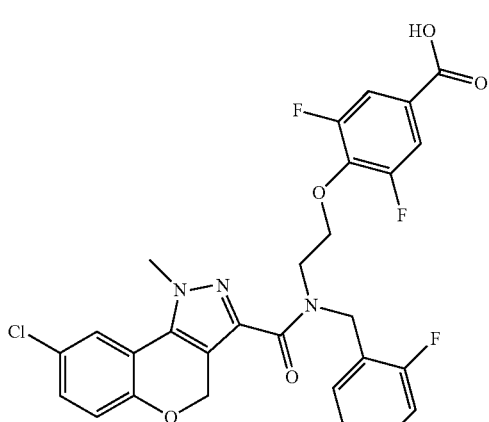 | MS (m/z): 572.2/574.2 (M + H)+ (chlorine isotope pattern); r.t. = 1.690 |

| Compound | Structure | Characterization Data |
|---|---|---|
| 51 | 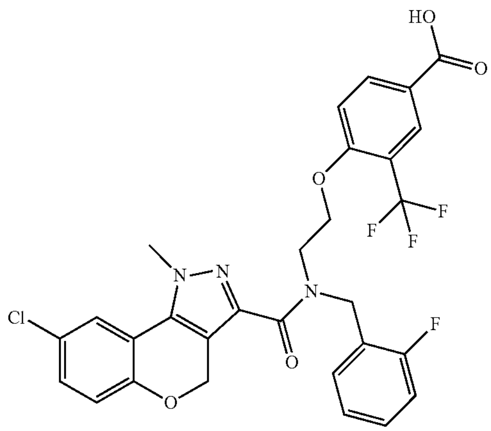 | MS (m/z): 604.3/606.3 (M + H)+ (chlorine isotope pattern); r.t. = 1.760 |
| 52 | 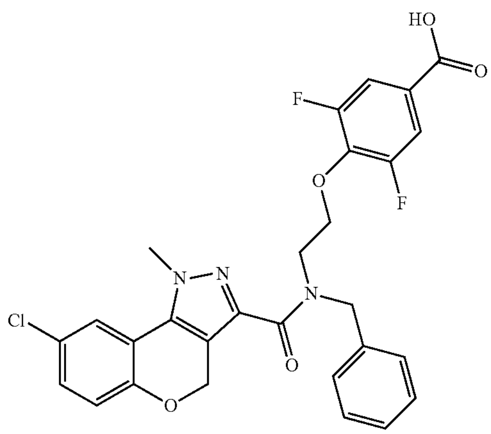 | ¹H NMR (400 MHz, d₄-MeOH): δ 7.59-7.15 (m, 9H), 6.78-6.73 (m, 1H), 5.38-5.24 (m, 3H), 4.85 (br s, 1H, partly obscured), 4.42-4.21 (m, 3H), 4.16-4.04 (m, 3H), 3.69 (app t J = 8.2 Hz, 1H). Mixture of rotamers. MS (m/z): 554.1/556.1 (M + H)+ (chlorine isotope pattern). |
| 53 | 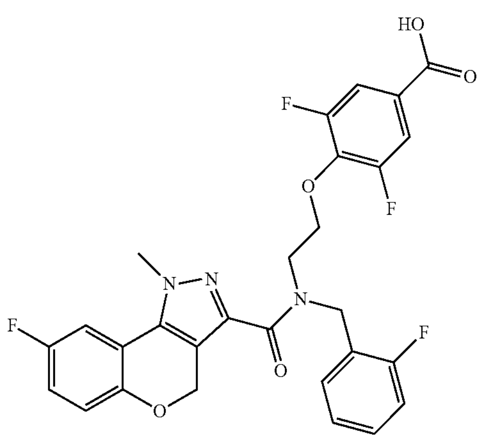 | MS (m/z): 556.2 (M + H)+; r.t. = 1.650 |

| Compound | Structure | Characterization Data |
|---|---|---|
| 54 | 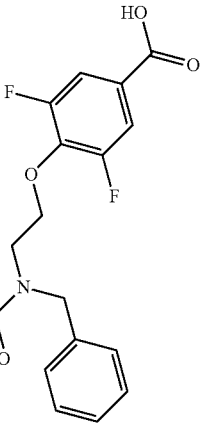 | $^1$H NMR (400 MHz, d$_4$-MeOH): δ 7.52-6.83 (m, 10H), 5.38-5.20 (m, 3H), 4.83 (br s, 1H), 4.43-3.87 (m, 7H). Mixture of rotamers. MS (m/z): 538.1 (M + H)$^+$. |

Example 9

4-(2-(N-benzyl-8-chloro-1-methyl-1,4-dihydro-chromeno[4,3-c]pyrazole-3-carboxamido)ethoxy)-3-fluorobenzoic acid (Compound 55)

Step 1

To a solution of 8-chloro-1-methyl-1,4-dihydrochromeno[4,3-c]pyrazole-3-carboxylic acid (I-4) (0.16 mmol) in anhydrous DMF (1 mL) were added HATU (0.18 mmol), DIEA (0.48 mmol) and methyl 4-(2-(benzylamino)ethoxy)-

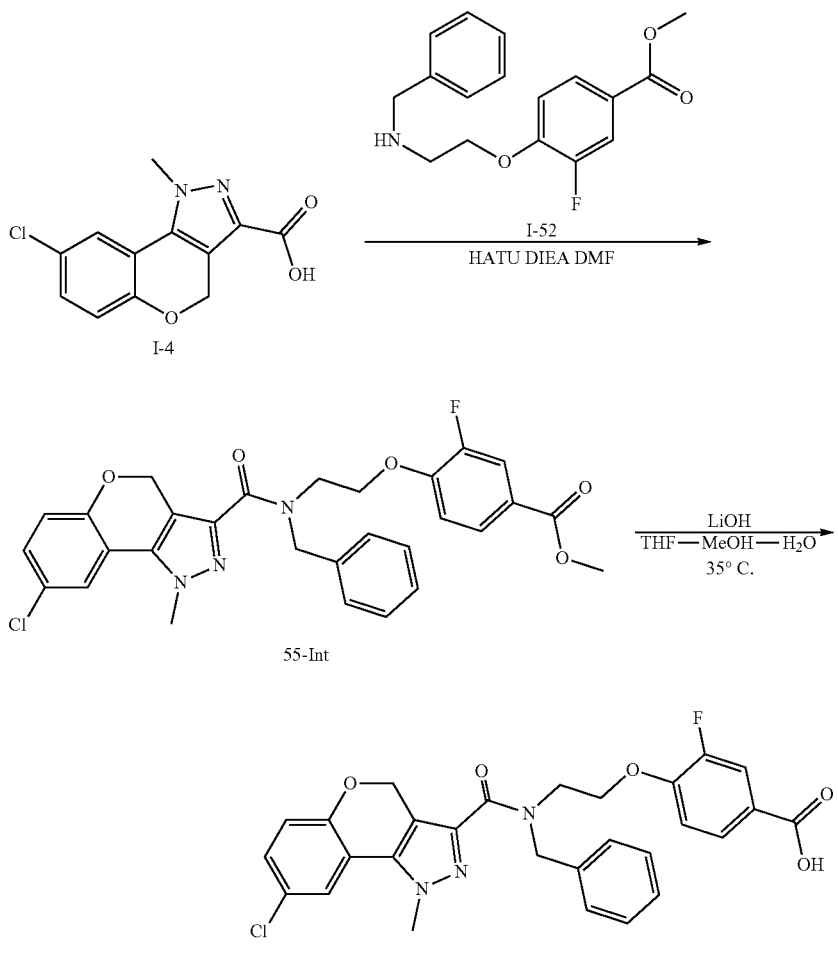

3-fluorobenzoate (I-52) (0.16 mmol) and the resulting mixture was stirred at room temperature until completion (2 hrs). The reaction mixture was then diluted with water (10 mL) and extracted with ethyl acetate (20 mL×3). The organic phase was washed with 1N HCl, water, brine, dried over Na$_2$SO$_4$ and concentrated in vacuum. The crude residue was triturated with MeOH to afford methyl 4-(2-(N-benzyl-8-chloro-1-methyl-1,4-dihydrochromeno[4,3-c]pyrazole-3-carboxamido)ethoxy)-3-fluorobenzoate as white solid (55-Int). MS (m/z): 550.1/552.1 (M+H)$^+$ (chlorine isotope pattern).

Step 2

A suspension of 4-(2-(N-benzyl-8-chloro-1-methyl-1,4-dihydrochromeno[4,3-c]pyrazole-3-carboxamido)ethoxy)-3-fluorobenzoic acid (61-int) (20 mg, 0.036 mmol) in a 3:2:1 THF-MeOH—H$_2$O solution (2 mL) was treated with a 6M solution of LiOH (100 uL) and the resulting mixture was stirred at 35° C. until complete conversion (3 hrs). The reaction mixture was then concentrated under reduced pressure. The crude residue was dissolved in water and 50% acetic acid was added until pH 5 at which point a white solid separated out. The solid was collected by filtration, washed with water and dried under high vacuum to give 4-(2-(N-benzyl-8-chloro-1-methyl-1,4 dihydrochromeno[4,3-c] pyrazole-3-carboxamido)ethoxy)-3-fluorobenzoic acid. $^1$H NMR (400 MHz, DMSO): δ 7.75-6.98 (m, 11H), 5.44-5.30 (m, 5H), 4.45-3.99 (m, 6H). Mixture of rotamers. MS (m/z): 536.2/538.2 (M+H)$^+$ (chlorine isotope pattern).

The following compounds were prepared according to the procedures described in Example 9 using the appropriate intermediates.

| Compound | Structure | Characterization Data |
|---|---|---|
| 56 | 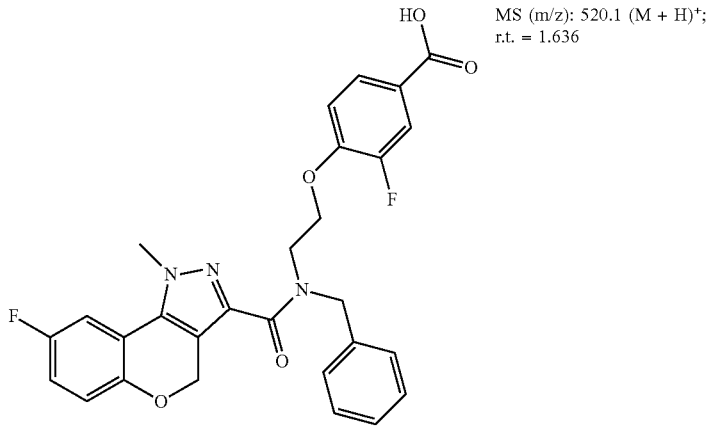 | MS (m/z): 520.1 (M + H)$^+$; r.t. = 1.636 |
| 57 | 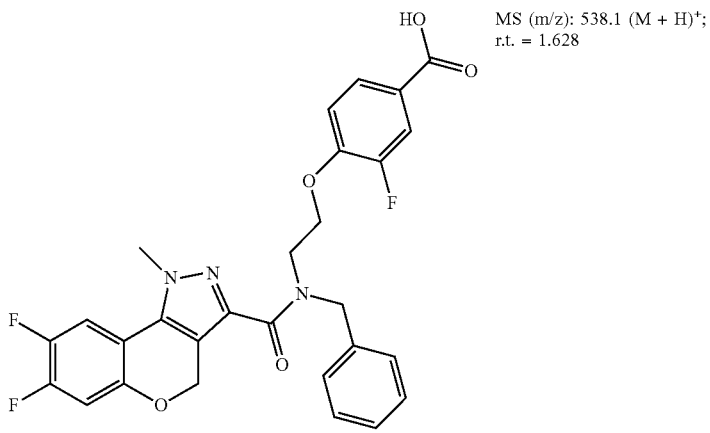 | MS (m/z): 538.1 (M + H)$^+$; r.t. = 1.628 |

| Compound | Structure | Characterization Data |
|---|---|---|
| 58 | 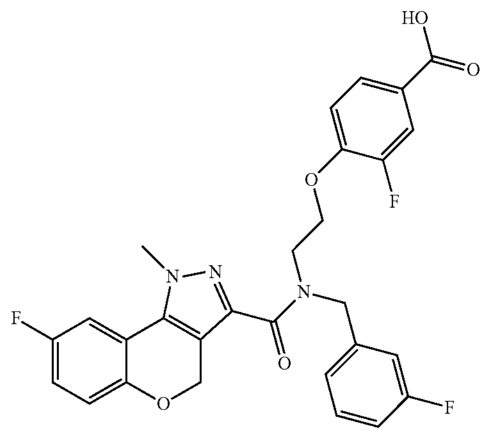 | $^1$H NMR (400 MHz, DMSO): δ 7.75-7.03 (m, 11H), 5.41-5.26 (m, 2H), 4.81 (s, 1H), 4.44-4.34 (m, 3H), 4.20-3.98 (m, 4H), 3.82-3.65 (m, 1H). Mixture of rotamers. MS (m/z): 538.1 (M + H)$^+$ |
| 59 | 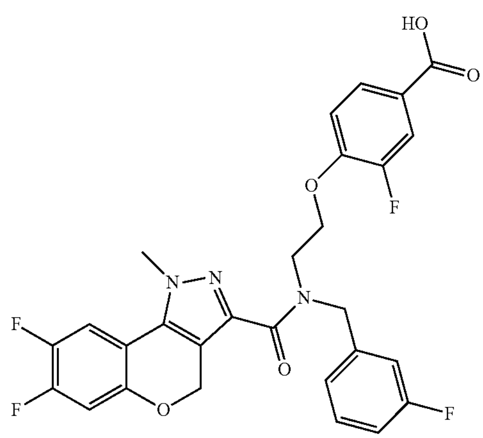 | $^1$H NMR (400 MHz, DMSO): δ 7.85-7.07 (m, 10H), 5.43-5.26 (m, 2H), 4.81 (s, 1H), 4.44-4.28 (m, 3H), 4.14-3.96 (m, 4H), 3.79-3.68 (m, 1H). Mixture of rotamers. MS (m/z): 556.1 (M + H)$^+$ |
| 60 | 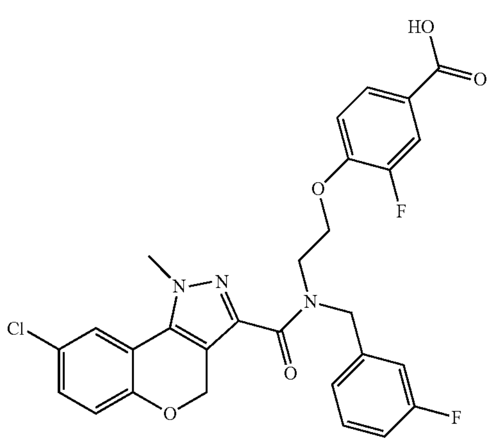 | MS (m/z): 554.1/556.1 (M + H)$^+$ (chlorine isotope pattern); r.t. = 1.667 |

Example 10

3-fluoro-4-(2-(8-fluoro-N-(2-fluorobenzyl)-1-methyl-1,4-dihydrochromeno[4,3-c]pyrazole-3-carboxamido)ethoxy)benzoic acid (Compound 61)

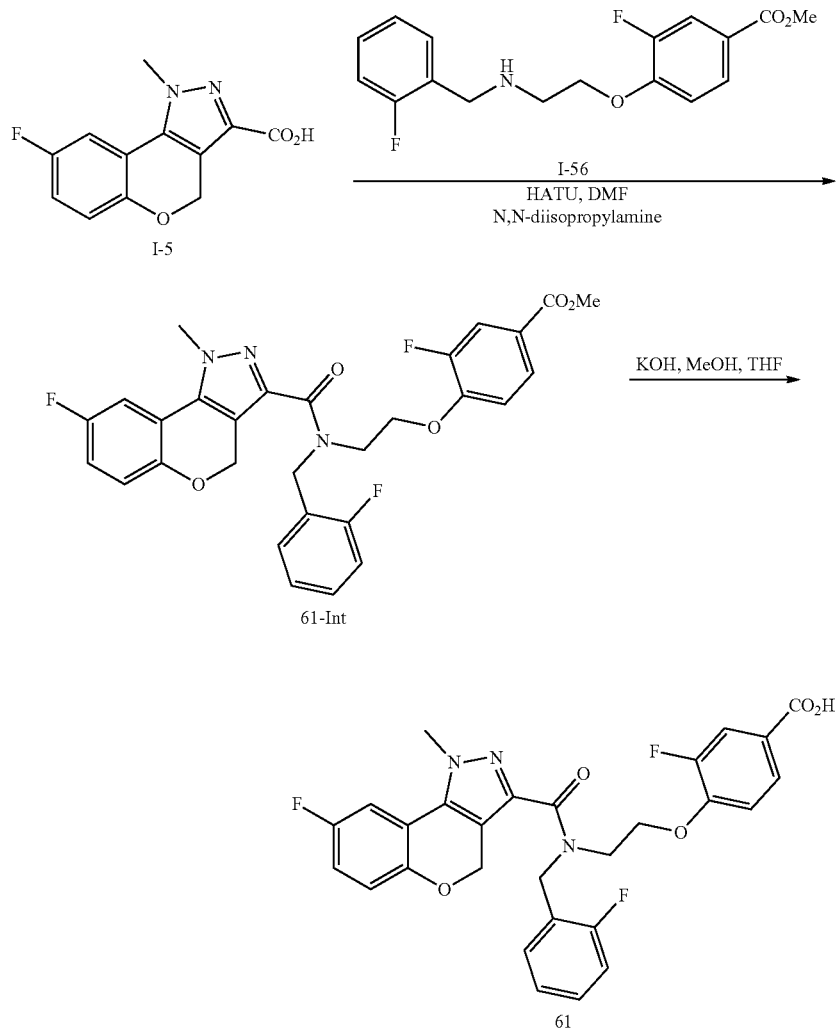

Step 1

HATU (0.22 mmol) was added to a mixture of 8-fluoro-1-methyl-1,4-dihydrochromeno[4,3-c]pyrazole-3-carboxylic acid (I-5) (0.20 mmol), N,N-diisopropylamine (0.44 mmol) and DMF (2 mL) at room temperature. After stirring for 20 mins, amine (I-56) (0.20 mmol) in DMF (1 mL) was added and the reaction mixture was stirred for 4 hrs at room temperature. The mixture was diluted with H$_2$O (10 mL) and EtOAc (10 mL), the layers were separated, and the H$_2$O layer was washed with EtOAc (×2, 10 mL). The combined organic extracts were washed with H$_2$O (10 mL), brine (10 mL), and then dried (MgSO$_4$). After removal of solvent, the crude material was purified by chromatography (solid load, silica gel, 0-60% EtOAc/hexanes) to give methyl 3-fluoro-4-(2-(8-fluoro-N-(2-fluorobenzyl)-1-methyl-1,4-dihydrochromeno[4,3-c]pyrazole-3-carboxamido)ethoxy)benzoate (61-Int) as a white solid. $^1$H NMR (400 MHz, CDCl$_3$): δ 7.84-7.64 (m, 2H), 7.43-7.29 (m, 1H), 7.21-7.13 (m, 1H), 7.13-7.02 (m, 2H), 7.01-6.87 (m, 3H), 5.60-5.54 (m, 1H), 5.50-5.43 (m, 2H), 5.30 (s, 3H), 5.01-4.94 (m, 1H), 4.45-4.37 (m, 2H), 4.37-4.30 (m, 1H), 4.09-4.06 (m, 3H), 3.91-3.84 (m, 2H).

Step 2

KOH (1.0 M in H$_2$O, 1.0 mmol) was added to a solution of methyl 3-fluoro-4-(2-(8-fluoro-N-(2-fluorobenzyl)-1-methyl-1,4-dihydrochromeno[4,3-c]pyrazole-3-carboxamido)ethoxy) benzoate (61-Int) (0.2 mmol) in THF (4.0 mL) and MeOH (1.0 mL) and the solution was stirred at 50° C. for 2 hrs. After removal of solvent (aspirator), the crude residue was diluted with water (10 mL) and the solution was acidified with acetic acid (to pH ~5). The resulting white precipitate was collected by vacuum filtration, washed with H$_2$O (20 mL), and dried overnight on high vacuum to give 3-fluoro-4-(2-(8-fluoro-N-(2-fluorobenzyl)-1-methyl-1,4-dihydrochromeno[4,3-c]pyrazole-3-carboxamido)ethoxy) benzoic acid. $^1$H NMR (400 MHz, DMSO): δ 7.75-7.64 (m, 1H), 7.57-7.01 (m, 9H), 5.51-5.23 (m, 3H), 4.89-4.80 (m, 1H), 4.49-4.29 (m, 3H), 4.13-3.98 (m, 3H), 3.83-3.72 (m, 1H). MS (m/z): 538.2 (M+H)$^+$. Mixture of rotamers.

The following compound was prepared according to the procedures described in Example 10 using the appropriate intermediates.

| Compound | Structure | Characterization Data |
|---|---|---|
| 62 | 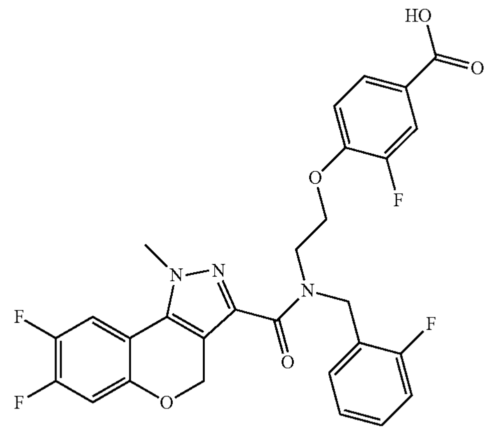 | $^1$H NMR (400 MHz, DMSO): δ 7.82-7.12 (m, 9H), 5.51-5.24 (m, 3H), 4.87-4.78 (m, 1H), 4.48-4.30 (m, 3H), 4.11-3.96 (m, 3H), 3.81-3.72 (m, 1H). Mixture of rotamers. MS (m/z): 556.2 (M + H)$^+$. |

Example 11

3-((2-(8-chloro-N-(2-fluorobenzyl)-1-methyl-1,4-dihydrochromeno[4,3-c]pyrazole-3-carboxamido)ethyl)amino)benzoic acid (Compound 63)

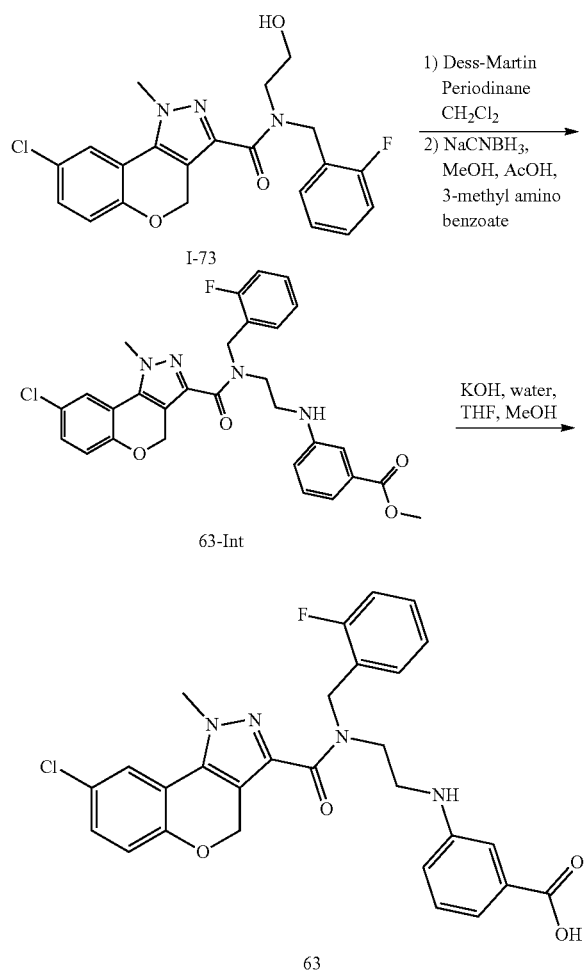

Step 1

To a 40 mL reaction vessel was charged 8-chloro-N-(2-fluorobenzyl)-N-(2-hydroxyethyl)-1-methyl-1,4-dihydrochromeno[4,3-c]pyrazole-3-carboxamide (I-73) (0.10 mmol) and CH$_2$Cl$_2$ (10 mL) followed by the addition of commercial Dess-Martin Periodinane (Sigma-Aldrich, 1,1,1-Tris(acetyloxy)-1,1-dihydro-1,2-benziodoxol-3-(1H)-one, 0.20 mmol) and buffered with solid sodium bicarbonate (0.20 mmol). The milky white suspension was rapidly stirred for 2 hrs and then the reaction was then directly diluted with ethyl acetate (150 mL) and washed with water (3×15 mL). The resulting organic extract was concentrated to a residue (in vacuo) and used directly without delay or further manipulation. The residue was dissolved in 9:1 MeOH/AcOH (5 mL) and treated with methyl-3-amino benzoate (0.40 mmol). The resulting reaction was then stirred at room temperature for 30 mins. and then treated with sodium cyanoborohydride (1.0 mmol, portion-wise over 30 mins.) followed by stirring at room temperature for an additional 1 hr. The resulting reaction was diluted with ethyl acetate (150 mL) and washed with water (3×25 mL). The resulting organic extracts were concentrated in vacuo and then directly subjected to reverse phase chromatography using TFA-modified (0.05%) water/ACN (35 to 80%). All fractions were reduced to dryness under vacuum and subjected to a free base event using polymer immobilized carbonate (SPE-CO$_3$H Varian cartridge, 0.90 nominal load with MeOH mobilizer, 10 mL) to give methyl 3-((2-(8-chloro-N-(2-fluorobenzyl)-1-methyl-1,4-dihydrochromeno[4,3-c]pyrazole-3-carboxamido)ethyl)amino) benzoate (63-Int) as a white solid. $^1$H NMR (400 MHz, d$_4$-MeOH): δ 7.48-7.19 (m, 8H), 7.03-6.92 (3H), 7.18 (app d, J=8.0 Hz, 1H), 6.62 (app dt, J=12.2, 8.0 Hz, 1H), 5.30-5.20 (m, 2H), 4.83 (br s, 2H), 4.21 (t, J=5.0 Hz, 2H), 3.85 (s, 3H), 3.74 (s, 3H), 3.38 (t, J=5.0 Hz, 2H). Mixture of rotamers. MS (m/z): 549.2/551.2 (M+H)$^+$ (chlorine isotope pattern).

Step 2

Methyl 3-(2-(8-chloro-N-(2-fluorobenzyl)-1-methyl-1,4-dihydrochromeno[4,3-c]pyrazole-3-carboxamido) acetamido)benzoate (63-Int) (0.075 mmol) was dissolved in THF (3 mL), MeOH (2 mL), and 1.0 M KOH (1.0 mmol). The resulting homogenous solution was heated to 60° C. for 2 hrs. At this time the reaction was cooled back to room temperature, quenched with AcOH (1.2 mmol, to pH=6 using Whatman-4 color-strip indicator paper to monitor). The reaction was then diluted with water (5 mL) and extracted with ethyl acetate (3×20 mL). The organic extracts were further washed with water (2×5 mL). The organic extracts were removed to dryness and allowed to precipitate from MeOH/water (3 mL, 9:1) to give 3-((2-(8-chloro-N-(2-fluorobenzyl)-1-methyl-1,4-dihydrochromeno[4,3-c]pyrazole-3-carboxamido)ethyl)amino) benzoic acid as a white solid. $^1$H NMR (400 MHz, d$_4$-MeOH): δ 7.48-7.10 (m, 7H), 7.02-6.90 (m, 3H), 6.61 (br d, J=8.0 Hz, 1H), 5.40-5.20 (m, 2H), 4.80 (br s, 2H), 4.21 (t, J=7.5 Hz, 2H), 3.91 (br s, 3H), 3.38 (t, J=7.5 Hz, 2H). Mixture of rotamers. MS (m/z): 535.2/537.2 (M+H)$^+$ (chlorine isotope pattern).

Example 12

3-(2-(8-chloro-N-(2-fluorobenzyl)-1-methyl-1,4-dihydrochromeno[4,3-c]pyrazole-3-carboxamido)acetamido)-4-fluorobenzoic acid (Compound 64)

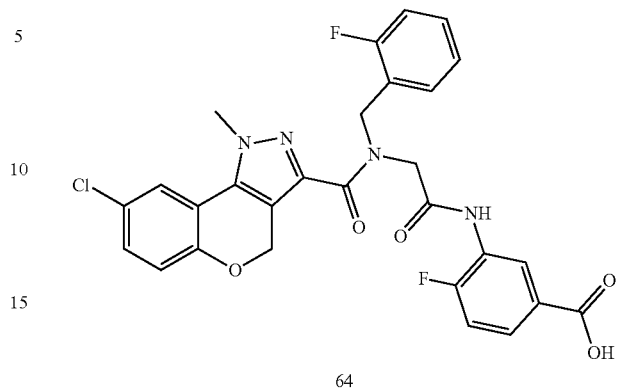

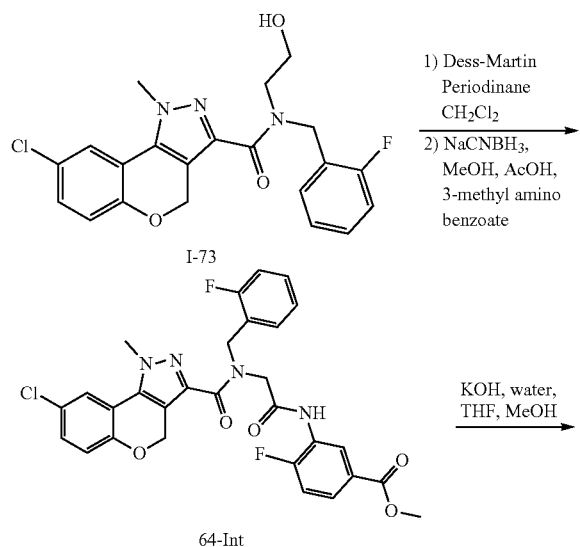

3-(2-(8-chloro-N-(2-fluorobenzyl)-1-methyl-1,4-dihydrochromeno[4,3-c]pyrazole-3-carboxamido)acetamido)-4-fluorobenzoic acid was prepared according to the procedures described in Example 3 for 3-(2-(8-chloro-N-(2-fluorobenzyl)-1-methyl-1,4-dihydrochromeno[4,3-c]pyrazole-3-carboxamido)acetamido)benzoic acid, using methyl 3-amino-4-fluorobenzoate in place of methyl-3-amino benzoate in step 1. MS (m/z): 567.2/569.1 (M+H)$^+$ (chlorine isotope pattern); r.t.=1.734.

Example 13

3-((2-(8-chloro-N-(3-fluorobenzyl)-1-methyl-1,4-dihydrochromeno[4,3-c]pyrazole-3-carboxamido)ethyl)amino)-4-fluorobenzoic acid (Compound 65)

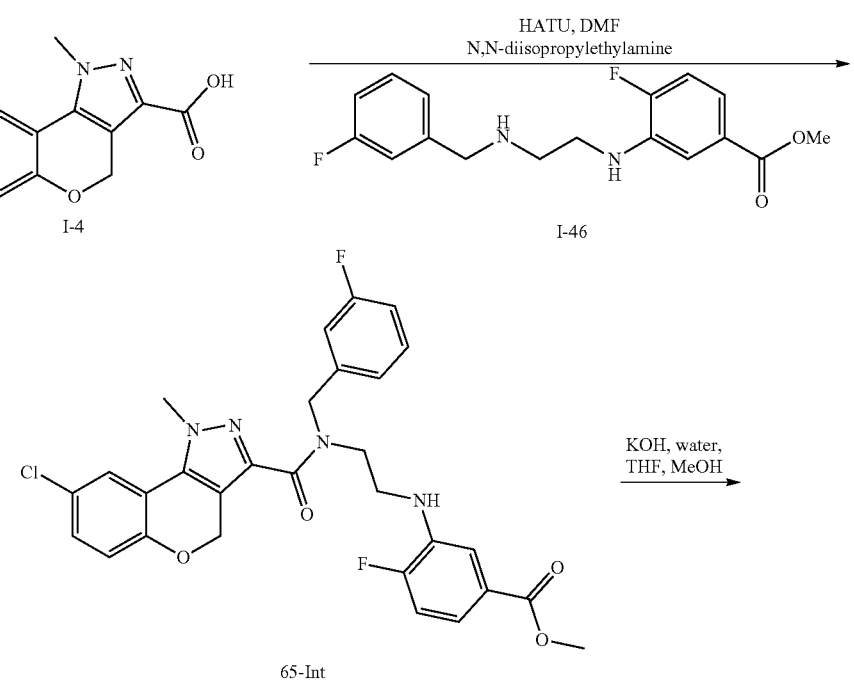

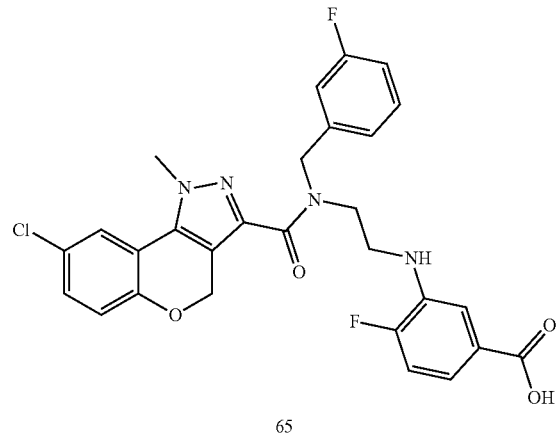

65

Step 1

HATU (1.2 mmol) was added to a mixture of 8-chloro-1-methyl-1,4-dihydrochromeno[4,3-c]pyrazole-3-carboxylic acid (I-4) (1.1 mmol), Hunigs Base (2.4 mmol) and DMF (5 mL). A solution of methyl 4-fluoro-3-((2-((3-fluorobenzyl)amino)ethyl)amino) benzoate (I-46) (1.1 mmol) in DMF (3 mL) was added and the reaction mixture stirred at room temperature for 4 hrs. The mixture was diluted with water and ethyl acetate. The layers were separated and the aqueous phase was washed with ethyl acetate. The combined organic extracts were washed with water, brine, and then dried over MgSO$_4$. The material was purified by chromatography (silica, 0-60% ethyl acetate/hexanes) to give methyl 3-((2-(8-chloro-N-(3-fluorobenzyl)-1-methyl-1,4-dihydrochromeno[4,3-c]pyrazole-3-carboxamido)ethyl)amino)-4-fluorobenzoate (65-Int). $^1$H NMR (400 MHz, DMSO): δ 7.61-7.29 (m, 2H), 7.23-6.86 (m, 8H), 6.20-5.89 (m, 1H), 5.45-4.65 (m, 4H), 4.14-3.95 (m, 4H), 3.84-3.77 (m, 3H), 3.58-3.46 (m, 1H), 3.46-3.37 (m, 2H).

Step 2

1N KOH (4 mmol, 5 equiv.) was added to a solution of methyl 3-((2-(8-chloro-N-(3-fluorobenzyl)-1-methyl-1,4-dihydrochromeno[4,3-c]pyrazole-3-carboxamido)ethyl)amino)-4-fluorobenzoate (65-Int) (0.80 mmol) in THF (4 mL) and MeOH (2 mL) and the solution was stirred at 50° C. for 2 hrs. The solvent was removed and the crude residue was diluted with water. The aqueous solution was acidified with acetic acid (pH ~5) to give the title compound as a white precipitate. $^1$H NMR (400 MHz, DMSO): δ 7.61-6.76 (m, 10H), 6.21-5.77 (m, 1H), 5.46-3.94 (m, 9H), 3.56-3.38 (m, 2H). Mixture of rotamers. MS (m/z): 537.2 (M+H)$^+$.

The following compounds were prepared according to the procedures described in Example 13 using the appropriate intermediates.

| Compound | Structure | Characterization Data |
|---|---|---|
| 66 | (structure shown) | $^1$H NMR (400 MHz, DMSO): δ 7.77-7.52 (m, 1H), 7.38-6.81 (m, 9H), 6.12-5.82 (m, 1H), 5.49-3.94 (m, 9H), 3.40 (s, 2H), 2.25 (s, 3H). Mixture of rotamers. MS (m/z): 549.3/551.3 (M + H)$^+$ (chlorine isotope pattern). |

-continued
| Compound | Structure | Characterization Data |
|---|---|---|
| 67 | 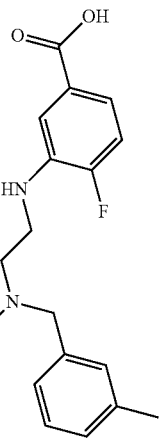 | $^1$H NMR (400 MHz, DMSO): δ 7.12 (m, 11H), 6.14-5.81 (m, 1H), 5.47-3.82 (m, 9H), 3.40 (s, 2H), 2.25 (s, 3H). Mixture of rotamers. MS (m/z): 533.3 (M + H)$^+$. |
| 68 | 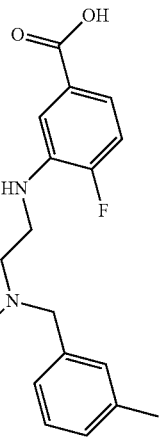 | $^1$H NMR (400 MHz, DMSO): δ 7.88-7.60 (m, 1H), 7.37-6.84 (m, 8H), 6.20-5.90 (m, 1H), 5.48-3.76 (m, 9H), 3.52-3.37 (m, 2H), 2.25 (s, 3H). Mixture of rotamers. MS (m/z): 551.3 (M + H)$^+$. |
| 69 | 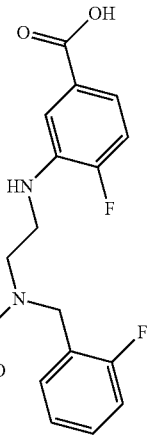 | $^1$H NMR (400 MHz, DMSO): δ 7.56-6.75 (m, 10H), 5.93 (m, 1H), 5.43-5.09 (m, 2H), 4.76 (s, 1H), 4.20-3.90 (m, 5H), 3.56 (m, 1H), 3.40 (dd, J = 16.7 Hz, 2H). Mixture of rotamers. MS (m/z): 537.3 (M + H)$^+$. |

-continued

| Compound | Structure | Characterization Data |
|---|---|---|
| 70 | 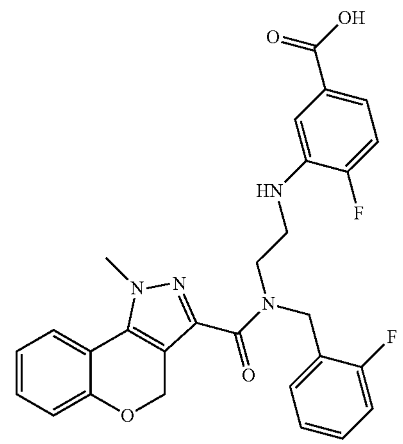 | ¹H NMR (400 MHz, DMSO): δ 7.77-6.72 (m, 11H), 6.09-5.81 (m, 1H), 5.41-5.21 (m, 2H), 4.81-4.71 (m, 1H), 4.26-3.86 (m, 5H), 3.61-3.53 (m, 1H), 3.46-3.37 (m, 2H). Mixture of rotamers. MS (m/z): 519.2 (M + H)⁺. |
| 71 | 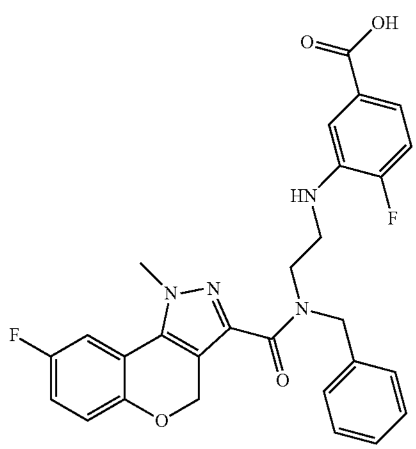 | MS (m/z): 519.2 (M + H)⁺; r.t. = 1.812 |
| 72 | 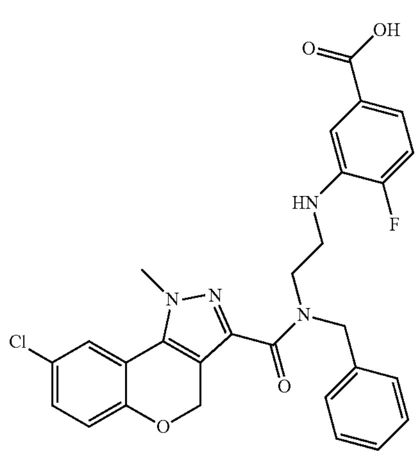 | MS (m/z): 535.1/537.1 (M + H)⁺ (chlorine isotope pattern); r.t = 1.771 |

-continued
| Compound | Structure | Characterization Data |
|---|---|---|
| 73 | 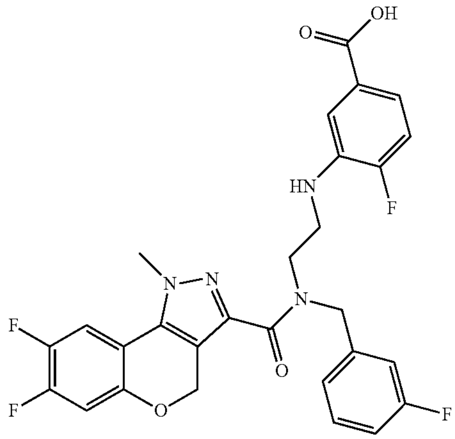 | $^1$H NMR (400 MHz, DMSO): δ 12.62 (br s, 1H), 7.92-7.23 (m, 7H), 6.89 (app d, J = 7.4 Hz, 1H), 6.78 (app t, J = 7.8 Hz, 1H), 5.58 (br s 1H, NH), 5.30-5.20 (m, 2H), 4.89 (br s, 2H), 4.33-3.97 (m, 5H), 3.62-3.54 (m, 2H). Mixture of rotamers. MS (m/z): 555.2 (M + H)$^+$. |
| 74 | 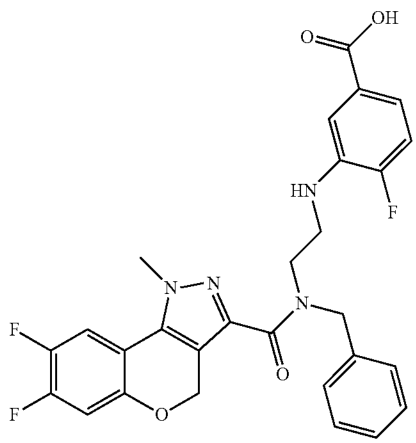 | MS (m/z): 537.1 (M + H)$^+$; r.t = 1.698 |
Example 14
4-((N-benzyl-8-chloro-1-methyl-1,4-dihydrochromeno[4,3-c]pyrazole-3-carboxamido)methyl)benzoic acid (Compound 75)
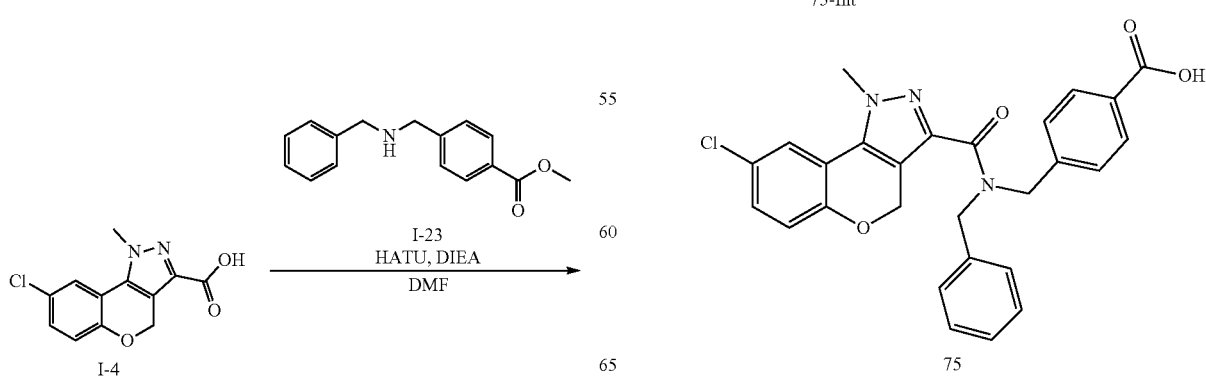

Step 1

HATU (43.1 mmol) (Oakwood) was added to a solution of the 8-chloro-1-methyl-1,4-dihydrochromeno[4,3-c]pyrazole-3-carboxylic acid (I-4) (39 mmol) and DIEA (15 mL) (Aldrich) in DMF (300 mL) at room temperature. After stirring for 20 mins, methyl 4-((benzylamino)methyl)benzoate (I-23) (39 mmol) was added neat as an oil followed by a rinse of DMF (20 mL) and the reaction mixture was stirred for 2 hrs. The mixture was poured onto ice and the resulting precipitate was filtered, rinsed with $H_2O$ (~200 mL). The solid was dissolved in DCM (300 mL), washed with $NaHCO_3$ (sat.), $H_2O$ and dried ($MgSO_4$). The crude material was purified by chromatography (silica gel, loaded neat with DCM rinse, 10-100% EtOAc/Hexanes) and after removal of solvent, an oil was obtained. The oil was suspended in EtOH (~100 mL) and the mixture was heated to reflux while stirring. After stirring for 1 hr, the mixture was cooled to room temperature and the resulting solid was filtered and rinsed with cold EtOH (~50 mL). The filtrate was concentrated (aspirator) and the crystallization was repeated to give methyl 4-((N-benzyl-8-chloro-1-methyl-1,4-dihydrochromeno[4,3-c]pyrazole-3-carboxamido)methyl)benzoate. $^1$H NMR (400 MHz, DMSO): δ 7.99-7.87 (m, 2H), 7.75-7.65 (m, 1H), 7.45-7.22 (m, 8H), 7.12-7.02 (m, 1H), 5.48-5.41 (m, 2H), 5.30-5.21 (m, 2H), 4.64-4.55 (m, 2H), 4.19-4.05 (m, 3H), 3.85 (s, 3H). MS (m/z): 502.0/504.0 $(M+H)^+$ (chlorine isotope pattern).

Step 2

1.0 M potassium hydroxide (53 mmol) was added to a solution of methyl 4-((N-benzyl-8-chloro-1-methyl-1,4-dihydrochromeno[4,3-c]pyrazole-3-carboxamido)methyl)benzoate (17.5 mmol) in THF (56 mL) and methanol (14 mL) and the mixture was heated to 50° C. for 2 hr. After cooling to room temperature, the solvent was removed (aspirator). The crude residue was diluted with water and the aqueous solution was acidified with acetic acid (to pH ~6) resulting in a precipitate. The precipitate was collected by vacuum filtration and dried overnight under high vacuum. The solid was collected and EtOH (125 mL) was added. The mixture was stirred at 85° C. for 2 hrs and then cooled to room temperature. The solid was filtered, rinsed with cold EtOH (~75 mL) and dried overnight under high vacuum to give 4-((N-benzyl-8-chloro-1-methyl-1,4-dihydrochromeno[4,3-c]pyrazole-3-carboxamido)methyl)benzoic acid. $^1$H NMR (400 MHz, DMSO): δ 7.96-7.85 (m, 2H), 7.74-7.67 (m, 1H), 7.42-7.20 (m, 8H), 7.12-6.97 (m, 1H), 5.46-5.42 (m, 2H), 5.28-5.21 (m, 2H), 4.62-4.49 (m, 2H), 4.18-4.07 (m, 3H). Mixture of rotamers. MS (m/z) 488.2/490.2 $(M+H)^+$ (chlorine isotope pattern).

Methanol (400 mL) was added to a mixture of 4-((N-benzyl-8-chloro-1-methyl-1,4-dihydrochromeno[4,3-c]pyrazole-3-carboxamido)methyl)benzoic acid (8.20 mmol) and TRIS (8.20 mmol). The reaction was heated to 70° C. for 0.5 hr. After cooling to room temperature, the solvent was removed in vacuum. The residue was sonicated in dichloromethane (10 mL) and concentrated again. The resulting white solid was dried under the vacuum pump overnight. The crude material was crystallized by slurring the solid residue in a 4:1 mixture of acetonitrile and methanol (5 mL). The mixture was stirred at room temperature for 24 hrs to give 4-((N-benzyl-8-chloro-1-methyl-1,4-dihydrochromeno[4,3-c]pyrazole-3-carboxamido)methyl)benzoic acid TRIS salt as a white precipitate. Melting point (195.6° C.). $^1$H NMR (400 MHz, DMSO): δ 7.92-7.80 (m, 2H), 7.78-7.64 (m, 1H), 7.41-7.19 (m, 8H), 7.13-7.00 (m, 1H), 5.44 (s, 2H), 5.25-5.14 (m, 2H), 4.61-4.48 (m, 2H), 4.18-4.03 (m, 3H), 3.39 (s, 7H).

In one embodiment, 4-((N-benzyl-8-chloro-1-methyl-1,4-dihydrochromeno[4,3-c]pyrazole-3-carboxamido)methyl)benzoic acid (30.6 mmol) was added to 150 mL acetone to give a white suspension. To the suspension was gradually added 75 mL meglumine (34 mmol) water solution. The resulting mixture was stirred at 50° C. for 4 h and then at room temperature for 12 hrs to give 4-((N-benzyl-8-chloro-1-methyl-1,4-dihydrochromeno[4,3-c]pyrazole-3-carboxamido)methyl)benzoic acid meglumine monohydrate salt as a white solid, which dehydrated at about 71° C. as determined by DSC.

In another embodiment, further heating of the meglumine monohydrate salt at 80° C., 0% relative humidity in an oven for 30 min. gave a white crystalline solid having a melting point (Tm onset) of 167.5° C. Alternatively, 4-((N-benzyl-8-chloro-1-methyl-1,4-dihydrochromeno[4,3-c]pyrazole-3-carboxamido)methyl)benzoic acid meglumine monohydrate salt (0.1 mmol) was added to 1 mL 1:1 (v/v) acetone/water. The resulting mixture was equilibrated at 50° C. for one week to give a white solid, which dehydrated at about 61° C. as determined by DSC.

In yet another embodiment, methanol (100 mL) was added to 4-((N-benzyl-8-chloro-1-methyl-1,4-dihydrochromeno[4,3-c]pyrazole-3-carboxamido)methyl)benzoic acid (4.1 mmol) and meglumine base (4.1 mmol). The resulting suspension was refluxed at 80° C. for 24 hrs then cooled to room temperature to give 4-((N-benzyl-8-chloro-1-methyl-1,4-dihydrochromeno[4,3-c]pyrazole-3-carboxamido)methyl)benzoic acid meglumine salt as a white solid. Melting point (180.6° C.).

The following compounds were prepared according to the procedures described in Example 14 using the appropriate intermediates.

| Compound | Structure | Characterization Data |
|---|---|---|
| 76 | 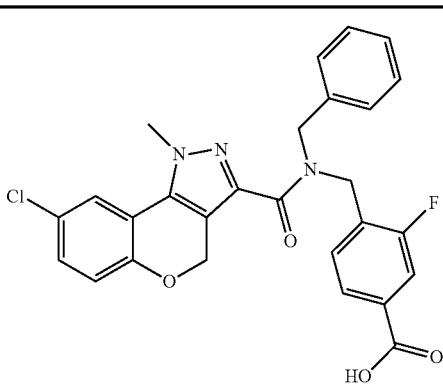 | $^1$H NMR (400 MHz, DMSO): δ 7.74-7.66 (m, 1H), 7.61-7.54 (m, 1H), 7.51-7.42 (m, 1H), 7.39-7.23 (m, 6H), 7.18-7.02 (m, 2H), 5.48-5.39 (m, 2H), 5.22 (s, 2H), 4.59-4.48 (m, 2H), 4.18-4.06 (m, 3H). Mixture of rotamers. MS (m/z): 506.2/508.2 $(M + H)^+$ (chlorine isotope pattern). |

| Compound | Structure | Characterization Data |
|---|---|---|
| 77 | 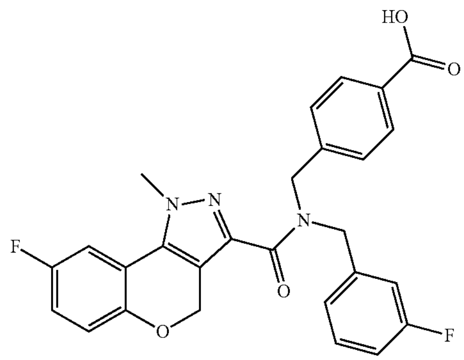 | $^1$H NMR (400 MHz, DMSO): δ 7.94-7.86 (m, 2H), 7.58-7.51 (m, 1H), 7.37 (m, 3H), 7.19-7.02 (m, 5H), 5.40 (s, 2H), 5.33-5.22 (m, 2H), 4.67-4.55 (m, 2H), 4.15-4.05 (m, 3H). Mixture of rotamers. MS (m/z): 490.2 (M + H)$^+$. |
| 78 | 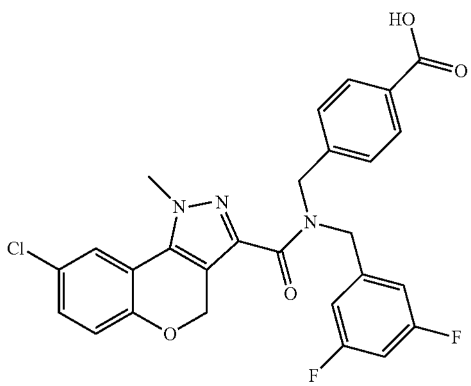 | $^1$H NMR (400 MHz, DMSO): δ 7.93-7.85 (m, 2H), 7.71 (m, 1H), 7.34 (m, 3H), 7.03 (m, 4H), 5.44 (s, 2H), 5.28 (m, 2H), 4.62 (m, 2H), 4.13 (s, 3H). Mixture of rotamers. MS (m/z): 524.2/526.2 (M + H)$^+$ (chlorine isotope pattern). |
| 79 | 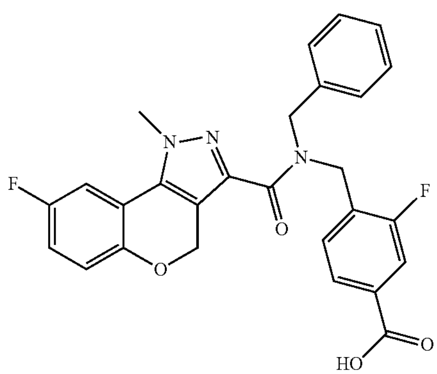 | $^1$H NMR (400 MHz, DMSO): δ 7.77-7.71 (m, 1H), 7.65-7.60 (m, 1H), 7.60-7.52 (m, 1H), 7.43-7.24 (m, 6H), 7.19-7.11 (m, 1H), 7.10-7.03 (m, 1H), 5.42-5.37 (m, 2H), 5.33-5.27 (m, 2H), 4.65-4.59 (m, 2H), 4.16-4.06 (m, 3H). Mixture of rotamers. MS (m/z): 490.2 (M + H)$^+$. |
| 80 | 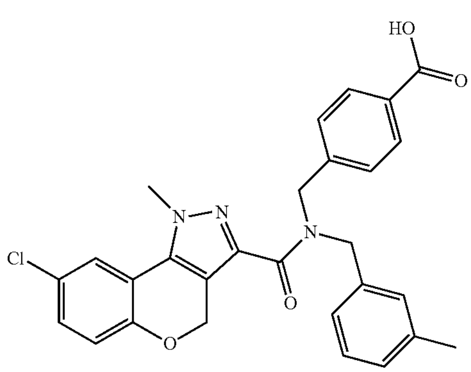 | $^1$H NMR (400 MHz, DMSO): δ 7.94-7.88 (m, 2H), 7.73-7.69 (m, 1H), 7.41-7.31 (m, 3H), 7.23 (s, 1H), 7.11-7.03 (m, 4H), 5.47-5.41 (m, 2H), 5.28-5.17 (m, 2H), 4.62-4.51 (m, 2H), 4.17-4.07 (m, 3H), 2.28 (s, 3H). Mixture of rotamers. MS (m/z): 502.2/504.2 (M + H)$^+$ (chlorine isotope pattern). |

| Compound | Structure | Characterization Data |
|---|---|---|
| 81 | 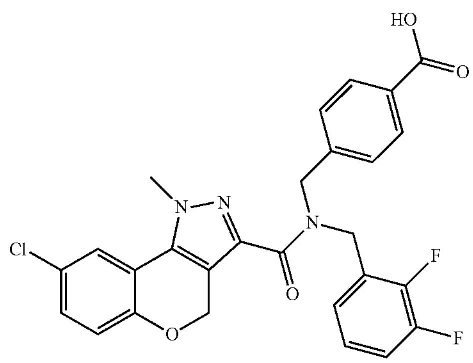 | ¹H NMR (400 MHz, DMSO): δ 7.95-7.84 (m, 2H), 7.71 (s, 1H), 7.44-7.27 (m, 4H), 7.22-7.00 (m, 3H), 5.44 (s, 2H), 5.39-5.31 (m, 2H), 4.74-4.60 (m, 2H), 4.17-4.05 (m, 3H). Mixture of rotamers. MS (m/z): 524.2/526.2 (M + H)⁺ (chlorine isotope pattern). |
| 82 | 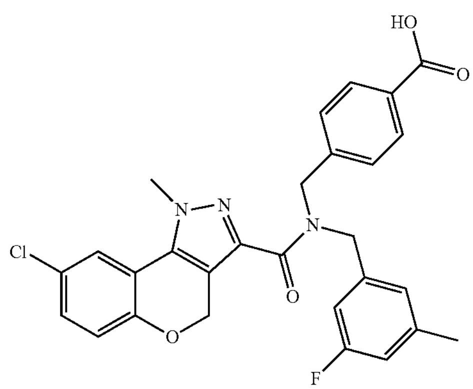 | ¹H NMR (400 MHz, DMSO): δ 7.95-7.84 (m, 2H), 7.71 (s, 1H), 7.44-7.27 (m, 4H), 7.22-7.00 (m, 3H), 5.44 (s, 2H), 5.39-5.31 (m, 2H), 4.74-4.60 (m, 2H), 4.17-4.05 (m, 3H), 2.28 (s, 3H). Mixture of rotamers. MS (m/z): 520.2/522.2 (M + H)⁺ (chlorine isotope pattern). |
| 83 | 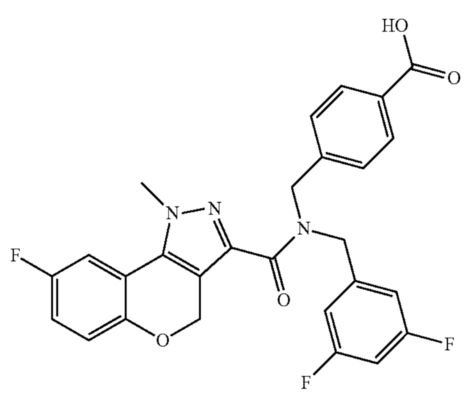 | ¹H NMR (400 MHz, DMSO): δ 7.90 (m, 2H), 7.56 (m, 1H), 7.39 (m, 2H), 7.20-6.91 (m, 5H), 5.40 (s, 2H), 5.37-5.19 (m, 2H), 4.72-4.52 (m, 2H), 4.12 (s, 3H). Mixture of rotamers. MS (m/z): 508.2 (M + H)⁺. |
| 84 | 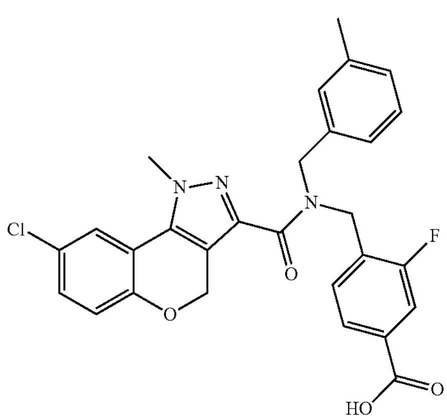 | ¹H NMR (400 MHz, DMSO): δ 7.77-7.68 (m, 2H), 7.65-7.59 (m, 1H), 7.45-7.31 (m, 2H), 7.26-7.19 (m, 1H), 7.12-7.03 (m, 4H), 5.48-5.39 (m, 2H), 5.34-5.18 (m, 2H), 4.67-4.46 (m, 2H), 4.21-3.90 (m, 3H), 2.27 (s, 3H). Mixture of rotamers. MS (m/z): 520.2/522.2 (M + H)⁺ (chlorine isotope pattern). |

| Compound | Structure | Characterization Data |
|---|---|---|
| 85 | 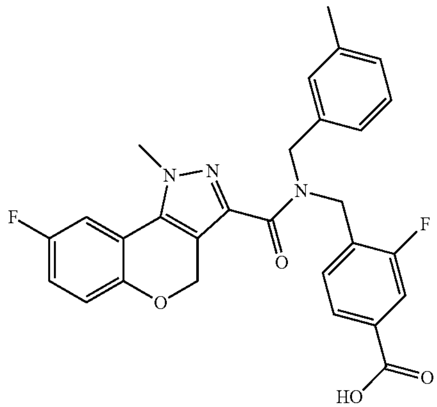 | ¹H NMR (400 MHz, DMSO): δ 7.79-7.68 (m, 1H), 7.65-7.50 (m, 2H), 7.45-7.36 (m, 1H), 7.27-7.02 (m, 6H), 5.43-5.34 (m, 2H), 5.34-5.21 (m, 2H), 4.68-4.50 (m, 2H), 4.20-3.94 (m, 3H), 2.27 (s, 3H). Mixture of rotamers. MS (m/z): 504.2 (M + H)⁺. |
| 86 | 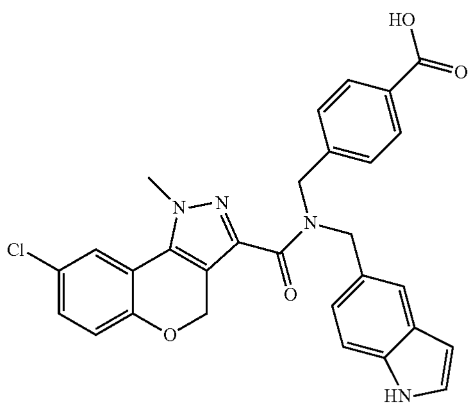 | ¹H NMR (400 MHz, DMSO): δ 11.22-11.02 (m, 1H), 7.97-7.87 (m, 2H), 7.76-7.66 (m, 1H), 7.46-7.30 (m, 6H), 7.10-6.99 (m, 9.8, 2H), 6.43-6.37 (m, 1H), 5.51-5.41 (m, 2H), 5.31-5.16 (m, 2H), 4.66-4.54 (m, 2H), 4.22-4.05 (m, 3H). Mixture of rotamers. MS (m/z): 527.2 (M + H)⁺. |
| 87 | 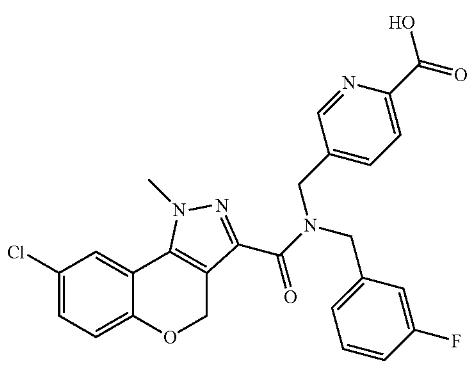 | ¹H NMR (400 MHz, DMSO): δ 8.65-8.53 (m, 1H), 8.03-7.95 (m, 1H), 7.90-7.78 (m, 1H), 7.74-7.68 (m, 1H), 7.43-7.31 (m, 2H), 7.19-7.04 (m, 4H), 5.47-5.40 (m, 2H), 5.34-5.27 (m, 2H), 4.70-4.61 (m, 2H), 4.17-4.07 (m, 3H). Mixture of rotamers. MS (m/z): 507.2 (M + H)⁺. |
| 88 | 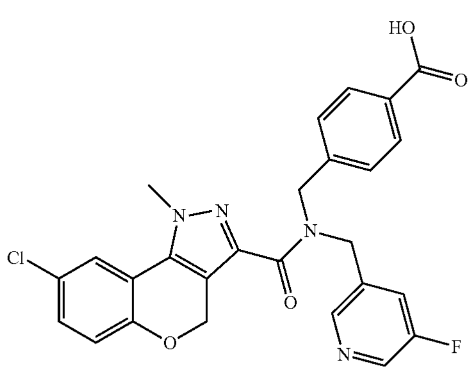 | ¹H NMR (400 MHz, DMSO): δ 8.50-8.44 (m, 1H), 8.43-8.32 (m, 1H), 7.94-7.83 (m, 2H), 7.73-7.68 (m, 1H), 7.68-7.54 (m, 1H), 7.45-7.39 (m, 1H), 7.39-7.30 (m, 2H), 7.10-7.02 (m, 1H), 5.48-5.24 (m, 4H), 4.73-4.59 (m, 2H), 4.16-4.08 (m, 3H). Mixture of rotamers. MS (m/z): 507.1 (M + H)⁺. |

| Compound | Structure | Characterization Data |
|---|---|---|
| 89 | 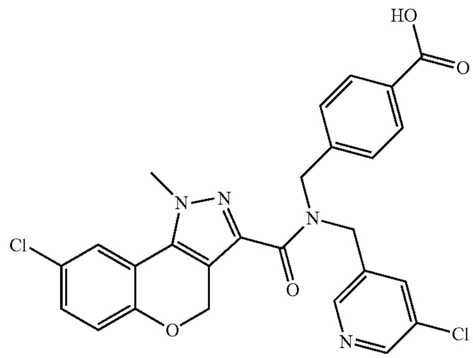 | ¹H NMR (400 MHz, DMSO): δ 8.53-8.40 (m, 2H), 7.93-7.68 (m, 4H), 7.46-7.30 (m, 3H), 7.09-7.02 (m, 1H), 5.48-5.22 (m, 4H), 4.74-4.57 (m, 2H), 4.17-4.05 (m, 3H). Mixture of rotamers. MS (m/z): 523.2 (M + H)⁺. |
| 90 | 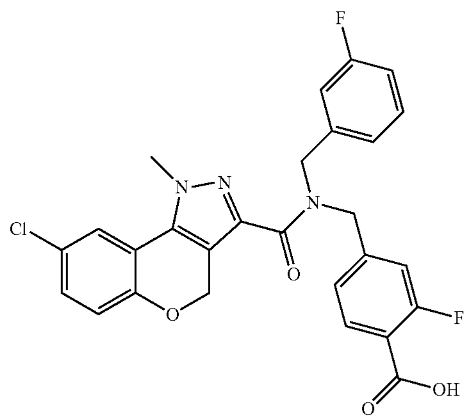 | ¹H NMR (400 MHz, CDCl₃): δ 7.82 (dd, J = 8.1, 17.0 Hz, 1H), 7.70 (dd, J = 2.5, 6.6 Hz, 1H), 7.43-7.28 (m, 2H), 7.13 (ddd, J = 7.8, 22.1, 26.9 Hz, 6H), 5.44 (d, J = 4.6 Hz, 2H), 5.28 (s, 2H), 4.61 (s, 2H), 4.12 (d, J = 15.7 Hz, 3H). MS (m/z): 524.2/526.2 (M + H)⁺ (chlorine isotope pattern). |
| 91 | 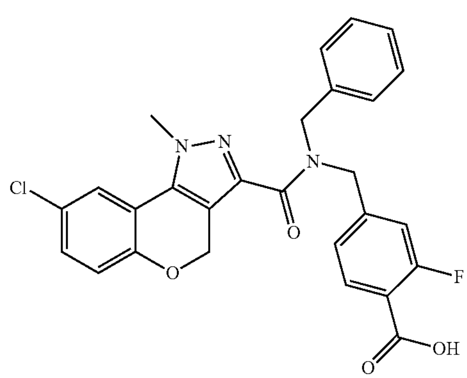 | ¹H NMR (400 MHz, DMSO): δ 7.83 (dd, J = 7.9, 17.5 Hz, 1H), 7.71 (dd, J = 2.5, 9.4 Hz, 1H), 7.32 (ddd, J = 4.7, 12.1, 20.5 Hz, 6H), 7.24-7.00 (m, 3H), 5.44 (d, J = 7.0 Hz, 2H), 5.26 (d, J = 11.9 Hz, 2H), 4.59 (d, J = 4.5 Hz, 2H), 4.13 (d, J = 22.5 Hz, 3H). Mixture of rotamers. MS (m/z): 506.2/508.2 (M + H)⁺ (chlorine isotope pattern). |
| 92 | 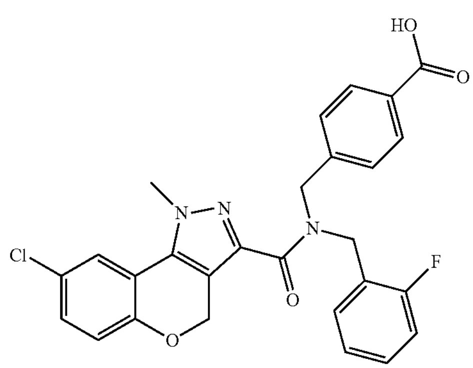 | ¹H NMR (400 MHz, DMSO): δ 7.92 (app d, J = 8.0 Hz, 2H), 7.72 (br s, 1H), 7.46-7.22 (m, 5 H), 7.16-7.08 (m, 2H), 7.04 (dd, J = 1.3, 8.0 Hz, 1H), 5.42 (br s, 2H), 5.32 (br s, 2H), 4.62-4.54 (m, 2H), 4.14-4.05 (m, 3H). Mixture of rotamers. MS (m/z): 506.1/508.1 (M + H)⁺ (chlorine isotope pattern). |

| Compound | Structure | Characterization Data |
|---|---|---|
| 93 | 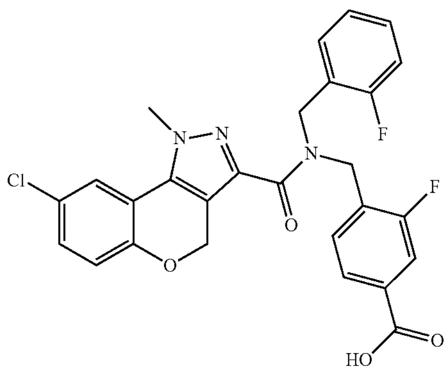 | MS (m/z): 524.1/526.1 (M + H)+ (chlorine isotope pattern). r.t = 1.709 |
| 94 | 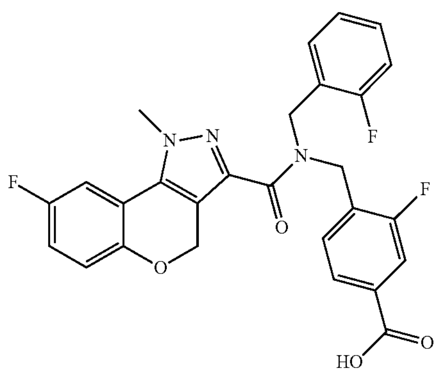 | ¹H NMR (400 MHz, DMSO): δ 12.03 (m, 1H), 7.68 (d, J = 7.5 Hz, 1H), 7.56 (d, J = 8.3 Hz, 1H), 7.48 (dd, J = 1.8, 7.5 Hz, 1H), 7.39-7.32 (m, 2H), 7.28-7.11 (m, 4H), 7.02 (dd, J = 1.9, 8.4 Hz, 1H), 5.33 (br s, 2H), 5.26 (s, 2H), 4.72 (br s, 2H), 3.98 (s, 3H). MS (m/z): 508.1 (M + H)+. |
| 95 | 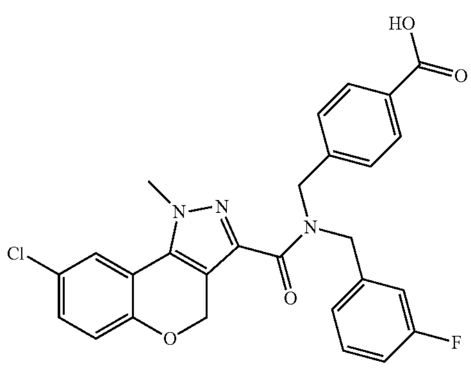 | MS (m/z): 506.1/508.1 (M + H)+ (chlorine isotope pattern); r.t = 1.801 |
| 96 | 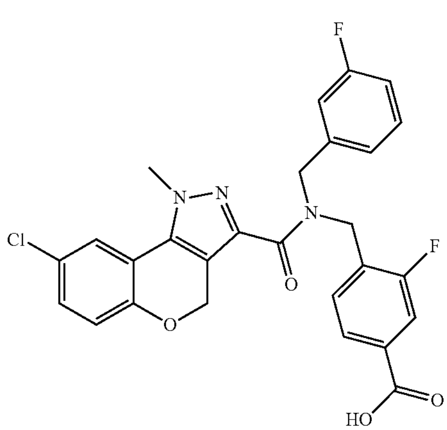 | ¹H NMR (400 MHz, DMSO): δ 12.33 (m, 1H), 7.83 (app t, J = 7.9 Hz, 2H), 7.76 (d, J = 8.3 Hz, 1H), 7.48-7.42 (m, 3H), 7.24-7.01 (m, 4H), 5.38 (br s, 2H), 5.28 (s, 1H), 5.20 (s, 1H), 4.70 (br s, 2H), 4.06-4.00 (m, 3H). Mixture of rotamers. MS (m/z): 524.1/526.1 (M + H)+ (chlorine isotope pattern). |

| Compound | Structure | Characterization Data |
|---|---|---|
| 97 | 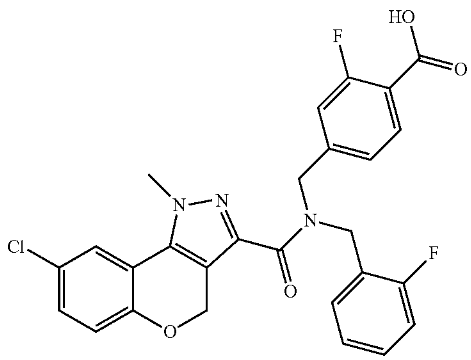 | MS (m/z): 524.1/526.1 (M + H)+ (chlorine isotope pattern); r.t = 1.751 |
| 98 | 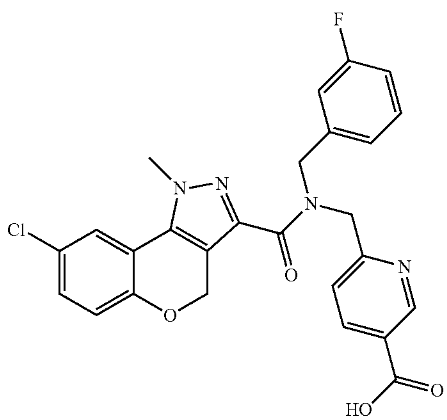 | ¹H NMR (400 MHz, d₄-MeOH): δ 9.01 (br s, 1H), 8.42 (app t, J = 8.2 Hz, 1H), 7.66-7.58 (m, 2H), 7.28-6.89 (m, 6H), 5.37-5.31 (m, 4H), 4.74 (br s, 1H), 4.68 (br s, 1H), 4.04-3.98 (m, 3H, NMe rotamers visible). Mixture of rotamers. MS (m/z): 507.1/509.1 (M + H)+ (chlorine isotope pattern). |
| 99 | 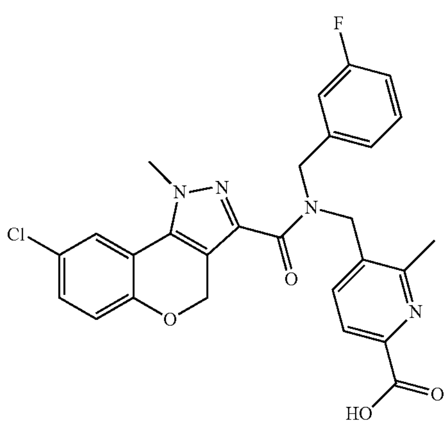 | ¹H NMR (400 MHz, DMSO): δ 12.54 (br s, 1H), 7.78 (d, J = 7.6 Hz, 1H), 7.72-7.64 (m, 1H), 7.54 (app dd, J = 1.5 Hz, 7.8 Hz, 1H), 7.39-7.22 (m, 2H), 7.19-7.08 (m, 3H), 6.98 (app d, J = 8.0 Hz, 1H), 5.38 (app d, J = 10 Hz, 2H), 5.24 (br s, 2H), 4.73 (br s, 1H), 4.64 (br s, 1H), 4.13-3.97 (m, 3H), 2.45 (app d, J = 11.2 Hz, 3H). Mixture of rotamers. MS (m/z): 521.1/523.1 (M + H)+ (chlorine isotope pattern). |

Example 15

4-Fluoro-3-((2-(8-fluoro-N-(3-fluorobenzyl)-1-methyl-1,4-dihydrochromeno[4,3-c]pyrazole-3-carboxamido)ethyl)amino)benzoic acid (Compound 100)

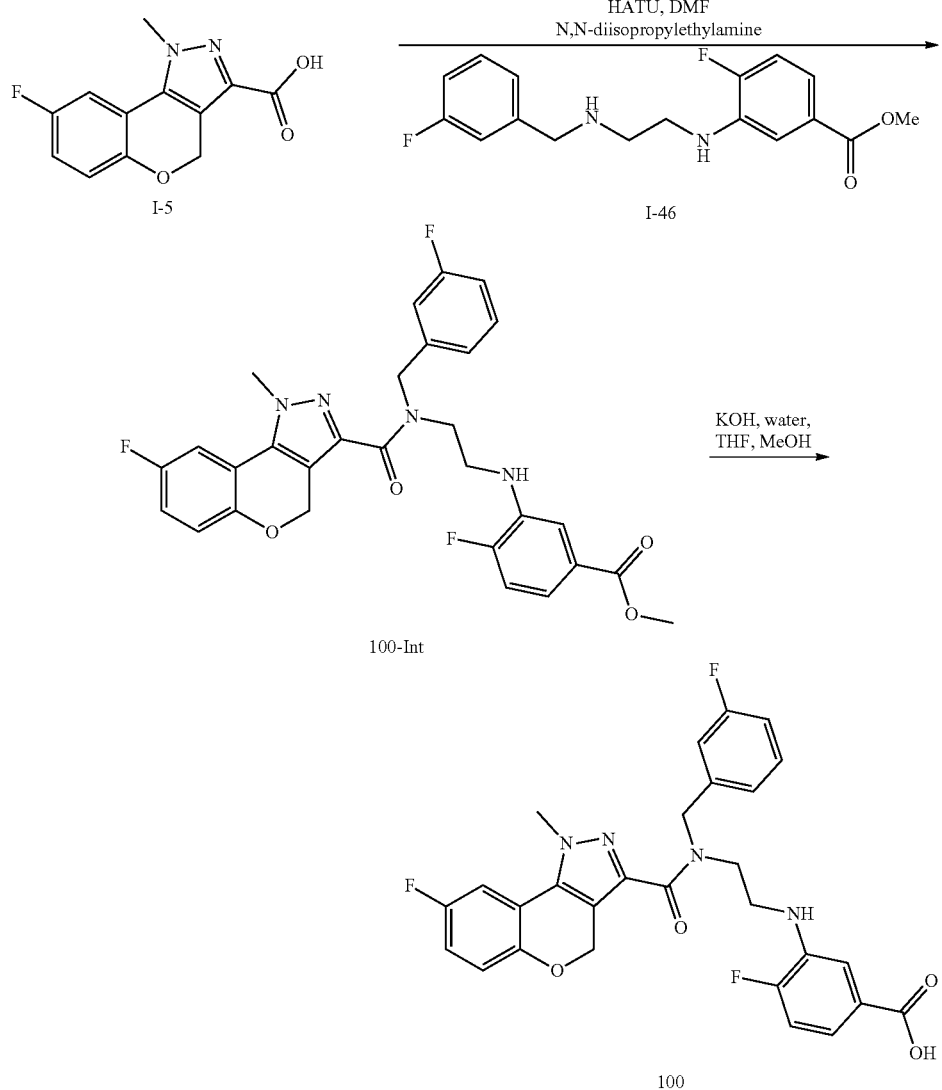

Step 1

HATU (1.2 mmol) was added to a mixture of 8-fluoro-1-methyl-1,4-dihydrochromeno[4,3-c]pyrazole-3-carboxylic acid (I-5) (1.1 mmol), Hunigs Base (2.4 mmol) and DMF (5 mL). A solution of methyl 4-fluoro-3-((2-((3-fluorobenzyl)amino)ethyl)amino)benzoate (I-46) (1.1 mmol) in DMF (3 mL) was added and the reaction mixture stirred at room temperature for 4 hrs. The mixture was diluted with water and ethyl acetate. The layers were separated and the aqueous phase was washed with ethyl acetate. The combined organic extracts were washed with water, brine, and then dried over MgSO$_4$. The material was purified by chromatography (silica, 0-60% ethyl acetate/hexanes) to give methyl 4-fluoro-3-((2-(8-fluoro-N-(3-fluorobenzyl)-1-methyl-1,4-dihydrochromeno[4,3-c]pyrazole-3-carboxamido)ethyl)amino)benzoate (100-Int).

Step 2

1N KOH (4 mmol, 5 equiv.) was added to a solution of methyl 4-fluoro-3-((2-(8-fluoro-N-(3-fluorobenzyl)-1-methyl-1,4-dihydrochromeno[4,3-c]pyrazole-3-carboxamido)ethyl)amino)benzoate (100-Int) (0.80 mmol) in THF (4 mL) and MeOH (2 mL) and the solution was stirred at 50° C. for 2 hrs. The solvent was removed and the crude residue was diluted with water. The aqueous solution was acidified with acetic acid (pH ~5) to give 4-fluoro-3-((2-(8-fluoro-N-(3-fluorobenzyl)-1-methyl-1,4-dihydrochromeno[4,3-c]pyrazole-3-carboxamido)ethyl)amino)benzoic acid as a white precipitate. $^1$H NMR (400 MHz, DMSO): δ 7.61-7.26 (m, 2H), 7.20-6.82 (m, 9H), 6.11-5.81 (m, 1H), 5.43-4.70 (m, 4H), 4.15-3.94 (m, 4H), 3.53 (t, J=6.6 Hz, 1H), 3.44-3.39 (m, 2H). MS (m/z): 537.2 (M+H)$^+$; r.t.=1.618; Elemental Analysis: calcd. for 0.50, $C_{28}H_{22}F_3N_4O$·0.52H$_2$O: C, 61.65; H, 4.43; N, 10.45). found: C, 61.75; H, 4.21; N, 10.31.

4-Fluoro-3-((2-(8-fluoro-N-(3-fluorobenzyl)-1-methyl-1,4-dihydrochromeno[4,3-c]pyrazole-3-carboxamido)ethyl)amino)benzoic acid (7.5 mmol) added to a solution of TRIS (7.5 mmol) in MeOH (400 mL). The reaction was stirred at 60° C. for 30 mins. After cooling to room temperature, the solvent was removed and the crude material was azeotroped with dichloromethane (2×). The resulting glassy solid was slurred in ethyl acetate (200 mL). The slurry was stirred at room temperature for 24 hrs. The resulting solid was collected by filtration to give 4-fluoro-3-((2-(8-fluoro-N-(3-fluorobenzyl)-1-methyl-1,4-dihydrochromeno[4,3-c]pyrazole-3-carboxamido)ethyl)amino)benzoic acid TRIS salt as a solid. Melting point (160° C.). $^1$H NMR (600 MHz, DMSO): δ 7.62-6.70 (m, 10H), 5-90-5.80 (m, 1H), 5.45-5.15 (m, 2H), 4.75-4.55 (m, 2H), 4.16-3.5 (m, 4H), 3.41-3.39 (m, 1H), 3.30-3.25 (m, 13H). Anal. Calcd for $C_{32}H_{34}F_3N_5O_7 \cdot 1.3H_2O$: C, 56.36; H, 5.42; N, 10.27.1H$_2$O Found: C, 56.25; H, 5.29; N, 10.32.

A solution of L-arginine (0.20 mmol) in deionized water (3 mL) was added to a suspension 4-fluoro-3-((2-(8-fluoro-N-(3-fluorobenzyl)-1-methyl-1,4-dihydrochromeno[4,3-c]pyrazole-3-carboxamido)ethyl)amino)benzoic acid (0.20 mmol) in MeOH (12 mL). The mixture was stirred at 70° C. for 0.5 hr and then stirred for 2 hrs at room temperature. The solvent was removed under vacuum and the crude material was crystallized by slurring the solid residue in acetonitrile (5 mL). The mixture was stirred at room temperature for additional 24 hrs to give 4-fluoro-3-((2-(8-fluoro-N-(3-fluorobenzyl)-1-methyl-1,4-dihydrochromeno[4,3-c]pyrazole-3-carboxamido)ethyl)amino) benzoic acid L-arginine salt as a white precipitate. Melting point (161° C.).

Example 16

3-((2-(8-chloro-N-(2-fluorobenzyl)-1-methyl-1,4-dihydrochromeno[4,3-c]pyrazole-3-carboxamido)ethyl)amino)-4-fluorobenzoic acid (Compound 101)

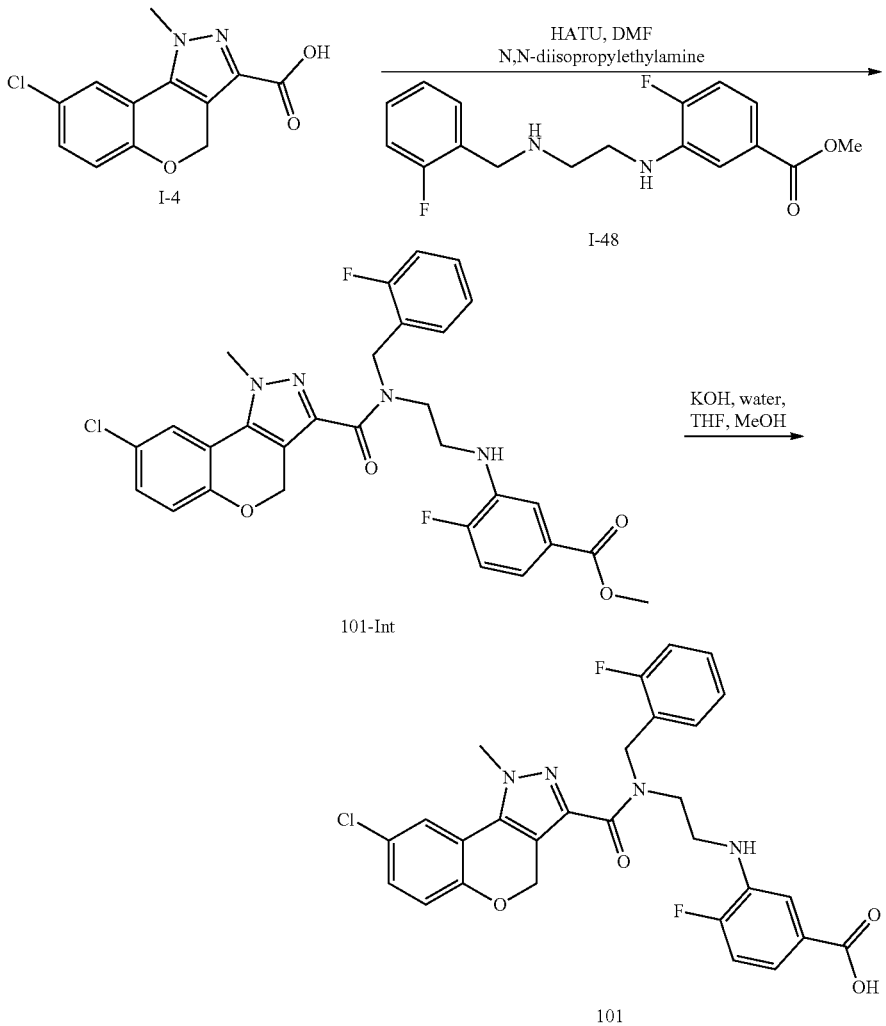

3-((2-(8-chloro-N-(2-fluorobenzyl)-1-methyl-1,4-dihydrochromeno[4,3-c]pyrazole-3-carboxamido)ethyl)amino)-4-fluorobenzoic acid was prepared according to the procedure described in Example 13 using the appropriate intermediates. MS (m/z): 553.2/555.2 (M+H)$^+$ (chlorine isotope pattern); r.t.=1.871.

BIOLOGICAL ASSAYS

Human GST-FXR LBD Co-Activator Interaction Assay

The FXR HTRF assay is a biochemical assay measuring the interaction between FXR and a coactivator protein (SRC1). The ligand-induced interaction with a coactivator protein is a critical step in transcriptional activation by FXR. Thus, this is an assay designed to measure FXR agonist activity of the test compounds.

Recombinant human Farnesoid X Receptor (FXR) ligand binding domain (amino acids 193-472) fused to glutathione S-transferase (GST) purified protein (GST-FXR LBD) was purchased (Invitrogen). The ligand-dependent interaction between GST-FXR LBD and a peptide derived from Steroid Receptor Coactivator-1 (SRC-1) was monitored by Fluorescence Resonance Energy Transfer (FRET). GST-FXR LBD was mixed with a biotin-labeled SRC-1 peptide (Biotin-CPSSHSSLTERHKILHRLLQEG-SPS-CONH2 (SEQ ID NO:1), American Peptide) in assay buffer (50 mM Tris.HCl, pH 7.4, 50 mM NaCl, 1 mM TCEP and 0.2% bovine serum albumen) and plated in 384 black Proxi plates (Greiner Bio-One). Test compounds (in DMSO solution) and detection reagents (anti-GST-Cryptate labeled antibody and Streptavidin-XL665 conjugate; CisBio) were added in assay buffer containing 50 mM KF. Plates are incubated at room temperature in the dark for 2.5 hrs before reading on an Envision (PerkinElmer) at 665 nm and 590 nm. The HTRF assay results were calculated from the 665 nm/590 nm ratio (ratio=(A665 nm/A590 nm)×$10^4$) and expressed in Delta F %=(Ratiosample−Rationegative)/Rationegative×100.

A negative control (without Streptavidin-XL665) was run with each assay and represented the background fluorescence. A reference FXR agonist, (E)-3-(2-chloro-4-((3-(2,6-dichlorophenyl)-5-isopropylisoxazol-4-yl)methoxy)styryl) benzoic acid (Compound GW4064), was included in each experiment as positive control. The efficacy of each test compound was compared to that of GW4064. At each concentration, the relative activity of the test compound was expressed as Response %=($R_{sample}$−$R_{DMSO}$)/($R_{positive}$−$R_{DMSO}$), where $R_{sample}$ is the HTRF response (expressed in Delta F %) for the test compound, $R_{positive}$ is the maximal response for GW4064 at saturating concentrations, and $R_{DMSO}$ is the response for DMSO control. The $EC_{50}$ values were calculated using GraphPad Prism (GraphPad Software) using non-linear regression curve fit (log(agonist) vs. response-variable slope (four parameters)).

Table 1 summarizes $EC_{50}$ values for the compounds of the invention in human GST-FXR LBD co-activator interaction assay.

TABLE 1

| Compound Number | FXR coactivator interaction assay (HTRF) (µM) |
|---|---|
| 1 | 0.0012 |
| 2 | 0.0006 |
| 3 | 0.00051 |
| 4 | 0.00075 |
| 5 | 0.00080 |
| 6 | 0.0024 |
| 7 | 0.0010 |
| 8 | 0.0033 |
| 9 | 0.0036 |
| 10 | 0.0017 |
| 11 | 0.0033 |
| 12 | 0.0054 |
| 13 | 0.00080 |
| 14 | 0.00084 |
| 15 | 0.00222 |
| 16 | 0.0034 |
| 17 | 0.0010 |
| 18 | 0.0004 |
| 19 | 0.0005 |
| 20 | 0.0005 |
| 21 | n.d. |
| 22 | n.d. |
| 23 | n.d. |
| 24 | 0.0032 |
| 25 | 0.0007 |
| 26 | n.d. |
| 27 | 0.0014 |
| 28 | 0.00038 |
| 29 | 0.00067 |
| 30 | 0.00060 |
| 31 | 0.00047 |
| 32 | 0.00074 |
| 33 | 0.0015 |
| 34 | 0.0021 |
| 35 | 0.00077 |
| 36 | 0.033 |
| 37 | 0.024 |
| 38 | 0.0026 |
| 39 | 0.0059 |
| 40 | 0.0086 |
| 41 | 0.0040 |
| 42 | 0.0025 |
| 43 | 0.018 |
| 44 | 0.011 |
| 45 | 0.015 |
| 46 | 0.0032 |
| 47 | 0.00053 |
| 48 | 0.061 |
| 49 | 0.017 |
| 50 | 0.011 |
| 51 | 0.0098 |
| 52 | 0.0026 |
| 53 | 0.017 |
| 54 | 0.021 |
| 55 | 0.013 |
| 56 | 0.040 |
| 57 | 0.030 |
| 58 | 0.022 |
| 59 | 0.028 |
| 60 | n.d. |
| 61 | 0.089 |
| 62 | 0.074 |
| 63 | 0.0060 |
| 64 | 0.00060 |
| 65 | 0.007 |
| 66 | n.d. |
| 67 | n.d. |
| 68 | n.d. |
| 69 | 0.025 |
| 70 | 0.081 |
| 71 | 0.022 |
| 72 | 0.0026 |
| 73 | 0.020 |
| 74 | 0.055 |
| 75 | 0.006 |
| 76 | 0.0096 |
| 77 | 0.0079 |
| 78 | 0.0083 |
| 79 | 0.022 |
| 80 | 0.016 |
| 81 | 0.021 |
| 82 | 0.012 |
| 83 | 0.014 |
| 84 | 0.018 |
| 85 | 0.035 |
| 86 | 0.012 |
| 87 | 0.028 |
| 88 | 0.015 |
| 89 | n.d. |
| 90 | 0.005 |
| 91 | 0.0065 |
| 92 | 0.014 |
| 93 | 0.013 |
| 94 | 0.032 |
| 95 | 0.0035 |
| 96 | 0.0036 |
| 97 | 0.017 |
| 98 | n.d. |
| 99 | 0.029 |

TABLE 1-continued

| Compound Number | FXR coactivator interaction assay (HTRF) (μM) |
|---|---|
| 100 | 0.024 |
| 101 | 0.0055 | n.d. = not determined

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound according to formula (I), or a pharmaceutical acceptable salt thereof, wherein, $R^0$ is Ring A or $C_{1-6}$ alkyl;

Ring A is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring A is unsubstituted or substituted by 1-2 substituents independently represented by $R^2$;

Ring B is aryl; 5-10 membered heteroaryl comprising 1-3 N, O or S heteroatoms; 4-6 membered heterocycle comprising 1-2 N, O or S heteroatoms; or $C_{3-7}$ cycloalkyl; and said Ring B is unsubstituted or substituted by 1-2 substituents independently represented by $R^2$;

X is —$(CR^4R^5)$— or —C(O)—;

Y is —O—, —$(CR^4R^5)$—, *—O$(CR^4R^5)$— or —NR—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *$^1$—$(CR^4R^5)_{1-2}$- or *$^1$—$(CR^4R^5)$—C(O)—NR—, wherein "*$^1$" indicates the point of attachment of $L^1$ to N;

$L^2$ is *$^2$—$(CR^4R^5)_{1-2}$—, *$^2$—$(CR^4R^5)$—C(O)—, *$^2$—$(CR^4R^5)$—C(O)—NR—, *$^2$—$(CR^4R^5)_2$—O—, *$^2$—$(CR^4R^5)_2$—NR—, *$^2$—$(CR^4R^5)_2$—$SO_2$—, *$^2$—$(CR^4R^5)_2$—NR—C(O)—, or *$^2$—$(CR^4R^5)$—C(O)—NR—$(CR^4R^5)$—;

wherein "*$^2$" indicates the point of attachment of $L^2$ to N;

$L^3$ is —$(CR^4R^5)$— or —C(O)—;

each $R^2$ is independently halo, hydroxyl, $C_{1-6}$ alkyl, or halo-substituted $C_{1-6}$ alkyl;

each $R^3$ is independently hydrogen, halo, or $C_{1-6}$ alkyl; and

R, $R^4$ and $R^5$ are independently hydrogen or $C_{1-6}$ alkyl.

2. The compound of claim 1, wherein, $R^0$ is Ring A or $C_{1-6}$ alkyl;

Ring A is aryl; 5-10 membered heteroaryl comprising 1-3 N, O or S heteroatoms; or $C_{3-7}$ cycloalkyl; and said Ring A is unsubstituted or substituted by 1-2 substituents independently represented by $R^2$;

Ring B is aryl; 5-10 membered heteroaryl comprising 1-3 N, O or S heteroatoms; or $C_{3-7}$ cycloalkyl; and said Ring B is unsubstituted or substituted by 1-2 substituents independently represented by $R^2$;

X is —$(CR^4R^5)$—;

Y is —O—, —$(CR^4R^5)$—, or *—O$(CR^4R^5)$—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is *$^1$—$(CR^4R^5)_{1-2}$— wherein "*$^1$" indicates the point of attachment of $L^1$ to N;

$L^2$ is $*^2$—$(CR^4R^5)_{1\text{-}2}$—, $*^2$—$(CR^4R^5)$—$C(O)$—$NR$—, $*^2$—$(CR^4R^5)_2$—$O$—, $*^2$—$(CR^4R^5)_2$—$NR$— or $*^2$—$(CR^4R^5)$—$C(O)$—$NR$—$(CR^4R^5)$—; wherein "$*^2$" indicates the point of attachment of $L^2$ to N;

$L^3$ is —$C(O)$—;

each $R^2$ is independently halo, $C_{1\text{-}6}$ alkyl, or halo-substituted $C_{1\text{-}6}$ alkyl;

each $R^3$ is independently hydrogen, halo, or $C_{1\text{-}6}$ alkyl;

R, $R^4$ and $R^5$ are independently hydrogen or $C_{1\text{-}6}$ alkyl.

3. The compound of claim 1, wherein the compound is of Formula (II):

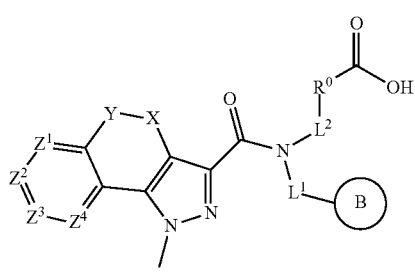

(II)

or a pharmaceutically acceptable salt thereof; wherein, $R^0$ is Ring A or $C_{1\text{-}6}$ alkyl; wherein Ring A is phenyl, pyridyl or cyclopropyl, each of which is unsubstituted or substituted by 1-2 substituents independently represented by $R^2$;

Ring B is selected from phenyl, pyridyl, 1H-indolyl, and $C_{3\text{-}7}$ cycloalkyl, each of which is unsubstituted or substituted by 1-2 substituents independently represented by $R^2$;

X is —$(CR^4R^5)$—;

Y is —O—, —$(CR^4R^5)$— or *—$O(CR^4R^5)$—, wherein "*" indicates the point of attachment of Y to the ring containing the Z ring atoms;

$Z^1$, $Z^2$, $Z^3$, and $Z^4$ are each independently —$CR^3$— or —N—;

$L^1$ is $*^1$—$(CR^4R^5)_{1\text{-}2}$— wherein "$*^1$" indicates the point of attachment of $L^1$ to N;

$L^2$ is $*^2$—$(CR^4R^5)_{1\text{-}2}$—, $*^2$—$(CR^4R^5)$—$C(O)$—$NR$—, $*^2$—$(CR^4R^5)_2$—$O$—, $*^2$—$(CR^4R^5)_2$—$NR$— or $*^2$—$(CR^4R^5)$—$C(O)$—$NR$—$(CR^4R^5)$—; where "$*^2$" indicates the point of attachment of $L^2$ to N;

each $R^2$ is independently halo, $C_{1\text{-}6}$ alkyl, or halo-substituted $C_{1\text{-}6}$ alkyl;

each $R^3$ is independently hydrogen, halo, or $C_{1\text{-}6}$ alkyl; and

R, $R^4$ and $R^5$ are independently hydrogen or $C_{1\text{-}6}$ alkyl.

4. The compound of claim 1, wherein $R^0$ is selected from $*^3$—$CH_2C(CH_3)_2$—, $*^3$—$CH_2CH(CH_3)$—, and $*^3$-cyclopropane-1,1,-diyl, wherein "$*^3$" indicates the point of attachment of $R^0$ to $L^2$.

5. The compound of claim 1, wherein the compound is of Formula (III):

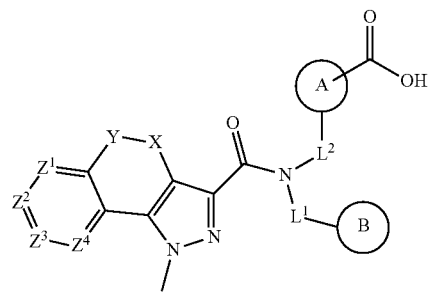

(III)

or a pharmaceutically acceptable salt thereof; wherein

Ring A is phenyl or pyridyl, each of which is unsubstituted or substituted by 1-2 substituents independently represented by $R^2$;

Ring B is selected from phenyl, pyridyl, 1H-indolyl, and cyclopentyl, each of which is unsubstituted or substituted by 1-2 substituents independently represented by $R^2$;

$L^1$ is —$(CR^4R^5)$—;

$L^2$ is selected from —$(CH_2)$—, $*^2$—$CH_2C(O)NH$—, $*^2$—$CH(CH_3)C(O)NH$—, $*^2$—$CH_2C(O)NHCH_2$—, $*^2$—$(CH_2)_2O$—, and $*^2$—$(CH_2)_2NH$—; wherein "$*^2$" indicates the point of attachment of $L^2$ to N;

X is $CH_2$;

Y is selected from —O—, —$CH_2$—, —$C(CH_3)_2$— and *—O—$CH_2$—, wherein "*" indicates the point of attachment of Y to the ring containing the Z ring atoms;

$Z^1$ is $CR^3$ or N;

$Z^2$ is $CR^3$;

$Z^3$ is $CR^3$;

$Z^4$ is $CR^3$ or N;

each $R^2$ is independently selected from halo, methyl, and trifluoromethyl;

each $R^3$ is independently hydrogen, halo, or $C_{1\text{-}6}$ alkyl; and each of $R^4$ and $R^5$ is independently hydrogen or methyl.

6. The compound of claim 1, wherein Y is —O—.

7. The compound of claim 1, wherein $L^1$ is —$CH_2$—.

8. The compound of claim 1, wherein $L^2$ is selected from —$(CH_2)$—, $*^2$—$CH_2C(O)NH$—, $*^2$—$(CH_2)_2O$—, and $*^2$—$(CH_2)_2NH$—; wherein "$*^2$" indicates the point of attachment of $L^2$ to N.

9. The compound of claim 1, wherein $L^2$ is —$CH_2$—.

10. The compound of claim 1, wherein each $R^2$ is independently fluoro or methyl.

11. The compound of claim 1, wherein each $R^3$ is independently selected from hydrogen, fluoro, chloro, and methyl.

12. The compound of claim 1, wherein $Z^1$ is selected from CH, CF, $CCH_3$, and N;

$Z^2$ is selected from CH, CF, CCl, and $CCH_3$;

$Z^3$ is selected from CH, CF, CCl, and $CCH_3$; and $Z^4$ is CH or N.

13. The compound of claim 1, wherein said compound is of Formula (IV):

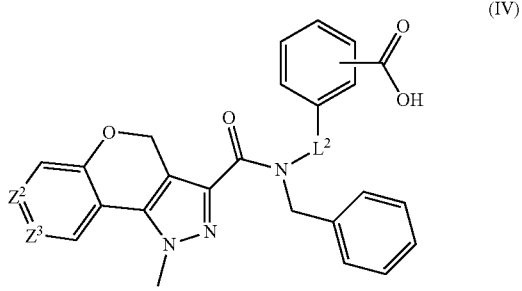

(IV)

or a pharmaceutically acceptable salt thereof; wherein each phenyl ring is optionally further substituted by 1-2 substituents independently represented by $R^2$, wherein $R^2$ is fluoro or methyl;

$L^2$ is selected from —$CH_2$—, $*^2$—$CH_2CH_2NH$—, $*^2$—$CH_2CH_2O$—, and $*^2$—$CH_2C(O)NH$—, wherein "$*^2$" indicates the point of attachment of $L^2$ to N;

$Z^2$ is selected from CH, CF, CCl, and $CCH_3$; and
$Z^3$ is selected from CH, CF, CCl, and $CCH_3$.

14. The compound of claim 1 selected from:
4-fluoro-3-(2-(8-fluoro-N-(2-fluorobenzyl)-1-methyl-1, 4-dihydrochromeno[4,3-c]pyrazole-3-carboxamido) acetamido)benzoic acid;
4-fluoro-3-(2-(8-fluoro-N-(3-fluorobenzyl)-1-methyl-1, 4-dihydrochromeno[4,3-c]pyrazole-3-carboxamido) acetamido)benzoic acid;
3-(2-(8-chloro-1-methyl-N-(3-methylbenzyl)-1,4-dihydrochromeno[4,3-c]pyrazole-3-carboxamido)acetamido)-4-fluorobenzoic acid;
4-fluoro-3-(2-(1-methyl-N-(3-methylbenzyl)-1,4-dihydrochromeno[4,3-c]pyrazole-3-carboxamido)acetamido)benzoic acid;
3-(2-(N-(2-fluorobenzyl)-1,8-dimethyl-1,4-dihydrochromeno[4, 3-c]pyrazole-3-carboxamido)acetamido) benzoic acid;
3-(2-(N-(2-fluorobenzyl)-1,6-dimethyl-1,4-dihydrochromeno[4, 3-c]pyrazole-3-carboxamido)acetamido) benzoic acid;
3-(2-(8-fluoro-N-(2-fluorobenzyl)-1-methyl-1,4-dihydrochromeno[4,3-c]pyrazole-3-carboxamido)acetamido) benzoic acid;
3-(2-(7-fluoro-N-(2-fluorobenzyl)-1-methyl-1,4-dihydrochromeno[4,3-c]pyrazole-3-carboxamido)acetamido) benzoic acid;
3-(2-(7-chloro-N-(2-fluorobenzyl)-1-methyl-1,4-dihydrochromeno[4, 3-c]pyrazole-3-carboxamido)acetamido)benzoic acid;
N-(2-fluorobenzyl)-1-methyl-1,4-dihydrochromeno[4,3-c]pyrazole-3-carboxamido)acetamido)benzoic acid;
3-(2-(6,8-difluoro-N-(2-fluorobenzyl)-1-methyl-1,4-dihydrochromeno[4,3-c]pyrazole-3-carboxamido)acetamido)benzoic acid;
3-(2-(N-(2-fluorobenzyl)-1-methyl-1,4-dihydrochromeno[4,3-c]pyrazole-3-carboxamido)acetamido)benzoic acid;
3-(2-(8-chloro-N-(2-fluorobenzyl)-1,7-dimethyl-1,4-dihydrochromeno[4,3-c]pyrazole-3-carboxamido)acetamido)benzoic acid;
3-(2-(8-chloro-N-(2-fluorobenzyl)-1,6-dimethyl-1,4-dihydrochromeno[4,3-c]pyrazole-3-carboxamido)acetamido)benzoic acid;
3-(2-(8-chloro-6-fluoro-N-(2-fluorobenzyl)-1-methyl-1, 4-dihydrochromeno[4,3-c]pyrazole-3-carboxamido) acetamido)benzoic acid;
4-fluoro-3-(2-(N-(2-fluorobenzyl)-1-methyl-1,4-dihydrochromeno[4,3-c]pyrazole-3-carboxamido)acetamido) benzoic acid;
3-(2-(7,8-difluoro-N-(2-fluorobenzyl)-1-methyl-1,4-dihydrochromeno[4,3-c]pyrazole-3-carboxamido)acetamido)-4-fluorobenzoic acid;
3-(2-(7,8-difluoro-N-(3-fluorobenzyl)-1-methyl-1,4-dihydrochromeno[4,3-c]pyrazole-3-carboxamido)acetamido)-4-fluorobenzoic acid;
3-(2-(N-benzyl-7,8-difluoro-1-methyl-1,4-dihydrochromeno[4,3-c]pyrazole-3-carboxamido)acetamido)-4-fluorobenzoic acid;
4-fluoro-3-(2-(8-fluoro-1-methyl-N-(3-methylbenzyl)-1, 4-dihydrochromeno[4,3-c]pyrazole-3-carboxamido) acetamido)benzoic acid;
4-fluoro-3-(2-(N-(2-fluorobenzyl)-1-methyl-4,5-dihydro-1H-pyrazolo[4,3-h]quinoline-3-carboxamido)acetamido)benzoic acid;
4-fluoro-3-(2-(N-(2-fluorobenzyl)-1-methyl-4,5-dihydro-1H-pyrazolo[3,4-f]quinoline-3-carboxamido)acetamido)benzoic acid;
(S)-4-fluoro-3-(2-(8-fluoro-N-(2-fluorobenzyl)-1-methyl-1,4-dihydrochromeno[4,3-c]pyrazole-3-carboxamido)propanamido)benzoic acid;
3-(2-(8-chloro-N-(2-fluorobenzyl)-1-methyl-4,5-dihydro-1H-benzo[g]indazole-3-carboxamido)acetamido)benzoic acid;
3-(2-(8-chloro-7-fluoro-N-(2-fluorobenzyl)-1-methyl-1, 4-dihydrochromeno[4,3-c]pyrazole-3-carboxamido) acetamido)benzoic acid;
4-fluoro-3-(2-(N-(3-fluorobenzyl)-1,5,5-trimethyl-4,5-dihydro-1H-benzo[g]indazole-3-carboxamido)acetamido)benzoic acid;
4-fluoro-3-(2-(N-(3-fluorobenzyl)-1-methyl-1,4-dihydrochromeno[4,3-c]pyrazole-3-carboxamido)acetamido) benzoic acid;
3-(2-(8-chloro-N-(3-fluorobenzyl)-1-methyl-1,4-dihydrochromeno[4, 3-c]pyrazole-3-carboxamido)acetamido)-4-fluorobenzoic acid;
3-(2-(N-benzyl-8-chloro-1-methyl-1,4-dihydrochromeno [4,3-c]pyrazole-3-carboxamido)acetamido)-4-fluorobenzoic acid;
3-(2-(8-chloro-N-(2-fluorobenzyl)-1-methyl-1,4-dihydrochromeno[4, 3-c]pyrazole-3-carboxamido)acetamido)-4-fluorobenzoic acid;
3-(2-(N-benzyl-8-chloro-1-methyl-1,4-dihydrochromeno [4,3-c]pyrazole-3-carboxamido)acetamido)benzoic acid;
3-(2-(N-benzyl-8-fluoro-1-methyl-1,4-dihydrochromeno [4,3-c]pyrazole-3-carboxamido)acetamido)-4-fluorobenzoic acid;
3-(2-(N-benzyl-1-methyl-1,4-dihydrochromeno[4,3-c] pyrazole-3-carboxamido)acetamido)-4-fluorobenzoic acid;
3-(2-(9-chloro-N-(2-fluorobenzyl)-1-methyl-4,5-dihydro-1H-benzo[2,3]oxepino[4,5-c]pyrazole-3-carboxamido)acetamido)-4-fluorobenzoic acid;
3-(2-(8-chloro-N-(2-fluorobenzyl)-1-methyl-1,4-dihydrochromeno[4, 3-c]pyrazole-3-carboxamido)acetamido)benzoic acid;
3-(2-(8-chloro-N-(cyclopentylmethyl)-1-methyl-1,4-dihydrochromeno[4,3-c]pyrazole-3-carboxamido)acetamido)-4-fluorobenzoic acid;

3-(2-(8-chloro-N-(cyclopentylmethyl)-1-methyl-1,4-dihydrochromeno[4,3-c]pyrazole-3-carboxamido)acetamido)benzoic acid;
3-(2-(8-chloro-N-(2-fluorobenzyl)-1-methyl-1,4-dihydrochromeno[4, 3-c]pyrazole-3-carboxamido)acetamido)-5-fluorobenzoic acid;
3-(2-(8-chloro-N-(2-fluorobenzyl)-1-methyl-1,4-dihydrochromeno[4, 3-c]pyrazole-3-carboxamido)acetamido)-4-methylbenzoic acid;
3-(2-(8-chloro-N-(2-fluorobenzyl)-1-methyl-1,4-dihydrochromeno[4, 3-c]pyrazole-3-carboxamido)acetamido)-2-methylpropanoic acid;
3-(2-(8-chloro-N-(2-fluorobenzyl)-1-methyl-1,4-dihydrochromeno[4, 3-c]pyrazole-3-carboxamido)acetamido)-2,2-dimethylpropanoic acid;
1-((2-(8-chloro-N-(2-fluorobenzyl)-1-methyl-1,4-dihydrochromeno[4, 3-c]pyrazole-3-carboxamido)acetamido)methyl)cyclopropanecarboxylic acid;
4-(2-(8-chloro-N-(2-fluorobenzyl)-1-methyl-1,4-dihydrochromeno[4, 3-c]pyrazole-3-carboxamido)ethoxy)-3-fluorobenzoic acid;
3-(2-(8-chloro-N-(2-fluorobenzyl)-1-methyl-1,4-dihydrochromeno[4, 3-c]pyrazole-3-carboxamido)ethoxy)benzoic acid;
4-(2-(8-chloro-N-(2-fluorobenzyl)-1-methyl-1,4-dihydrochromeno[4, 3-c]pyrazole-3-carboxamido)ethoxy)benzoic acid;
N-(2-fluorobenzyl)-1-methyl-1,4-dihydrochromeno[4,3-c]pyrazole-3-carboxamido)ethoxy)-3-methylbenzoic acid;
4-(2-(8-chloro-N-(2-fluorobenzyl)-1-methyl-1,4-dihydrochromeno[4, 3-c]pyrazole-3-carboxamido)ethoxy)-3,5-dimethylbenzoic acid;
3-(2-(8-chloro-N-(2-fluorobenzyl)-1-methyl-1,4-dihydrochromeno[4, 3-c]pyrazole-3-carboxamido)ethoxy)-4-fluorobenzoic acid;
4-(2-(8-chloro-N-(cyclopentylmethyl)-1-methyl-1,4-dihydrochromeno[4,3-c]pyrazole-3-carboxamido)ethoxy)-3,5-dimethylbenzoic acid;
4-(2-(8-chloro-N-(2-fluorobenzyl)-1-methyl-1,4-dihydrochromeno[4, 3-c]pyrazole-3-carboxamido)ethoxy)-3,5-difluorobenzoic acid;
4-(2-(8-chloro-N-(2-fluorobenzyl)-1-methyl-1,4-dihydrochromeno[4, 3-c]pyrazole-3-carboxamido)ethoxy)-3-(trifluoromethyl)benzoic acid;
4-(2-(N-benzyl-8-chloro-1-methyl-1,4-dihydrochromeno[4,3-c]pyrazole-3-carboxamido)ethoxy)-3,5-difluorobenzoic acid;
3,5-difluoro-4-(2-(8-fluoro-N-(2-fluorobenzyl)-1-methyl-1,4-dihydrochromeno[4,3-c]pyrazole-3-carboxamido)ethoxy)benzoic acid;
4-(2-(N-benzyl-8-fluoro-1-methyl-1,4-dihydrochromeno[4,3-c]pyrazole-3-carboxamido)ethoxy)-3,5-difluorobenzoic acid;
4-(2-(N-benzyl-8-chloro-1-methyl-1,4-dihydrochromeno[4,3-c]pyrazole-3-carboxamido)ethoxy)-3-fluorobenzoic acid;
4-(2-(N-benzyl-8-fluoro-1-methyl-1,4-dihydrochromeno[4,3-c]pyrazole-3-carboxamido)ethoxy)-3-fluorobenzoic acid;
4-(2-(N-benzyl-7,8-difluoro-1-methyl-1,4-dihydrochromeno[4,3-c]pyrazole-3-carboxamido)ethoxy)-3-fluorobenzoic acid;
3-fluoro-4-(2-(8-fluoro-N-(3-fluorobenzyl)-1-methyl-1,4-dihydrochromeno[4,3-c]pyrazole-3-carboxamido)ethoxy)benzoic acid;
4-(2-(7,8-difluoro-N-(3-fluorobenzyl)-1-methyl-1,4-dihydrochromeno[4,3-c]pyrazole-3-carboxamido)ethoxy)-3-fluorobenzoic acid;
4-(2-(8-chloro-N-(3-fluorobenzyl)-1-methyl-1,4-dihydrochromeno[4, 3-c]pyrazole-3-carboxamido)ethoxy)-3-fluorobenzoic acid;
3-fluoro-4-(2-(8-fluoro-N-(2-fluorobenzyl)-1-methyl-1,4-dihydrochromeno[4,3-c]pyrazole-3-carboxamido)ethoxy)benzoic acid;
4-(2-(7,8-difluoro-N-(2-fluorobenzyl)-1-methyl-1,4-dihydrochromeno[4,3-c]pyrazole-3-carboxamido)ethoxy)-3-fluorobenzoic acid;
3-((2-(8-chloro-N-(2-fluorobenzyl)-1-methyl-1,4-dihydrochromeno[4, 3-c]pyrazole-3-carboxamido)ethyl)amino)benzoic acid;
3-(2-(8-chloro-N-(2-fluorobenzyl)-1-methyl-1,4-dihydrochromeno[4, 3-c]pyrazole-3-carboxamido)acetamido)-4-fluorobenzoic acid;
3-((2-(8-chloro-N-(3-fluorobenzyl)-1-methyl-1,4-dihydrochromeno[4, 3-c]pyrazole-3-carboxamido)ethyl)amino)-4-fluorobenzoic acid;
3-((2-(8-chloro-1-methyl-N-(3-methylbenzyl)-1,4-dihydrochromeno[4,3-c]pyrazole-3-carboxamido)ethyl)amino)-4-fluorobenzoic acid;
4-fluoro-3-((2-(8-fluoro-1-methyl-N-(3-methylbenzyl)-1,4-dihydrochromeno[4,3-c]pyrazole-3-carboxamido)ethyl)amino)benzoic acid;
3-((2-(7,8-difluoro-1-methyl-N-(3-methylbenzyl)-1,4-dihydrochromeno[4,3-c]pyrazole-3-carboxamido)ethyl)amino)-4-fluorobenzoic acid;
4-fluoro-3-((2-(8-fluoro-N-(2-fluorobenzyl)-1-methyl-1,4-dihydrochromeno[4,3-c]pyrazole-3-carboxamido)ethyl)amino)benzoic acid;
4-fluoro-3-((2-(N-(2-fluorobenzyl)-1-methyl-1,4-dihydrochromeno[4,3-c]pyrazole-3-carboxamido)ethyl)amino)benzoic acid;
3-((2-(N-benzyl-8-fluoro-1-methyl-1,4-dihydrochromeno[4,3-c]pyrazole-3-carboxamido)ethyl)amino)-4-fluorobenzoic acid;
3-((2-(N-benzyl-8-chloro-1-methyl-1,4-dihydrochromeno[4,3-c]pyrazole-3-carboxamido)ethyl)amino)-4-fluorobenzoic acid;
3-((2-(7,8-difluoro-N-(3-fluorobenzyl)-1-methyl-1,4-dihydrochromeno[4,3-c]pyrazole-3-carboxamido)ethyl)amino)-4-fluorobenzoic acid;
3-((2-(N-benzyl-7,8-difluoro-1-methyl-1,4-dihydrochromeno[4,3-c]pyrazole-3-carboxamido)ethyl)amino)-4-fluorobenzoic acid;
4-((N-benzyl-8-chloro-1-methyl-1,4-dihydrochromeno[4, 3-c]pyrazole-3-carboxamido)methyl)benzoic acid;
4-((N-benzyl-8-chloro-1-methyl-1,4-dihydrochromeno[4, 3-c]pyrazole-3-carboxamido)methyl)-3-fluorobenzoic acid;
4-((8-fluoro-N-(3-fluorobenzyl)-1-methyl-1,4-dihydrochromeno[4,3-c]pyrazole-3-carboxamido)methyl)benzoic acid;
4-((8-chloro-N-(3,5-difluorobenzyl)-1-methyl-1,4-dihydrochromeno[4,3-c]pyrazole-3-carboxamido)methyl)benzoic acid;
4-((N-benzyl-8-fluoro-1-methyl-1,4-dihydrochromeno[4, 3-c]pyrazole-3-carboxamido)methyl)-3-fluorobenzoic acid;
4-((8-chloro-1-methyl-N-(3-methylbenzyl)-1,4-dihydrochromeno[4,3-c]pyrazole-3-carboxamido)methyl)benzoic acid;

4-((8-chloro-N-(2,3-difluorobenzyl)-1-methyl-1,4-dihydrochromeno[4,3-c]pyrazole-3-carboxamido)methyl)benzoic acid;
4-((8-chloro-N-(3-fluoro-5-methylbenzyl)-1-methyl-1,4-dihydrochromeno[4,3-c]pyrazole-3-carboxamido)methyl)benzoic acid;
4-((N-(3,5-difluorobenzyl)-8-fluoro-1-methyl-1,4-dihydrochromeno[4,3-c]pyrazole-3-carboxamido)methyl)benzoic acid;
4-((8-chloro-1-methyl-N-(3-methylbenzyl)-1,4-dihydrochromeno[4,3-c]pyrazole-3-carboxamido)methyl)-3-fluorobenzoic acid;
3-fluoro-4-((8-fluoro-1-methyl-N-(3-methylbenzyl)-1,4-dihydrochromeno[4,3-c]pyrazole-3-carboxamido)methyl)benzoic acid;
4-((N-((1H-indol-5-yl)methyl)-8-chloro-1-methyl-1,4-dihydrochromeno[4,3-c]pyrazole-3-carboxamido)methyl)benzoic acid;
5-((8-chloro-N-(3-fluorobenzyl)-1-methyl-1,4-dihydrochromeno[4,3-c]pyrazole-3-carboxamido)methyl)picolinic acid;
4-(8-chloro-N-((5-fluoropyridin-3-yl)methyl)-1-methyl-1,4-dihydrochromeno[4,3-c]pyrazole-3-carboxamido)methyl)benzoic acid;
4-((8-chloro-N-((5-chloropyridin-3-yl)methyl)-1-methyl-1,4-dihydrochromeno[4,3-c]pyrazole-3-carboxamido)methyl)benzoic acid;
4-((8-chloro-N-(3-fluorobenzyl)-1-methyl-1,4-dihydrochromeno[4,3-c]pyrazole-3-carboxamido)methyl)-2-fluorobenzoic acid;
4-((N-benzyl-8-chloro-1-methyl-1,4-dihydrochromeno[4,3-c]pyrazole-3-carboxamido)methyl)-2-fluorobenzoic acid;
N-benzyl-N-(4-carbamoylbenzyl)-8-chloro-1-methyl-1,4-dihydrochromeno[4,3-c]pyrazole-3-carboxamide;
4-((8-chloro-N-(2-fluorobenzyl)-1-methyl-1,4-dihydrochromeno[4,3-c]pyrazole-3-carboxamido)methyl)benzoic acid;
4-((8-chloro-N-(2-fluorobenzyl)-1-methyl-1,4-dihydrochromeno[4,3-c]pyrazole-3-carboxamido)methyl)-3-fluorobenzoic acid;
3-fluoro-4-((8-fluoro-N-(2-fluorobenzyl)-1-methyl-1,4-dihydrochromeno[4,3-c]pyrazole-3-carboxamido)methyl)benzoic acid;
4-((8-chloro-N-(3-fluorobenzyl)-1-methyl-1,4-dihydrochromeno[4,3-c]pyrazole-3-carboxamido)methyl)benzoic acid;
4-((8-chloro-N-(3-fluorobenzyl)-1-methyl-1,4-dihydrochromeno[4,3-c]pyrazole-3-carboxamido)methyl)-3-fluorobenzoic acid
4-((8-chloro-N-(2-fluorobenzyl)-1-methyl-1,4-dihydrochromeno[4,3-c]pyrazole-3-carboxamido)methyl)-2-fluorobenzoic acid;
6-((8-chloro-N-(3-fluorobenzyl)-1-methyl-1,4-dihydrochromeno[4,3-c]pyrazole-3-carboxamido)methyl) nicotinic acid;
5-((8-chloro-N-(3-fluorobenzyl)-1-methyl-1,4-dihydrochromeno[4,3-c]pyrazole-3-carboxamido)methyl)-6-methylpicolinic acid;
4-fluoro-3-((2-(8-fluoro-N-(3-fluorobenzyl)-1-methyl-1,4-dihydrochromeno[4,3-c]pyrazole-3-carboxamido)ethyl)amino)benzoic acid; and
3-((2-(8-chloro-N-(2-fluorobenzyl)-1-methyl-1,4-dihydrochromeno[4, 3-c]pyrazole-3-carboxamido)ethyl) amino)-4-fluorobenzoic acid;
or a pharmaceutically acceptable salt thereof.

15. The compound of claim 1 selected from:
4-fluoro-3-(2-(8-fluoro-N-(2-fluorobenzyl)-1-methyl-1,4-dihydrochromeno[4,3-c]pyrazole-3-carboxamido)acetamido)benzoic acid;
4-fluoro-3-(2-(8-fluoro-N-(3-fluorobenzyl)-1-methyl-1,4-dihydrochromeno[4,3-c]pyrazole-3-carboxamido)acetamido)benzoic acid;
3-(2-(7-chloro-N-(2-fluorobenzyl)-1-methyl-1,4-dihydrochromeno[4, 3-c]pyrazole-3-carboxamido)acetamido)benzoic acid;
3-(2-(7,8-difluoro-N-(2-fluorobenzyl)-1-methyl-1,4-dihydrochromeno[4,3-c]pyrazole-3-carboxamido)acetamido)-4-fluorobenzoic acid;
3-(2-(8-chloro-N-(2-fluorobenzyl)-1-methyl-1,4-dihydrochromeno[4, 3-c]pyrazole-3-carboxamido)ethoxy)benzoic acid;
3-((2-(8-chloro-N-(2-fluorobenzyl)-1-methyl-1,4-dihydrochromeno[4, 3-c]pyrazole-3-carboxamido)ethyl)amino)benzoic acid;
3-((2-(8-chloro-N-(3-fluorobenzyl)-1-methyl-1,4-dihydrochromeno[4, 3-c]pyrazole-3-carboxamido)ethyl)amino)-4-fluorobenzoic acid;
4-((N-benzyl-8-chloro-1-methyl-1,4-dihydrochromeno[4, 3-c]pyrazole-3-carboxamido)methyl)benzoic acid;
4-((8-chloro-N-(2-fluorobenzyl)-1-methyl-1,4-dihydrochromeno[4,3-c]pyrazole-3-carboxamido)methyl)benzoic acid;
4-((8-chloro-N-(3-fluorobenzyl)-1-methyl-1,4-dihydrochromeno[4,3-c]pyrazole-3-carboxamido)methyl)benzoic acid; and
4-fluoro-3-((2-(8-fluoro-N-(3-fluorobenzyl)-1-methyl-1,4-dihydrochromeno[4,3-c]pyrazole-3-carboxamido)ethyl)amino)benzoic acid;
or a pharmaceutically acceptable salt thereof.

16. An compound of Formula (V)

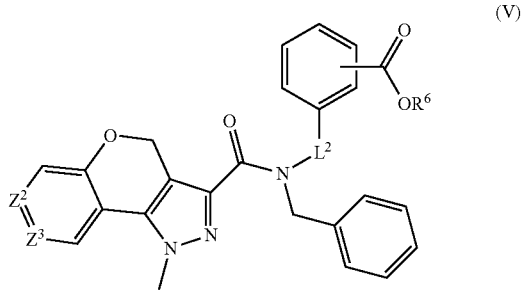

(V)

wherein each phenyl ring is optionally further substituted by 1-2 substituents independently represented by $R^2$, wherein $R^2$ is fluoro or methyl;
$L^2$ is selected from —CH$_2$—, *²—CH$_2$CH$_2$NH—, *²—CH$_2$CH$_2$O—, and *²—CH$_2$C(O)NH—, wherein "*²" indicates the point of attachment of $L^2$ to N;
$Z^2$ is selected from CH, CF, CCl, and CCH$_3$;
$Z^3$ is selected from CH, CF, CCl, and CCH$_3$; and
$R^6$ is $C_{1-6}$ alkyl.

17. A pharmaceutical composition comprising a therapeutically effective amount of a compound of claim 1 or a pharmaceutically acceptable salt thereof, and a pharmaceutically acceptable carrier.

18. A combination comprising a therapeutically effective amount of a compound of claim 1 or a pharmaceutically acceptable salt thereof, and a second therapeutic agent.

19. A method for treating a condition mediated by farnesoid X receptors (FXR) in a subject suffering therefrom, comprising administering to the subject a therapeutically effective amount of a compound of claim 1 or a pharmaceutically acceptable salt thereof, and optionally in combination with a second therapeutic agent.

20. The method of claim 19, wherein said condition mediated by FXR is a liver disease or a gastrointestinal disease.

21. The method of claim 20, wherein said condition mediated by FXR is a liver disease selected from intrahepatic cholestasis, estrogen-induced cholestasis, drug-induced cholestasis, cholestasis of pregnancy, parenteral nutrition-associated cholestasis, progressive familial cholestasis (PFIC), Alagille syndrome, primary biliary cirrhosis (PBC), primary sclerosing cholangitis, ductopenic liver transplant rejection, liver transplant associated graft versus host disease, cystic fibrosis liver disease, non-alcoholic fatty liver disease (NAFLD), non-alcoholic steatohepatitis (NASH), alcoholic liver disease, and parenteral nutrition-associated liver disease.

22. The method of claim 20, wherein said condition mediated by FXR is a gastrointestinal disease selected from primary bile acid diarrhea, secondary bile acid diarrhea, bile reflux gastritis, and inflammatory bowel disease.

23. The compound of claim 1 or a pharmaceutically acceptable salt thereof, wherein said compound is

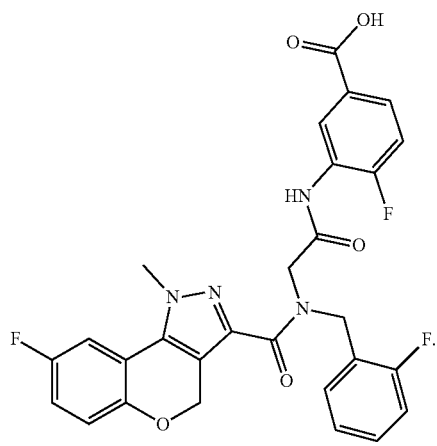

24. The compound of claim 1 or a pharmaceutically acceptable salt thereof, wherein said compound is

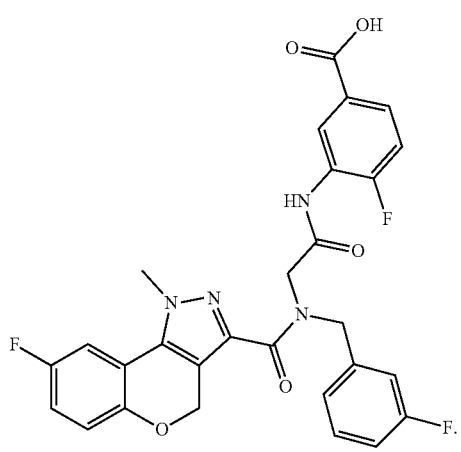

25. The compound of claim 1 or a pharmaceutically acceptable salt thereof, wherein said compound is

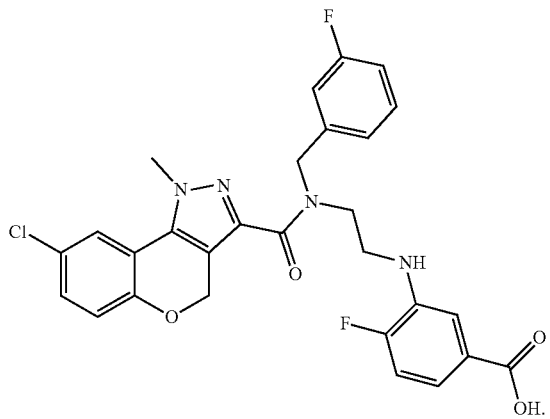

26. The compound of claim 1 or a pharmaceutically acceptable salt thereof, wherein said compound is

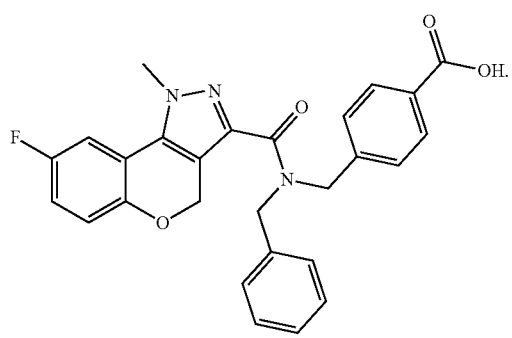

27. The compound of claim 1 or a pharmaceutically acceptable salt thereof, wherein said compound is

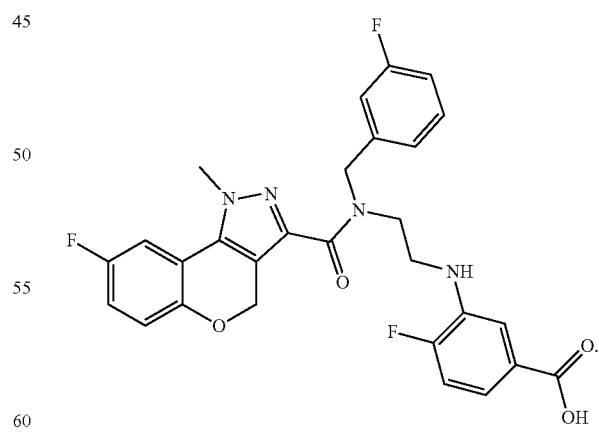

* * * * *

UNITED STATES PATENT AND TRADEMARK OFFICE
CERTIFICATE OF CORRECTION

PATENT NO. : 9,682,939 B2  
APPLICATION NO. : 15/034280  
DATED : June 20, 2017  
INVENTOR(S) : Chianelli et al.

Page 1 of 1

It is certified that error appears in the above-identified patent and that said Letters Patent is hereby corrected as shown below:

In Claim 26, please replace the compound structure with the following compound structure:

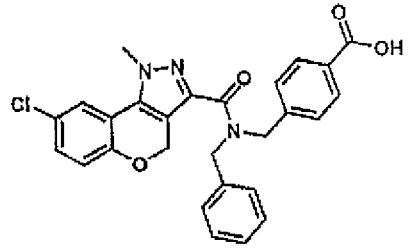

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: biotinylated peptide derived from Steroid
      Receptor Coactivator-1
<220> FEATURE:
<221> NAME/KEY: MOD_RES
<222> LOCATION: (1)..(1)
<223> OTHER INFORMATION: Biotinylated

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25
```